(12) United States Patent
Caravan et al.

(10) Patent No.: US 9,386,938 B2
(45) Date of Patent: Jul. 12, 2016

(54) METHODS FOR COLLAGEN IMAGING

(75) Inventors: Peter D. Caravan, Cambridge, MA (US); Andrew Kolodziej, Winchester, MA (US); Zhaoda Zhang, Andover, MA (US); Stephane Dumas, Cambridge, MA (US); Biplab Kumar Das, Boston, MA (US); Vincent Jacques, Somerville, MA (US); Richard Looby, Reading, MA (US); Steffi K. Koerner, Somerville, MA (US); Wei-Chuan Sun, Acton, MA (US); David R. Buckler, Sudbury, MA (US); Aida Abujoub, Winchester, MA (US); Aaron K. Sato, Richmond, CA (US)

(73) Assignee: Collagen Medical, LLC, Belmont, MA (US)

( * ) Notice: Subject to any disclaimer, the term of this patent is extended or adjusted under 35 U.S.C. 154(b) by 810 days.

(21) Appl. No.: 13/229,900

(22) Filed: Sep. 12, 2011

(65) Prior Publication Data
US 2012/0114557 A1 May 10, 2012

Related U.S. Application Data

(63) Continuation of application No. 11/618,458, filed on Dec. 29, 2006, now Pat. No. 8,034,898.

(60) Provisional application No. 60/755,710, filed on Dec. 29, 2005, provisional application No. 60/755,709, filed on Dec. 29, 2005, provisional application No. 60/845,118, filed on Sep. 15, 2006, provisional application No. 60/844,768, filed on Sep. 15, 2006.

(51) Int. Cl.
*A61B 5/05* (2006.01)
*A61B 5/055* (2006.01)
*A61B 5/00* (2006.01)

(52) U.S. Cl.
CPC .............. *A61B 5/055* (2013.01); *A61B 5/4519* (2013.01); *A61B 5/7289* (2013.01); *A61B 5/7292* (2013.01)

(58) Field of Classification Search
None
See application file for complete search history.

(56) References Cited

U.S. PATENT DOCUMENTS

| | | | |
|---|---|---|---|
| 5,402,785 | A | 4/1995 | Leigh et al. |
| 6,026,317 | A | 2/2000 | Verani |
| 6,295,465 | B1 | 9/2001 | Simonetti |
| 6,549,798 | B2 | 4/2003 | Stefancik et al. |
| 2002/0034476 | A1 | 3/2002 | Lauffer et al. |
| 2003/0028101 | A1 | 2/2003 | Weisskoff et al. |
| 2003/0180222 | A1* | 9/2003 | Zhang et al. ............ 424/9.34 |
| 2003/0216320 | A1* | 11/2003 | Koerner et al. ............ 514/16 |
| 2003/0220563 | A1 | 11/2003 | Schutt |
| 2003/0232013 | A1* | 12/2003 | Sieckman et al. ........... 424/1.69 |

FOREIGN PATENT DOCUMENTS

| | | |
|---|---|---|
| WO | WO 96/23526 | 8/1996 |
| WO | WO 01/08712 | 2/2001 |
| WO | WO 01/09188 | 2/2001 |

OTHER PUBLICATIONS

"2001 Guidelines for Authors" *J. Org. Chem.*, 2001, 66(1):24A.
Brechbiel et al., "Synthesis of 1-(p-Isothiocyanatobenzyl) Derivatives of DTPA and EDTA. Antibody Labeling and Tumor-Imaging Studies," *Inorg. Chem.*, 1986, 25:2772-2781.
Caravan et al., "Gadolinium(III) Chelates as MRI Contrast Agents: Structure, Dynamics, and Applications," *Chem. Rev.*, 1999, 99(9):2293-2352.
Cerqueira et al., "Standardized myocardial segmentation and nomenclature for tomographic imaging of the heart: a statement for healthcare professionals from the Cardiac Imaging Committee of the Council on Clinical Cardiology of the American Heart Association," *Circulation*, 2002, 105:539-542.
Chen et al., "MicroPET imaging of brain tumor angiogenesis with 18F-labeled PEGylated RGD peptide," *Eur. J. Nucl. Med. Mol. Imaging*, 2004, 31:1081-1089.
Cho et al., "An oral endothelin-A receptor antagonist blocks collagen synthesis and deposition in advanced rat liver fibrosis," *Gastroenterology*, 2000, 118:1169-1178.
Corson et al., "Efficient Multigram Synthesis of the Bifunctional Chelating Agent (S)-1-p-Isothiocyanatobenzyl-diethylenetetraminepentaacetic Acid," *Bioconjug. Chem.*, 2000, 11:292.
de Bruin et al., "1-[3-(2-[18F]fluoropyridin-3-yloxy)propyl]pyrrole-2,5-dione: design, synthesis, and radiosynthesis of a new [18F]fluoropyridine-based maleimide reagent for the labeling of peptides and proteins," *Bioconjug. Chem.*, 2005, 16:406-420.
Goodman et al., "Nanomolar small molecule inhibitors for alphav(beta)6, alphav(beta)5, and alphav(beta)3 integrins," *J. Med. Chem.*, 2002, 45:1045-1051.
Guenther et al., "Synthesis and in vitro evaluation of 18F- and 19F-labeled insulin: a new radiotracer for PET-based molecular imaging studies," *J. Med. Chem.*, 2006, 49:1466-1474.
Jones, "A Short Guide to Abbreviations and Their Use in Peptide Science," *J. Peptide. Sci.*, 1999, 5:465-471.
Murru et al., "Luminescence Behaviour of Stable Europium and Terbium Complexes of Tetraaza Phosphinates: Efficient Through-space Energy Transfer from Phenyl to Terbium," *J. Chem. Soc. Chem. Comm.*, 1993, 1116-1118.
Rockey et al., "Noninvasive measures of liver fibrosis," *Hepatology*, 2006, 43:S113-120.
Verrecchio et al., "Design of Peptides with High Affinities for Heparin and Endothelial Cell Proteoglycans," *J. Biol. Chem.*, 2000, 275:7701-7707.
Virmani et al., "Vulnerable Plaque: The Pathology of Unstable Coronary Lesions," *J. Interv. Cardiol.*, 2002, 15:439-446
Wagner et al., "Contrast-enhanced MRI and routine single photon emission computed tomography (SPECT) perfusion imaging for detection of subendocardial myocardial infarcts: an imaging study," *Lancet*, 2003, 361:374-379.

(Continued)

*Primary Examiner* — Julie Ha
*Assistant Examiner* — Kristina M Hellman
(74) *Attorney, Agent, or Firm* — Fish & Richardson P.C.

(57) ABSTRACT

Diagnostic compositions and methods for imaging and/or assessing collagen are described. The diagnostic compositions can include collagen binding peptides.

18 Claims, 8 Drawing Sheets

(56) References Cited

OTHER PUBLICATIONS

Wester et al., "PET imaging of somatostatin receptors: design, synthesis and preclinical evaluation of a novel 18F-labelled, carbohydrated analogue of octreotide," *Eur. J. Nucl. Med. Mol. Imaging*, 2003, 30(1):117-122.

Autorized Officer B. Copenheaver. International Search Report and Written Opinion in International Application No. PCT/US2006/62760, mailed Oct. 23, 2007, 12 pages.

Friedman and Rutenburg, "Preparation of I131 Labelled Iodoacetamide and N-Iodoacetyl Amino Acids," Jul. 1950, 72:3285-3286.

Krasikova et al., "4-[18F]Fluoroglutamic Acid (BAY 85/8050), a New Amino Acid Radiotracer for PET Imaging of Tumors: Synthesis and in Vitro Characterization," *J. Med. Chem.*, 2011, 54: 406-410.

Pimm et al., "Strategies for Labelling Branched Polypeptides with a Poly(L-Lysine) Backbone with Radioiodines (123I, 125I, 131I) and Radiometals (111In, 51Cr) for Biodistribution Studies and Radiopharmaceutical Development," *Journal of Labelled Compounds and Radiopharmaceuticals*, 1995, 157-172.

Samnick et al., "Investigation of iodine-123-labelled amino acid derivatives for imaging cerebral gliomas: uptake in human glioma cells and evaluation in stereotactically implanted C6 glioma rats," *European Journal of Nuclear Medicine*, 2000, 1-10.

Vaidyanathan et al., "An Alternative and Expedient Synthesis of Radioiodinated 4-Iodophenylalanine," *Appl Radiat Isot*, Oct. 2011, 69(10): 1401-1406.

Yan et al., "A new 18F-labeled BBN-RGD peptide heterodimer with a symmetric linker for prostate cancer imaging," *Amino Acids*, Jul. 2011, 41(2): 439-447.

* cited by examiner

A

B

C　　　　　　　D

US 9,386,938 B2

METHODS FOR COLLAGEN IMAGING

CLAIM OF PRIORITY

This application is a continuation of U.S. patent application Ser. No. 11/618,458, filed Dec. 29, 2006, which claims priority under 35 USC §119(e) to U.S. Provisional Application Ser. No. 60/755,709, filed on Dec. 29, 2005, U.S. Provisional Application Ser. No. 60/755,710, filed on Dec. 29, 2005, U.S. Provisional Application Ser. No. 60/844,768, filed on Sep. 15, 2006, and U.S. Provisional Application Ser. No. 60/845,118, filed on Sep. 15, 2006, all of which are incorporated by reference in their entirety herein.

TECHNICAL FIELD

This disclosure relates to compositions containing diagnostic agents that are capable of binding to and thus imaging collagen, and more particularly to the use of such compositions for myocardial imaging and perfusion measurements.

BACKGROUND

Collagens are a class of extracellular matrix proteins that represent 30% of total body protein and shape the structure of tendons, bones, and connective tissues. Abnormal or excessive accumulation of collagen in organs such as the liver, lungs, kidneys, or breasts, and vasculature can lead to fibrosis of such organs (e.g., cirrhosis of the liver), lesions in the vasculature or breasts, collagen-induced arthritis, Dupuytren's disease, rheumatoid arthritis, and other collagen vascular diseases. It would be useful to have both therapeutic and diagnostic agents that could assist in the treatment or diagnosis of such disorders.

Diagnostic imaging techniques, such as magnetic resonance imaging (MRI), X-ray, nuclear radiopharmaceutical imaging, ultraviolet-visible-infrared light imaging, and ultrasound, have been used in medical diagnosis for a number of years. Contrast media additionally have been used to improve or increase the resolution of the image or to provide specific diagnostic information.

Complexes between gadolinium or other paramagnetic ions and organic ligands are widely used to enhance and improve MRI contrast. Gadolinium complexes increase contrast by increasing the nuclear magnetic relaxation rates of protons found in the water molecules that are accessible to the diagnostic compositions during MRI (Caravan, P., et al., *Chem. Rev.* 99, 2293 (1999)). The relaxation rate of the protons in these water molecules increases relative to protons in other water molecules that are not accessible to the diagnostic composition. This change in relaxation rate leads to improved contrast of the images. In addition, this increase in relaxation rate within a specific population of water molecule protons can result in an ability to collect more image data in a given amount of time. This in turn results in an improved signal to noise ratio.

Imaging may also be performed using light, in which case an optical dye is chosen to provide signal. In particular, light in the 600-1300 nm (visible to near-infrared) range passes relatively easily through biological tissues and can be used for imaging purposes. The light that is transmitted through, or scattered by, reflected, or re-emitted (fluorescence), is detected and an image generated. Changes in the absorbance, reflectance, or fluorescence characteristics of a dye, including an increase or decrease in the number of absorbance peaks or a change in their wavelength maxima, may occur upon binding to a biological target, thus providing additional tissue contrast. In some situations, for example the diagnosis of disease close to the body surface, UV or visible light may also be used.

Ischemic heart disease is a leading cause of death in the developed world. Efforts in the detection of the disease often focus on the patency of major blood vessels such as the coronary arteries, and recent paradigms have emphasized the importance of the coronary microvasculature in providing blood flow, including collateral blood flow, to injured myocardial tissue. Since cardiac catheterization assessing the patency of coronary arteries is an expensive and risky procedure, noninvasive techniques that assess the likelihood of coronary artery disease have flourished, especially nuclear medicine based myocardial perfusion studies.

The most widely used techniques for measuring myocardial perfusion are SPECT (single photon computed tomography) imaging protocols using injectable nuclear agents (e.g., "hot" radiotracers), such as thallium isotope or technetium Sestamibi (MIBI). Frequently the patient is required to undergo a stress test (e.g., a treadmill exercise stress test) to aid in the SPECT evaluation of myocardial perfusion. The cardiac effect of exercise stress can also be simulated pharmacologically by the intravenous administration of a coronary vasodilator. Typically, after injection of the nuclear agent during stress, the myocardium is imaged. A second redistribution rest image is then obtained after an appropriate rest period (approximately 3-4 hours). Alternatively, the patient may be given a second, 2× concentrated dose of the nuclear agent during the rest phase and a second rest image is then acquired. The clinician compares the two image sets to diagnose ischemic areas as "cold" spots on the stress image. SPECT imaging, however, may result in inconclusive perfusion data due to attenuation artifacts and/or from the relatively low spatial resolution compared to other modalities. For instance, subendocardial defects may not be adequately visualized. Moreover, SPECT imaging exposes the patient to ionizing radiation.

Recently, magnetic resonance imaging (MRI) techniques have also been proposed to assess myocardial perfusion. In general, MRI is appealing because of its noninvasive character, ability to provide improved spatial resolution, and ability to derive other important measures of cardiac performance, including cardiac morphology, wall motion and ejection fraction in a single sitting. Current MRI perfusion imaging techniques require rapid imaging of the myocardium during the first pass (after bolus injection) of an extracellular fluid (ECF) or intravascular MR diagnostic composition; this technique is referred to as MRFP (magnetic resonance first pass) perfusion imaging. On T1-weighted images, the ischemic zones appear with a delayed and lower signal enhancement (e.g., hypointensity) as compared with normally perfused myocardium. Myocardial signal intensity versus time curves can then be analyzed to extract perfusion parameters. Intensity differences, however, rapidly decrease as the MR diagnostic composition is diluted in the systemic circulation after the first pass. Furthermore, because of the rapid timing requirement of MRFP perfusion imaging, the patient must undergo pharmacologically-induced stress while positioned inside the MRI apparatus. Rapid imaging may also limit the resolution of the perfusion maps obtained and may result in poor quantification of perfusion.

Because ischemically-injured myocardium contains both reversibly and irreversibly injured regions, accurate characterization of myocardial injury, in particular the differentiation between non-viable, necrotic (necrotic, acutely infarcted myocardium or chronically infarcted myocardium), ischemic, and viable myocardial tissue, is an important factor in proper patient management. This characterization can be aided by an analysis of the perfusion and/or reperfusion state of myocardial tissue adjacent to coronary microvessels either before or after an ischemic event (e.g., an acute myocardial infarction).

SUMMARY

Peptides described herein exhibit an affinity for collagen, and can be used to treat, prevent, ameliorate, or evaluate physiologic functions, manifestations, or disorders where collagens are present in either normal or atypically high concentrations. Examples include the use of collagen-specific agents to treat, prevent, ameliorate, or evaluate fibrosis in the lungs, liver, kidneys, joints, or breasts, or lesions in the vasculature, or heart. Use of such agents can also affect the remodeling of myocardial tissue after an ischemic event. The compositions thus may be useful for both diagnostic and therapeutic purposes.

The disclosure is based on peptides and peptide-targeted diagnostic compositions, including multimeric diagnostic compositions, for MR, optical, SPECT, nuclear medicine, and radionuclide imaging, wherein a peptide can function both as a targeting group and a point of attachment for one or more chelates at one or more of the internal amino acids, N-, and/or C-termini, either directly or via an optional intervening linker. Diagnostic compositions maintain binding affinity for biological targets such as collagen. Diagnostic compositions have a sufficient half-life following in vivo administration such that effective imaging studies can be performed.

The disclosure is also based on the discovery of MR-based methods and diagnostic compositions for measuring myocardial perfusion that provide enhanced anatomical detail and accurate perfusion maps. The methods and diagnostic compositions allow maximum flexibility in the induction of stress in a patient prior to imaging and permit an extended time period for MR signal acquisition post-stress induction. Use of the methods and diagnostic compositions allow the differentiation of ischemia from infarct. Diagnostic compositions are also useful for imaging the myocardium or physiologic states having high concentrations of collagen. Diagnostic compositions can be useful for characterizing atherosclerotic plaque as fibrotic or not, and/or to assess the presence or absence of vulnerable plaque.

A diagnostic composition can include the following formula:

$$[EMTG]_n\text{-}[L]_m\text{-}[C]_p$$

wherein m and p are independently one to ten; n is one to five; C is a physiologically compatible metal chelating group; L is a linker; and EMTG is an Extracellular Matrix Targeting Group.

In other embodiments, a diagnostic composition can include the following formula:

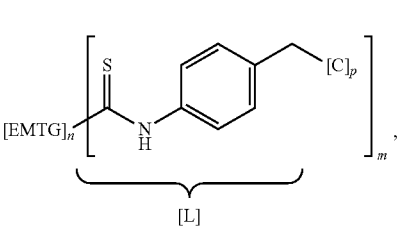

wherein m and p are independently one to ten; n is one to five; C is a physiologically compatible metal chelating group; L is a linker; and EMTG is an Extracellular Matrix Targeting Group.

In certain embodiments, C can be complexed to a paramagnetic metal ion. The paramagnetic metal ion can be selected from the group consisting of: Gd(III), Fe(III), Mn(II), Mn(III), Cr(III), Cu(II), Dy(III), Ho(III), Er(III), Pr(III), Eu(II), Eu(III), Tb(III), and Tb(IV), and the physiologically compatible metal chelating group (C) can include a cyclic or an acyclic organic chelating agent. In some cases, the cyclic or acyclic organic chelating agent can be selected from the group consisting of DTPA, DOTA, HP-DO3A, NOTA, DOTAGA, Glu-DTPA, DTPA-BMA, and derivatives thereof. In other cases, the cyclic or acyclic organic chelating agent comprises Glu-DTPA, DOTAGA, DOTA, or derivatives thereof, and wherein said paramagnetic metal ion complexed to the metal chelate is Gd(III).

In some embodiments, L can include a linear, branched, or cyclic peptide. In specific cases, L can include a linear dipeptide having the sequence G-G or P-P. In other cases, L can include a linear, branched, or cyclic alkane, alkene, or alkyne, or a phosphodiester moiety. Additionally, L can be substituted with at least one functional group selected from the group consisting of ketones, esters, amides, ethers, carbonates, sulfonamides, ureas, and carbamates.

In other embodiments, EMTG can include a cyclic peptide wherein L caps the N-terminus of the peptide as an amide moiety; or EMTG can include a cyclic peptide wherein L caps the C-terminus of said peptide as an amide moiety.

In certain embodiments, m can be one or two; n can be one to four or alternatively, n can be one to two; p can be one to four or p can be one to two.

In other embodiments the EMTG includes any of the cyclic amino acid sequences set forth in Tables 1-16, 18-41, 44, and 45. In further embodiments, the EMTG can include a cyclic peptide including the amino acid sequence W-X1-C-(X2)$_n$-W-X3-C (SEQ ID NO: 806), wherein n is 5-7; X1, X2, and X3 are any amino acid; and wherein the peptide has a length of 11 to 30 amino acids. In some embodiments, n can be 5, 6, or 7. In certain embodiments, X1 is selected from K, Q, Y, T, E, D, L, R, H, I, V, N, M, and A; and X2 is selected from R, E, D, S, H, K, N, Y, M, V, I, Q, and G.

In certain embodiments, the EMTG can include a cyclic peptide including the amino acid sequence W-X1-C-X2-G*-X3-X4-X5-X6-W-X7-C (SEQ ID NO: 807), wherein X1 is selected from any amino acid; X2 is selected from S, V, T, H, R, Y, and D; G* is selected from G and any amino acid in D form; X3 is selected from D and N, independently in D or L form; X4 is selected from any amino acid in D or L form; X5 is selected from any amino acid in D or L form; X6 is selected from T, K, H, D, A, R, Y, and E; and X7 is selected from Y, K, H, V, S, M, and N; wherein the peptide has a total length of 12 to 30 amino acids. In some cases, the cyclic peptide includes the amino acid sequence W-X1-C-X2-G*-X3-X4-X5-X6-W-X7-C-X8-X9 (SEQ ID NO: 808), wherein X8 is selected from N, L, I, R, K, and A; and X9 is selected from Y, F, M, R, and H, independently in D or L form. In other cases, X3 is D; X1 is T; X2 is selected from S, T and V; X4 is selected from E, H, I, S, and A; X5 is selected from Y, K, L, F, A, and P; X6 is T; X7 is selected from H and K; X8 is selected from N, K, and A; and X9 is selected from Y and F. In certain embodiments, the cyclic peptide includes one of the following amino acid sequences W-T-C-S-G-D-E-Y-T-W-H-C (SEQ ID NO: 809); W-T-C-V-G-D-H-K-T-W-K-C (SEQ ID NO: 810); W-Y-C-S-G-D-H-L-D-W-K-C (SEQ ID NO: 811); and W-E-C-H-G-N-E-F-E-W-N-C (SEQ ID NO: 812).

The EMTG can include a cyclic peptide including the amino acid sequence Q-W-H-C-T-T-R-F-P-H-H-Y-C-L-Y-G (SEQ ID NO: 74), wherein the peptide has a total length of 16 to 30 amino acids.

In other embodiments, the EMTG can include a cyclic peptide including the amino acid sequence C-Y-Q-X1-X2-C-W-X3-W (SEQ ID NO: 813), wherein X1 is any amino acid; X2 is any amino acid; X3 is any amino acid; wherein each C, Y, Q, W, X1, X2, or X3, independently, can be in the D form; and wherein the peptide contains 9 to 30 amino acids. In certain cases, X1 is selected from A, G, I, L, V, F, and P; X2 is selected from G, A, I, L, V, F, and P; and X3 is selected from I, A, G, L, V, F, and P. The cyclic peptide can include the amino acid sequence C-Y-Q-A-G-C-W-1-W (SEQ ID NO: 814) in any combination of D or L forms for the individual amino acids; or C-Y-Q-A-G-C-W-1-W (SEQ ID NO: 814) in all L-form.

In certain embodiments, the EMTG can include a cyclic peptide including the amino acid sequence Y-X1-X2-C-Y-Q-X3-X4-C-W-X5-W (SEQ ID NO: 815), wherein X1 is any amino acid; X2 is any amino acid; X3 is any amino acid; X4 is any amino acid; X5 is I, G, L, V, F, or P; and wherein the peptide contains 12 to 30 amino acids. In some embodiments, X1 is selected from H, R, K, E, D, Q, or N; X2 is selected from A, G, I, L, V, F, or P; X3 is selected from A, G, I, L, V, F, or P; X4 is selected from G, A, I, L, V, F, or P; and X5 is selected from I, L, V, or F.

In some embodiments, the EMTG can include a cyclic peptide including the amino acid sequence C*-X1-X2-X3-X4-X5-X6-X7-X8-C* (SEQ ID NO: 816), wherein X1, X2, X3, X4, X5, X6, X7, and X8 are independently any amino acid; C* is C or Pen in D or L form; and wherein the peptide has a length of 10 to 30 amino acids. In certain embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, A, Y, E, R, L, Bip, F(4-CF$_3$), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, A, Y, D, R, T, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), b-h-W, in D or L form; and X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form. In other cases, X1 is selected from T or S; X2 is selected from T or G; X3 is selected from R or D; X4 is selected from F or E; X5 is selected from P or Y; X6 is selected from H or T; X7 is selected from H or W; and X8 is selected from Y or H. Alternatively, the cyclic peptide can include one of the following amino acid sequences: C-T-T-S-F-P-H-H-Y-C (SEQ ID NO: 817); C-T-T-K-F-P-H-H-Y-C (SEQ ID NO: 818); C-Y-T-Y-F-P-H-H-Y-C (SEQ ID NO: 819); C-T-T-R-F-P-H-H-Y-C (SEQ ID NO: 820); and C-S-G-D-E-Y-T-W-H-C (SEQ ID NO: 821).

In other embodiments, the EMTG can include a cyclic peptide including the amino acid sequence C*-X1-X2-X3-X4-X5-X6-X7-X8-C*-X9-X10-X11 (SEQ ID NO: 822), wherein X1, X2, X3, X4, X5, X6, X7, X8, X9, X10, and X11 are independently any amino acid; C* is C or Pen, in D or L form; and wherein the peptide has a length of 13 to 30 amino acids. In some cases, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, A, Y, E, R, L, Bip, F(4-CF$_3$), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, A, Y, D, R, T, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form X9 is selected from L, A, I, K, V, F, N, Y, P, Aib, Hse, Hfe, Bpa, 2-Nal, Y(3-Cl), Dip, or F(4-NH2), in D or L form; X10 is selected from Y, A, F, E, Bpa, 2-Nal, Y(3-Cl), Dip, F(4-NH2), or Y(3-I), in D or L form; and X11 is selected from G, E, Y, F, V, Bip, F(4-NH2), or Aib, in D or L form. In other cases, X9 is selected from L or N, preferably L; X10 is Y; and X11 is selected from G or E.

The EMTG can include a cyclic peptide including the amino acid sequence C*-X1-X2-X3-X4-X5-X6-X7-X8-C*-X9-X10-X11-X12 (SEQ ID NO: 823), wherein X1, X2, X3, X4, X5, X6, X7, X8, X9, X10, and X11 are independently any amino acids; X12 is any one or two amino acids; C* is C or Pen, in D or L form; and wherein the peptide has a length of 14 to 30 amino acids. In further embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, A, Y, D, R, T, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X9 is selected from L, A, I, K, V, F, N, Y, P, Aib, Hse, Hfe, Bpa, 2-Nal, Y(3-Cl), Dip, or F(4-NH2), in D or L form; X10 is selected from Y, A, F, E, Bpa, 2-Nal, Y(3-Cl), Dip, F(4-NH2), or Y(3-I), in D or L form; X11 is selected from G, E, Y, F, V, Bip, F(4-NH2), or Aib, in D or L form; and X12 is selected from K, KK, Peg K, PEG(1×O), 1,4-AMB, 1,3-AMB, 1,6-Hex, PEG, or GTE, in D or L form. In other cases, X12 is K.

In certain embodiments, the EMTG can include a cyclic peptide including the amino acid sequence X14-X13-C*-X1-X2-X3-X4-X5-X6-X7-X8-C* (SEQ ID NO: 824), wherein X1, X2, X3, X4, X5, X6, X7, X8, X13, and X14 are independently any amino acid; C* is C or Pen, in D or L form; and wherein the peptide has a length of 12 to 30 amino acids. In various embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, A, Y, D, R, T, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X13 is selected from H, A, S, K, N, D, Y, T, P, or Aib, in D or L form; and X14 is selected from W, A, Y, 1-Nal, 2-Nal, thien-W, Tic, or W(5-OH), in D or L form. In certain cases, X13 is selected from H or T; and X14 is W.

In some embodiments, the EMTG can include a cyclic peptide including the amino acid sequence X16-X15-X14-X13-C*-X1-X2-X3-X4-X5-X6-X7-X8-C* (SEQ ID NO: 825), wherein X1, X2, X3, X4, X5, X6, X7, X8, X13, and X14 are independently any amino acid; X15 and X16 independently comprise one to three amino acids; C* is C or Pen, in D or L form; and wherein the peptide has a length of 14 to 30 amino acids. In other embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, A, Y, D, R, T, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X13 is selected from H, A, S, K, N, D, Y, T, P, or Aib, in D or L form; X14 is selected from W, A, Y, 1-Nal, 2-Nal, thien-W, Tic, or W(5-OH), in D or L form; X15 is selected from Q, G, A, D, S, P, K, GQ, K(G), K(Y.G), K(V.G). K(F.G), K(H.H), KK(K), Dpr, or Aib, in D or L form; and X16 is selected from G, K, PP, GY, GV, GF, GH, GK(G), KK(K), Dpr, EAG, or PPG, in D or L form. In other cases, X15 is selected from Q, D, or K(G); and X16 is G.

In further embodiments, the EMTG can include a cyclic peptide including the amino acid sequence G-Q-W-H-C-T-T-S-F-P-H-H-Y-C-L-Y-G (SEQ ID NO: 264); G-K(G)-W-H-C-T-T-K-F-P-H-H-Y-C-L-Y-Bip (SEQ ID NO: 400); or K-K-W-H-C-Y-T-Y-F-P-H-H-Y-C-V-Y-G (SEQ ID NO: 408).

In additional embodiments, the EMTG can include a cyclic peptide including the amino acid sequence X1-X2-X3-C*-X4-T-X5-X6-P*-X7-H-X8-C-X9-X10-X11 (SEQ ID NO: 826), wherein X1, X2, X3, X4, X5, X6, X7, X8, X9, X10, and X11 are independently any amino acid; C* is C or Pen; P* is P, L-hydroxyproline, piperidine-2-carboxylic acid, or 4-hydroxypiperidine-2-carboxylic acid; and; and wherein the peptide has a length of 16 to 30 amino acids. In certain cases, X1 is selected from any amino acid in L form; X2 is selected from W or W*; X3 is selected from H, A, K, or S; X4 is selected from T, Y, G, K, or Y*; X5 is selected from any amino acid in L form; X6 is selected from F, Y, or Y*; X7 is selected from H, A, or Y; X8 is selected from Y or Y*; X9 is selected from L, V, L*, or Y*; X10 is selected from Y, F, or Y*; and X11 is selected from G, Y, Bip, or Y*; wherein W* is 1-Nal, 2-Nal, Bpa, thien-W, W(5-OH), 7-aza-Trp, 1-methyl-Trp, 5-bromo-Tryp, 5-chloro-Tryp, 5-fluor-Trp, 7-methyl-trp, 6-methyl-Trp, 6-fluoro-Trp, or 6-hydroxy-trp; Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine; L* is I, V, A, L, G, Tle, L-norvaline, L-norleucine, L-dehydroleucine, L-abu (2-aminobutyric acid), L-tert-leucine, beta-cyclohexyl-L-alanine, L-homoleucine, or L-homo-cyclohexylalanine; and the substituent can be independently selected from alkyl, aryl, halogen, alkoxy, cyano, nitro, carboxy, amino, methoxy, or hydroxy. In certain cases, X1 is selected from Q or K(G); and X5 is selected from R, Y, L, D, or K.

The EMTG can include a cyclic peptide including the amino acid sequence X1-X2-X3-C-X4-X5-D-X6-X7-X8-W-X9-C-X10-X11-X12 (SEQ ID NO: 827), wherein X1, X2, X3, X4, X5, X6, X7, X8, X9, X10, X11, and X12 are any amino acid; and wherein the peptide has a length of 16 to 30 amino acids. In certain embodiments, X1 is selected from any amino acid in L form; X2 is selected from W or W*; X3 is selected from T, A, or W; X4 is selected from S, Y, A, V, or Y*; X5 is selected from G or D*; X6 is selected from E, A, or H; X7 is selected from Y, L, or Y*; X8 is selected from T, Y, A, or S; X9 is selected from H, S, or Y; X10 is selected from N or A; X11 is selected from Y or Y*; X12 is selected from any amino acid in L form; W* is 1-Nal, 2-Nal, Bpa, thien-W, W(5-OH), 7-aza-Trp, 1-methyl-Trp, 5-bromo-Tryp, 5-chloro-Tryp, 5-fluor-Trp, 7-methyl-trp, 6-methyl-Trp, 6-fluoro-Trp, or 6-hydroxy-trp; Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine; D* is any amino acid in D form; and the substituent can be independently selected from alkyl, aryl, halogen, alkoxy, cyano, nitro, carboxy, amino, methoxy, or hydroxy. In some embodiments, X1 is selected from Q or D; and X12 is selected from E or G.

In other embodiments, the diagnostic composition can include any of the sequences set forth in Tables 18-41, 44, and 45. In some cases, the diagnostic composition can have a structure set forth in Table 17, 42, or 43. In further embodiments, the diagnostic composition can be selected from Compound ID 800, Compound ID 801, Compound ID 802, Compound ID 803, Compound ID 807, Compound ID 808, Compound ID 816, Compound ID 813, Compound ID 815, Compound ID 1014, Compound ID 1004, or Compound ID 1013.

Also provided herein is a method of distinguishing fibrotic from non-fibrotic pathologies in an animal, the method includes: a) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for collagen; b) acquiring a T1-weighted image of a tissue of said animal at from about 1 minute to about 10 minutes after administration of the MR-based diagnostic composition; c) acquiring a second T1-weighted image of the tissue of said animal at a time from about 10 minutes to about 2 hours after administration of the MR-based diagnostic composition; and d) evaluating differences between the images acquired in steps b) and c), wherein a non-fibrotic pathology exhibits greater loss in enhancement from the image collected in step b) to that in step c) as compared to a fibrotic pathology.

In another embodiment, the method of distinguishing fibrotic from non-fibrotic pathologies in an animal includes: a) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for collagen; b) acquiring a series of T1-weighted images of the tissue of said animal for a time from about 1 minute to about 2 hours after administration of the MR-based diagnostic composition; and c) evaluating differences between the images acquired in step b), wherein a non-fibrotic pathology exhibits greater loss in enhancement in an image collected earlier in time compared to an image collected later in time, as compared to a fibrotic pathology.

In the above methods, the pathology can be selected from cancer, liver fibrosis, kidney fibrosis, pulmonary fibrosis, and myocardial infarction. In some cases, the collagen can be type I or type III collagen.

In alternative embodiments, a method of imaging a myocardial infarct in an animal is disclosed. The method includes: a) optionally acquiring a baseline image of the myocardium of said animal; b) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for collagen; c) acquiring an image of the myocardium during administration to about 2 hours after administration of the MR-based diagnostic composition; and d) identifying infarcted regions of the myocardium by enhancement of signal in the image of step c) as compared to other regions of the myocardium and/or the optional baseline image of step a). In some cases, the MR-based diagnostic composition is administered as a bolus. The image of step c) can be obtained within about 10 minutes, from about 10 minutes to about 40 minutes, or about one hour following administration of the MR-based diagnostic composition.

In some embodiments, a cardiac-gated gradient inversion recovery sequence is used to obtain the image. Enhancement can be at least 10 times greater than that observed in an optional baseline image.

Additionally, a method of distinguishing a benign from a malignant breast tumor in an animal is provided, the method includes: a) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for the component of an extracellular matrix of the tumor tissue; b) acquiring a series of T1-weighted image of the breast tissue of said animal for a time from about 1 minutes to about 2 hours after administration of the MR-based diagnostic composition; and c) evaluating differences between the images acquired in steps b), wherein a malignant tumor exhibits greater loss in enhancement in an image collected earlier in time compared to an image collected later in time, as compared to a benign tumor.

In another embodiment, the method of distinguishing a benign from a malignant breast tumor in an animal includes: a) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for the component of an extracellular matrix of the tumor tissue; b) acquiring a T1-weighted image of the breast tissue of said animal at from about 1 minute to about 10 minutes after administration of the MR-based diagnostic composition; c) acquiring a second T1-weighted image of the breast tissue of said animal at a time from about 10 minutes to about 2 hours after administration of the MR-based diagnostic composition; and d) evaluating differences between the images acquired in steps b) and c), wherein a malignant tumor exhibits greater loss in enhancement from the image collected in step b) to that in step c) as compared to a benign tumor.

In an additional embodiment, a method of imaging fibrosis in an animal includes: a) optionally acquiring a baseline image of a tissue of said animal; b) administering to the animal an effective amount of an MR-based diagnostic composition, the diagnostic composition comprising An Extracellular Matrix Targeting Group (EMTG) and a physiologically compatible metal chelating group (C), wherein the EMTG exhibits an affinity for collagen; c) acquiring an image of the tissue during administration to about 2 hours after administration of the MR-based diagnostic composition; d) identifying infarcted regions of fibrosis by enhancement of signal in the image of step c) as compared to other regions of the tissue and/or the optional baseline image of step a).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the methods, materials, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
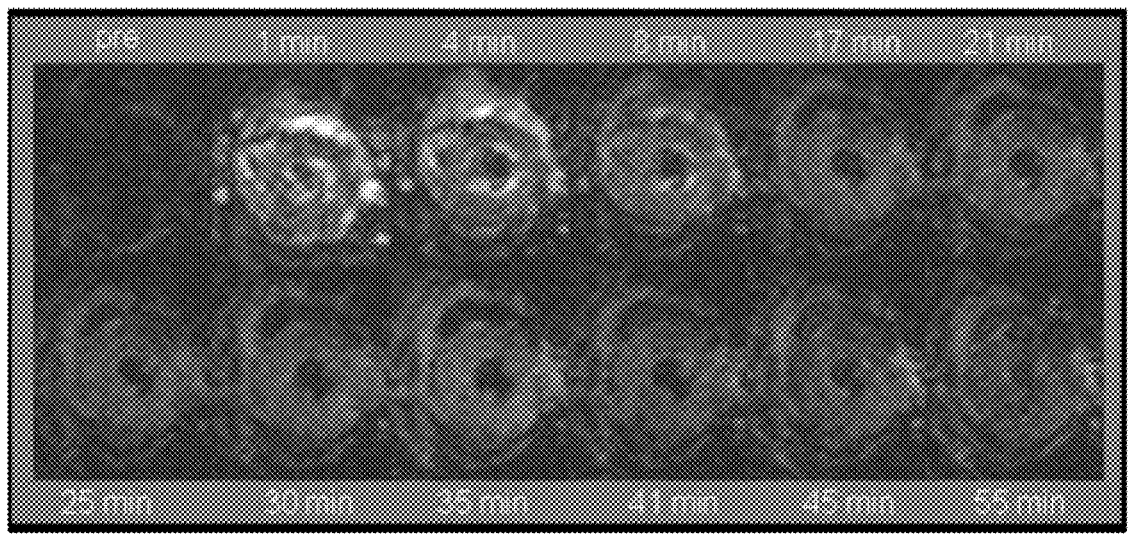
FIG. 1 is in vivo short-axis images from a mouse heart pre- and post-injection of compound ID 800.

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org. Chem.* 66(1), 24A (2001), "A Short Guide to Abbreviations and Their Use in Peptide Science" *J. Peptide. Sci.* 5, 465-471 (1999).

For the purposes of this application, the term "aliphatic" describes any acyclic or cyclic, saturated or unsaturated, branched or unbranched carbon compound, excluding aromatic compounds.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term "alkyl" includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "arylalkyl" moiety is an alkyl substituted with an aryl (e.g., phenylmethyl(benzyl)). The term "alkyl" also includes the side chains of natural and unnatural amino acids. The term "n-alkyl" means a straight chain (i.e., unbranched) unsubstituted alkyl group.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

In general, the term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, such as naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics." An aryl group may be substituted at one or more ring positions with substituents.

For the purposes of this application, "DTPA" refers to a chemical compound comprising a substructure composed of diethylenetriamine, wherein the two primary amines are each covalently attached to two acetyl groups and the secondary amine has one acetyl group covalently attached according to the following formula:

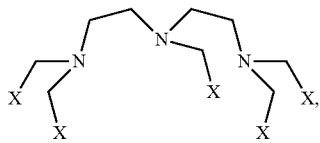

wherein each X is independently a functional group capable of coordinating a metal cation, preferably COO⁻, COOH, $C(O)NH_2$, C(O)NHR, C(O)NRR', $PO_3^{2-}$, $PO_3R^-$, $P(R)O_2^-$ or NHR, or OR wherein R is any aliphatic group. When each X group is the tert-butoxy ($^t$Bu) carboxylate ester (COO$^t$Bu), the structure may be referred to as "DTPE" ("E" for ester).

For the purposes of this application, "DOTA" refers to a chemical compound comprising a substructure composed of 1,4,7,11-tetraazacyclododecane, wherein the amines each have one acetyl group covalently attached according to the following formula:

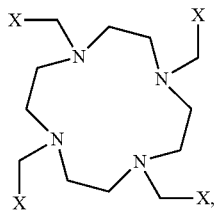

wherein X is defined above.

For the purposes of this application, "NOTA" refers to a chemical compound comprising a substructure composed of 1,4,7-triazacyclononane, wherein the amines each have one acetyl group covalently attached according to the following formula:

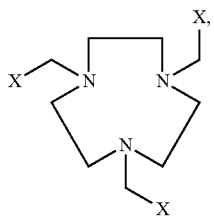

wherein X is defined above.

For the purposes of this application, "DO3A" refers to a chemical compound comprising a substructure composed of 1,4,7,11-tetraazacyclododecane, wherein three of the four amines each have one acetyl group covalently attached and the other amine has a substituent having neutral charge according to the following formula:

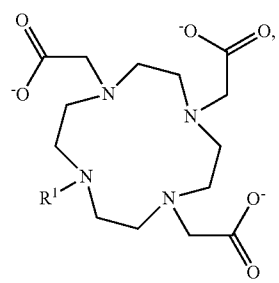

wherein $R^1$ is an uncharged chemical moiety, preferably hydrogen, any aliphatic, alkyl group, or cycloalkyl group, and uncharged derivatives thereof. The chelate "HP"-DO3A has $R^1$=—$CH_2$(CHOH)$CH_3$.

In each of the four structures above, the carbon atoms of the indicated ethylenes may be referred to as "backbone" carbons. The designation "bbDTPA" may be used to refer to the location of a chemical bond to a DTPA molecule ("bb" for "back bone"). Note that as used herein, bb(CO)DTPA-Gd means a C=O moiety bound to an ethylene backbone carbon atom of DTPA.

The terms "chelating ligand," "chelating moiety," and "chelate moiety" may be used to refer to any polydentate ligand which is capable of coordinating a metal ion, including DTPA (and DTPE), DOTA, DO3A, DOTAGA, Glu-DTPA, or NOTA molecule, or any other suitable polydentate chelating ligand as is further defined herein, that is either coordinating a metal ion or is capable of doing so, either directly or after removal of protecting groups. The term "chelate" refers to the actual metal-ligand complex, and it is understood that the polydentate ligand will eventually be coordinated to a medically useful metal ion.

The term "specific binding affinity" as used herein, refers to the capacity of a peptide or composition to be taken up by, retained by, or bound to a particular biological component to a greater degree than other components. Peptides that have this property are said to be "targeted" to the "target" component. Peptides that lack this property are said to be "non-specific" or "non-targeted" agents. The binding affinity for a target is expressed in terms of the equilibrium dissociation constant "Kd" or as a percentage of the compound bound to the target under a defined set of conditions.

The term "relaxivity" as used herein, refers to the increase in either of the MRI quantities 1/T1 or 1/T2 per millimolar (mM) concentration of paramagnetic ion, contrast agent, therapeutic agent, or diagnostic composition, wherein T1 is the longitudinal or spin-lattice, relaxation time, and T2 is the transverse or spin-spin relaxation time of water protons or other imaging or spectroscopic nuclei, including protons found in molecules other than water. Relaxivity is expressed in units of $mM^{-1} s^{-1}$.

As used herein, the term "purified" refers to a peptide that has been separated from either naturally occurring organic molecules with which it normally associates or, for a chemically-synthesized peptide, separated from any other organic molecules present in the chemical synthesis. Typically, the polypeptide is considered "purified" when it is at least 70%

(e.g., 70%, 80%, 90%, 95%, or 99%), by dry weight, free from any other proteins or organic molecules. The terms "purified" and "isolated" are used interchangeably herein.

As used herein, the term "peptide" refers to a chain of amino acids that is about 2 to about 75 amino acids in length (e.g., 3 to 50 amino acids, 1 to 50 amino acids, 3 to 30 amino acids, 2 to 25 amino acids, 10-25 amino acids, 10-50 amino acids, 15-25 amino acids, 8-20 amino acids, 8-15 amino acids, 16-17 amino acids). All peptide sequences herein are written from the N to C terminus. Additionally, peptides containing two or more cysteine residues can form disulfide bonds under non-reducing conditions. Formation of the disulfide bond can result in the formation of a cyclic peptide. The cyclic peptide may represent all or a portion of the peptide sequence. A peptide as described herein can be branched, e.g., have additional amino acids linked to one or more of the side chains of an amino acid in the chain. For example, a lysine residue having an additional lysine residue off of the ε-amino group, such a functionality is represented as K(K), wherein the group in the parentheses is that which is linked off of a side chain. Where more than one amino acid is bound off of the side chain, it is represented with a period separating the two amino acids, e.g., K(Y.G). In certain embodiments, a chelating group or a metal containing chelating group may be linked to one or more side chains of an amino acid. For example, a lysine residue having a GdDTPA complex off of the ε-aminogroup, such a functionality is represented as K(Gd$^{DTPA}$), wherein the group in parenthesis is that which is linked off of a side chain.

Additionally, an amino acid can be substituted. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "arylalkyl" moiety is an alkyl substituted with an aryl (e.g., phenylmethyl(benzyl)). The term "alkyl" also includes the side chains of natural and unnatural amino acids. The term "n-alkyl" means a straight chain (i.e., unbranched) unsubstituted alkyl group.

As used herein, the term "natural" or "naturally occurring" amino acid refers to one of the twenty most common occurring amino acids. Natural amino acids modified to provide a label for detection purposes (e.g., radioactive labels, optical labels, or dyes) are considered to be natural amino acids. Natural amino acids are referred to by their standard one- or three-letter abbreviations. Natural amino acids can be in their D or L form. As used herein, a lower case one or two letter abbreviation refers to the D-form of an amino acid.

The terms "target binding" and "binding" for purposes herein refer to non-covalent interactions of a peptide with a target. These non-covalent interactions are independent from one another and may be, inter alia, hydrophobic, hydrophilic, dipole-dipole, pi-stacking, hydrogen bonding, electrostatic associations, or Lewis acid-base interactions.

As used herein, all references to "Gd," "gado," or "gadolinium" mean the Gd(III) paramagnetic metal ion.

Collagen Binding Peptides

Isolated peptides described herein have an affinity for an extracellular matrix protein, such as collagen, including human collagen type I. In some embodiments, an isolated peptide has a specific binding affinity for an extracellular matrix protein such as collagen relative to serum proteins, such as human serum albumin (HSA) and/or fibrinogen. In these embodiments, the peptide may exhibit a smaller dissociation constant for an extracellular matrix protein relative to the dissociation constant for a serum protein.

Extracellular matrix proteins include soluble and insoluble proteins, polysaccharides, including heteropolysaccharides and polysaccharides covalently bound to proteins, and cell-surface receptors. For example, extracellular matrix proteins can be collagens (Types I, II, III, IV, V, and VI), elastin, decorin, glycosoaminoglycans, and proteoglycans.

Collagens are particularly useful extracellular matrix proteins to target. For example, collagens I and III are the most abundant components of the extracellular matrix of myocardial tissue, representing over 90% of total myocardial collagen and about 5% of dry myocardial weight. The ratio of collagen I to collagen III in the myocardium is approximately 2:1, and their total concentration is approximately 100 μM in the extracellular matrix. Human collagen type I is a trimer of two chains with an [α1(I)]$_2$[α2(I)] stoichiometry characterized by a repeating G-X-Y sequence motif, where X is most frequently proline and Y is frequently hydroxyproline. Thus, in some embodiments, a peptide has an affinity for human and/or rat collagen type I.

Peptides useful for inclusion in the diagnostic compositions described herein can include natural or unnatural amino acids which may be in the D or L form. In some embodiments, all of the amino acids are natural amino acids. In some embodiments, all of the amino acids are in the L form. The peptides can be synthesized according to standard synthesis methods such as those disclosed in, e.g., WO 01/09188 and WO 01/08712. Charged groups on the peptides can be neutralized if desired. For example, the C-terminal carboxylate moiety can be amidated with an —NH$_2$ group, yielding a C(=O)NH$_2$ moiety. In certain embodiments, the C-terminus is amidated via cleavage of the peptide from the resin; see the Examples, below. For ease of synthesis and cost considerations, it is preferred that the peptides have between 3 to 75 amino acids (e.g., 3 to 50, 1 to 50, 10 to 50, 10 to 30, 3 to 30, 3 to 20, 3 to 15, 5 to 30, 3 to 25, 16 to 17, 5 to 25, 5 to 20, 5 to 15, 11 to 25, 11 to 50, 11 to 40, 10 to 12, 8 to 30, 8 to 20, or 8 to 15 amino acids in length).

Amino acids with many different protecting groups appropriate for immediate use in the solid phase synthesis of peptides are commercially available. Concatemers of peptides (2-5 or more) can increase binding affinity and specificity for an extracellular matrix protein (Verrecchio, A., Germann, M. W., Schick, B. P., Kung, B., Twardowski, T., and San Antonio, J. D. J. Biol. Chem. (2000) 275, 7701-7707).

Peptides can be assayed for affinity to the appropriate extracellular matrix protein by methods as disclosed in WO 01/09188 and WO 01/08712, and as described below. For example, peptides can be screened for binding to an extracellular matrix protein by methods well known in the art, including equilibrium dialysis, affinity chromatography, and inhibition or displacement of probes bound to the matrix protein. For example, peptides can be evaluated for their ability to bind to collagen, such as dried human collagen type I or dried rat collagen type I. In certain cases, a peptide can exhibit a percent binding to dried human collagen type I or dried rat collagen type I (see assays described below) of greater than 10%, e.g., greater than 12%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, or greater than 85%. In some embodiments, a peptide can exhibit a percent binding to dried human collagen in the range of from about 10% to about 50%, or from about 20% to about 60%, or from about 30% to about 60%, or from about 40% to about 90%. Certain peptides useful for inclusion in the diagnostic compositions herein can exhibit an affinity for collagen. Such peptides can be identified through phage display experiments; see the Examples, below.

Collagen binding peptides can be derivatized with nonmetallic radionuclides for PET or SPECT imaging. For instance the tyrosine amino acid can be iodinated with I-123, I-125, or I-131 as described in the Examples. Flourine-18 can be incorporated into the peptide using fluorination and bioconjugation techniques as described in the literature (see e.g. Guenther K J, Yoganathan S, Garofalo R, Kawabata T, Strack T, Labiris R, Dolovich M, Chirakal R, Valliant J F. "Synthesis and in vitro evaluation of 18F- and 19F-labeled insulin: a new radiotracer for PET-based molecular imaging studies." J Med Chem. 2006 49:1466-74; de Bruin B, Kuhnast B, Hinnen F, Yaouancq L, Amessou M, Johannes L, Samson A, Boisgard R, Tavitian B, Dolle F. "1-[3-(2-[18F]fluoropyridin-3-yloxy)propyl]pyrrole-2,5-dione: design, synthesis, and radiosynthesis of a new [18F]fluoropyridine-based maleimide reagent for the labeling of peptides and proteins." Bioconjug Chem. 2005 16:406-20; Chen X, Park R, Hou Y, Khankaldyyan V, Gonzales-Gomez I, Tohme M, Bading J R, Laug W E, Conti P S. "MicroPET imaging of brain tumor angiogenesis with 18F-labeled PEGylated RGD peptide." Eur J Nucl Med Mol. Imaging. 2004 31:1081-9; Wester H J, Schottelius M, Scheidhauer K, Meisetschlager G, Herz M, Rau F C, Reubi J C, Schwaiger M. "PET imaging of somatostatin receptors: design, synthesis and preclinical evaluation of a novel 18F-labelled, carbohydrated analogue of octreotide." Eur J Nucl Med Mol. Imaging. 2003 30(1):117-22).

Peptides disclosed herein can include the amino acid sequence W-X1-C-(X2)$_n$-W-X3-C (SEQ ID NO: 806), wherein n=5-7; X1, X2, and X3 are any amino acid; and wherein the peptide has a length of 11 to 50 amino acids. In some embodiments, the peptide can have a length of 11 to 30 amino acids, 11 to 35 amino acids, 11 to 25 amino acids, 11 to 20 amino acids, or 11 to 15 amino acids. In certain embodiments, X1 is selected from K, Q, Y, T, E, D, L, R, H, I, V, N, M, and A. Similarly, X2 is in some cases selected from R, E, D, S, H, K, N, Y, M, V, I, Q, and G. In certain cases, X1 is selected from M, K, Q, T, Y, and R, and X3 is selected from Y, K, H, V, S, N, and M.

A purified peptide can include the amino acid sequence W-X1-C-X2-G*-X3-X4-X5-X6-W-X7-C (SEQ ID NO: 807), wherein X1 is any amino acid; X2 can be S, V, T, H, R, Y, or D; G* is G or any amino acid in D form; X3 can be D or N, independently in D or L form; X4 can be any amino acid in D or L form; X5 can be any amino acid in D or L form; X6 can be T, K, H, D, A, R, Y, or E; and X7 can be Y, K, H, V, S, M, or N, wherein the peptide has a total length of 12 to 50 amino acids. The peptide length can vary, as indicated previously, e.g., 12 to 25 amino acids, 12 to 30 amino acids, 12 to 40 amino acids, 12 to 20 amino acids, and 12 to 15 amino acids. In some cases, G* is selected from G and the D form of the amino acids A, S, R, Y, and L.

In some embodiments, such a purified peptide can include the amino acid sequence: W-X1-C-X2-G*-X3-X4-X5-X6-W-X7-C-X8-X9 (SEQ ID NO: 808), wherein X1 to X6 and G* are as defined above for SEQ ID NO: 807; X8 can be N, L, I, R, K, or A; and X9 can be Y, F, M, R, or H, independently in D or L form. In some cases, X3 can be D. In some embodiments, X1 can be T; X2 can be S, T or V; X4 can be E, H, I, S, or A; X5 can be Y, K, L, F, A, or P; X6 is T; X7 is H or K; X8 is N, K, or A; and X9 is Y or F. In some embodiments, the peptide can include one of the following amino acid sequences:

```
W-T-C-S-G-D-E-Y-T-W-H-C;        (SEQ ID NO: 809)

W-T-C-V-G-D-H-K-T-W-K-C;        (SEQ ID NO: 810)

W-Y-C-S-G-D-H-L-D-W-K-C;        (SEQ ID NO: 811)
and

W-E-C-H-G-N-E-F-E-W-N-C.        (SEQ ID NO: 812)
```

A purified peptide can include any of the amino acid sequences in Tables 1-16, 18-41, 44, and 45. In some embodiments, such peptides have a total length of 50 amino acids or less, e.g., 45 amino acids or less, 40 amino acids or less, 35 amino acids or less, 30 amino acids or less, 25 amino acids or less, 20 amino acids or less, or 15 amino acids or less.

A purified peptide can include the amino acid sequence Q-W-H-C-T-T-R-F-P-H-H-Y-C-L-Y-G (SEQ ID NO: 74), wherein the peptide has a total length of 16 to 50 amino acids, e.g., 16 to 40 amino acids, 16 to 30 amino acids, 16 to 20 amino acids, or 16 to 18 amino acids.

In other cases, a purified peptide can include the amino acid sequence C-Y-Q-X1-X2-C-W-X3-W (SEQ ID NO: 813), wherein X1 is any amino acid; X2 is any amino acid; X3 is any amino acid; wherein each C, Y, Q, W, X1, X2, or X3, independently, can be in the D form; and wherein the peptide contains 9 to 50 amino acids, such as 9 to 40 amino acids, 9 to 30 amino acids, 9 to 20 amino acids, or 9 to 15 amino acids. In some cases, X1 is selected from A, G, I, L, V, F, and P; X2 is selected from G, A, I, L, V, F, and P; and X3 is selected from I, A, G, L, V, F, and P. In certain embodiments, the peptide includes the amino acid sequence C-Y-Q-A-G-C-W-1-W (SEQ ID NO: 814) in any combination of D or L forms for the individual amino acids. For example, a peptide can include SEQ ID NO: 814 in all L-form.

A purified peptide can include amino acid sequence Y-X1-X2-C-Y-Q-X3-X4-C-W-X5-W (SEQ ID NO: 815), wherein X1 is any amino acid; X2 is any amino acid; X3 is any amino acid; X4 is any amino acid; X5 is I, G, L, V, F, or P; and wherein the peptide contains 12 to 50 amino acids, such as 12 to 40 amino acids, 12 to 30 amino acids, 12 to 25 amino acids, 12 to 20 amino acids, or 12 to 15 amino acids. In some embodiments, X1 is selected from H, R, K, E, D, Q, or N; X2 is selected from A, G, I, L, V, F, or P; X3 is selected from A, G, I, L, V, F, or P; X4 is selected from G, A, I, L, V, F, or P; and X5 is selected from I, L, V, or F. For example, a purified peptide can include SEQ ID NO:1, SEQ ID NO: 132, or SEQ ID NO: 135. Other peptides are set forth in the accompanying claims.

A purified peptide can include the amino acid sequence C*-X1-X2-X3-X4-X5-X6-X7-X8-C* (SEQ ID NO: 816), wherein X1, X2, X3, X4, X5, X6, X7, and X8 are any amino acid; C* is C or Pen in D or L form; and the peptide has a length of 10 to 50 amino acids, such as 10 to 20 amino acids, 10 to 30 amino acids, 10 to 40 amino acids, and 10 to 15 amino acids. In some cases, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), and Aib, in D or L form; X2 is selected from T, A, N, S, Y, R, V, I, K, D, G, b-h-G, Orn, and Dpr, in D or L form; X3 is selected from R, A, S, L, Y, D, K, G, P, Aib, Y(3-Cl), I, Cha, Abu, F(4-F), Dopa, Tle, Cit, b-h-D, and K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, and b-h-E, in D or L form; X5 is selected from P, A, Y, D, R, T, P(3-OH), ΔPro, Pip, N-Me-A, P(3-OH), Y(3-I), b-h-Y, and Aib, in D or L form; X6 is selected from H, A, S, K, N, Y, T, D, R, W, P, Aib, and b-h-T, in D or L form; X7 is selected from H, A, S, N, D, Y, W, Aib, Dpr, 2-Pal, 1-Nal, thien-W, W(5-OH), and b-h-W, in D or L form; and X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form. For example, a peptide can be C-T-T-S-F-P-H-H-Y-C (SEQ ID NO: 817), C-T-T-K-F-P-H-H-Y-C (SEQ ID NO: 818), C-Y-T-Y-F-P-H-H-Y-C (SEQ ID NO: 819), C-T-T-R-F-P-H-H-Y-C (SEQ ID NO: 820), or C-S-G-D-E-Y-T-W-H-C (SEQ ID NO: 821).

A purified peptide can include the amino acid sequence C*-X1-X2-X3-X4-X5-X6-X7-X8-C* (SEQ ID NO: 828), wherein C* is C or Pen in D or L form; X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), or b-h-W, in D or L form; and X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; wherein the peptide has a length of 10 to 20 amino acids.

In another embodiment, a purified peptide can include the amino acid sequence C*-X1-X2-X3-X4-X5-X6-X7-X8-C*-X9-X10-X11 (SEQ ID NO: 822), wherein X1, X2, X3, X4, X5, X6, X7, X8, X9, X10, and X11 are any amino acid; C* is C or Pen, in D or L form; and the peptide has a length of 13 to 50 amino acids, such as 13 to 40 amino acids, 13 to 30 amino acids, 13 to 20 amino acids, and 13 to 17 amino acids. In certain embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), and Aib, in D or L form; X2 is selected from T, A, N, S, Y, R, V, I, K, D, G, b-h-G, Orn, and Dpr, in D or L form; X3 is selected from R, A, S, L, Y, D, K, G, P, Aib, Y(3-Cl), I, Cha, Abu, F(4-F), Dopa, Tle, Cit, b-h-D, and K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, and b-h-E, in D or L form; X5 is selected from P, A, Y, D, R, T, P(3-OH), ΔPro, Pip, N-Me-A, P(3-OH), Y(3-I), b-h-Y, and Aib, in D or L form; X6 is selected from H, A, S, K, N, Y, T, D, R, W, P, Aib, and b-h-T, in D or L form; X7 is selected from H, A, S, N, D, Y, W, Aib, Dpr, 2-Pal, 1-Nal, thien-W, W(5-OH), and b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), and Aib, in D or L form; X9 is selected from L, A, I, K, V, F, N, Y, P, Aib, Hse, Hfe, Bpa, 2-Nal, Y(3-Cl), Dip, and F(4-NH2), in D or L form; X10 is selected from Y, A, F, E, Bpa, 2-Nal, Y(3-Cl), Dip, F(4-NH2), and Y(3-I), in D or L form; and X11 is selected from G, E, Y, F, V, Bip, F(4-NH2), and Aib, in D or L form.

A purified peptide can include the amino acid sequence C*-X1-X2-X3-X4-X5-X6-X7-X8-C*-X9-X10-X11 (SEQ ID NO: 829), wherein C* is C or Pen in D or L form; X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, P(3-OH), ΔPro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), or b-h-W, in D or L form; and X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; and X9, X10, and X11 are any amino acid; wherein the peptide has a length of 13 to 20 amino acids.

A purified peptide can include the amino acid sequence C*-X1-X2-X3-X4-X5-X6-X7-X8-C*-X9-X10-X11-X12 (SEQ ID NO: 823), wherein X1, X2, X3, X4, X5, X6, X7, X8, X9, X10, and X11 are any amino acids; X12 is any one or two amino acids; C* is C or Pen, in D or L form; and wherein the peptide has a length of 14 to 50 amino acids, such as 14 to 40 amino acids, 14 to 30 amino acids, 14 to 20 amino acids, and 14 to 17 amino acids. In some embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), and Aib, in D or L form; X2 is selected from T, A, N, S, Y, R, V, I, K, D, G, b-h-G, Orn, and Dpr, in D or L form; X3 is selected from R, A, S, L, Y, D, K, G, P, Aib, Y(3-Cl), I, Cha, Abu, F(4-F), Dopa, Tle, Cit, b-h-D, and K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, and b-h-E, in D or L form; X5 is selected from P, A, Y, D, R, T, P(3-OH), ΔPro, Pip, N-Me-A, P(3-OH), Y(3-I), b-h-Y, and Aib, in D or L form; X6 is selected from H, A, S, K, N, Y, T, D, R, W, P, Aib, and b-h-T, in D or L form; X7 is selected from H, A, S, N, D, Y, W, Aib, Dpr, 2-Pal, 1-Nal, thien-W, W(5-OH), and b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), and Aib, in D or L form; X9 is selected from L, A, I, K, V, F, N, Y, P, Aib, Hse, Hfe, Bpa, 2-Nal, Y(3-Cl), Dip, and F(4-NH2), in D or L form; X10 is selected from Y, A, F, E, Bpa, 2-Nal, Y(3-Cl), Dip, F(4-NH2), and Y(3-I), in D or L form; X11 is selected from G, E, Y, F, V, Bip, F(4-NH2), and Aib, in D or L form; and X12 is selected from K, KK, Peg K, PEG(1×O), 1,4-AMB, 1,3-AMB, 1,6-Hex, PEG, and GTE, in D or L form.

In some embodiments, the cyclic peptide includes the amino acid sequence C*-X1-X2-X3-X4-X5-X6-X7-X8-C*-X9-X10-X11-X12 (SEQ ID NO: 832), wherein C* is C or Pen in D or L form; X1 is T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is T, A, N, S, Y, R, V, I, K, D, G, b-h-G, Orn, or Dpr, in D or L form; X3 is R, A, S, L, Y, D, K, G, P, Aib, Y(3-Cl), I, Cha, Abu, F(4-F), Dopa, Tle, Cit, b-h-D, or K(Boc), in D or L form; X4 is F, Bip, F(4-CF3), 4-Pal, 1-Nal, F(4-NO2), Hfe, Bpa, F(4-CN), F(4-NH2), F(3, 4-OMe), 2-Nal, Y(3-Cl), Aib, or b-h-E, in D or L form; X5 is P, P(3-OH), ΔPro, Pip, N-Me-A, P(3-OH), Y(3-I), b-h-Y, or Aib, in D or L form; X6 is H, A, S, K, N, Y, T, D, R, W, P, Aib, or b-h-T, in D or L form; X7 is H, A, S, N, D, Y, W, Aib, Dpr, 2-Pal, 1-Nal, thien-W, W(5-OH), or b-h-W, in D or L form; X8 is Y, A, R, T, V, H, D, S, P, 1-Nal, Bip, DOPA, H-Tyr, H-Tyr(Me), F(3-OMe), Y(3-Cl), Y(2,6-Me2), Dip, F(4-

NH2), or Aib, in D or L form; X9, X10, and X11 are any amino acid; and X12 is any one or two amino acids; wherein the peptide has a length of 14 to 20 amino acids.

In some embodiments, the cyclic peptide includes the amino acid sequence C*-X1-X2-X3-X4-X5-X6-X7-X8-C*-X9-X10-X11-X12 (SEQ ID NO: 833), wherein C* is C or Pen in D or L form; X1 is T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is T, A, N, S, Y, R, V, I, K, D, G, b-h-G, Orn, or Dpr, in D or L form; X3 is R, A, S, L, Y, D, K, G, P, Aib, Y(3-Cl), I, Cha, Abu, F(4-F), Dopa, Tle, Cit, b-h-D, or K(Boc), in D or L form; X4 is F, Bip, F(4-CF3), 4-Pal, 1-Nal, F(4-NO2), Hfe, Bpa, F(4-CN), F(4-NH2), F(3, 4-OMe), 2-Nal, Y(3-Cl), Aib, or b-h-E, in D or L form; X5 is P, P(3-OH), APro, Pip, N-Me-A, P(3-OH), Y(3-I), b-h-Y, or Aib, in D or L form; X6 is H, A, S, K, N, Y, T, D, R, W, P, Aib, or b-h-T, in D or L form; X7 is H, A, S, N, D, Y, W, Aib, Dpr, 2-Pal, 1-Nal, thien-W, W(5-OH), or b-h-W, in D or L form; X8 is Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X9 and X10 are any amino acid; X11 is G, E, Y, F, V, Bip, F(4-NH2), or Aib, in D or L form; and is any amino acid; and X12 is K, KK, Peg K, PEG(1×O), 1,4-AMB, 1,3-AMB, 1,6-Hex, PEG, or GTE, in D or L form; wherein the peptide has a length of 14 to 20 amino acids.

In another embodiment, a purified peptide includes the amino acid sequence X14-X13-C*-X1-X2-X3-X4-X5-X6-X7-X8-C* (SEQ ID NO: 824), wherein X1, X2, X3, X4, X5, X6, X7, X8, X13, and X14 are any amino acid; C* is C or Pen, in D or L form; and wherein the peptide has a length of 12 to 50 amino acids, such as 12 to 40 amino acids, 12 to 30 amino acids, 12 to 20 amino acids, and 12 to 17 amino acids. In certain embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), and Aib, in D or L form; X2 is selected from T, A, N, S, Y, R, V, I, K, D, G, b-h-G, Orn, and Dpr, in D or L form; X3 is selected from R, A, S, L, Y, D, K, G, P, Aib, Y(3-Cl), I, Cha, Abu, F(4-F), Dopa, Tle, Cit, b-h-D, and K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, and b-h-E, in D or L form; X5 is selected from P, A, Y, D, R, T, P(3-OH), ΔPro, Pip, N-Me-A, P(3-OH), Y(3-I), b-h-Y, and Aib, in D or L form; X6 is selected from H, A, S, K, N, Y, T, D, R, W, P, Aib, and b-h-T, in D or L form; X7 is selected from H, A, S, N, D, Y, W, Aib, Dpr, 2-Pal, 1-Nal, thien-W, W(5-OH), and b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), and Aib, in D or L form; X13 is selected from H, A, S, K, N, D, Y, T, P, and Aib, in D or L form; and X14 is selected from W, A, Y, 1-Nal, 2-Nal, thien-W, Tic, or W(5-OH), in D or L form.

A purified peptide can include the amino acid sequence X14-X13-C*-X1-X2-X3-X4-X5-X6-X7-X8-C* (SEQ ID NO: 830), wherein C* is C or Pen in D or L form; X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is selected from T, A, N, S, Y, R, V, I, K, D, G, b-h-G, Orn, or Dpr, in D or L form; X3 is selected from R, A, S, L, Y, D, K, G, P, Aib, Y(3-Cl), I, Cha, Abu, F(4-F), Dopa, Tle, Cit, b-h-D, or K(Boc), in D or L form; X4 is selected from F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is selected from P, P(3-OH), APro, Pip, N-Me-A, P(3-OH), Y(3-I), b-h-Y, or Aib, in D or L form; X6 is selected from H, A, S, K, N, Y, T, D, R, W, P, Aib, or b-h-T, in D or L form; X7 is selected from H, A, S, N, D, Y, W, Aib, Dpr, 2-Pal, 1-Nal, thien-W, W(5-OH), or b-h-W, in D or L form; and X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; and X13 and X14 are any amino acid; wherein the peptide has a length of 12 to 20 amino acids.

A purified peptide can include the amino acid sequence X16-X15-X14-X13-C*-X1-X2-X3-X4-X5-X6-X7-X8-C* (SEQ ID NO: 825), wherein X1, X2, X3, X4, X5, X6, X7, X8, X13, and X14 are any amino acid; X15 and X16 comprise one to three amino acids; C* is C or Pen, in D or L form; and wherein the peptide has a length of 14 to 50 amino acids, such as 14 to 40 amino acids, 14 to 30 amino acids, 14 to 20 amino acids, and 14 to 17 amino acids. In some embodiments, X1 is selected from T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), and Aib, in D or L form; X2 is selected from T, A, N, S, Y, R, V, I, K, D, G, b-h-G, Orn, and Dpr, in D or L form; X3 is selected from R, A, S, L, Y, D, K, G, P, Aib, Y(3-Cl), I, Cha, Abu, F(4-F), Dopa, Tle, Cit, b-h-D, and K(Boc), in D or L form; X4 is selected from F, A, Y, E, R, L, Bip, F(4-CF3), 4-Pal, 1-Nal, F(4-NO2), Hfe, Bpa, F(4-CN), F(4-NH2), F(3, 4-OMe), 2-Nal, Y(3-Cl), Aib, and b-h-E, in D or L form; X5 is selected from P, A, Y, D, R, T, P(3-OH), ΔPro, Pip, N-Me-A, P(3-OH), Y(3-I), b-h-Y, and Aib, in D or L form; X6 is selected from H, A, S, K, N, Y, T, D, R, W, P, Aib, and b-h-T, in D or L form; X7 is selected from H, A, S, N, D, Y, W, Aib, Dpr, 2-Pal, 1-Nal, thien-W, W(5-OH), and b-h-W, in D or L form; X8 is selected from Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), and Aib, in D or L form; X13 is selected from H, A, S, K, N, D, Y, T, P, and Aib, in D or L form; X14 is selected from W, A, Y, 1-Nal, 2-Nal, thien-W, Tic, or W(5-OH), in D or L form; X15 is selected from Q, G, A, D, S, P, K, GQ, K(G), K(Y.G), K(V.G). K(F.G), K(H.H), KK(K), Dpr, and Aib, in D or L form; and X16 is selected from G, K, PP, GY, GV, GF, GH, GK(G), KK(K), Dpr, EAG, and PPG, in D or L form.

In some embodiments, the collagen binding peptide includes a cyclic peptide including the amino acid sequence X16-X15-X14-X13-C*-X1-X2-X3-X4-X5-X6-X7-X8-C* (SEQ ID NO: 834), wherein C* is C or Pen in D or L form; X1 is T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is T, A, N, S, Y, R, V, I, K, D, G, b-h-G, Orn, or Dpr, in D or L form; X3 is R, A, S, L, Y, D, K, G, P, Aib, Y(3-Cl), I, Cha, Abu, F(4-F), Dopa, Tle, Cit, b-h-D, or K(Boc), in D or L form; X4 is F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is P, P(3-OH), APro, Pip, N-Me-A, P(3-OH), Y(3-I), b-h-Y, or Aib, in D or L form; X6 is H, A, S, K, N, Y, T, D, R, W, P, Aib, or b-h-T, in D or L form; X7 is H, A, S, N, D, Y, W, Aib, Dpr, 2-Pal, 1-Nal, thien-W, W(5-OH), or b-h-W, in D or L form; X8 is Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X13 and X14 are any amino acid; X15 and X16 comprise one to three amino acids; and wherein the peptide has a length of 14 to 20 amino acids.

In some embodiments, the collagen binding peptide includes a cyclic peptide including the amino acid sequence X16-X15-X14-X13-C*-X1-X2-X3-X4-X5-X6-X7-X8-C* (SEQ ID NO: 835), wherein C* is C or Pen in D or L form; X1 is T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is T, A, N, S, Y, R, V, I, K, D, G, b-h-G, Orn, or Dpr, in D or L form; X3 is R, A, S, L, Y, D, K, G, P, Aib, Y(3-Cl), I, Cha, Abu, F(4-F), Dopa, Tle, Cit, b-h-D, or K(Boc), in D or L form; X4 is F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is P, P(3-OH), APro, Pip, N-Me-A, P(3-OH), Y(3-I), b-h-Y, or Aib, in D or L form; X6 is H, A, S, K, N, Y, T, D, R, W, P, Aib, or b-h-T, in D or L form; X7 is H, A, S, N, D, Y, W, Aib, Dpr, 2-Pal, 1-Nal, thien-W, W(5-OH), or b-h-W, in D or L form; X8 is Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X13 and X14 are any amino acid; X15 is Q, G, A, D, S, P, K, GQ, K(G), K(Y.G), K(V.G). K(F.G), K(H.H), KK(K), Dpr, or Aib, in D or L form; X16 is G, K, PP, GY, GV, GF, GH, GK(G), KK(K), Dpr, EAG, or PPG, in D or L form; and wherein the peptide has a length of 14 to 20 amino acids.

In some embodiments, the collagen binding peptide includes a cyclic peptide including the amino acid sequence X16-X15-X14-X13-C*-X1-X2-X3-X4-X5-X6-X7-X8-C* (SEQ ID NO: 836), wherein C* is C or Pen in D or L form; X1 is T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form; X2 is T, A, N, S, Y, R, V, I, K, D, G, b-h-G, Orn, or Dpr, in D or L form; X3 is R, A, S, L, Y, D, K, G, P, Aib, Y(3-Cl), I, Cha, Abu, F(4-F), Dopa, Tle, Cit, b-h-D, or K(Boc), in D or L form; X4 is F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form; X5 is P, P(3-OH), APro, Pip, N-Me-A, P(3-OH), Y(3-I), b-h-Y, or Aib, in D or L form; X6 is H, A, S, K, N, Y, T, D, R, W, P, Aib, or b-h-T, in D or L form; X7 is H, A, S, N, D, Y, W, Aib, Dpr, 2-Pal, 1-Nal, thien-W, W(5-OH), or b-h-W, in D or L form; X8 is Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; X13 and X14 are any amino acid; X15 is Q, D, or K(G); X16 is G.

In other embodiments, a purified peptide can include the amino acid sequence X1-X2-X3-C*-X4-T-X5-X6-P*-X7-H—X8-C-X9-X10-X11 (SEQ ID NO: 826), wherein X1, X2, X3, X4, X5, X6, X7, X8, X9, X10, and X11 are any amino acid; C* is C or Pen; P* is P in D or L form; and wherein the peptide has a length of 16 to 50 amino acids, such as 16 to 40 amino acids, 16 to 30 amino acids, 16 to 20 amino acids, and 16 to 17 amino acids. In certain embodiments, X1 is selected from any amino acid in L form; X2 is selected from W or W*; X3 is selected from H, A, K, or S; X4 is selected from T, Y, G, K, and Y*; X5 is selected from any amino acid in L form; X6 is selected from F, Y, and Y*; X7 is selected from H, A, and Y; X8 is selected from Y and Y*; X9 is selected from L, V, L*, and Y*; X10 is selected from Y, F, and Y*; and X11 is selected from G, Y, Bip, and Y*; wherein W* is 1-Nal, 2-Nal, Bpa, thien-W, W(5-OH), 7-aza-Trp, 1-methyl-Trp, 5-bromo-Tryp, 5-chloro-Tryp, 5-fluor-Trp, 7-methyl-trp, 6-methyl-Trp, 6-fluoro-Trp, or 6-hydroxy-trp; Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine; and L* is I, V, A, L, G, Tle, L-norvaline, L-norleucine, L-dehydroleucine, L-abu (2-aminobutyric acid), L-tert-leucine, beta-cyclohexyl-L-alanine, L-homoleucine, or L-homo-cyclohexylalanine.

In some embodiments, a purified peptide can include the amino acid sequence X1-X2-X3-C*-X4-T-X5-X6-P*-X7-H-X8-C-X9-X10-X11 (SEQ ID NO: 831), wherein C* is C or Pen in D or L form; X1 is selected from any amino acid in L form; X2 is selected from W or W*; X3 is selected from H, A, K, or S; X4 is selected from T, Y, G, K, or Y*; X5 is selected from any amino acid in L form; X6 is selected from F, Y, Y*; X7 is selected from H, A, or Y; X8 is selected from Y or Y*; X9 is selected from L, V, L*, or Y*; X10=Y, F, or Y*; and X11 is selected from G, Y, Bip, or Y*; wherein W* is 1-Nal, 2-Nal, Bpa, thien-W, W(5-OH), 7-aza-Trp, 1-methyl-Trp, 5-bromo-Tryp, 5-chloro-Tryp, 5-fluor-Trp, 7-methyl-trp, 6-methyl-Trp, 6-flouro-Trp, or 6-hydroxy-trp; Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine; L* is I, V, A, L, G, Tle, L-norvaline, L-norleucine, L-dehydroleucine, L-abu (2-aminobutyric acid), L-tert-leucine, beta-cyclohexyl-L-alanine, L-homoleucine, or L-homo-cyclohexylalanine; and P* is P, L-hydroxyproline, piperidine-2-carboxylic acid, or 4-hydroxypiperidine-2-carboxylic acid; wherein the peptide has a length of 16 to 20 amino acids.

In a further embodiment, a purified peptide can include the amino acid sequence X1-X2-X3-C-X4-X5-D-X6-X7-X8-W-X9-C-X10-X11-X12 (SEQ ID NO: 827), wherein X1, X2, X3, X4, X5, X6, X7, X8, X9, X10, X11, and X12 are any amino acid; and wherein said peptide has a length of 16 to 50 amino acids, such as 16 to 40 amino acids, 16 to 30 amino acids, 16 to 20 amino acids, and 16 to 17 amino acids. In some cases, X1 is selected from any amino acid in L form; X2 is selected from W and W*; X3 is selected from T, A, or W; X4 is selected from S, Y, A, V, and Y*; X5 is selected from G or D*; X6 is selected from E, A, and H; X7 is selected from Y, L, or Y*; X8 is selected from T, Y, A, and S; X9 is selected from H, S, and Y; X10 is selected from N and A; X11 is selected from Y and Y*; X12 is selected from any amino acid in L form; wherein W* is 1-Nal, 2-Nal, Bpa, thien-W, W(5-OH), 7-aza-Trp, 1-methyl-Tip, 5-bromo-Tryp, 5-chloro-Tryp, 5-fluor-Trp, 7-methyl-trp, 6-methyl-Tip, 6-fluoro-Trp, or 6-hydroxy-trp; Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine; and D* is any amino acid in D form.

Any of the peptides described herein can be capable of forming a disulfide bond under non-reducing conditions, as known to those having ordinary skill in the art. In certain cases, any of the peptides described herein include a disulfide bond, and form a cyclized peptide structure. Any of the peptides can exhibit specific binding affinity for collagen, e.g., collagen type I from human or rat.

Specific peptides and peptide linker combinations are also set forth in Tables 1-16, 18-41, 44, and 45 and in the Examples, below.

Diagnostic Compositions

Diagnostic compositions (e.g., diagnostic compositions suitable for MR imaging, nuclear imaging, PET imaging, SPECT imaging, or optical imaging), which can be used for detecting pathologies where abnormal or excessive proliferation of collagen is implicated, are described herein. Typically such diagnostic compositions will include one or more imaging moieties (IEMs) coupled, such as through a linker (L), to an Extracellular Matrix Targeting Group (EMTG).

Extracellular Matrix Targeting Group

Generally, the Extracellular Matrix Targeting Group (EMTG) has an affinity for an extracellular matrix component, such as collagen. For example, the EMTG can bind the extracellular matrix component with a dissociation constant of less than 100 µM (e.g., less than 50 µM, less than 10 µM, less than 5 µM, less than 1 µM, or less than 100 nM). In some embodiments, the EMTG has a specific binding affinity for an extracellular matrix component relative to serum proteins, such as human serum albumin (HSA) and fibrinogen, to result in decreased background signal (e.g., background signal of blood). In these embodiments, the EMTG may exhibit a smaller dissociation constant for an extracellular matrix component relative to the dissociation constant for a serum protein.

Extracellular matrix components of the myocardium include soluble and insoluble proteins, polysaccharides, including heteropolysaccharides and polysaccharides covalently bound to proteins, and cell-surface receptors. For example, extracellular matrix components can be collagens (Types I, II, III, IV, V, and VI), elastin, decorin, glycosoaminoglycans, and proteoglycans.

Collagens are particularly useful extracellular matrix components to target. For example, collagens I and III are the most abundant components of the extracellular matrix of myocardial tissue, representing over 90% of total myocardial collagen and about 5% of dry myocardial weight. The ratio of collagen I to collagen III in the myocardium is approximately 2:1, and their total concentration is approximately 100 µM in the extracellular matrix. Human collagen type I is a trimer of two chains with an $[\alpha 1(I)]_2[\alpha 2(I)]$ stoichiometry characterized by a repeating G-X-Y sequence motif, where X is most frequently proline and Y is frequently hydroxyproline. Thus, in some embodiments, human, pig, rabbit, mouse, and/or rat collagen type I is targeted.

Another extracellular matrix component suitable for targeting is elastin. The aorta and major blood vessels are 30% by dry weight elastin. Similarly, proteoglycans are also suitable for targeting, including proteoglycans present in the heart and blood vessels. For example, in non-human primates, proteoglycan distribution in the myocardium is approximately 62% heparan sulfates; 20% hyaluronin, and 16% chondroitan/dermatan sulfates. The choindroitan/dermatan sulfate fraction consists exclusively of biglycan and decorin.

In principal, the EMTG can be any compound that exhibits affinity for a component of the extracellular matrix, e.g., an extracellular matrix component of the myocardium, and can include small organic molecules, such as azo dyes or fluorophores, and peptides. Peptides can be particularly useful, both as EMTGs in diagnostic compositions as well as compositions, e.g., for therapeutic and/or diagnostic purposes. A peptide can also be a point of attachment for one or more chelates at one or both peptide termini, or at one or more side chains, optionally through the use of linkers. In some embodiments, a peptide can one described herein. Examples of such peptides are also set forth in the Examples, below.

Imaging Moieties

Diagnostic compositions can be prepared that incorporate any of the EMTGs described previously, including in particular the collagen binding peptides described above. Diagnostic compositions described herein typically include one or more physiologically compatible chelating groups (C) as Imaging Moieties, Extracellular Matrix Targeting Groups (EMTG), and optional linkers (L). The diagnostic compositions thus target an extracellular matrix component ("the target"), e.g., such as collagen present in the extracellular matrix of the myocardium, and bind to it, allowing imaging of collagen and/or the myocardium. In some cases, a diagnostic compositions will include one or more collagen binding peptides as the EMTG, one or more physiologically compatible metal chelating groups (C), and optionally one or more linkers (L) connecting the two (or more) moieties.

The C can be any of the many known in the art, and includes, for example, cyclic and acyclic organic chelating agents such as DTPA, DOTA, HP-DO3A, DOTAGA, NOTA, Glu-DTPA, and DTPA-BMA. For MRI, metal chelates such as gadolinium diethylenetriaminepentaacetate (DTPA.Gd), gadolinium tetraamine 1,4,7,10-tetraazacyclododecane-N,N',N'',N'''-tetraacetate (DOTA.Gd), gadolinium 1,4,7,10-tetraazacyclododecane-1,4,7-triacetate (DO3A.Gd), and bb(CO)DTPA.Gd are particularly useful. In certain embodiments, DOTAGA may be used. The structure of DOTAGA, shown complexed with Gd(III), is as follows:

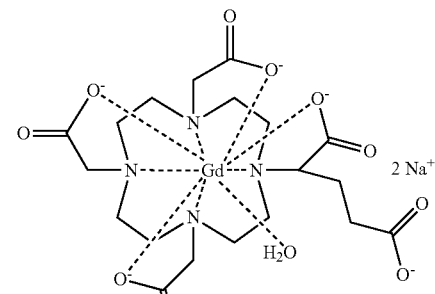

Na$_2$[GdDOTAGA]

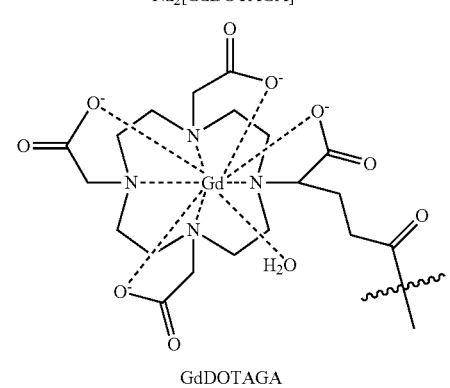

GdDOTAGA

In other cases, the C can be GluDTPA, which has the following structure (shown complexed with Gd(III):

Glu-DTPA-Gd = 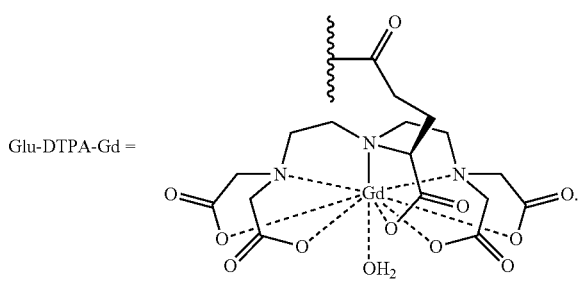

For MR applications, the C can be complexed to a paramagnetic metal ion, including Gd(III), Fe(III), Mn(II), Mn(III), Cr(III), Cu(II), Dy(III), Ho(III), Er(III), Pr(III), Eu(II), Eu(III), Tb(III), Tb(IV), Tm(III), and Yb(III). Additional information regarding C groups and synthetic methodologies for incorporating them into diagnostic compositions can be found in WO 01/09188, WO 01/08712, and U.S. patent application Ser. No. 10/209,183, entitled "Peptide-Based Multimeric Targeted Contrast Agents," filed Jul. 30, 2002.

For radionuclide imaging agents, radionuclides $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$, and $^{141}Ce$ are particularly useful, and can be complexed to the C's described previously.

Metal complexes with useful optical properties also have been described. See, Murru et al., *J. Chem. Soc. Chem. Comm.* 1993, 1116-1118. For optical imaging using chelates, lanthanide chelates such as La(III), Ce(III), Pr(III), Nd(III), Pn(III), Sm(III), Eu(III), Gd(III), Tb(III), Dy(III), Ho(III), Er(III), Tm(III), Yb(III) and Ln(III) are suitable. Eu(III) and Tb(III) are particularly useful.

Metal chelates should not dissociate metal to any significant degree during the imaging agent's passage through the body, including while bound to a target tissue.

Linkers

In some embodiments, a peptide and one or more Cs are covalently bound through a linker (L). A linker can be on the C-terminus, the N-terminus, or both, of a peptide. Additionally, a linker can be bound to the side chain of a peptide. If a peptide is bound to multiple Ls, each L can be different. A L can be covalently linked to a side chain of an amino acid, e.g., lysine, glutamine, cysteine, methionine, glutamate, aspartate, asparagine.

In some embodiments an amino acid side chain can serve as the linker. For example the epsilon amino group ($\epsilon$-NH$_2$) can be used to conjugate to a chelate for instance through an amide or thiourea linkage. Similarly the delta amino group of ornithine (orn), the gamma amino group of diaminobutyric acid (dab), or the beta amino group of diamino proprionic acid (dpr) can also act linkers. These amino acids may be at the C- or N-terminus of the peptide or they may be positioned within the peptide sequence.

An L can include, for example, a linear, branched or cyclic peptide sequence. For example, and L can be a peptide sequence having from 1 to 20, e.g., 1 to 10, or 2 to 5, prolines. Similarly, a L can be a peptide sequence having from 1 to 20, e.g., 1 to 10, or 2 to 5, glycines, Specific examples of L are a single G; the linear dipeptide sequence G-G (glycine-glycine); a single P (proline); the linear dipeptide sequence P-P (proline-proline); —NH(CH$_2$)$_2$O(CH$_2$)$_2$NH$_2$ (referred to as PEG-H herein, and typically on the C-terminal end of a peptide), and NH$_2$(CH$_2$)$_2$O(CH$_2$)$_2$O(CH$_2$)C(O)— (referred to as PEG2O and typically on the N-terminal end). In some cases, the L can cap the N-terminus of the peptide, the C-terminus, or both N- and C-termini, as an amide moiety. Other exemplary L capping moieties include sulfonamides, ureas, thioureas and carbamates. Ls can also include linear, branched, or cyclic alkanes, alkenes, or alkynes, and phosphodiester moieties. The L may be substituted with one or more functional groups, including ketone, ester, amide, ether, carbonate, sulfonamide, thiourea, or carbamate functionalities. Specific Ls contemplated also include —NH(CH$_2$)$_2$O(CH$_2$)$_2$)NH—, —NH—CO—NH—; and —CO—(CH$_2$)$_n$—NH—, where n=1 to 10; diaminopropionic acid (dpr); diaminobenzidine (dab); —NH-Ph-; —NH—(CH$_2$)$_n$—, where n=1 to 10; —CO—NH—; —(CH$_2$)$_n$—NH—, where n=1 to 10; —CO—(CH$_2$)$_n$—NH—, where n=1 to 10; and —CS—NH—. Additional examples of Ls and synthetic methodologies for incorporating them into diagnostic compositions, particularly diagnostic compositions comprising peptides, are set forth in WO 01/09188, WO 01/08712, and U.S. patent application Ser. No. 10/209,183, entitled "Peptide-Based Multimeric Targeted Contrast Agents," filed Jul. 30, 2002.

In some embodiments, the linker can have the following structure:

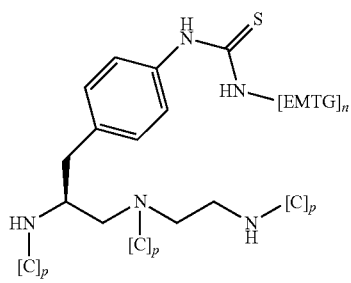

Structures of MR Diagnostic Compositions

An MR diagnostic composition (also referred to as an MR chelate or diagnostic composition) may have the following general formula:

[EMTG]$_n$-[L]$_m$-[C]$_p$, where n can range from 1 to 10, m can range from 0 to 10, and p can range from 1 to 20, and the EMTG, L, and C moieties are as described above. In some embodiments, the EMTG is a collagen binding peptide, as described previously.

In other embodiments, an MR diagnostic composition can have the following general formula:

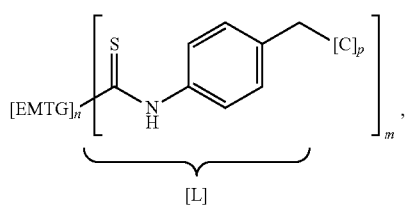

wherein n, m, p, EMTG, L and C are as defined above.

Examples of MR diagnostic compositions having such structures are set forth in the Examples, below, e.g., Table 17.

An MR diagnostic composition can also have the following general formula:

[C]$_p$-[L]$_m$-[EMTG]$_n$-[L]$_q$-[C]$_r$ where p and r can independently range from 1 to 20; m and q can independently be 0 or 1; and n can range from 1 to 10. For example, a diagnostic composition corresponding to such a generic structure is depicted in Example 2, below.

Table 17, 42, and 43, below, sets forth MR diagnostic compositions having affinity for collagen, e.g., dried human and/or rat collagen.

In certain embodiments, an MR diagnostic composition can also have the following general formula:

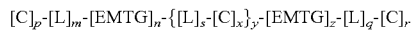

where p, x, and r can independently range from 1 to 20; m, s, and q can independently be 0 or 1; y can range from 1 to 10, and n and z can independently range from 1 to 10. The structure of other MR diagnostic compositions are set forth in the accompanying claims.

Multimeric Structures

MR diagnostic compositions can also exhibit multimeric structures of EMTGs, Cs, and Ls. For example, specifically contemplated herein are diagnostic composition structures as shown in U.S. patent application Ser. No. 10/209,183, entitled PEPTIDE-BASED MULTIMERIC TARGETED CONTRAST AGENTS, filed Jul. 30, 2002, wherein a collagen binding peptide would substitute for the fibrin binding peptides disclosed therein.

Properties of Diagnostic Compositions

Certain diagnostic compositions can be more stable with respect to degradation by endogenous enzymes than the parent peptide (i.e., a collagen binding peptide without any attached chelates). To estimate in vivo stability, test compounds can be incubated with rat liver homogenates. After selected intervals, the reactions can be quenched and centrifuged, and the supernatant can be analyzed by liquid chromatography-mass spectrometry to quantitate the amount of compound remaining. Alternately, plasma samples can be analyzed for metabolites after administration of the test compound.

Diagnostic compositions can also bind an extracellular matrix component, such as collagen. For example, at least 10% (e.g., at least 15%, 20%, 25%, 30%, 35%, 40%, 45%, 50%, 60%, 65%, 70%, 75%, 80%, 85%, 90%, 92%, 94%, or 96%) of the diagnostic composition can be bound to the desired component at physiologically relevant concentrations of diagnostic composition and target. The extent of binding of a diagnostic composition to a target can be assessed by a variety of equilibrium binding methods, e.g., ultrafiltration methods; equilibrium dialysis; affinity chromatography; or competitive binding inhibition or displacement of probe compounds. For example, the binding of a diagnostic composition to collagen can be assessed by monitoring the inhibition of von Willebrand Factor binding to collagen by the diagnostic composition.

In some cases, peptides can be evaluated for their ability to bind to collagen using assays described herein or as indicated in the cross-referenced application, such as dried human collagen or dried rat collagen assays. For example, in certain cases, a peptide can exhibit a percent binding to dried human collagen or dried rat collagen (see assays described in the cross-referenced case) of greater than 10%, e.g., greater than 12%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, or greater than 85%. In some embodiments, a peptide can exhibit a percent binding to dried human collagen in the range of from about 10% to about 50%, or from about 20% to about 60%, or from about 30% to about 60%, or from about 40% to about 90%.

Alternatively, the extraction of the diagnostic composition into myocardial tissue using a perfused heart model can be assessed. See the Examples, below.

MR diagnostic compositions can exhibit high relaxivity as a result of target binding (e.g., to collagen), which can lead to better image resolution. The increase in relaxivity upon binding is typically 1.5-fold or more (e.g., at least a 2, 3, 4, 5, 6, 7, 8, 9, or fold increase in relaxivity). Targeted MR diagnostic compositions having 7-8 fold, 9-10 fold, or even greater than 10 fold increases in relaxivity are particularly useful. Typically, relaxivity is measured using an NMR spectrometer. The preferred relaxivity of an MRI diagnostic composition at 20 MHz and 37° C. is at least 8 mM$^{-1}$ s$^{-1}$ per paramagnetic metal ion (e.g., at least 10, 15, 20, 25, 30, 35, 40, or 60 mM$^{-1}$ s$^{-1}$ per paramagnetic metal ion). MR diagnostic compositions having a relaxivity greater than 60 mM$^{-1}$ s$^{-1}$ at 20 MHz and 37° C. are particularly useful.

As described herein, targeted MR diagnostic compositions can be taken up selectively by areas in the body having higher concentrations of an extracellular matrix component target (e.g., collagen) relative to other areas. Selectivity of uptake of targeted agents can be determined by comparing the uptake of the agent by myocardium as compared to the uptake by blood. The selectivity of targeted diagnostic compositions also can be demonstrated using MRI and observing enhancement of myocardial signal as compared to blood signal.

Use of Diagnostic Compositions

MR diagnostic compositions prepared according to the disclosure herein may be used in the same manner as conventional MRI diagnostic compositions and are useful for imaging extracellular matrix components of the myocardium. Typically, the MR diagnostic composition is administered to a patient (e.g., an animal, such as a human) and an MR image of the patient is acquired. Generally, the clinician will acquire an image of an area having the extracellular matrix component that is targeted by the agent. For example, the clinician may acquire an image of the heart, a joint, a bone, or an organ if the diagnostic composition targets collagen or locations of abnormal collagen accumulation in a disease state. The clinician may acquire one or more images at a time before, during, or after administration of the MR diagnostic composition.

Certain MR techniques and pulse sequences may be preferred in the methods of the present disclosure. Both 2-dimensional and 3-dimensional T1-weighted acquisitions are desirable. For example spin-echo and fast spin echo sequences with short repetition times (TR), or gradient recalled echo sequences with short TR. Inversion recovery sequences may be particularly useful for highlighting T1 changes, as well as the use of an inversion prepulse combined with a T1-weighted sequence. For cardiac imaging methods of cardiac gating, either prospective or retrospective methods, can be applied to freeze cardiac motion. Similarly artifacts from respiratory motion can be reduced using breath-hold methodologies or free-breathing navigator techniques. In some instances it may be desirable to obtain additional contrast and the T1-weighted sequence can be combined with fat suppression, or blood flow suppression, or by using a magnetization transfer prepulse. Similarly, those of skill in the art will recognize other suitable MR-based methods for detecting infarct, e.g., T2 weighted imaging, delayed hyperenhancement imaging following extracellular contrast agent, and myocardial imaging.

In some embodiments, a contrast-enhancing imaging sequence that preferentially increases a contrast ratio of a magnetic resonance signal of the myocardium having a MR diagnostic composition bound thereto relative to the magnetic resonance signal of background or flowing blood is used. These techniques include, but are not limited to, black blood angiography sequences that seek to make blood dark, such as fast spin echo sequences; flow-spoiled gradient echo sequences; and out-of-volume suppression techniques to suppress in-flowing blood. These methods also include flow independent techniques that enhance the difference in contrast due to the T1 difference between contrast-enhanced myocardium and blood and tissue, such as inversion-recovery prepared or saturation-recovery prepared sequences that will increase the contrast between the myocadium and background tissues. Methods of preparation for T2 techniques may also prove useful. Finally, preparations for magnetization transfer techniques may also improve contrast with MR diagnostic compositions.

Methods may be used that involve the acquisition and/or comparison of contrast-enhanced and non-contrast images and/or the use of one or more additional MR diagnostic compositions. The additional MR diagnostic compositions may also exhibit affinity for an extracellular matrix component of the myocardium, as described herein. For example, a series of images may be obtained with an MR diagnostic composition that binds to collagen, while another series of images may be obtained with an MR diagnostic composition that binds to elastin. Alternatively, an additional MR diagnostic composition may be used that is nonspecific or that may exhibit an affinity for fibrin or HSA. For example, methods as set forth in U.S. patent application Ser. No. 09/778,585, entitled MAGNETIC RESONANCE ANGIOGRAPHY DATA, filed Feb. 7, 2001 and U.S. patent application Ser. No. 10/209,416, entitled SYSTEMS AND METHODS FOR TARGETED MAGNETIC RESONANCE IMAGING OF THE VASCULAR SYSTEM, filed Jul. 30, 2002 may be used. Similarly, fibrin targeted agents are described in U.S. patent application Ser. No. 10/209,183, entitled PEPTIDE-BASED MULTIMERIC TARGETED CONTRAST AGENTS, filed Jul. 30, 2002. Diagnostic compositions for binding HSA are described in WO 96/23526.

In addition, MR diagnostic compositions are useful for monitoring and measuring myocardial perfusion. Certain methods, although not all, include the step of obtaining an MR image of the myocardial tissue of an animal while the animal is in a pre-hyperemic state. As used herein, the term "pre-hyperemic state" refers to a resting physiologic state of the animal. In some methods, peak hyperemia can be induced in the animal, either before or after the step of obtaining a pre-hyperemic MR image. As used herein, the term "peak hyperemia" means the point approaching maximum increased blood supply to an organ or blood vessel for physiologic reasons. Peak hyperemia can be exercise-induced or pharmacologically-induced. Exercise-induced peak hyperemia can be achieved through what is commonly known as a "stress test," and has several clinically relevant endpoints, including excessive fatigue, dyspnea, moderate to severe angina, hypotension, diagnostic ST depression, or significant arrhythmia. If exercise is used to induce peak hyperemia, the animal can exercise for at least one additional minute before the administration of a diagnostic composition, as described below. The cardiac effect of exercise-induced peak hyperemia can also be simulated pharmacologically (e.g., by the intravenous administration of a coronary vasodilator, such as Dipyridamole (Persantine™)) or adenosine.

After or during the induction of peak hyperemia, an effective amount of an MR-diagnostic composition as described above can be administered to the animal. An MR image of the animal's myocardial tissue after the induction of peak hyperemia can then be acquired. Generally, the acquisition of the image begins at a time frame at least 2 times greater than that required for a first pass distribution of the MR diagnostic composition. In humans, with venous injection of an MR diagnostic composition, the bolus typically passes through the right heart after approximately 12 sec., and through the left heart after about another 12 sec. Thus, from time of injection to the first pass of the MR diagnostic composition through the entire heart, approximately 24-30 seconds have passed usually. The second pass of the MR diagnostic composition usually is seen approximately 45 sec. later. In some embodiments, the MR image of the myocardial tissue of the animal after the induction of peak hyperemia may begin at a time frame at least 5, 10, or 30 times greater than that required for a first pass distribution of the MR diagnostic composition. Typically, the acquisition of the MR image of the myocardial tissue after the induction of peak hyperemia begins in a time period from about 5 to about 60 minutes after the induction of peak hyperemia. For example, in some embodiments, peak hyperemia is induced in the patient outside of an MR scanner, the MR diagnostic composition is injected at or after peak hyperemia, and the patient is put inside the MR scanner to acquire the MR image of the myocardium after peak hyperemia.

In certain embodiments, the MR images of the myocardium, whether at peak or pre-hyperemia, are T1-weighted images. In some embodiments, T2-weighted images of the myocardium in a pre-hyperemic state are obtained. A T2 weighted image of the myocardium at rest (pre-hyperemic) would give an enhancement of infarcted tissue.

In certain cases, the MR image of the myocardial tissue of the animal in the pre-hyperemic state, if obtained, are compared with the MR image of the myocardial tissue after the induction of peak hyperemia in order to evaluate myocardial perfusion. Zones of abnormal, or low, perfusion will be hypointense (less intense) compared to normal myocardium in the peak hyperemia image.

Certain methods employ a second MR diagnostic composition. In these methods, peak hyperemia can be induced in an animal and an effective amount of a first MR-based diagnostic composition, as described herein, is administered. An MR image of the animal's myocardial tissue after the induction of peak hyperemia is acquired, as described previously. An effective amount of a second MR-based diagnostic composition can then be administered. In some embodiments, the first and second MR-based diagnostic compositions are administered together. The second MR diagnostic composition may be any MR-based diagnostic composition including ECF agents or the diagnostic compositions described herein. Suitable examples of Gd(III)-complexed MR diagnostic compositions include Gd(III)-DTPA, Gd(III)-DOTA; Gd(III)-HP-DO3A, Gd(III)-DTPA-BMA, Gd(III)-DTPA-BMEA, Gd(III)-BOPTA, Gd(III)-EOB-DTPA, Gd(III)-MS-325, Gd(III)-Gadomer-17, or the Gd(III)-complex of the first MR diagnostic composition administered in the method. Other examples of useful diagnostic compositions are described in WO 96/23526. The administration of the second MR diagnostic composition can occur after a time frame sufficient to return the animal to a pre-hyperemic state. For example, the animal may immediately return to a pre-hyperemic state, or the administration of the second diagnostic composition can occur on a time frame typically ranging from 15 min. to approximately 4 hours after the induction of peak hyperemia. An MR image of the myocardial tissue of the animal in the pre-hyperemic state is then acquired. As one of skill in the art can recognize, the order of the above-referenced steps can be altered, e.g., the administration of the "second" MR diagnostic composition and acquisition of the pre-hyperemic image can be performed first, while the administration of the "first" MR diagnostic composition and peak hyperemic scan could be acquired second.

An MR image of the myocardial tissue of the animal in the pre-hyperemic state can be compared with the MR image of the myocardial tissue after the induction of peak hyperemia. Zones of abnormal, or low, perfusion will be hypointense compared to normal myocardium in the peak hyperemia image. Both ischemic and infarct zones appear as hypointense in the peak hyperemia image. In the pre-hyperemic image acquired with the second diagnostic composition, however, the ischemic zones appear with normal to hyperintensity, while infarct zones initially appear as hypointense (e.g., after a short time period after injection of the second diagnostic composition) and then as hyperintense after a longer delay after injection. A comparison of the two images thus allows the characterization of abnormal, or low, perfusion as either ischemia or infarct.

In other methods of evaluating myocardial perfusion, peak hyperemia is induced and an MR diagnostic composition is administered. An MR image of the animal's myocardial tissue after the induction of peak hyperemia is acquired. The animal is allowed to return to a pre-hyperemic state, and the myocardial tissue is imaged again. The two images can then be compared and examined for zones of ischemia and/or infarct.

Administering an MR diagnostic composition as described herein (e.g., a collagen targeted agent) at peak hyperemia should yield an MR image where healthy tissue is bright, while inducibly ischemic and infarcted tissue is dark, for T1 weighted scans. If there is a dark (hypointense region), one can distinguish whether it is viable tissue (inducible ischemia) or if it is an infarct by comparing the image to an image of the myocardium obtained using one or more of several other methods. For example, one method would be to acquire a T2-weighted scan of the myocardium at rest (e.g., either before or after the induction of peak hyperemia). Infarct appears bright relative to normal diagnostic composition as described herein (e.g., a collagen targeted MR agent) at rest (pre-hyperemia) and to obtain a pre-hyperemic MR scan of the myocardium, as described previously above; this administration could be performed either before or after the peak hyperemia MR scan. In such a pre-hyperemic scan, normal and inducibly ischemic tissue would enhance, but infarct would not (analogously to nuclear medicine protocols). A third approach would be to administer an extracellular fluid MR diagnostic composition (ECF), e.g., GdDTPA or GdDOTA, or others as known to those having ordinary skill in the art, at pre-hyperemia, and to obtain an MR image of the myocardium from about 2 to about 60 (e.g., 2 to 20, 2 to 10, 5 to 10, 5 to 20, 10 to 30, 5 to 40, or 8 to 50) minutes after administration of the ECF, e.g., a delayed enhancement image. In this case the infarct would enhance, but the ischemic area would not. Finally, a fourth approach would be to administer an ECF agent at pre-hyperemia and to perform a first pass (MRFP) dynamic perfusion exam to determine if hypointense areas as seen in the targeted MR agent hyperemia scans enhance as quickly and intensely as normal myocardium, which would indicate inducible ischemia.

MRI diagnostic compositions containing small organic molecules as IEMs may also be useful as optical diagnostic compositions. Due to the difference in sensitivity between optical and MR techniques, such dual MR/optical diagnostic compositions can be used, for example, to image areas of both high and low concentration of the myocardial extracellular matrix component. Alternatively, a dual agent may be useful to image areas where there is reduced resolution or signal due to an aspect of the alternative imaging modality.

Small organic molecules included in the compositions typically have an optical signal. The optical signal can be any signal that can be detected, including transmission or absorption of a particular wavelength of light (e.g., near-infrared), fluorescence or phosphorescence absorption and emission, reflection, changes in absorption amplitude or maxima, and elastically scattered radiation. Generally, the optical signal is a near-infrared or fluorescence emission spectrum. Methods of detection include catheters equipped with an appropriate optical detector.

The diagnostic compositions of the present disclosure may function to distinguish benign from malignant breast lesions or tumors. The compositions may be small enough to freely extravasate from the blood vessels and into the interstitial space of the lesion. This may allow enhancement of all lesions, akin to that of contrast agents used clinically, such as GdDTPA. Benign lesions such as fibroadenomas and fibrocystic tissue contain significant concentrations of type I collagen. Carcinomas are also collagen rich compared to normal breast tissue, but also contain high collagenase concentrations which serve to degrade collagen.

In certain embodiments, a diagnostic composition of the present disclosure (e.g., compound ID 800) may be used. In some embodiments, a T1-weighted imaging is performed after injection of the diagnostic composition, and a dynamic phase shows all lesions enhanced. The diagnostic composition is retained in the collagen-rich benign lesions, but washes out of the carcinoma. An image is then acquired at a later time point (e.g., 10 minutes or more post injection) and the benign lesion remains enhanced whereas the carcinoma is not enhanced at this late time point.

In another embodiment, the dynamic contrast-enhanced magnetic resonance imaging (DCE-MRI) approach is used with the diagnostic compositions (e.g., compound ID 800). Collagen binding alters the signal intensity vs time curve, especially at later time points where the wash-out from the benign lesion is much slower than from the carcinoma.

Compound ID 800

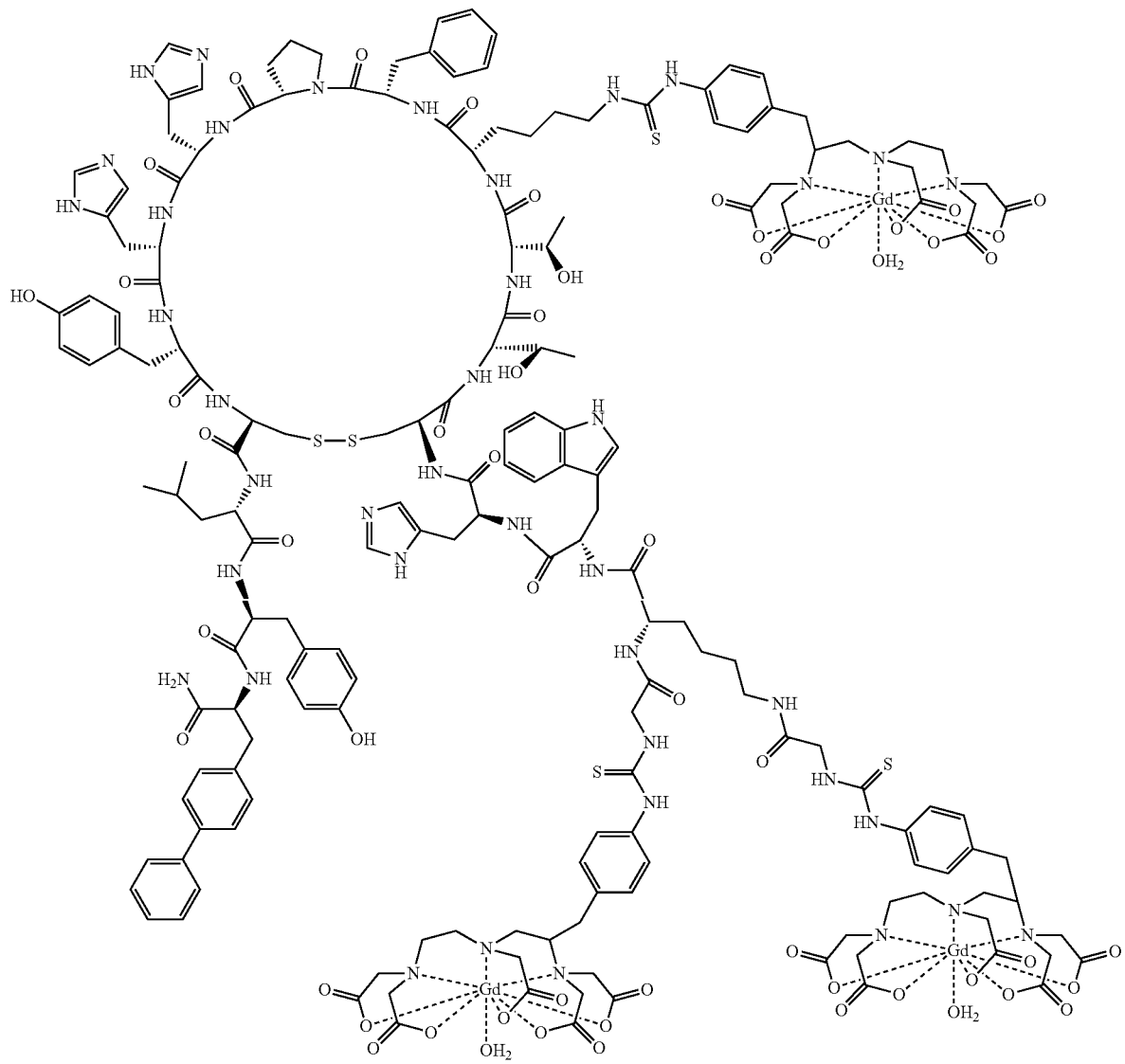

It is also contemplated that the diagnostic compositions set forth in this disclosure may be useful in the following applications:

1. Atherosclerosis, High Risk/Vulnerable Plaque.

It has become established that certain atherosclerotic lesions are at risk for rupture, thereby creating a thrombogenic surface. Plaque rupture leads to thrombosis which can result in myocardial infarction or stroke. The precursor lesion of plaque rupture has been defined (Virmani et al, J Interv Cardiol. 2002, 15:439-46) as "thin-cap fibroatheroma" (TCFA). Morphologically, TCFAs have a necrotic core with an overlying thin fibrous cap (<65 mm) consisting of collagen type I, which is infiltrated by macrophages. These lesions are most frequent in the coronary tree of patients dying with acute myocardial infarction. In TCFAs, necrotic core length is approximately 2-17 mm (mean 8 mm) and the underlying cross-sectional luminal narrowing in over 75% of cases is <75% (<50% diameter stenosis). The area of the necrotic core in at least 75% of cases is ≤3 $mm^2$. Clinical studies of TCFAs are limited as angiography and intravascular ultrasound (IVUS) catheters cannot precisely identify these lesions. Identification of these precursor lesions of plaque rupture is therefore a great unmet medical need.

Stable lesions, on the other hand, have a thick fibrous (collagenous) cap. The ability to identify and distinguish atherosclerotic plaques based on cap thickness would be of great value. A collagen type I targeted imaging agent such as those described in this application, would bind to the fibrous cap in a collagen-dependent manner. Stable plaques would be seen by T1-weighted MRI as hyperenhanced regions in the lumen and vessel wall. Unstable or at risk plaques (the TCFA) would be seen as a thin hyperenhanced complex zone appearing along the vessel wall.

2. Myocardial Infarct Imaging and Myocardial Viability.

It has been demonstrated that delayed enhancement of infarcted myocardium with GdDTPA enhanced MRI is useful for detecting both transmural and subendocardial infarcts (e.g. Wagner et al. Lancet 2003, 361:374-9). Myocardial infarcts (MI) are typically classified by their EKG response and are grouped into Q-wave MI and non-Q-wave MI. Non-Q- wave infarcts are typically smaller infarcts, however they are associated with a morbidity and mortality associated with larger infarcts. Wagner et al. showed that delayed contrast enhancement MRI was much better at detecting subendocardial infarcts than single photon emission computed tomography (SPECT). Improving the detection of infarct to identify smaller MI would result in a change in treatment for these patients whose MI would otherwise have been missed and would likely improve prognosis. MI results in cardiac remodeling and an increased collagen content. A specific collagen targeted contrast agent would be able to better delineate infarcted regions and improve specificity for infarct.

3. Renal Fibrosis—Diagnosis, and Monitoring Response to Therapy.

Renal fibrosis is a final common process of many chronic renal diseases. It is characterized by overdeposition of the extracellular matrix, notabl collagen, which eventually leads to the end-stage renal disease (ESRD). Several renal disorders such as diabetic nephropathy, chronic glomerulonephritis, tubulointerstitial fibrosis and hypertensive nephrosclerosis can result into ESRD. Early detection of renal fibrosis would be valuable in order to start treatments earlier and improve the likelihood of reversing the disease. Moreover an imaging agent that allows monitoring of fibrosis would be valuable in assessing response to therapy.

4. Pulmonary Fibrosis—Diagnosis, and Monitoring Response to Therapy.

Pulmonary fibrosis is a pathology whereby the lung tissue becomes scarred with deposits of fibrotic (collagen) tissue. As fibrosis increases there is a decrease in the lung's ability to transfer oxygen to the blood resulting in considerable morbidity and a high likelihood of mortality. There are many causes of pulmonary fibrosis: environmental pollutants/toxins such as cigarette smoke, asbestos; diseases such as scleroderma, sarcoidosis, lupus, rheumatoid arthritis; side effects of radiation treatment or chemotherapy (e.g. bleomycin treatment) for cancer. Early detection and accurate characterization of pulmonary fibrosis can improve patient outcomes. Moreover, as new antifibrotic therapies become available there is a need for means of non-invasively monitoring pulmonary fibrosis and the patient's response to therapy.

5. Liver Fibrosis—Diagnosis, and Monitoring Response to Therapy.

Liver fibrosis is a common result of many diseases which attack the liver: hepatitis B and C; non-alcoholic steato hepatitis (NASH); cirrhosis; and occurs in a fraction of patients with fatty liver. Fibrosis in the liver can be diagnosed but only at an advanced stage with current non-invasive procedures. Biopsy can detect fibrosis at an earlier stage but liver biopsy is not well suited to screening/monitoring disease because of its cost, associated morbidity and known lack of accuracy because of sampling variation, Rockey D C, Bissell D M. "Noninvasive measures of liver fibrosis" Hepatology. 2006 43:S113-20. Early detection and accurate characterization of liver fibrosis can improve patient outcomes. For patients with NASH, diet changes can reverse the disease if caught early enough. Moreover, as new antifibrotic therapies become available there is a need for means of non-invasively monitoring pulmonary fibrosis and the patient's response to therapy.

Therapeutic Compositions

Peptides described herein can be included in compositions for treating, ameliorating, preventing, or prophylaxis of pathologies or disorders associated with abnormal or excessive accumulation of collagen or for treating, ameliorating, preventing, or prophylaxis of pathologies or disorders associated with collagen vascular or tissue diseases. For example, a therapeutic composition can include a peptide as shown herein conjugated to a therapeutic agent, such as collagenase, a collagenase activator, an anti-inflammatory, or an antithrombotic (e.g., a platelet gpIIb/IIIa inhibitor, a Factor Xa inhibitor, and a thrombin inhibitor). In cases where a collagenase or collagenase activator is conjugated, the therapeutic composition can be useful to alter (e.g., increase or improve) the myocardial remodeling process after a myocardial infarction. Antifibrotics can include inhibitors of transforming growth factor beta-1 (TGF β1), angiotensin converting enzyme (ACE) inhibitors (e.g. captopril), endothelin A receptor antagonists (e.g. LU 135252, Cho J J, Hocher B, Herbst H, Jia J D, Ruehl M, Hahn E G, Riecken E O, Schuppan D. "An oral endothelin-A receptor antagonist blocks collagen synthesis and deposition in advanced rat liver fibrosis", Gastroenterology. 2000 118:1169-78), antioxidants, PPAR-γ agonists, and integrin antagonists to inhibit activation of TGF-β (e.g. EMD409849, an anti $\alpha_v\beta_6$ antagonist, Goodman S L, Holzemann G, Sulyok G A, Kessler H., Nanomolar small molecule inhibitors for alphav(beta)$_6$, alphav(beta)$_5$, and alphav(beta)$_3$ integrins" J Med. Chem. 2002 45:1045-51).

Peptides can be linked or fused to a therapeutic agent in known ways, using the linkers discussed below with respect to constructing diagnostic compositions. Conjugation to a therapeutic agent can be achieved by standard chemical techniques including the formation of amide, ester, disulfide, thiourea, and thioether bonds. For example, a peptide can be covalently linked, either directly or through a linker, to a protein by forming an amide bond between the peptide or the linker and the lysine residues on the surface of the protein. Surface lysine residues are usually distant from enzymatic catalytic sites. Therefore, a tethered moiety is less likely to interfere with the enzyme's catalytic activity. In particular, a coupling agent or an activated ester can be used to achieve amide bond formation between a lysine on a protein therapeutic agent and the peptide. Multiple ligation can be achieved in a single step. The ratio of the peptide to the therapeutic agent can be controlled by adjusting the stoichiometry of the ligation chemistry. Multiple ligation is particularly useful in the case of a moderately strongly binding peptide because higher binding affinity can be realized through the so called "avidity" effect. Alternatively, a peptide can be incorporated into the hybrid molecule using recombinant DNA technology.

Pharmaceutical Compositions

Pharmaceutical compositions can include any of the diagnostic or therapeutic compositions described previously, and can be formulated as a pharmaceutical composition in accordance with routine procedures. As used herein, pharmaceutical compositions can include pharmaceutically acceptable salts or derivatives thereof. "Pharmaceutically acceptable" means that the agent can be administered to an animal without unacceptable adverse effects. A "pharmaceutically acceptable salt or derivative" means any pharmaceutically acceptable salt, ester, salt of an ester, or other derivative of composition that, upon administration to a recipient, is capable of providing (directly or indirectly) a composition of the present disclosure or an active metabolite or residue thereof. Other derivatives are those that increase the bioavailability when administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the therapeutic or diagnostic compositions or compositions of this disclosure include counter ions derived from pharmaceutically acceptable inorganic and organic acids and bases known in the art, e.g., sodium, calcium, N-methylglutamine, lithium, magnesium, potassium, etc.

Pharmaceutical compositions can be administered by any route, including both oral, intranasal, inhalation, or parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the therapeutic or diagnostic compositions of the present disclosure and pharmaceutically acceptable salts thereof, with any pharmaceutically acceptable ingredient, excipient, carrier, adjuvant or vehicle.

A pharmaceutical composition is preferably administered to the patient in the form of an injectable composition. The method of administering a therapeutic or diagnostic composition is preferably parenterally, meaning intravenously, intra-arterially, intrathecally, interstitially or intracavitarilly. Pharmaceutical compositions can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

EXAMPLES

1. Phage Display Identification of Peptides that Bind to Collagen

A. Selection Strategies

Collagen I selections were conducted using cyclic peptide sub-libraries as well as a linear library (Ln20) (Dyax, Inc., Cambridge, Mass.) in the following panning formats:
1. Biotinylated collagen I on streptavidin (SV) beads selection
2. Biotinylated collagen I immobilized on SV beads with human serum in selection
3. Collagen I (non-biotinylated) immobilized on immunotubes
4. Collagen I (non-biotinylated) immobilized on immunotubes with human serum in selection
5. Collagen I (non-biotinylated) immobilized on carboxylic acid (CA) beads Since cross reactivity with human serum albumin (HSA) was not desired, phage aliquots were depleted against HSA (bound to SV beads) before selecting on collagen I. For each of the selections above, three rounds were performed. Selections 1 and 2 above consisted of 2 arms each, where binding time for phage and targets was varied between either 5- or 60-minutes. All other selections were performed using 60-minutes binding time. Based on pre-screening ELISA on round 2 and round 3 selection outputs, a specific set of selection arms was chosen for high throughput screening. ELISA positive isolates were re-arrayed and sequenced. Unique sequences were re-arrayed, and secondary ELISA with collagen from different species (bovine, rabbit, rat, pig) was performed. Sequence motif analysis was performed on unique sequences.

Target Validation:

Biotinylated collagen and non-biotinylated collagen were analyzed to confirm that target was effectively immobilized prior to phage selection. The analyses included: a.) SDS PAGE verification of SV beads pull-down experiment for biotinylated collagen, b.) ELISA on CA beads coated with non-biotinylated collagen (using anti-collagen antibody), and c.) Immunotubes ELISA after coating tubes with non-biotinylated collagen (using anti-collagen antibody).

Results Summary:

From selection and screening using collagen, the cyclic and linear peptide libraries produced over 200 total unique peptide sequences from all selection modes, none of which cross-reacted in ELISA with HSA. Using sequence alignment and analysis, motifs were identified for the libraries. Cross-species ELISA showed that many clones bound effectively to collagens from rat, rabbit, bovine and pig; and 15 isolates showed binding to all 5 species. Many isolates (226) showed binding to h-Collagen but not HSA in the presence of serum.

ELISA Analyses:

To determine the relative binding affinity and binding specificity of individual phage clones to collagen, individual phage colonies obtained after the phage screen were hand-picked at random for amplification in 96-well plates. The procedure for growing liquid cultures of phage was as follows:
1. From an overnight culture of (*E. coli*) MRF', dilute 1:100 in NZCYM/12.5 µg/mL tetracycline and grow to mid-log stage (OD 0.5, 600 nm);
2. Aliquot mid-log cells into 96-well microtiter plates (200 uL per well)
3. Pick plaques (by hand for pre-screening or with automated picker for high-throughput) into individual wells of microtiter plates from step 2 above
4. Seal plates using adhesive film seal and incubate with shaking at 37° C. overnight Amplified phage in liquid culture were then tested for their ability to bind to collagen using a phage ELISA procedure. In this method, biotinylated human collagen was immobilized to the wells of a 96-well microtiter plate coated with streptavidin. Phage were incubated either in the plate in either buffer (PBST) or in human serum. Unbound phage were washed from the plate and the presence of bound phage was detected by anti-M13 antibody coupled to horse radish peroxidase. Plates were developed with the colorimetric substrates TMB/ $H_2O_2$ and the absorbance of the plate was measured at 630 nm. High absorbance values were associated with high-binding phage colonies. To determine the specificity of the interaction, phage ELISAs were conducted to determine binding to streptavidin alone or to human serum albumin. In both cases, the protein target was passively adsorbed to the plate in buffer (100 mM bicarbonate, pH 8.5 for streptavidin; PBS for HSA).

The protocol used was as follows:
1. Coat plates with Streptavidin (2 μg/mL in 100 mM bicarbonate, pH 8.5, 100 uL per well) overnight at 4° C.
2. Next morning, block all plates with 1% (w/v) BSA in 100 mM bicarbonate, pH 8.5, 2 hr at 37° C.
3. Wash 3×100 uL PBST (PBS with Triton X-100).
4. Add biotinylated-collagen at 1 μg/mL (100 μL per well); for background plates use streptavidin and bio-HSA. Incubate 2 hr RT.
5. Wash all plates 3×PBST.
6. Spin overnight cultures of amplified phage in 96-well plates from step 4 in the previous section at 1200 rpm for 5 min.
7. Add 70 μL PBST and 30 μL amplified phage culture to each well; incubate 1.5 hr at RT.
8. Wash plates 5×100 uL with PBST.
9. Add anti-M13 monoclonal antibody-HRP conjugate (1:5000 dilution in PBST, 100 μL/well). Incubate 1 hr RT
10. Wash plates 7×100 uL with PBST.
11. Develop with TMB/$H_2O_2$.
12. Read plates on plate reader at 630 nm.
13. For cross-species ELISA: the same procedure was used, wells were coated with designated collagen (rabbit, bovine, rat or pig) at 1 ug/mL in PBST (100 uL per well).
14. For ELISA with serum: same procedure is used but serum was added at the same time phage was added; final concentration of serum was 50% (v/v) per well.
15. For phage ELISA vs. Streptavidin or HSA, plates were prepared following steps 1 and 2 above.

Approximately 211 peptide sequences were identified from the phage display protocol by DNA sequencing of positive clones.

B. Peptide Sequences

Approximately 140 synthetic peptides were prepared using standard peptide synthesis methods. The percent binding to dried human collagen (assay described below), for certain peptides are set forth below.

TABLE 1

TN-6 Peptides, all peptides are cyclic with disulfide bond between the two cysteines:

| SEQ ID NO. | Dried Human Collagen Binding | Sequence |
|---|---|---|
| 1 | 56% | Y H A C Y Q A G C W I W |

TABLE 2

TN-8 Peptides, all peptides are cyclic with disulfide bond between the two cysteines:

| SEQ ID NO. | Dried Human Collagen Binding | Sequences |
|---|---|---|
| 2 | 14% | W G W C E W A Q N N C W N Y |
| 3 | 2% | P W W C H E M P S M C F G F |

TABLE 3

TN-9 Peptides, all peptides are cyclic with disulfide bond between the two cysteines:

| SEQ ID NO. | Dried Human Collagen Binding | Sequences |
|---|---|---|
| 4 | 45% | T W M C V D P P L W R C W V Q |
| 5 | 24% | N W K C W G V V K W E C I W A |
| 6 | 20% | T W Q C S G N Q K W S C E W F |
| 7 | 11% | N W Y C T G T K S W E C F W K |
| 8 | 9% | G W Q C F G A S D W H C T W V |
| 9 | 7% | T W N C Y G V T E W H C Y M I |
| 10 | 9% | L T V C H P P Y Y G R C N F V |
| 11 | 9% | P L V C H P P Y S G S C S L H |
| 12 | 7% | P M I C H A P Y V G K C N F L |

TABLE 4

TN-10 Peptides, all peptides are cyclic with disulfide bond between the two cysteines:

| SEQ ID NO. | Dried Human Collagen Binding | Sequences |
|---|---|---|
| 13 | 78-85% | Q W T C S G D E Y T W H C N Y E |
| 14 | 83% | D W T C R G D E Y T W H C N Y E |
| 15 | 83% | D W T C Y G D E Y T W H C N Y E |
| 16 | 83% | D W T C S G D E Y Y W H C N Y E |
| 17 | 78% | D W T C S G D E Y T W H C N Y E |
| 18 | 78% | D W T C S G D E Y T W Y C N Y E |
| 19 | 70% | D W T C S G D E Y R W H C N Y E |
| 20 | 64% | P W Y C S G D H L D W K C I Y Q |
| 21 | 57% | D W T C V G D H K T W K C N F H |
| 22 | 55% | D W E C H G N E F E W N C L M R |
| 23 | 44% | A W D C S G N I P T W Y C R R L |
| 24 | 43% | E W L C V G D S L K W Y C K H S |
| 25 | 39% | I W L C T G G A A T W N C K F D |
| 26 | 25% | W R C D G D A H D W H C D W F |
| 27 | 24% | S W H C F G D N E N W M C N L R |
| 28 | 20% | S W I C T G D N I D W N C R F A |
| 29 | 16% | D W I C H G D F D T W K C D L Q |
| 30 | 16% | G W D C Q G T D N I W E C V R K |
| 31 | 15% | G W V C G G D H T T W E C H L Q |
| 32 | 12% | N W V C S G D H A D W S C A L I |
| 33 | 12% | A W T G V G G E K T W G G V W N |
| 34 | 11% | M W D C T G N S A E W R C E M Q |

TABLE 4-continued

TN-10 Peptides, all peptides are cyclic with disulfide bond between the two cysteines:

| SEQ ID NO. | Dried Human Collagen Binding | Sequences |
|---|---|---|
| 35 | 8% | Y W V C G G D H Q S W H C S H P |
| 36 | 7% | S W S C G G D H N A W K C Q Y S |
| 37 | 7% | L W N C H G T D A N W K C V L N |
| 38 | 6% | G W S C H G D A A D W P C Q W S |
| 39 | 6% | G W Q C S G D A S V W N C D W I |
| 40 | 3% | E W R C R G D S S W L C D Y T |
| 41 | 1% | V W A C R G G T T N W H C D L |
| 42 | 40% | T W R C D Q F K G K W V C R G G |
| 43 | 30% | P W Q C Y S D K T S W V C N L Y |
| 44 | 28% | G W N C Y E Y D S Q W I C D H L |
| 45 | 25% | E W Q C T Q Y A N Q W N C K Y N |
| 46 | 23% | G W V C L Q K G P K W V C D W D |
| 47 | 22% | P W T C R M T E N T W V C D L N |
| 48 | 22% | A W S C W I V E G R W N C S D I |
| 49 | 19% | A W F C S Q K N R L W S C G E T |
| 50 | 18% | K W F C E L M Q D Q W Q C G S K |
| 51 | 18% | K W F C E L M H D Q W Q C G S K |
| 52 | 15% | R W S C W L D E N G W K C D G T |
| 53 | 12% | G W F C K L V D G N W E C S T K |
| 54 | 12% | M W N C T M T K S G W R C F E K |
| 55 | 12% | S W N C H W R N Q G W L C S G G |
| 56 | 11% | S W N C H M I R N E W R C T G H |
| 57 | 11% | R W T C D L Q R G D W Q C S T I |
| 58 | 10% | G W V C M M R E T D W N C S I |
| 59 | 10% | H W Q C R L T D Y G W N C D E R |
| 60 | 10% | E W H C V L N D F R W T C G G D |
| 61 | 9% | K W S C Y M V D H Q W Y C R E F |
| 62 | 9% | H W S C Y L G D N G W N C H D R |
| 63 | 8% | N W Y C S Q A L D N W S C K L R |
| 64 | 8% | T W I C S H N D K G W T C G D Q |
| 65 | 7% | K W E C V H T K G E W Y C E T K |
| 66 | 6% | R W S C V L D A D G W V C S D N |
| 67 | 5% | G W S C H S M D M Q W H C D F S |
| 68 | 5% | S W H C F L E N H H W M C S D H |
| 69 | 3% | H W Q C G E K M S F W S C E L V |
| 70 | 3% | F W R C A L L D G H W Q C T D H |
| 71 | 3% | S W H C A L M G S R W V C G Q N |
| 72 | 1% | E W H C V F I Q G D W L C N S G |
| 73 | 1% | S W H C A L V E N S W Q C S E A |
| 74 | 67-69% | Q W H C T T R F P H H Y C L Y G |
| 75 | 10% | E R N C V L N D F R W T C G G D |
| 76 | 1% | F G A C D I F P T F H T C P G V |

TABLE 5

TN-11 Peptides, all peptides are cyclic with disulfide bond between the two cysteines:

| SEQ ID NO. | Dried Human Collagen Binding | Sequences |
|---|---|---|
| 77 | 12% | G W Q C Q G T D S L D W K C L Y M |
| 78 | 8% | T W A C D L D E Y G G W Q C Y T G |
| 79 | 8% | F W T C E L D F R Q S W Y C Y D K |
| 80 | 6% | S W Y C N N G S Y G Q W H C E H R |
| 81 | 3% | Q W F C E M D E Y G K W N C G M M |
| 82 | 3% | L W T C S M D R N Y D W V C G E K |
| 83 | 3% | G W A C N T T S K G D W E C T N L |
| 84 | 3% | H W S C D L A M D N E W F C S T K |
| 85 | 3% | G W T C S Q P G A N V W N C T M Q |
| 86 | 2% | S W Y C D W D D R K G W M C G S D |
| 87 | 1% | H W T C D Q A K G G A W S C S S T |
| 88 | 1% | F W T C M R D Q V G E W H C G T E |
| 89 | 1% | K W H C E L D S H M E W S C S G H |
| 90 | 34% | T W A C G W T T T G W D N C R W I |
| 91 | 28% | T W A C G W T T A G W D N C R W I |
| 92 | 34% | T W A C G W T T T G W D N C R W I |
| 93 | 5% | W W A C Q K G Q H D W E K C H W L |
| 94 | 21% | W T D C Q W M D E Q L W T C R W D |
| 95 | 5% | W T D C Q W M D E Q I W T C R W D |
| 96 | 17% | W Q L C S S R N D H V A Y C F V S |
| 97 | 13% | W I S C E S S E E K I S Y C W R A |
| 98 | 5% | W Q V C A D S P G V I T Y C Y T Y |
| 99 | 3% | A K K C W Y N D G G H L R C R T L |

TABLE 6

TN-12 Dried Collagen Binders, all peptides are cyclic with disulfide bond between the two cysteines:

| SEQ ID NO. | Dried Human Collagen Binding | Sequences |
|---|---|---|
| 100 | 67% | W W G C R Q G T G E H W S H C M W F |
| 101 | 56% | W W T C H M T W S G Q W D S C K W H |
| 102 | 31% | W A Y C M T D P S G K Y R Y C Q N W |
| 103 | 2% | Y P A C D D Q T H L W N L A C W P A |

2. Synthesis of Peptides

Peptides described herein were synthesized using the generic protocol described below.

Peptides are synthesized on an automated peptide synthesizer "Symphony" (Rainin Inc.) using 1 to 12 batch reactors loaded with 0.1 mmol of commercially available Rink amide resin (~0.20 mmol/g). A double coupling cycle is used for each amino acid and a 5-fold excess of amino acids is used per coupling to synthesize the peptide on the resin. Standard Fmoc chemistry is used to elongate the peptide on the resin. The Fmoc is removed with a solution of 20% piperidine in DMF. Each amino acid dissolved in a 0.2 M solution of 1-hydroxybenzotriazole in (N-methylpyrrolidone) NMP is coupled to the peptide using a 0.2 M solution of diisopropylcarbodiimide in NMP. After each deprotection or coupling step the resin is washed alternatively three times with DMF and MeOH. The completed peptide/resin is washed with $CH_2Cl_2$ and dried under nitrogen.

After the synthesis of the peptide on the resin is complete, the peptide is cleaved from the resin using the following cleavage cocktail: TFA/TIS/$H_2O$ 95:2.5:2.5 (5 mL per 100 µmoles of peptide). The solution of fully deprotected peptide is then concentrated to a tenth of its initial volume and the peptide is precipitated with cold ether (20 mL). The peptide solid is isolated after centrifugation and then re-dissolved in a 1:1 mixture of DMSO/$H_2O$ (1 mL per 25 mg of peptide) and the pH is adjusted to 5 with a 1N NaOH solution. The cyclization is monitored by LC-MS (12 to 24 h). The cyclic peptide is purified by reverse phase preparative HPLC on a C-18 column using a gradient of 1% TFA in water to 1% TFA in acetonitrile. The fractions of pure peptide are pooled and lyophilized to give the final peptide moiety.

3. Screening of Phage-Display Identified Peptides

Peptides identified using the phage-display protocol were screened using dried collagen assays (DCA) as described in A.-D. below.

A. Preparation of Human Collagen:

Acid soluble human collagen extracted from placenta (Sigma, cat#C7774, lot#083K375) is dissolved in 15 mM HCl (3.5 mg/ml) by vortexing and gently shaking for 3-4 hours at 4° C. The acid soluble collagen is dissolved against PBS, pH 7.4 (three buffer exchanges are used). The $NaH_2PO_4$ protein concentration is determined by the BCA method (Pierce, Cat #23225) using bovine collagen (Vitrogen, cat #FXP-019) as a reference standard. Percent gelation (fibril formation) of the collagen is determined by incubating 10 µM collagen (3.3 mg/ml) at 37° C. for 6 hours. A typical percent gelation is 60%.

B. Preparation of Rat Collagen:

Rat collagen (acid soluble, type I, rat tail, Upstate USA, Inc, cat#08-115) is dialyzed against 10 mM Phosphate ($NaH_2PO_4$), pH 4.2 with three changes of the dialysis buffer. For the final assay, a 1:10 volume of 10×PBS (100 mM $NaH_2PO_4$, 1.5 M NaCl pH 7.4) is added to the collagen solution (final 1×PBS) and incubated at 37° C. for 2 hours. The gelation is typically 90%.

C. Preparation of Microliter Plate:

Collagen solutions are gelled and dried down in the wells of a 96 well microtiter plate (non-binding polystyrene, VWR, cat#29445-142) or polypropylene plate (Coaster, cat #29444-100, code 3364). 75 µl of 10 µM human collagen is aliquoted into each well and the plate is incubated at 37° C. for 6 hours to form a gel. The collagen gels are evaporated overnight to dryness at 37° C. Ungelled collagen is removed by washing the collagen films with 200 µL PBS (four times, 15 min per wash). The thin collagen fibril film remains, coating the bottom of each well. The final well content of gelled collagen is 150 µg. After washing by PBS the plate is again dried at 37° C. for 2 hours and is stored at −20° C.

D. Binding Assay:

600 µL of 5 µM peptide solution is prepared in PBS, pH 7.4. 90 µl of the 5 µM peptide solution is added to two collagen containing wells, and in addition, an empty well to control for nonspecific binding to the plate. An additional 90 µL is reserved in a HPLC glass vial as a measure of the total concentration. The plate is then incubated on a shaker table (300 rpm) for 2 hours at room temperature to allow the compound to bind. After 2 hours the supernatant from each well (with or without collagen) is transferred to an HPLC glass vial. The relative amount of free, unbound compound in the sample supernatants and the amount of compound in the reserved (total) sample are determined by HPLC (Agilent, 1100 series). The compounds are chromatographed on a Kromasil C-4 column (AKZONOBEL, cat #E 22840), and eluted use a two buffer system (buffer A, 1% TFA in distilled water, buffer B 1% TFA in Acetonitrile). Each sample (30 µl) is injected onto the column and the compound (peptide or other compound) is eluted by a 10-40% gradient of buffer B (3 min, 5 ml/min). The peak area of the compound in each sample is determined by integration using the ChemStation software. Values for the supernatant samples ([Free]) after incubation with collagen and the total sample are averaged. The percent bound, % B, is calculated from the formula: % B=([Total]−[Free])/[Total].

4. Modification of Peptides and Screening

Peptides identified in the phage display protocol were modified in order to assess the effects of amino acid type and location on binding; the results are shown below.

A. Various Amino Acid Substitutions

TABLE 7

TN-6 Peptides, all peptides are cyclic with disulfide bond between the two cysteines:

| SEQ ID NO. | % Collagen Binding Dried Human | % Collagen Binding Dried Rat | Sequences |
|---|---|---|---|
| 104 | 12 | 19 | Y H A C Y Q A G' C W I W |
| 105 | 9 | 23 | Y H A C Y Q A' G C W I W |
| 106 | 9 | 24 | Y H A C Y Q A G C W I Y |
| 107 | 9 | 6 | Y H A C Y Q A G C Y I W |

TABLE 7-continued

TN-6 Peptides, all peptides are cyclic with disulfide bond between the two cysteines:

| SEQ ID NO. | % Collagen Binding Dried Human | Dried Rat | Sequences |
|---|---|---|---|
| 108 | 5 | 12 | Y H A C Y Q A G C Y I Y |
| 109 | 21 | 37 | Y S A C Y Q A G C W I W |
| 110 | 10 | 2 | Y S A C Y Q A G C Y I Y |
| 111 | 0 | 24 | Y H A S Y Q A G S W I W |

Note that G' and A' are the N-methyl derivatives of G and A, respectively.

TABLE 8

TN-9 Peptides, all peptides are cyclic with disulfide bond between the two cysteines:

| SEQ ID NO. | Dried Human Collagen Binding | Sequences |
|---|---|---|
| 112 | 9% | A K A C S V H D E F G C L I S |
| 113 | 3% | F S E C V W V N A Y Q C E Y F |

TABLE 9

TN-10 Peptides, all peptides are cyclic with disulfide bond between the two cysteines:

| SEQ ID NO. | % Collagen Binding Dried Human | Dried Rat | Sequences |
|---|---|---|---|
| 114 | 19 | 14 | W T C S G D E Y T W H C N Y E |
| 115 | 39 | 23 | D W T C S G D P Y T W H C N Y E |
| 116 | 58 | 35 | D W T C S G D H L T W H C N Y G |
| 117 | 38 | 24 | D W T C S G D H L T W K C N Y G |
| 118 | 68 | 67 | D W T C S G N H L T W Y C N Y G |
| 119 | 55 | 55 | D W T C S G D E F T W H C N Y E |
| 120 | 38 | 28 | D W T C S G D E Y A W H C N Y e |
| 121 | 57 | 72 | P W T C S G D E Y A W H C N Y e |

TABLE 10

TN-10 Peptides with the Linker-G- at the N terminus (G-peptide); all peptides are cyclic with disulfide bond between the two cysteines:

| SEQ ID NO. | % Collagen Binding Dried Human | Dried Rat | Sequences (L = G at N-terminus) |
|---|---|---|---|
| 122 | 71 | 71 | Q W T C S G D E Y T W H C N Y E |
| 123 | 59 | 72 | Q W T C S G D E Y T W H C N Y |

TABLE 10-continued

TN-10 Peptides with the Linker-G- at the N terminus (G-peptide); all peptides are cyclic with disulfide bond between the two cysteines:

| SEQ ID NO. | % Collagen Binding Dried Human | Dried Rat | Sequences (L = G at N-terminus) |
|---|---|---|---|
| 124 | 24 | 17 | Q W T C S G D E Y a W H C N A e |
| 125 | 85 | 86 | Q W T C S G D E Y S W H C N Y e |
| 126 | 68 | 73 | Q W T C S G D E Y A W H C N Y e |
| 127 | 80 | 73 | Q W T C S G D E Y T W S C N Y E |
| 128 | 80 | 72 | Q W T C S G D A Y T W H C A Y E |
| 129 | 87 | 84 | A W T C S G D E Y T W H C N Y E |

TABLE 11

TN-11 Peptides, all peptides are cyclic with disulfide bond between the two cysteines:

| SEQ ID NO. | Dried Human Collagen Binding | Sequences |
|---|---|---|
| 130 | 32% | W W A C Q K G R H D W E K C R W L |

B. Alanine Scanning

Alanine scanning was used to also probe the effect of amino acid position and type on binding. The results are shown below.

TABLE 12

TN-6 Peptides, all peptides are cyclic with disulfide bond between the two cysteines:

| SEQ ID No. | % Collagen Binding Dried Human | Dried Rat | Sequences |
|---|---|---|---|
| 131 | 7 | 12 | A H A C Y Q A G C W I W |
| 132 | 53 | 37 | Y A A C Y Q A G C W I W |
| 133 | 4 | 5 | Y H A C A Q A G C W I W |
| 134 | 14 | 1 | H A C Y A A G C W I I W |
| 135 | 72 | 88 | Y H A C Y Q A A C W I W |
| 136 | 2 | 2 | Y H A C Y Q A G C A I W |
| 137 | 4 | 7 | Y H A C Y Q A G C W A W |
| 138 | 2 | 1 | Y H A C Y Q A G C W I A |

TABLE 13

TN-10 Peptides, all peptides are cyclic with disulfide bond between the two cysteines:

| SEQ ID NO. | % Collagen Binding Dried Human | % Collagen Binding Dried Rat | Sequences (all have a -G- Linker at the N-terminus) |
|---|---|---|---|
| 139 | 1 | 0 | Q A T C S G D E Y T W H C N Y E |
| 140 | 84 | 77 | Q W A C S G D E Y T W H C N Y E |
| 141 | 87 | 83 | Q W T C A G D E Y T W H C N Y E |
| 142 | 9 | 6 | Q W T C S A D E Y T W H C N Y E |
| 143 | 66 | 51 | Q W T C S G A E Y T W H C N Y E |
| 144 | 87 | 77 | Q W T C S G D A Y T W H C N Y E |
| 145 | 68 | 50 | Q W T C S G D E A T W H C N Y E |
| 146 | 82 | 77 | Q W T C S G D E Y A W H C N Y E |
| 147 | 5 | 1 | Q W T C S G D E Y T A H C N Y E |
| 148 | 66 | 73 | Q W T C S G D E Y T W A C N Y E |
| 149 | 82 | 82 | Q W T C S G D E Y T W H C A Y E |
| 150 | 16 | 9 | Q W T C S G D E Y T W H C N A E |
| 151 | 87 | 81 | Q W T C S G D E Y T W H C N Y A |

C. D-Amino Acid Scanning

Peptides having D-amino acids at certain positions were also prepared and assayed for collagen binding. The results are shown below. Note that a lower-case letter indicates the D-form of the amino acid.

TABLE 14

TN-6 Peptides, all peptides are cyclic with disulfide bond between the two cysteines:

| SEQ ID No. | % Collagen Binding Dried Human | % Collagen Binding Dried Rat | Sequences |
|---|---|---|---|
| 152 | | | y H A C Y Q A G C W I W |
| 153 | 0 | 0 | Y h A C Y Q A G C W I W |
| 154 | 24 | 21 | Y H a C Y Q A G C W I W |
| 155 | 15 | 11 | Y H A c Y Q A G C W I W |
| 156 | 38 | 48 | Y H A C y Q A G C W I W |
| 157 | 37 | 35 | Y H A C Y q A G C W I W |
| 158 | 56 | 66 | Y H A C Y Q a G C W I W |
| 159 | 7 | 27 | Y H A C Y Q A G c W I W |
| 160 | 20 | 12 | Y H A C Y Q A G C w I W |
| 161 | 8 | 10 | Y H A C Y Q A G C W i W |
| 162 | 18 | 14 | Y H A C Y Q A G C W I w |
| 163 | 37 | 53 | y h a c y q a G c w i w |

TABLE 15

TN-10 Peptides, all peptides are cyclic with disulfide bond between the two cysteines:

| SEQ ID NO. | % Collagen Binding Dried Human | % Collagen Binding Dried Rat | Sequences (all have a -G- Linker at the N-terminus) |
|---|---|---|---|
| 164 | 46 | 31 | q W T C S G D E Y T W H C N Y E |
| 165 | 2 | 4 | Q w T C S G D E Y T W H C N Y E |
| 166 | 2 | 3 | Q W t C S G D E Y T W H C N Y E |
| 167 | 4 | 0 | Q W T c S G D E Y T W H C N Y E |
| 168 | 3 | 2 | Q W T C s G D E Y T W H C N Y E |
| 169 | 11 | 4 | Q W T C S G d E Y T W H C N Y E |
| 170 | 49 | 35 | Q W T C S G D e Y T W H C N Y E |
| 171 | 13 | 6 | Q W T C S G D E y T W H C N Y E |
| 172 | 9 | 8 | Q W T C S G D E Y t W H C N Y E |
| 173 | 5 | 4 | Q W T C S G D E Y T w H C N Y E |
| 174 | 5 | 0 | Q W T C S G D E Y T W h C N Y E |
| 175 | 2 | 2 | Q W T C S G D E Y T W H c N Y E |
| 176 | 2 | 2 | Q W T C S G D E Y T W H C n Y E |

TABLE 15-continued

TN-10 Peptides, all peptides are cyclic
with disulfide bond between the two cysteines:

| SEQ ID NO. | % Collagen Binding Dried Human | Dried Rat | Sequences (all have a -G- Linker at the N-terminus) |
|---|---|---|---|
| 177 | 30 | 27 | Q W T C S G D E Y T W H C N y E |
| 178 | 90 | 87 | Q W T C S G D E Y T W H C N Y e |

TABLE 16

TN-10 Peptides, all peptides are cyclic with
disulfide bond between the two cysteines:

| SEQ ID NO. | % Collagen Binding Dried Human | Dried Rat | Sequences |
|---|---|---|---|
| 179 | 81% | 75% | D W T C S a D E Y T W H C N Y E |
| 180 | 81% | 72% | D W T C S s D E Y T W H C N Y E |
| 181 | 87% | 86% | D W T C S r D E Y T W H C N Y E |
| 182 | 89% | 86% | D W T C S y D E Y T W H C N Y E |
| 183 | 73% | 63% | D W T C S l D E Y T W H C N Y E |

5. Iodination of SEQ ID NO: 144

SEQ ID NO: 144 was iodinated with radioactive 1-125 at GE Healthcare at either tyrosine residue using the lactoperoxidase method of iodination. Two products were identified and purified by HPLC, presumably corresponding to iodination at each tyrosine. The iodinated material was mixed with SEQ ID NO: 144 to a concentration of 5 µM and analyzed using the dried collagen assay; the fraction that bound to collagen as determined using a radiotracer that was similar to the fraction bound for SEQ ID NO: 144 without the radiotracer was used, as set forth below.

6. Biodistribution Analysis of SEQ ID NO: 144 as Compared to GdDTPA

Conscious male Sprague-Dawley rats ranging in weight from 270 to 320 grams were administered a solution containing SEQ ID NO: 144 (0.5 µmol/kg) with radiolabeled (1-125) SEQ ID NO: 144 (Example 5) (8-10 µCi), GdDTPA (0.5 µmol/kg), and radiolabeled (Tc-99m) DTPA (8-10 µCi) via tail vein injection. At either one or five minutes post injection the animals were sacrificed and the blood and heart collected. The heart was rinsed in a saline and blotted dry before analysis. The organs were then weighed and the radioactivity measured with a Packard Cobra 5003 Gamma Scintillation counter. The Tc-99m counts were measured in the window 128-165 keV; the 1-125 counts were measured in the window 15-75 keV with a 5% correction for spillover from the technetium. An aliquot of the injection solution was also weighed and counted. Concentration estimates were decay corrected. Studies were performed at least in duplicate.

Results:

| Compound | N | Time (min) | Heart (% ID/g) | Blood (% ID/g) | Heart:Blood |
|---|---|---|---|---|---|
| SEQ ID NO: 144 | 2 | 1 | 0.68 ± 0.01 | 1.8 ± 0.2 | 0.38 |
| GdDTPA | 2 | 1 | 0.32 ± 0.02 | 1.2 ± 0.2 | 0.26 |
| SEQ ID NO: 144 | 3 | 5 | 0.50 ± 0.16 | 0.46 ± 0.07 | 1.08 |
| GdDTPA | 3 | 5 | 0.17 ± 0.08 | 0.67 ± 0.12 | 0.26 |

Conclusion:

The collagen binding peptide (SEQ ID NO: 144) shows positive uptake in the heart relative to the GdDTPA negative control. This collagen binding peptide is retained in the heart at 5 minutes compared to the GdDTPA control.

7. Langendorff Heart Model

A. General Langendorff preparation

After deep anesthesia with pentobarbital (80 mg/kg ip), the chest cavity of a male Sprague Dawley rat (300 g) was opened, retracted and the heart was removed immediately and placed in an ice-cold normal Krebs-Henseleit (K-H) solution (NaCl, 118 mM; KCl, 4.7 mM; $CaCl_2$, 2.5 mM; $MgSO_4$, 1.2 mM; $KH_2PO_4$, 1.2 mM; $NaHCO_3$, 25 mM; glucose, 5.5 mM). A K-H buffer filled 20 Gauge needle was inserted into the apex of the heart penetrating into the bottom of the chamber. This was attached to a pressure transducer used to record and monitor heart function. Perfusion pressure (~60 mmHg) was monitored using a second transducer. The heart was perfused at a constant flow rate of 10-12 mL/min with 37° C. Krebs-Henseleit buffer saturated with a mixture of 95% $O_2$ and 5% $CO_2$ gas. The heart was paced at 300 beats/min.

B. Equilibrium Binding to Perfused Langendorff Rat Heart

Two peptide test articles, a high collagen binding peptide (SEQ ID NO: 144) and a low collagen binding peptide (SEQ ID NO: 173), are compared to GdDTPA. The appropriate test article was added to the K-H buffer solution to a total concentration of either 3 or 30 µM. Also added to the K-H buffer was a radiotracer analog of each peptide or GdDTPA. For the peptides, the radiotracer was an aliquot of the appropriate 1-125 labeled peptide derivative (see Example 5 for protocol). For GdDTPA, the tracer added was Tc-99m labeled DTPA. The amount of radioactivity added to the buffer solution was 1-5 µCi.

The heart was perfused for a period of 10 minutes and the perfusion solution was recycled through the heart. The total volume of K-H buffer used was 50-60 mL. After 10 min, the heart was removed from the apparatus and any connective tissue was removed. The heart was opened, fluid in the chambers drained, and the interior blotted dry with filter paper. The heart was then weighed and the radioactivity in the heart measured with a Packard Cobra 5003 Gamma Scintillation counter. An aliquot of the K-H buffer was also weighed and counted. Studies were performed at least in duplicate.

Results:

| Compound | N | Heart (nmol/g) | Buffer (μM) | Heart:Buffer |
|---|---|---|---|---|
| SEQ ID NO: 144 | 5 | 9.8 ± 2.3 | 3.0 | 3.3 ± 0.8 |
| SEQ ID NO: 173 | 3 | 1.1 ± 0.2 | 3.0 | 0.37 ± 0.08 |
| GdDTPA | 6 | 1.3 ± 0.3 | 3.0 | 0.42 ± 0.06 |
| SEQ ID NO: 144 | 3 | 120 ± 50 | 30 | 4.0 ± 1.7 |
| GdDTPA | 2 | 14 ± 1.0 | 30 | 0.46 ± 0.03 |

Conclusion:

GdDTPA is a marker of extracellular space. It is used as a negative control. The amount of GdDTPA in the heart is representative of the buffer present in the heart. SEQ ID NO: 173, a peptide with weak collagen binding, exhibits similar heart concentrations as GdDTPA, indicating no specific uptake. SEQ ID NO: 144, a peptide with good collagen binding, exhibits about 10 times more heart uptake than GdDTPA. This indicates specific heart uptake for the collagen binding peptide.

C. Washout Kinetics of the Collagen Binding Peptide (SEQ ID NO: 144) from Perfused Langendorff Rat Heart A Langendorff rat heart preparation was perfused with K-H buffer at a rate of 10-12 mL/min. A one mL solution containing SEQ ID NO: 144 (300 μM), radiolabeled (I-125) SEQ ID NO: 144 (1-6 μCi), GdDTPA (300 μM), and radiolabeled (Tc-99m) DTPA (5-8 μCi) was infused into the heart at a rate of 1 mL/min. After the infusion was finished, the heart was either removed or perfusion was allowed to continue for an additional 10 minutes and then the heart was removed. The perfusion buffer was not recirculated through the heart. After removal of any connective tissue, the heart was opened, fluid in the chambers drained, and the interior blotted dry with filter paper. The heart was then weighed and the radioactivity in the heart measured with a Packard Cobra 5003 Gamma Scintillation counter. The Tc-99m counts were measured in the window 128-165 keV; the 1-125 counts were measured in the window 15-75 keV with a 5% correction for spillover from the technetium. An aliquot of the K-H buffer was also weighed and counted. Concentration estimates were decay corrected. Studies were performed at least in duplicate.

Results:

| Compound | N | Time after infusion (min) | Heart (% ID/g) |
|---|---|---|---|
| SEQ ID NO: 144 | 3 | 0 | 4.6 ± 1.1 |
| GdDTPA | 3 | 0 | 2.9 ± 1.5 |
| SEQ ID NO: 144 | 2 | 10 | 3.1 ± 1.6 |
| GdDTPA | 2 | 10 | 0.014 ± 0.002 |

Conclusion:

The collagen binding peptide (SEQ ID NO: 144) is significantly retained in the heart after perfusion with buffer for 10 minutes. At 10 minutes after infusion of the compounds, 68% of the peptide that was present at 0 minutes post infusion remains, compared to only 0.5% for GdDTPA. This indicates that the collagen binding peptide (SEQ ID NO: 144) binds to and is retained by the heart.

8. Diagnostic Composition Synthesis

A. General Scheme for the Preparation of N-Terminus Chelate-Functionalized Glu-DTPA-Gd Peptides:

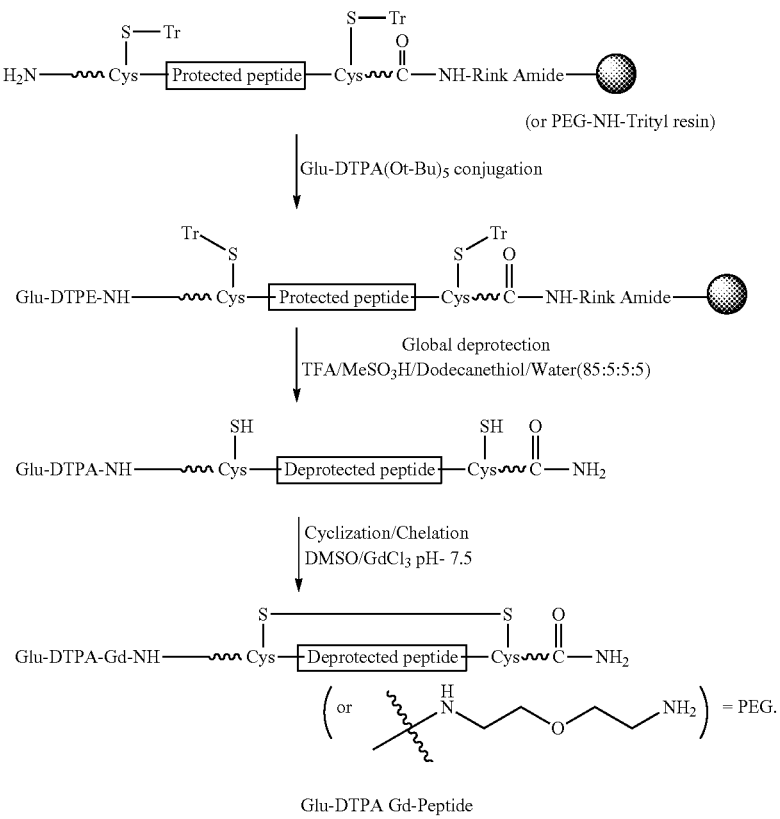

Glu-DTPA Gd-Peptide

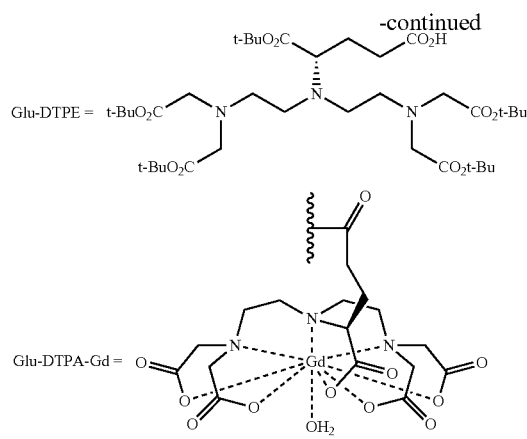

B. General Procedure for the Preparation of N-Terminus Chelate-Functionalized Glu-DTPA-Gd Peptides:

Peptide of interest was dissolved in DMF (5-7 mL/100 mg of resin). In a separate vial, 1.5-2 eq of Glu-DTPE, HOBt and PyBop were added to DMF (10% volume of peptide mixture). DIEA was added until pH≈8 (measured with wet pH paper). After 5 to 10 minutes of pre-activation, the DTPA mixture was added to peptide and the pH was adjusted to ~8 with DIEA. The mixture was agitated at RT for 4-18 hours.

The reaction was monitored by performing a mini-cleavage and global deprotection on a small aliquot of resin. The resin was first washed with DMF (2 times) and ether (3 times). The peptide and the DTPA penta-ester was fully deprotected using a deprotection cocktail (TFA/MeSO$_3$H/Dodecanethiol/Water 85:5:5:5) for 30-120 minutes. The deprotection was monitored by LCMS.

The bulk of the reaction was deprotected after the monitoring showed less than 5% of starting peptide remained using the same deprotection cocktail (5-7 ml/100 mg resin). The linear deprotected peptide ligand was precipitated and triturated in ether to give a white solid.

Crude linear peptide-ligand was dissolved in DMSO (4-7 mL/100 mg solid). Water was added until the solution started to become cloudy and then a little more DMSO was added to clear the solution. The pH was adjusted to ~7.5 with 1.0 N NaOH. The gadolinium chelate was prepared by adding 1.2 eq GdCl$_3$ (based on initial loading of resin). The pH was adjusted to ~7.5-8-with 1N NaOH. Completion of reaction was determined by LC/MS (ammonium formate/Acetonitrile). Excess GdCl$_3$ was scavenged with 2 eq of EDTA to scavenge.

Cyclic peptide-chelate was purified by preparative-HPLC using Kromasil C4 or C18 columns and either bufferless conditions or 50 mM Ammonium. Formate/90:10 ACN: 50 mM Ammonium. Formate. The product was characterized by LC-MS.

The following peptides were derivatized on their N-terminus and/or C-terminus using the general procedure:

1. Glu-DTPA-Gd-W.W.T.C.H.M.T.W.S.G.Q.W.D-.S.C.K.W.H-CONH$_2$ (Compound ID 1020; SEQ ID NO: 184) was prepared following the general procedure above to give 0.3 mg of product with the correct molecular mass. The C-terminus is capped with an —NH$_2$.

2. Glu-DTPA-Gd-G.Q.W.T.C.S.G.D.E.Y.T.W.H.C.NY.E-PEG-H (Compound ID 1021; SEQ ID NO: 185), having an N-terminal G linker and PEG-H at the C-terminus, was prepared following the general procedure to give 19.5 mg of product with the correct molecular mass.

3. Glu-DTPA-Gd-G.Q.W.H.C.T.T.R.F.P.H.H.Y.C.L.Y.G-PEG-H (Compound ID 1022; SEQ ID NO: 186), having an N-terminal G linker and PEG-H at the C-terminus, was prepared following the general procedure (see additional details, below) to give 78 mg of product with the correct molecular mass.

4. Glu-DTPA-Gd-G.G.D.W.T.C.V.G.D.H.K.T.W.K.C-.N.F.H-CONH$_2$ (Compound ID 1023; SEQ ID NO: 187), having an N-terminal G-G linker and a C-terminus capped with —NH$_2$, was prepared following the general procedure to give 143 mg of product with the correct molecular mass.

C. General Scheme for the Preparation of N- and C-Termini Chelate-Functionalized Glu-DTPA-Gd Peptides:

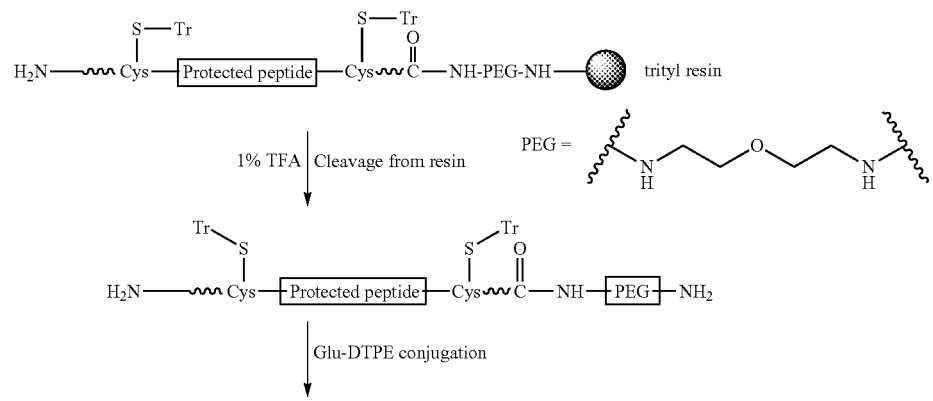

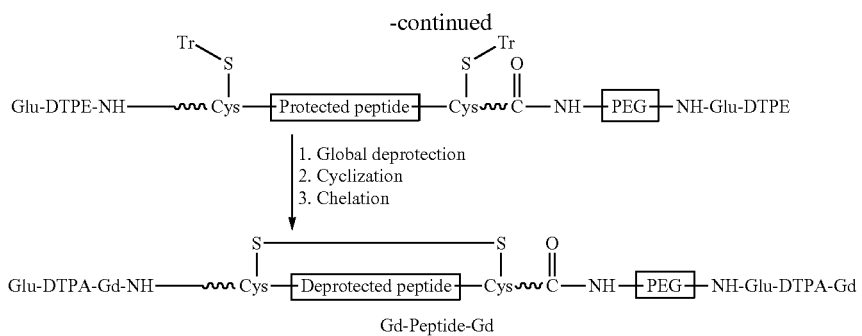
Gd-Peptide-Gd
D. Synthesis of MR Phantom Study Contrast Agent, SEQ ID NO: 186
SEQ ID NO: 186, an MR contrast agent having the structure Gd-Glu-DTPA-GQWHCTTRFPHHYCLYG-PEG-H, where G is the N-terminal linker and PEG-H is the C-terminal capping moiety, was prepared as described below to give 78 mg of product with the correct molecular mass.

General Scheme:
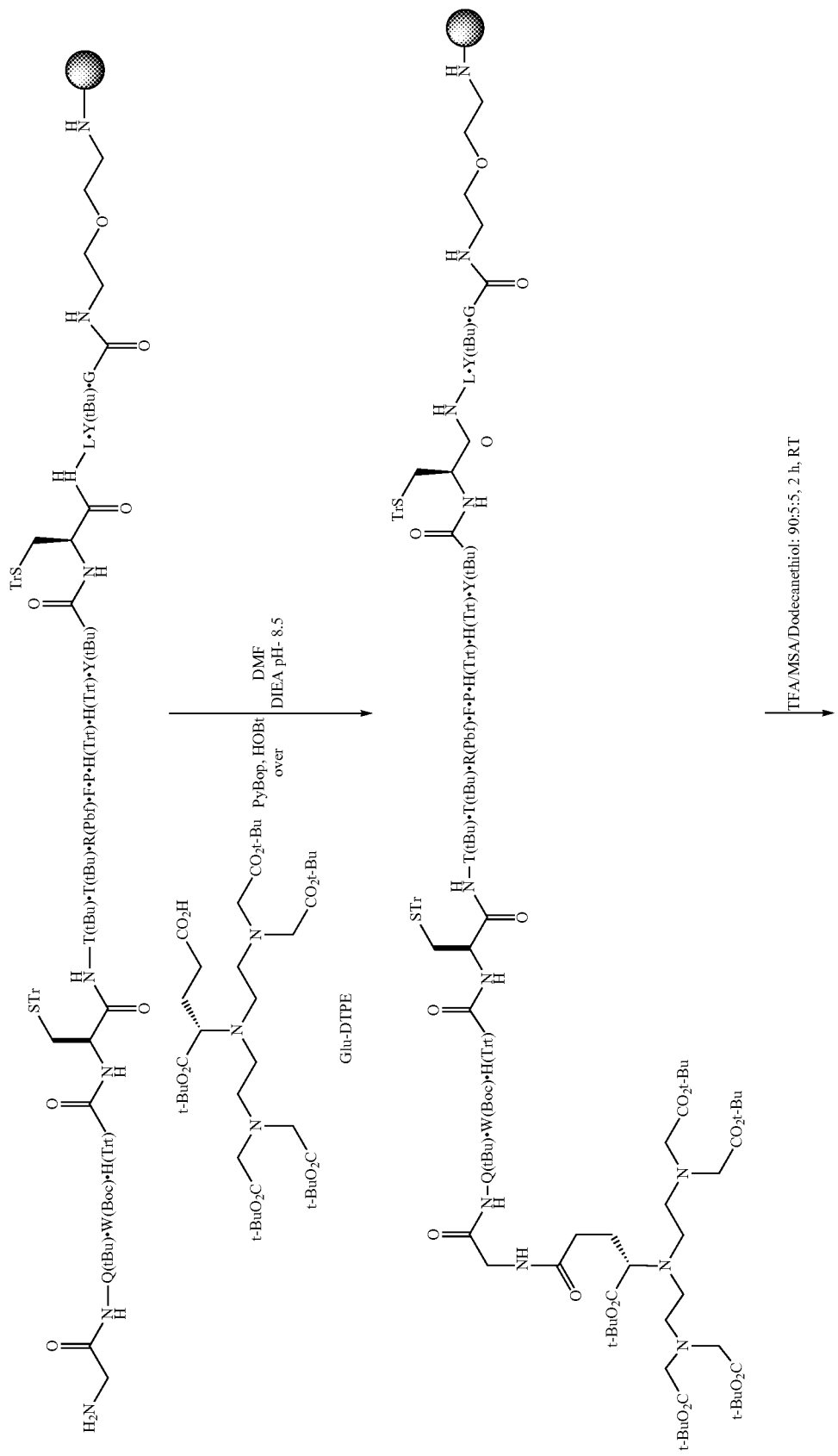

-continued
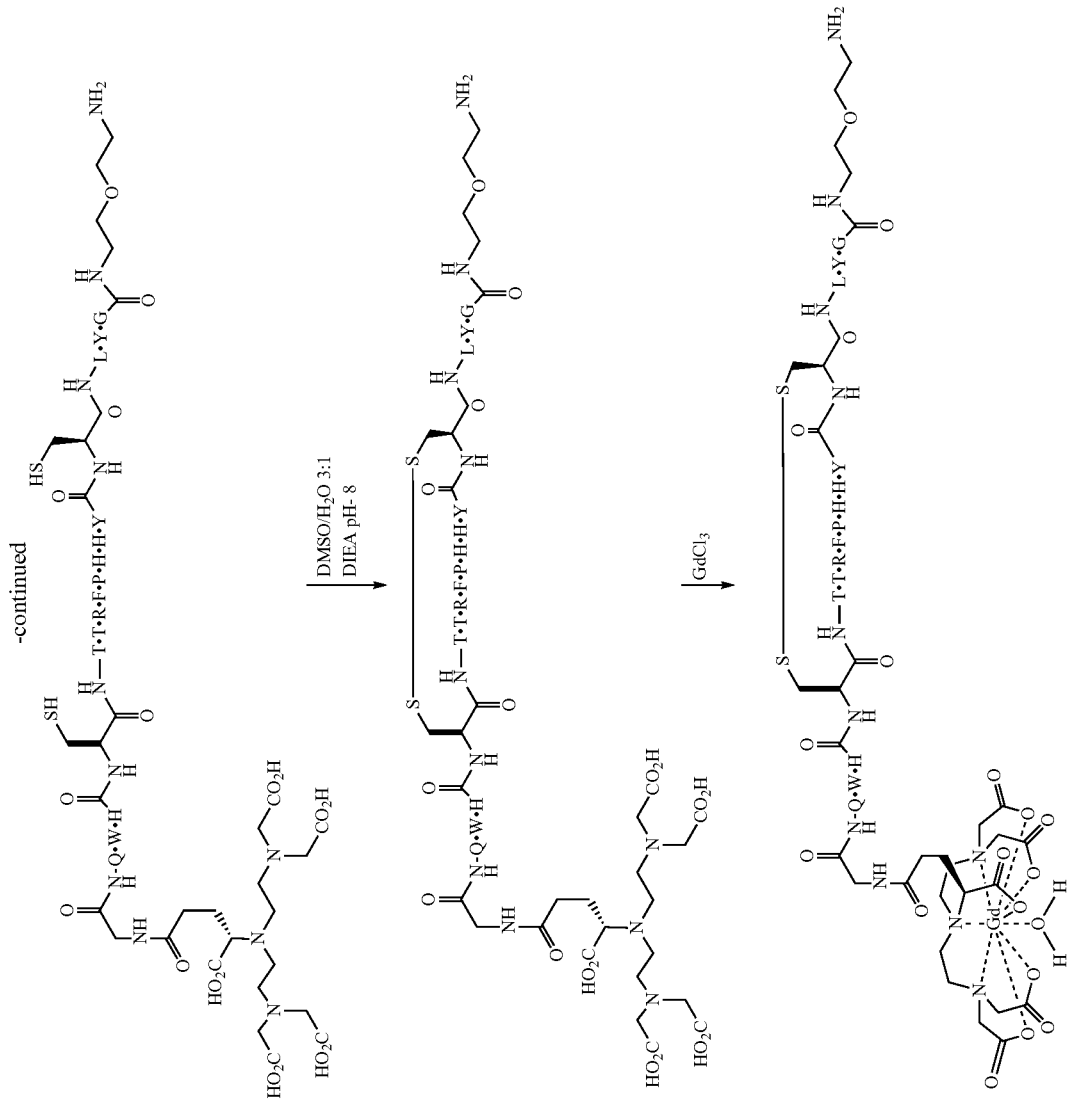

Protected peptide on resin (4.2 g, 0.6 mmol) was suspended in 40 mL of DMF. The pH was adjusted to ≈8.5 with DIEA (wet pH paper test). Glu-DTPE acid (488 mg, 0.65 mmol., 1.1 eq.) dissolved in DMF (2 mL) was added followed by PyBOP (0.33 g, 0.63 mmol., 1.05 eq.) and HOBt mono hydrate (0.10 g, 0.74 mmol., 1.23 eq.). The reaction mixture was shaken on an orbital shaker overnight. The resin was filtered off and was successively washed with DMF (2 times) and ether (3 times). The peptide was cleaved from the resin and globally deprotected with 50 mL of deprotection cocktail (TFA/Methanesulfonic acid/dodecanethiol 90:5:5), at room temperature for 2 h. The resin was filtered off and the peptide was precipitated from the filtrate with ether to give an oily solid. The crude linear peptide was dissolved in a 3:1 mixture of DMSO and $H_2O$ (4-7 mL per 100 mg of linear peptide) and the pH was adjusted to 8 with DIEA. The cyclization was monitored by LC-MS.

The pH of the crude ligand solution was adjusted to 7.0 with 6N HCl and the ligand was titrated (Xylenol orange method). Gadolinium chloride (0.18 mmol., 1 eq.) was added and the pH was adjusted to 6.5 with 1N NaOH. The chelation was monitored by LC-MS. The cyclic peptide chelate was purified by reverse phase preparative HPLC using a gradient of 10 to 50% B (A:$H_2O$, B: Acetonitrile).

General Procedure:

Coupling Step:

The peptide on resin was suspended in DMF (5-7 mL/100 mg resin). In a separate vial, 1.5-2 eq of Glu-DTPE acid was activated by addition of HOBt, and PyBOP in DMF (10% of the volume of peptide mixture) for 5-10 min at pH≈8 obtained by addition of DIEA (measured with wet pH paper). Activated DTPE acid mixture was added to the solution of peptide and the pH was adjusted to ~8 with DIEA. The mixture was shaken at RT for 4-18 hours.

The reaction was monitored by taking an aliquot of resin in suspension in DMF from the reaction mixture. The resin was washed with DMF (2 times) and with ether (3 times). The peptide was cleaved from the resin and globally deprotected with the deprotection cocktail (TFA, MSA, DDT, Water 85:5:5:5) for 30-120 minutes. The reaction was stopped when less than 5% of the starting peptide was detected by LC-MS. Then the bulk of the reaction mixture was deprotected using the same conditions (5-7 ml of deprotection cocktail/100 mg resin). Crude peptide conjugate was precipitated with ether and triturated several times with ether to give the desired ligand as a white solid.

Cyclization/Chelation Step:

Linear peptide DTPA conjugate was dissolved in DMSO (4-7 mL/100 mg solid). Water was added until the solution became cloudy, and some DMSO was added to clear the solution. The pH was adjusted with 1.0 N NaOH to ~7.5. Gadolinium chloride was added (1.2 eq., based on initial loading of resin). The pH was maintained to ~7.5-8 with 1N NaOH during the reaction. Completion of reaction was determined by LC/MS (aqueous ammonium formate/acetonitrile gradient). Excess $GdCl_3$ was scavenged with EDTA (2 eq.) and then the peptide chelate DTPA conjugate was purified by reverse phase preparative HPLC using C-4 or C-18 Kromasil columns with a buffer (50 mM ammonium formate/90:10 acetonitrile/50 mM ammonium formate) or without a buffer. The pure fractions were pooled together based on the LC-MS analysis (neutral buffer method).

E. Preparation of Additional Contrast Agents

Other contrast agents prepared using the methods described above include:

1. Glu-DTPA-Gd-P-P-Q-W-H-C-T-T-R-F-P-H-H-Y-C-L-Y-G (Compound ID 1024; SEQ ID NO: 188), which includes a P-P linker on the N-terminus of the peptide; the C-terminus is capped with —$NH_2$.

2. Glu-DTPA-Gd-G-G-T-W-R-C-D-Q-F-K-G-K-W-V-C-R-G-G (Compound ID 1025; SEQ ID NO: 189), which includes a -G-G- linker on the N-terminus of the peptide; the C-terminus is capped with —$NH_2$.

3. Glu-DTPA-Gd-PEG(2O)-G-Q-W-T-C-S-G-D-E-Y-T-W-H-C-N-Y-e (Compound ID 1026; SEQ ID NO: 190), where e is the D-form of E, and which includes the Linker -PEG(2O)-G- on the N-terminus and the C-terminus capping moiety of —$NH_2$.

Other contrast agents that could also be made using the above protocol include:

4. Glu-DTPA-Gd-P-P-Q-W-T-C-S-G-D-E-Y-T-W-H-C-N-Y-E-P-P-Glu-DTPA-Gd (Compound ID 1027; SEQ ID NO: 191), which includes a P-P linker at both the N and C termini.

5. Glu-DTPA-Gd-G-Q-W-H-C-T-T-R-F-P-H-H-Y-C-L-Y-G (Compound ID 1028; SEQ ID NO: 192), which includes a G linker on the N-terminus of the peptide and a C-terminal capping moiety of —$NH_2$.

6. Glu-DTPA-Gd-G-Q-W-T-C-S-G-D-E-Y-T-W-H-C-N-Y-E (Compound ID 1029; SEQ ID NO: 193), which includes a G linker on the N-terminus of the peptide, and a C-terminal capping moiety of —$NH_2$.

7. Glu-DTPA-Gd-G-D-W-T-C-V-G-D-H-K-T-W-K-C-N-F-H (Compound ID 1030; SEQ ID NO: 194), which includes a G linker on the N-terminus of the peptide, and a C-terminal capping moiety of —$NH_2$.

The percent binding to human and rat collagen type I for various chelate-derivatized peptides are set forth below.

TABLE 17

| SEQ ID NO: | % Binding Collagen I | | Chelate Conjugates C-terminal | | | |
|---|---|---|---|---|---|---|
| | Human | Rat | Chelate | Linker | Peptide Sequence | Moiety |
| 188 | 70 | 55 | Glu-DTPA-Gd | PP | QWHCTTRFPHHYCLYG | $NH_2$ |
| 186 | 36 | 38 | Glu-DTPA-Gd | G | QWHCTTRFPHHYCLYG | PEG-H |
| 187 | 14 | 12 | Glu-DTPA-Gd | GG | DWTCVGDHKTWKCNFH | NH2 |

TABLE 17-continued

| SEQ ID NO: | % Binding Collagen I Human | % Binding Collagen I Rat | Chelate | Linker | Peptide Sequence | Chelate Conjugates C-terminal Moiety |
|---|---|---|---|---|---|---|
| 185 | 48 | 13 | Glu-DTPA-Gd | G | QWTCSGDEYTWHCNYE | PEG-H |
| 190 | 28 | 5 | Glu-DTPA-Gd | PEG(20)G | QWTCSGDEYTWHCNYe | $NH_2$ |
| 184 | 60 | 34 | Glu-DTPA-Gd | — | WWTCHMTWSGQWDSCKWH | $NH_2$ |
| 195 | 16 | 9 | Glu-DTPA-Gd | — | WWGCRQGTGEHWSHCMWF | PEG-Glu-DTPA-Gd |
| 196 | 60 | 34 | Glu-DTPA-Gd | — | WWTCHMTWSGQWDSCKWH | $NH_2$ |

9. MR Phantom Study Collagen Imaging with SEQ ID NO. 186, "Compound ID 1022"

A series of samples were prepared to demonstrate that a collagen binding peptide conjugated to a GdGluDTPA moiety could enhance the signal of collagen in an MR image. Compound ID 1022 was compared with GdDTPA alone to show that the peptide part of Compound ID 1022 was necessary for the contrast enhancement.

Collagen Stock Preparation:
Human Collagen Stock:
Acid soluble human collagen type I extracted from placenta (Sigma, cat#C7774, lot#083K375) was dissolved in 15 mM HCl (3.5 mg/mL) by vortexing and gently shaking for 3-4 hours at 4° C. The acid soluble collagen was dialyzed against PBS (pH 7.4). Protein concentration was determined by the BCA method (Pierce, Cat#23225) using bovine collagen (Vitrogen, cat#FXP-019) as a reference standard. The final collagen concentration for the stock solution was 9 µM.

Rat Collagen Stock:
Rat collagen (acid soluble, type I, rat tail, Upstate USA, Inc. Cat#08-115) was dialyzed against 10 mM Phosphate buffer ($NaH_2PO_4$, pH 4.2). The final collagen concentration for the stock solution was approx. 12 µM.

Samples:
1. 10 µM Compound ID 1022 in PBS, pH 7.4
2. 10 µM Compound ID 1022 in a solution of 5.0 µM rat type I collagen in 10 mM phosphate buffer, pH 5 incubated at 37° C. overnight to form a gel
3. 10 µM Compound ID 1022 in a solution of 7.5 µM human type I collagen in PBS, pH 7.4 incubated at 37° C. overnight to form a gel
4. Sample prepared as sample 2, but centrifuged to separate insoluble rat collagen gel
5. Sample prepared as sample 3, but centrifuged to separate insoluble human collagen gel
6. 27 µM GdDTPA solution in PBS, pH 7.4
7. 27 µM GdDTPA in a solution of 5.0 µM rat type I collagen in 10 mM phosphate buffer, pH 5 incubated at 37° C. overnight to form a gel
8. Sample prepared as in sample 7, but centrifuged to separate insoluble rat collagen gel
9. Homogeneous gel of 5 µM rat collagen
10. Homogeneous gel of 7.5 µM human collagen T1 was determined for samples 1, 2, 3, 6, 7, 9, 10 at 0.47 Tesla using a Bruker NMS120 minispec NMR analyzer operating at 37° C. The data are listed below:

| Sample number | T1 (s) |
|---|---|
| 1 - Compound ID 1022 in PBS | 2.375 |
| 2 - Compound ID 1022 in rat collagen gel | 2.370 |
| 3 - Compound ID 1022 in human collagen gel | 2.100 |
| 6 - GdDTPA in PBS | 2.437 |
| 7 - GdDTPA in rat collagen gel | 2.410 |
| 9 - rat collagen blank | 3.370 |
| 10 - human collagen blank | 3.120 |

The Table shows that the presence of Gd(III) reduces the relaxation times of the samples as compared to the collagen blanks. It also indicates that GdDTPA and Compound ID 1022 samples are matched in terms of their T1 values.

Imaging Experiments
Samples for imaging were placed in glass tubes that were in turn placed in tubes containing water. Images were acquired at 4.7 T on a Bruker Biospec Imager using a Multi-Slice Multi-Echo Method with variable Relaxation Delay (MS-MEVTR) experiment. The spin echo time and the relaxation delay were set to TE=11.2 ms and TR=500 ms, respectively with a flip angle of 30°. Images were acquired of sample 2, sample 4, sample 7, and sample 8. As compared to the uncentrifuged sample (sample 2), the pellet for sample 4 was much brighter than the supernatant, indicating that Compound ID 1022 is associated with the collagen gel. Sample 7 and 8 show uniform signal intensity. After the collagen gel is separated (sample 8), there is no increased concentration of GdDTPA in the gel relative to the supernatant. This demonstrates the specificity of Compound ID 1022 for collagen.

10. Myocardial Imaging with Compound ID 800

A 28 g C57BL/6 mouse was anesthetized using a 2% mixture of isoflurane in oxygen and anesthesia was maintained with a 1% mixture. The mouse forelimbs were shaved and fitted with pediatric ECG leads (Blue Sensor, BRS-50-

K/US, Ambu, Inc., Linthicum, Md.). The core body temperature and ECG were monitored with an SAII Model 1025 monitoring and gating system (Small Animal Instruments, Inc., Stony Brook, N.Y.). Temperature was maintained at 37° C. using tubing that contained circulating, thermostated water. An i.v. line was implanted in the tail vein and the mouse was placed in the magnet.

Images were acquired on a Varian 4.7-T Inova scanner. A cardiac-gated gradient echo inversion recovery sequence was used whereby the inversion time was set to null the signal from the myocardium. The inversion pulse was a non-selective sinc pulse with a TI of 430 ms and TR of 3 seconds. The excitation is slice selective at 90 degrees and 3 to 4 lines were acquired per TR. Scan time was 4-5 minutes.

Baseline images were acquired. Typically 3-4 short-axis slices were acquired. After satisfactory baseline images were obtained, compound ID 800 was administered by i.v. as a bolus at a dose of 25 µmol/kg and imaging commenced immediately post injection. Imaging was repeated out to an hour post injection.

Figure 2:
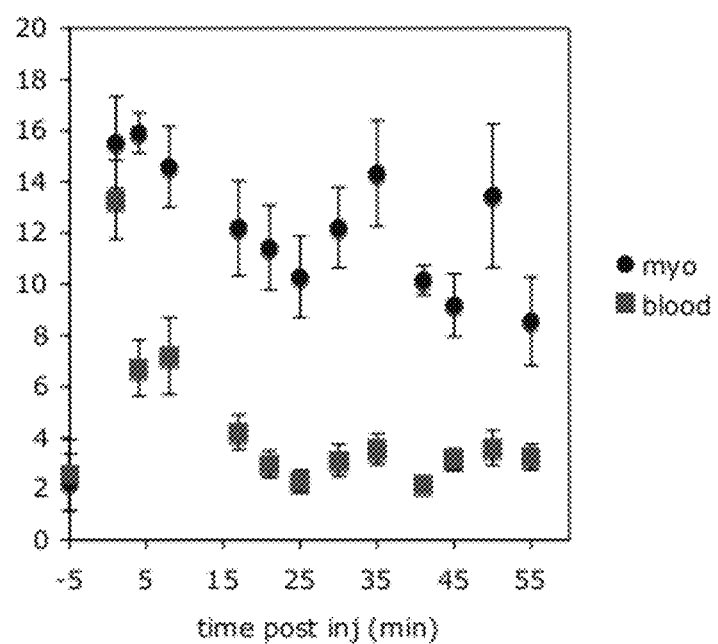
FIG. 2 is a graph demonstrating the signal to noise ratios (SNR) versus time for myocardium and blood generated from the images in FIG. 1.

A series of short-axis images are shown in FIG. 1. Immediately post injection the myocardium and the blood pool increased in signal intensity followed by signal washout from the blood and slower washout from the myocardium. To better quantify the images, region of interest (ROI) signal intensity (SI) measurements were made in the myocardium, in the left ventricle, and compared to the standard deviation (SD) of the noise. Four ROIs were measured in the myocardium and in the left ventricle and the average measurements was taken. Signal to noise ratios (SNR) were calculated as signal intensity in myocardium or blood divided by the standard deviation of the noise. FIG. 2 shows SNR curves versus time for the myocardium and blood pool before and after injection of compound ID 800. Contrast to noise ratios (CNR) for myocardium relative to blood pool was also calculated as:

$$CNR=(SI_{myocardium}-SI_{blood})/(SD_{noise}).$$

Figure 3:
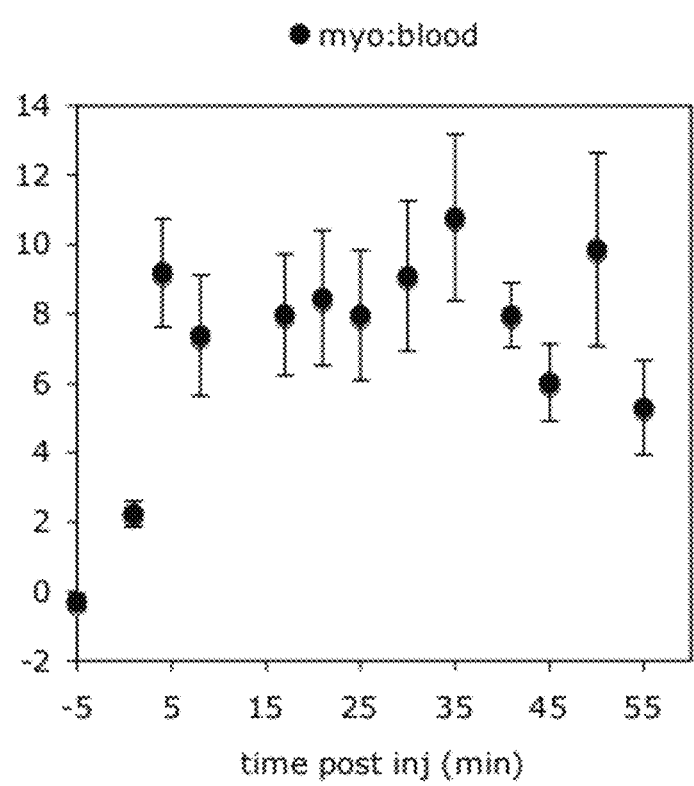
FIG. 3 is a graph displaying the contrast to noise ratios (CNR) for myocardium versus blood generated from the images in FIG. 1.

FIG. 3 shows CNR values versus time before and after injection of compound ID 800. These data show that compound ID 800 provides positive enhancement of the myocardium that persists for at least 1 hour.

11. Myocardial Infarction Imaging Using Compound ID 800

A myocardial infarct (MI) was induced in a 28 g C57BL/6 mouse by a 1-hr occlusion of the left anterior descending coronary artery, followed by reperfusion. The mouse was allowed to recover. Seven days post MI, the mouse was anesthetized using a 2% mixture of isoflurane in oxygen and anesthesia was maintained with a 1% mixture. The mouse forelimbs were shaved and fitted with pediatric ECG leads (Blue Sensor, BRS-50-K/US, Ambu, Inc., Linthicum, Md.). The core body temperature and ECG were monitored with an SAII Model 1025 monitoring and gating system (Small Animal Instruments, Inc., Stony Brook, N.Y.). Temperature was maintained at 37° C. using tubing that contained circulating, thermostated water. An i.v. line was implanted in the tail vein and the mouse was placed in the magnet.

Images were acquired on a Varian 4.7-T Inova scanner. A cardiac-gated gradient echo inversion recovery sequence was used whereby the inversion time was set to null the signal from the myocardium. The inversion pulse was a non-selective sinc pulse with a TI of 430 ms and TR of 3 seconds. The excitation is slice selective at 90 degrees and 3 to 4 lines were acquired per TR. Scan time was 4-5 minutes.

Baseline images were acquired. Typically 3-4 short-axis slices were acquired. After satisfactory baseline images were obtained, compound ID 800 was administered by i.v. as a bolus at a dose of 25 µmol/kg and imaging commenced immediately post injection. Imaging was repeated out to an hour post injection.

Figure 4:
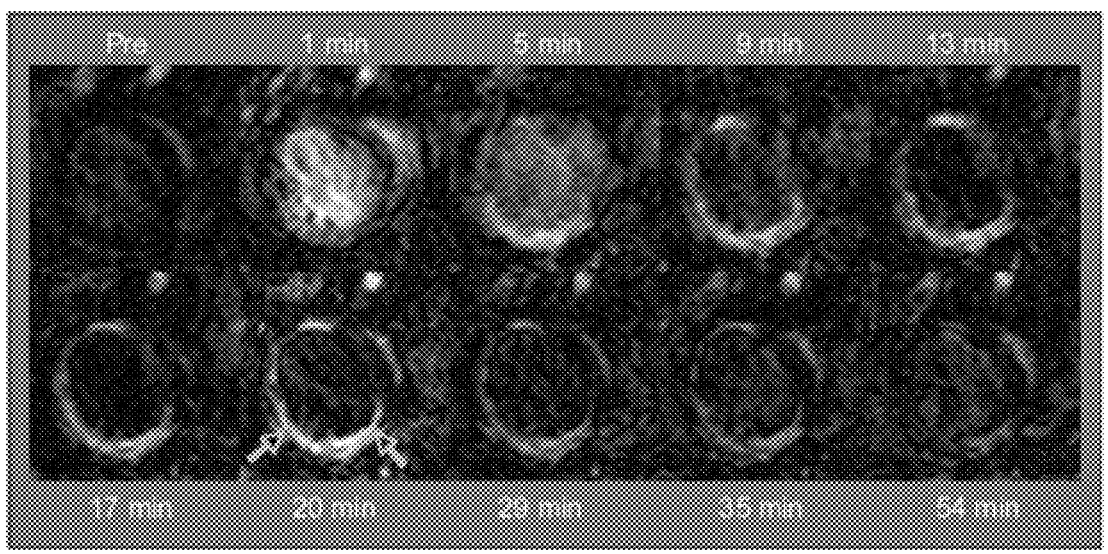
FIG. 4 is in vivo short-axis images from a mouse heart with a 7-day old infarction pre- and post-injection of compound ID 800.

A series of short-axis images are shown in FIG. 4. Immediately post injection the myocardium and the blood pool increased in signal intensity followed by signal washout from the blood and slower washout from the myocardium. In this case, the myocardium did not enhance uniformly. Infarcted regions of the heart were hyperenhanced as may be expected because of the increased collagen content in infarcted regions.

These data show that compound ID 800 provides positive enhancement of the myocardium and hyperenhancement of infarcted zones and that the enhancement persists for at least 1 hour.

12. Example of Heart Uptake Using Compound ID 800

Male BALB/c mice were anesthetized with pentobarbital (80 mg/kg ip). Following deep anesthesia, a longitudinal incision was made above the base of the abdomen up to just below the sternum. Internal organs were carefully moved out of the body cavity to the left, exposing the mesentery vein. Compound ID 800, at a dose of 10 mmol/kg, was injected directly into the vessel. The animals were sacrificed at 1, 5, 15, or 30 minutes post-injection. The heart and lungs were immediately removed and rinsed in saline, separated from each other and rinsed with saline again. Both were removed and carefully dried before being prepared for analysis. Organs were digested with nitric acid and gadolinium content determined by ICP-MS. Gadolinium concentration in the heart was 23.9±7.8, 33.9±4.5, 37±4.3, and 34.4±2.9 at 1, 5, 15, and 30 minutes post injection, respectively.

This data shows that compound ID 800 delivers gadolinium to the heart and that gadolinium is retained in the heart at least out to 30 minutes.

13. Further Synthesis of Peptides

Additional peptides were synthesized following the general protocol described in Example 2. Peptide sequences are shown in Tables 18-41. Note that lower-case letter indicates the D-form of the amino acid.

TABLE 18 all peptides are cyclic with disulfide bond between the two cysteines:

| SEQ ID NO. | Sequence |
|---|---|
| 197 | G A W H C T T R F P H H Y C L Y G |
| 198 | G Q A H C T T R F P H H Y C L Y G |
| 199 | G Q W A C T T R F P H H Y C L Y G |
| 200 | G Q W H C A T R F P H H Y C L Y G |
| 201 | G Q W H C T A R F P H H Y C L Y G |
| 202 | G Q W H C T T A F P H H Y C L Y G |
| 203 | G Q W H C T T R A P H H Y C L Y G |
| 204 | G Q W H C T T R F A H H Y C L Y G |

TABLE 18-continued all peptides are cyclic with disulfide bond between the two cysteines:

| SEQ ID NO. | Sequence |
|---|---|
| 205 | G Q W H C T T R F P A H Y C L Y G |
| 206 | G Q W H C T T R F P H A Y C L Y G |
| 207 | G Q W H C T T R F P H H A C L Y G |
| 208 | G Q W H C T T R F P H H Y C A Y G |
| 209 | G Q W H C T T R F P H H Y C L A G |

TABLE 19

| SEQ ID NO. | Sequence |
|---|---|
| 210 | G q W H C T T R F P H H Y C L Y G |
| 211 | G Q w H C T T R F P H H Y C L Y G |
| 212 | G Q W h C T T R F P H H Y C L Y G |
| 213 | G Q W H C t T R F P H H Y C L Y G |
| 214 | G Q W H C t T R F P H H Y C L Y G |
| 215 | G Q W H C T t R F P H H Y C L Y G |
| 216 | G Q W H C T T r F P H H Y C L Y G |
| 217 | G Q W H C T T R f P H H Y C L Y G |
| 218 | G Q W H C T T R F p H H Y C L Y G |
| 219 | G Q W H C T T R F P h H Y C L Y G |
| 220 | G Q W H C T T R F P H h Y C L Y G |
| 221 | G Q W H C T T R F P H H y C L Y G |
| 222 | G Q W H C T T R F P H H Y c L Y G |
| 223 | G Q W H C T T R F P H H Y C I Y G |
| 224 | G q w h c t t r f p h h y c I Y G |
| 225 | G Q W H C T T R F P H H Y C L y G |

TABLE 20

| SEQ ID NO. | Sequence |
|---|---|
| 226 | G Q 1-Nal H C T T R F P H H Y C L Y G |
| 227 | G Q 2-Nal H C T T R F P H H Y C L Y G |
| 228 | G Q thien-W H C T T R F P H H Y C L Y G |
| 229 | G Q Y H C T T R F P H H Y C L Y G |
| 230 | G Tic H C T T R F P H H Y C L Y G |
| 231 | G Q W(5-OH) H C T T S F P H H Y C L Y G |

TABLE 21

| SEQ ID NO. | Sequence |
|---|---|
| 232 | G Q W S C T T R F P H H Y C L Y G |
| 233 | G Q W Aib C T T R F P H H Y C L Y G |

TABLE 21-continued

| SEQ ID NO. | Sequence |
|---|---|
| 234 | cbz-G Q W K C T T R F P H H Y C L Y G |
| 235 | G Q W S C T T R F P H H Y C L Y G |
| 236 | G Q W N C T T L F P H H Y C L Y G |
| 237 | G Q W D C T T L F P H H Y C L Y G |
| 238 | G K(G) W Y C T T Y F P H H Y C L Y G |

TABLE 22

| SEQ ID NO. | Sequence |
|---|---|
| 239 | G Q W H C Aib T R F P H H Y C L Y G |
| 240 | cbz-G Q W H C K T R F P H H Y C L Y G |
| 241 | G Q W H C Aib T R F P H H Y C L Y G |
| 242 | G Q W H C V T L F P H H Y C L Y G |
| 243 | G Q W H C I T L F P H H Y C L Y G |
| 244 | G Q W H C S T L F P H H Y C L Y G |
| 245 | G Q W H C Y T L F P H H Y C L Y G |
| 246 | G Q W H C G T L F P H H Y C L Y G |
| 247 | G K(G) W H C Y(3-I) T Y F P H H Y C L Y G |

TABLE 23

| SEQ ID NO. | Sequence |
|---|---|
| 248 | G Q W H C T n R F P H H Y C L Y G |
| 249 | G Q W H C T s R F P H H Y C L Y G |
| 250 | G Q W H C T y R F P H H Y C L Y G |
| 251 | G Q W H C T r R F P H H Y C L Y G |
| 252 | G Q W H C T V L F P H H Y C L Y G |
| 253 | G Q W H C T I L F P H H Y C L Y G |
| 254 | G Q W H C T N L F P H H Y C L Y G |
| 255 | G Q W H C T Y L F P H H Y C L Y G |
| 256 | cbz-G Q W H C T Dpr R F P H H Y C L Y G |
| 257 | G Q W H C T Dpr R F P H H Y C L Y G |
| 258 | cbz-G Q W H C T K R F P H H Y C L Y G |
| 259 | G Q W H C T K R F P H H Y C L Y G |
| 260 | cbz-G Q W H C T Orn R F P H H Y C L Y G |
| 261 | G Q W H C T Orn R F P H H Y C L Y G |
| 262 | G Q W H C T D R F P H H Y C L Y G |
| 263 | G K(G) W H C Y K Y F P H H Y C L Y G |

TABLE 24

| SEQ ID NO. | Sequence |
|---|---|
| 264 | G Q W H C T T S F P H H Y C L Y G |
| 265 | G Q W H C T T D F P H H Y C L Y G |
| 266 | G Q W H C T T L F P H H Y C L Y G |
| 267 | G Q W H C T T Y F P H H Y C L Y G |
| 268 | cbz-G Q W H C T T K F P H H Y C L Y G |
| 269 | G Q W H C T T Aib F P H H Y C L Y G |
| 270 | G Q W H C T T Y(3-Cl) F P H H y C L Y G |
| 271 | G Q W H C T T I F P H H y C L Y G |
| 272 | G Q W H C T T Cha F P H H y C L Y G |
| 273 | G Q W H C T T Abu F P H H Y C L Y G |
| 274 | G Q W H C T T F(4-F) F P H H Y C L Y G |
| 275 | G Q W H C T T Dopa F P H H Y C L Y G |
| 276 | G Q W H C T T Tle F P H H Y C L Y G |
| 277 | G Q W H C T T Cit F P H H Y C L Y G |

TABLE 25

| SEQ ID NO. | Sequence |
|---|---|
| 278 | G Q W H C T T R Y P H H Y C L Y G |
| 279 | G Q W H C T T R Bip P H H Y C L Y G |
| 280 | G Q W H C T T R F(4-CF3) P H H Y C L Y G |
| 281 | G Q W H C T T R 4-PaI P H H Y C L Y G |
| 282 | G Q W H C T T R 1-NaI P H H Y C L Y G |
| 283 | G Q W H C T T R F(4-NO2) P H H Y C L Y G |
| 284 | G Q W H C T T R Hfe P H H Y C L Y G |
| 285 | G Q W H C T T D Bpa P H H Y C L Y G |
| 286 | G Q W H C T T D F(4-CN) P H H Y C L Y G |
| 287 | G Q W H C T T D F(4-NH2) P H H Y C L Y G |
| 288 | G Q W H C T T D F(3,4-OMe) P H H Y C L Y G |
| 289 | G Q W H C T T D 2-NaI P H H Y C L Y G |
| 290 | G Q W H C T T D Y(3-Cl) P H H Y C L Y G |

TABLE 26

| SEQ ID NO. | Sequence |
|---|---|
| 291 | P P Q W H C T T R F P(3-OH) H H Y C L Y G |
| 292 | G Q W H C T T S F ΔPro H H Y C L Y G |
| 293 | G Q W H C T T S F Pip H H Y C L Y G |
| 294 | G Q W H C T T R F N-Me-A H H Y C L Y G |
| 295 | D W S C T T D Y P(3-OH) A H y C L Y G |

TABLE 27

| SEQ ID NO. | Sequence |
|---|---|
| 296 | G Q W H C T T R F P S H Y C L Y G |
| 297 | cbz-G Q W H C T T R F P K H Y C L Y G |
| 298 | G Q W H C T T R F P Aib H Y C L Y G |
| 299 | G Q W H C T T L F P N H Y C L Y G |
| 300 | A W H C T T R F P A H Y C L Y G |
| 301 | G K(G) W H C T T Y F P Y H Y C L Y G |
| 302 | G Q W H C T T R F P H S Y C L Y G |
| 303 | G Q W H C T T R F P H Aib Y C L Y G |
| 304 | G Q W H C T T D F P H Dpr Y C L Y G |
| 305 | G Q W H C T T D F P H 2-Pal Y C L Y G |
| 306 | G Q W H C T T L F P H N Y C L Y G |
| 307 | G Q W H C T T L F P H D Y C L Y G |
| 308 | G K(G) W H C T T Y F P H Y Y C L Y G |
| 309 | G K(G) W H C T T Y F P H W Y C L Y G |

TABLE 28

| SEQ ID NO. | Sequence |
|---|---|
| 310 | G Q W H C T T R F P H H 1-NaI C L Y G |
| 311 | G Q W H C T T R F P H H Bip C L Y G |
| 312 | G Q W H C T T R F P H H r C L Y G |
| 313 | G Q W H C T T R F P H H bip C L Y G |
| 314 | G Q W H C T T R F P H H 1-nal C L Y G |

TABLE 28-continued

| SEQ ID NO. | Sequence |
|---|---|
| 315 | G Q W H C T T R F P H H t C L Y G |
| 316 | G Q W H C T T L F P H H 1-NaI C L Y G |
| 317 | G Q W H C T T S F P H H Dopa C L Y G |
| 318 | G Q W H C T T R F P H H h-Tyr C L Y G |
| 319 | G Q W H C T T R F P H H h-Tyr(Me) C L Y G |
| 320 | G Q W H C T T R F P H H F(3-OMe) C L Y G |
| 321 | G K(G) W H C T T Y F P H H Bip C L Y G |
| 322 | G K(G) W H C T T Y F P H H Y(3-Cl) C L Y G |
| 323 | G K(G) W H C T T Y F P H H Y(2,6-Me2) C L Y G |
| 324 | G K(G) W H C T T Y F P H H V C L Y G |
| 325 | G K(G) W H C T T L F P H H V C L Y G |
| 326 | G K(G) W H C T T Y F P H H Dip C L Y G |
| 327 | G K(G) W H C T T Y F P H H Dip C L Y G |
| 328 | G K(G) W H C T T Y F P H H F(4-NH2) C L Y G |
| 329 | G K(G) W H C Y T Y F P H H 1-NaI C L Y G |

TABLE 29

| SEQ ID NO. | Sequence |
|---|---|
| 330 | G Q W H Pen T T R F P H H Y C L Y G |
| 331 | G Q W H C T T R F P H H Y Pen L Y G |
| 332 | G Q W H Pen T T R F P H H Y Pen L Y G |

TABLE 30

| SEQ ID NO. | Sequence |
|---|---|
| 333 | cbz-G Q W H C T T R F P H H Y C K Y G |
| 334 | G Q W H C T T R F P H H Y C Aib Y G |
| 335 | G Q W H C T T L F P H H Y C I Y G |
| 336 | G Q W H C T T L F P H H Y C V Y G |
| 337 | G Q W H C T T L F P H H Y C Hse Y G |
| 338 | G Q W H C T T R F P H H Y C F Y G |
| 339 | G Q W H C T T R F P H H Y C Hfe Y G |

TABLE 31

| SEQ ID NO. | Sequence |
|---|---|
| 340 | G Q W H C T T D F P H H Y C L Bpa G |
| 341 | G Q W H C T T D F P H H Y C L F G |
| 342 | G Q W H C T T D F P H H Y C L 2-Nal G |
| 343 | G Q W H C T T D F P H H Y C L Y(3-Cl) G |
| 344 | G Q W H C T T L F P H H Y C L 2-Nal G |
| 345 | G K(G) W H C T T Y F P H H Y C L Dip G |
| 346 | G K(G) W H C T T Y F P H H Y C L F(4-NH2) G |

TABLE 32

| SEQ ID NO. | | | | | | Sequence | | | | | | | | | |
|---|---|---|---|---|---|---|---|---|---|---|---|---|---|---|---|
| 347 | G | Q | Y | T | C | S | G | D | E | Y | T | W | H | C N Y E |
| 348 | G | Q | 1-Nal | T | C | S | G | D | E | Y | T | W | H | C N Y E |
| 349 | | D | thien-W | T | C | S | G | D | E | Y | T | W | H | C N Y E |
| 350 | | D | W(5-OH) | T | C | S | G | D | E | Y | T | W | H | C N Y E |
| 351 | G | Q | W | T | C | S | G | D | E | Y | T | Y | H | C N Y E |
| 352 | G | Q | W | T | C | S | G | D | E | Y | T | 1-Nal | H | C N Y E |
| 353 | | D | W | T | C | S | G | D | E | Y | T | thien-W | H | C N Y E |
| 354 | | D | W | T | C | S | G | D | E | Y | T | W(5-OH) | H | C N Y E |
| 355 | | D | W | T | C | S | G | D | E | Y | T | b-h-W | H | C N Y E |
| 356 | | D | W | T | C | S | G | D | E | Y | T | H | H | C N Y E |

TABLE 33

| SEQ ID NO. | Sequence | | | | |
|---|---|---|---|---|---|
| 357 | D W T | C | R | G D E Y T W H | C N Y E |
| 358 | D W T | C | y | G D E Y T W H | C N Y E |
| 359 | D W T | C | P | G D E Y T W H | C N Y E |
| 360 | D W T | C | Y | G D E Y T W H | C N Y E |
| 361 | D W T | C | b-h-S | G D E Y T W H | C N Y E |
| 362 | D W T | C | L | G D E Y T W H | C N Y E |
| 363 | D W T | C | 3-NO2Y | G D E Y T W H | C N Y E |
| 364 | D W T | C | 3-NO2Y | G D E Y T W H | C N Y E |
| 365 | D W T | C | 4-Pal | G D E Y T W H | C N Y E |
| 366 | D W T | C | 4-CO2H-F | G D E Y T W H | C N Y E |
| 367 | D W T | C | 4-tBu-F | G D E Y T W H | C N Y E |
| 368 | D W T | C | F(4-NH2) | G D E Y T W H | C N Y E |
| 369 | D W T | C | Y(Bn,3-Cl) | G D E Y T W H | C N Y E |
| 370 | G Q W T | C | Y | G D E Y T W H | C N Y E |
| 371 | D W T | C | Aib | G D E Y T W H | C N Y E |

TABLE 34

| SEQ ID NO. | | | Sequence | | |
|---|---|---|---|---|---|
| 372 | PP | Q | W H C T T R F P H H Y C L | Y | G |
| 373 | G | Q | W H C T T R F Y T W H C N | | E |
| 374 | G | Q | W H C T T R F P H H Y C L | Y | G |
| 375 | G | Q | W H C T T R F P H H Y C L | Y | G |
| 376 | | | W H C T T R F P H H Y C L | Y | G |
| 377 | GK(G) | Q | W H C T T Y F P H H Y C L | Y | G |
| 378 | G | Q | W H C T T L F P H H Y C L | Y | G |
| 379 | G | A | W H C T T L F P H H y C L | Y | G |
| 380 | | A | W H C T T L F P H H y C L | Y | G |
| 381 | G | D | W H C T T L F P H H y C L | Y | G |
| 382 | G | S | W H C T T L F P H H y C L | Y | G |
| 383 | P | P | W H C T T L F P H H y C L | Y | G |
| 384 | G | Q | W H C T T Y F P H H y C L | Y | G |
| 385 | G | A | W H C T T Y F P H H y C L | Y | G |

TABLE 34-continued

| SEQ ID NO. | Sequence | | | | | | | | | | | | | | | |
|---|---|---|---|---|---|---|---|---|---|---|---|---|---|---|---|---|
| 386 | G. | K(G) | W | H | C | T | T | L | F | P | H | H | y | C | L | Y | G |
| 387 | G | Abu | W | H | C | T | T | S | F | P | H | H | y | C | L | Y | G |
| 388 | G | Cit | W | H | C | T | T | S | F | P | H | H | y | C | L | Y | G |
| 389 | G | K(G) | W | H | C | T | T | Y | F | P | H | H | y | C | L | Y | G |
| 390 | G | K(G) | W | H | C | T | T | Y | F | P | H | H | y | C | L | Y | G |
| 391 | G | K(G) | W | H | C | T | T | Y | F | P | H | H | y | C | L | Y | G |
| 392 | G | K(G) | W | H | C | T | T | Y | F | P | H | H | y | C | L | Y | Y |
| 393 | G | K(G) | W | H | C | T | T | Y | F | P | H | H | y | C | L | Y | Y |
| 394 | G | K(G) | W | H | C | T | T | Y | F | P | H | H | y | C | L | Y | Bip |
| 395 | KK(K) | GQ | W | H | C | T | T | Y | F | P | H | H | y | C | L | Y | G |
| 396 | G | K(G) | W | H | C | T | T | Y | F | P | H | H | y | C | L | Y | G |
| 397 | G | K(G) | W | H | C | T | T | Y | F | P | H | H | y | C | L | Y | G |
| 398 | G | K(G) | W | H | C | T | T | Y | F | P | H | H | y | C | L | Y | G |
| 399 | G | K(G) | W | H | C | T | T | Y | F | P | H | H | y | C | L | Y | F(4-NHS) |
| 400 | G | K(G) | W | H | C | T | T | K | F | P | H | H | y | C | L | Y | Bip |

TABLE 35

| SEQ ID NO. | Sequence | | | | | | | | | | | | | | | |
|---|---|---|---|---|---|---|---|---|---|---|---|---|---|---|---|---|
| 401 | G | K(G) | W | H | C | Y | T | K | F | P | H | H | Y | C | V | Y | G |
| 402 | G | K(G) | W | H | C | Y | T | K | F | P | H | H | Y | C | V | Y | Y |
| 403 | G | K(G) | W | H | C | T | T | K | F | P | H | H | Y | C | L | Y | Y |
| 404 | GY | K(Y.G) | W | H | C | T | T | Y | F | P | H | H | Y | C | L | Y | G |
| 405 | GV | K(V.G) | W | H | C | T | T | Y | F | P | H | H | Y | C | L | Y | G |
| 406 | GF | K(F.G) | W | H | C | T | T | Y | F | P | H | H | Y | C | L | Y | G |
| 407 | GH | K(H.G) | W | H | C | T | T | Y | F | P | H | H | Y | C | L | Y | G |
| 408 | K | K | W | H | C | Y | T | Y | F | P | H | H | Y | C | V | Y | G |
| 409 | Dpr | Dpr(Dpr) | W | H | C | Y | T | Y | F | P | H | H | Y | C | V | Y | G |
| 410 | | KK(K) | W | H | C | Y | T | Y | F | P | H | H | Y | C | V | Y | G |
| 411 | G | Q | W | T | C | S | G | D | E | P | H | H | Y | C | L | Y | G |
| 412 | G | Q | W | T | C | S | G | D | F | P | H | H | Y | C | L | Y | G |
| 413 | G | Q | W | T | C | S | G | D | F | P | H | H | Y | C | L | Y | G |
| 414 | G | Q | W | T | C | S | G | R | F | P | H | H | Y | C | L | Y | G |

TABLE 36

| SEQ ID NO. | Sequence | | | | | | | | | | | | | | | |
|---|---|---|---|---|---|---|---|---|---|---|---|---|---|---|---|---|
| 415 | cbz-G | Q | W | H | C | T | T | R | F | P | H | H | Y | C | L | Y | G | K |
| 416 | cbz-G | Q | W | H | C | T | T | R | F | P | H | H | Y | C | L | Y | G | k |
| 417 | cbz-G | Q | W | H | C | T | T | R | F | P | H | H | Y | C | L | Y | G | Peg K |
| 418 | cbz-G | Q | W | H | C | T | T | R | F | P | H | H | Y | C | L | Y | G | KK |
| 419 | G | Q | W | H | C | T | T | Y | F | P | H | H | Y | C | L | Y | G | peg(1xO) |
| 420 | G | Q | W | H | C | Y | T | L | F | P | H | H | Y | C | L | Y | G | 1,4-AMB |
| 421 | G | Q | W | H | C | Y | T | L | F | P | H | H | Y | C | L | Y | G | 1,4-AMB |
| 422 | G | Q | W | H | C | Y | T | L | F | P | H | H | Y | C | L | Y | G | 1,3-AMB |
| 423 | G | Q | W | H | C | T | T | Y | F | P | H | H | Y | C | L | Y | G | 1,4-AMB |
| 424 | G | Q | W | H | C | T | T | Y | F | P | H | H | Y | C | L | Y | G | 1,3-AMB |
| 425 | G | Q | W | H | C | T | T | Y | F | P | H | H | Y | C | L | Y | G | 1,3-AMB |
| 426 | G | K(G) | W | H | C | Y | T | Y | F | P | H | H | Y | C | V | Y | G | K |
| 427 | G | K(G) | W | H | C | Y | T | Y | F | P | H | H | Y | C | V | Y | Y | K |
| 428 | G | K(G) | W | H | C | Y | T | Y | F | P | H | H | Y | C | L | Y | Y | K |
| 429 | G | K(G) | W | H | C | Y | T | Y | F | P | H | H | Y | C | L | Y | Y | K |
| 430 | G | K(G) | W | H | C | Y | T | Y | F | P | H | H | Y | C | L | Y | Bip | K |
| 431 | G | K(G) | W | H | C | Y | T | Y | F | P | H | H | Y | C | V | Y | G | 1,4AMB |
| 432 | G | K(G) | W | H | C | Y | T | Y | F | P | H | H | Y | C | L | Y | F | K |
| 433 | G | K(G) | W | H | C | Y | T | Y | F | P | H | H | Y | C | L | Y | Y | K |
| 434 | G | K(G) | W | H | C | Y | T | Y | F | P | H | H | Y | C | L | Y | Y | K |
| 435 | G | K(G) | W | H | C | Y | T | Y | F | P | H | H | Y | C | L | Y | y | K |
| 436 | G | K(G) | W | H | C | Y | T | Y | F | P | H | H | Y | C | L | Y | V | K |
| 437 | G | K(G) | W | H | C | Y | T | Y | F | P | H | H | Y | C | L | Y | V | K |

TABLE 36-continued

| SEQ ID NO. | Sequence |
|---|---|
| 438 | G Q W H C Y T K F P H H Y C L Y G K |
| 439 | G Q W H C Y T Y F P H H Y C L Y G K |
| 440 | G K(G) W H C Y T Y F P H H Y C L Y G K |
| 441 | G K(G) W H C Y T Y F P H H Y C V Y G 1,6-Hex |
| 442 | G K(G) W H C Y T Y F P H H Y C V Y G PEG |

TABLE 37

| SEQ ID NO. | Sequence |
|---|---|
| 443 | D W T C S G P E Y T W H C N Y E |
| 444 | D W T C S G b-h-D E Y T W H C N Y E |
| 445 | D W T C S G L E Y T W H C N Y E |
| 446 | G Q W T C S G K(Boc) E Y T W H C N Y E |
| 447 | D W T C S G Aib E Y T W H C N Y E |

TABLE 38

| SEQ ID NO. | Sequence |
|---|---|
| 448 | D W T C S G D E D T W H C N Y E |
| 449 | D W T C S G D E R T W H C N Y E |
| 450 | D W T C S G D E P T W H C N Y E |
| 451 | D W T C S G D E Y(3-I) T W H C N Y E |
| 452 | D W T C S G D E b-h-y T W H C N Y E |
| 453 | D W T C S G D E Aib T W H C N Y E |
| 454 | D W T C S G D E Y T W H C N Y(3-I) E |

TABLE 39

| SEQ ID NO. | Sequence |
|---|---|
| 455 | E A G Q W T C S G D E Y T W H C N Y E |
| 456 | G Q W T C S G D E Y T W H C N Y E GTE |
| 457 | E A G Q W T C S G D E Y T W H C N Y E GTE |
| 458 | G Q W T C S G D E Y T W H C N Y e PEG(1xO) |
| 459 | G Q W T C S G D E Y T W H C N Y e K |
| 460 | P P G Q W T C S G D E Y T W H C N Y e K |

TABLE 40

| SEQ ID NO. | Sequence |
|---|---|
| 461 | P P G Q W T C S G D E Y T W H C N Y e |
| 462 | D W T C S G D Y T W H C N Y E |
| 463 | G q w t c s G d e y t w h c n y e |
| 464 | D W T C S G D E Y D W H C N Y E |
| 465 | D W T C S G D E Y R W H C N Y E |
| 466 | D W T C S G D R Y T W H C N Y E |
| 467 | D W T C S G D L Y T W H C N Y E |
| 468 | G Q W T C S G D E Y T W H C N |
| 469 | G Q W T C S G D E Y T W H C |
| 470 | G Q W T C S G D Y T W H C N Y E |
| 471 | D W T C S G D E Y P W H C N Y E |
| 472 | D W T C S G D E Y Y W H C N Y E |
| 473 | D W T C S G D E Y T W D C N Y E |
| 474 | D W T C S G D E Y T W Y C N Y E |
| 475 | P P Q W T C S G D E Y T W H C A Y E |
| 476 | P P Q W T C S G D A Y T W H C A Y E |
| 477 | G Q W T C S G D A Y T W S C N Y E |
| 478 | D W T C S G D E Y T W P C N Y E |
| 479 | D W T C S G D E Y T W H C N Y E |
| 480 | D W T C S G D E Y T W H C P Y E |
| 481 | D W T C S G D E Y L W H C N Y E |
| 482 | G Q W T C S G D A Y T W S C N Y E |
| 483 | D W P C S G D E Y T W H C N Y E |
| 484 | D W T C S G D Aib Y T W H C N Y E |
| 485 | G Q W T C S k D E Y T W H C N Y E |
| 486 | Aib W T C S G D E Y T W H C N Y E |
| 487 | D W Aib C S G D E Y T W H C N Y E |
| 488 | D W T C S G D E Aib T W H C N Y E |
| 489 | D W T C S G D E Y Aib W H C N Y E |
| 490 | D W T C S G D E Y T W Aib C N Y E |
| 491 | D W T C S G D E Y T W H C N Y Aib |

TABLE 41

| SEQ ID NO. | Sequence | | | | | | | | | | | | |
|---|---|---|---|---|---|---|---|---|---|---|---|---|---|
| 492 | D | W | T | C | Sb-h-G | D | E | Y | T | W | H | C | N Y E |
| 493 | D | W | T | C | S | G | D | b-h-E | Y | T | W | H | C N Y E |
| 494 | D | W | T | C | S | G | D | E | b-h-Y | T | W | H | C N Y E |
| 495 | D | W | T | C | S | G | D | E | Y | b-h-T | W | H | C N Y E |

The unnatural amino acids listed in Tables 18-41 are abbreviated as:

| Abbreviation | Name |
|---|---|
| 1-Nal | L-1-Naphthylalanine |
| 2-Nal | L-2-Naphthylalanine |
| 2-Pal | L-2-Pyridylalanine |
| 3-NO2 Y | L-3-Nitrotyrosine |
| 4-CO2H-F | L-4-carboxyphenylalanine |
| 4-Pal | L-4-Pyridylalanine |
| 4-tBu-F | L-4-tert-Butylphenylalanine |
| Abu | L-α-Aminobutyic acid |
| Aib | Aminoisobutyric acid |
| b-h-D | L-β-homoaspartic acid |
| b-h-S | L-β-homoserine |
| b-h-W | L-β-homotryptophan |
| b-h-Y | L-β-homotyrosine |
| Bip | L-Biphenylalanine |
| bip | D-Biphenylalanine |
| Bpa | L-4-Benzoylphenylalanine |
| Cha | L-Cyclohexylalanine |
| Cit | L-Citrulline |
| Dip | L-Diphenylalanine |
| Dopa | L-3,4-Dihydroxyphenylalanine |
| ΔPro | L-3,4-Dehydroproline |
| F(3,4-OMe2) | L-3,4-Dimethoxyphenylalanine |
| F(3-OMe) | L-3-Methoxyphenylalanine |
| F(4-CF3) | L-4-Trifluoromethylphenylalanine |
| F(4-CN) | L-4-Cyanophenylalanine |
| F(4-F) | L-4-Fluorophenylalanine |
| F(4-NH2) | L-4-Aminophenylalanine |
| F(4-NO2) | L-4-Nitrophenylalanine |
| Hfe | L-Homophenylalanine |
| Hse | L-Homoserine |
| h-Tyr | L-Homotyrosine |
| h-Tyr(Me) | L-O-methylhomotyrosine |
| N-Me-A | N-Methyl-L-alanine |
| Orn | L-Ornithine |
| P(3-OH) | L-3-Hydroxyproline |
| Pen | L-Penicillamine |
| Pip | L-Pipecolic acid |
| thien-W | L-3-Benzothienylalanine |
| Tic | L-1,2,3,4-Tetrahydroisoquinoline-3-carboxylic acid |
| Tle | L-tert-Leucine |
| W(5-OH) | L-5-Hydroxytryptophan |
| Y(2,6-Me2) | L-2,6-Dimethyltyrosine |
| Y(3-Cl) | L-3-Chlorotyrosine |
| Y(3-I) | L-3-Iodotyrosine |
| Y(Bn, 3-Cl) | L-3-Chloro-O-benzyltyrosine |

The full names of the abbreviation of linkers used in Tables 18-41 are given below:

| Abbreviation | Name |
|---|---|
| 1,3-AMB | 1,3-Bis(aminomethyl)benzene |
| 1,4-AMB | 1,4-Bis(aminomethyl)benzene |
| 1,6-Hex | 1,6-Diaminohexane |
| PEG | 8-Amino-3,6-dioxaoctanoic acid |
| peg(1xO) | 2,2'-Oxydiethylamine |
| PEG(1xO) | 2,2'-Oxydiethylamine |

All other non-natural amino acids are known to those of ordinary skill in the art.

12. Synthesis of GdDTPA-Peptide Conjugates with Thiourea Linkages

A. Preparation of GdDTPA-ITC Solution.

The ligand 2-(4-isothiocyanatobenzyl)-diethylenetriaminepentaacetic acid (DTPA-ITC) was purchased from Macrocyclics as the tris hydrochloride salt. DTPA-ITC, 1.72 g (2.65 mmol) was dissolved in 10 mL of distilled deionized water and the pH adjusted to 6 by addition of 1 M NaOH. $GdCl_3.6H_2O$, 781 mg (2.1 mmol) was added with stirring and the pH re-adjusted to 6 with 1 M NaOH. Another 186 mg (0.55 mmol) of $GdCl_3.6H_2O$ was added and the pH re-adjusted to 6. The reaction was complete as determined by LC-MS analysis. The final volume was 43.6 mL resulting in a concentration of 59.6 mM GdDTPA-ITC.

B. General Procedures for GdDTPA-Peptide Conjugates with Thiourea Linkages.

i. Microwave Synthesis.

Purified cyclized peptide (0.05 mmol) containing N primary amines is suspended in 10 mL pH 7.5 phosphate buffer (200 mM Pi). GdDTPA-ITC solution (59.6 mM) is added in excess (2×N amines×0.05 mmol peptide), typically 1-5 mL of solution. The mixture is heated to 80° C. for 20 min using an Emrys Optimizer microwave synthesizer. The solution is allowed to cool to room temperature and the conjugate purified and isolated by preparative HPLC (Kromasil C18 colum) using a gradient of increasing acetonitrile (ACN) into an aqueous ammonium formate (50 mM) mobile phase.

ii. Room Temperature Synthesis.

Purified cyclized peptide (0.05 mmol) containing N primary amines is suspended in 10 mL pH 9 borate buffer (100 mM). GdDTPA-ITC solution (59.6 mM) is added in excess (5×N amines×0.05 mmol peptide). The mixture is stirred at room temperature overnight. The conjugate is purified and isolated by preparative HPLC (Kromasil C18 colum) using a gradient of increasing acetonitrile (ACN) into an aqueous ammonium formate (50 mM) mobile phase.

C. Synthesis of Compound ID 800.

Peptide, SEQ ID NO. 400 (0.0133 mmol) was suspended in 3 mL of pH 9 borate buffer. Gd-DTPA-ITC (3.0 mL of a 59.6 mM solution, 0.18 mmol) was added and the solution stirred at room temperature for 69 hours. The product was isolated directly by preparative HPLC and elutes at approximately 35% ACN. Pure fractions were combined and salts were removed by loading the compound onto a 5 g C18 SepPak column and eluting the salts with water. The pure compound was eluted with 50% water/ethanol solution. After removal of solvent 16.2 mg of product was obtained with correct molecular weight by LC-MS.

Compound ID 800:

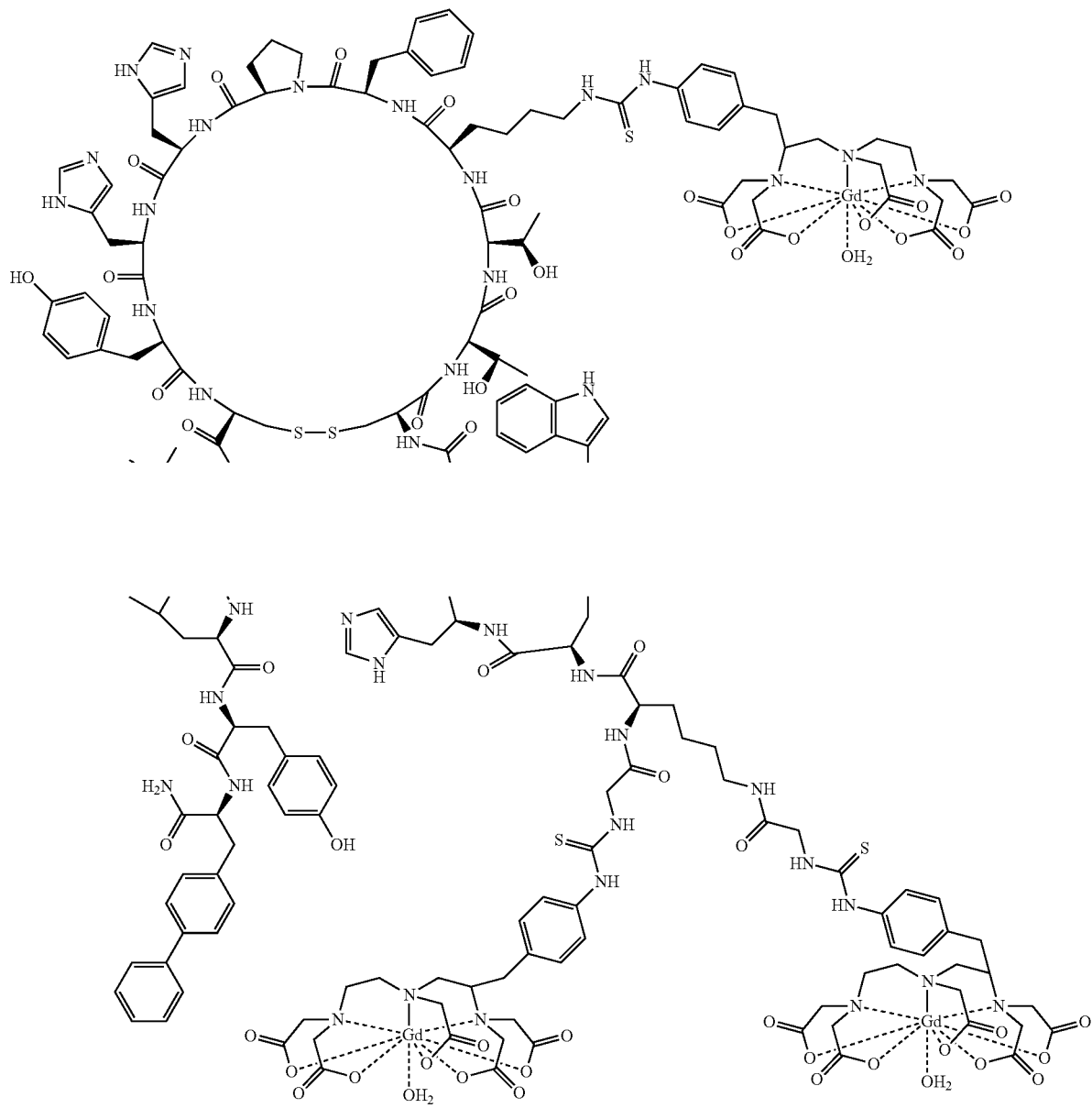

D. Synthesis of Compound ID 801.

Peptide, SEQ ID NO. 408 (0.043 mmol) was suspended in a mixture of 10 mL pH 7.5 phosphate buffer (200 mM) and 5 ml ACN in a microwave reaction vessel. Gd-DTPA-ITC (3.4 mL of a 59.6 mM solution, 0.203 mmol) was added. The mixture was heated in the microwave for 20 min at 80° C. A clear solution was obtained. The product was isolated directly by preparative HPLC and elutes between 20-30% acetonitrile. The product was analyzed by LC-MS and gave the correct mass.

Compound ID 801:

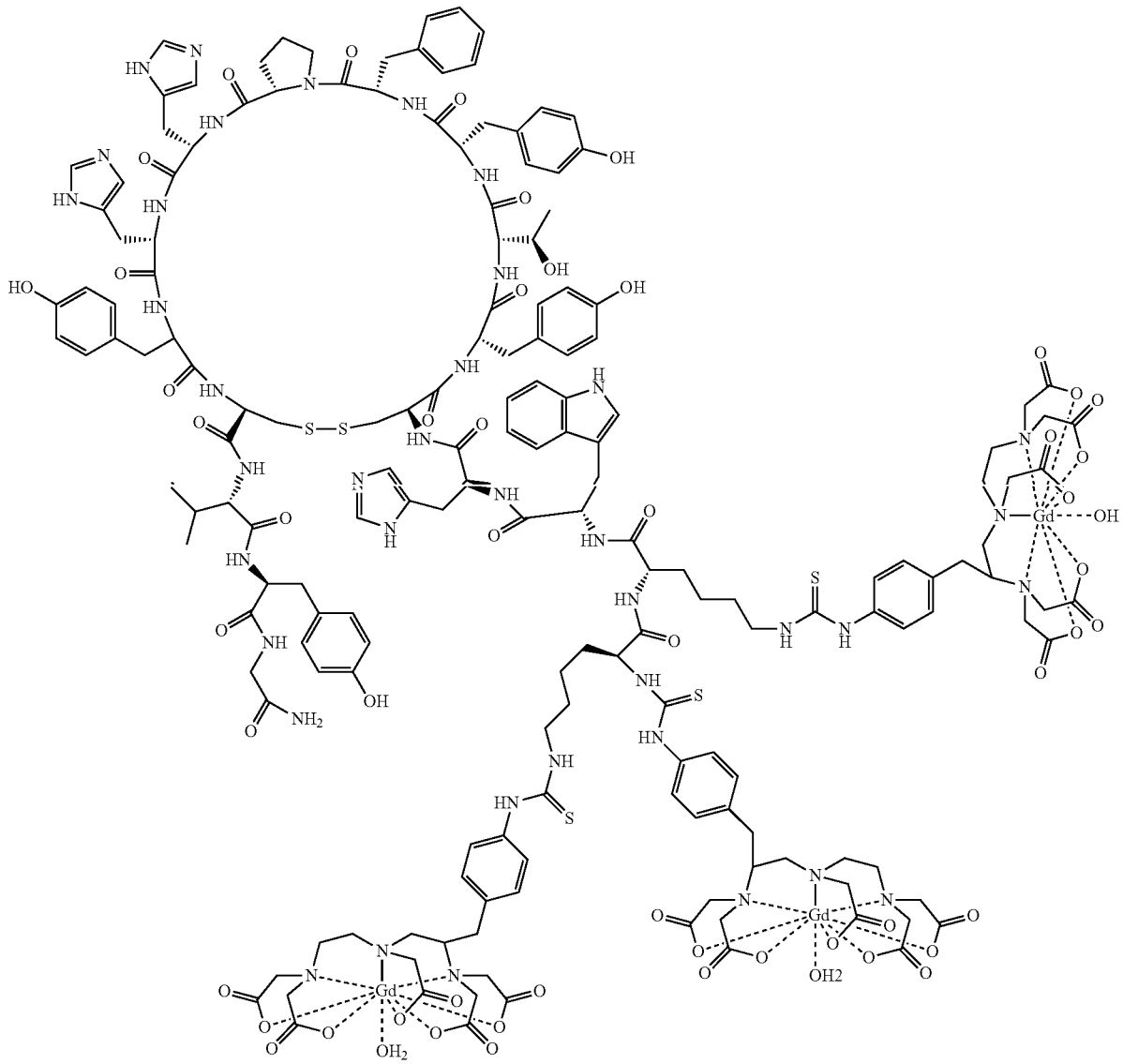

14. Synthesis of GdDOTAGA-Peptide Conjugates with Amide Linkages

A. General Procedure for Peptide-Gd-DOTAGA Conjugates.

Coupling:

The peptide (0.05 mmol) containing N primary amines is dissolved in DMF (15 ml). t-butyl protected DOTAGA-pentafluorophenylester (2×N primary amines×0.05 mmol) is added and the pH of the reaction mixture adjusted to 7.5 with di-isopropylethylamine (DIEA). The reaction is stirred overnight at room temperature and then the solvent is removed in vacuo. Conversion to product is confirmed by LC-MS and the product is used without further purification.

Deprotection:

The crude product, protected DOTAGA-peptide conjugate, is dissolved in a mixture of TFA/methanesulfonic acid/TIS/water/phenol (20 ml, 18:0.5:0.5:0.5:0.5) and stirred for 20 min at room temperature and then poured into ether giving a white precipitate. The precipitate was isolated by centrifugation followed by decanting the solvent. The crude deprotected DOTAGA-peptide conjugate was not purified.

Chelation:

The crude ligand is dissolved in H₂O and the pH adjusted to 6 with a 1 N NaOH solution. Solid GdCl₃.6H₂O (1.1×N primary amines×0.05 mmol peptide) is added at RT and the pH re-adjusted to 6.5. The reaction is allowed to proceed overnight and results in a cloudy suspension. The chelation reaction is checked by LC-MS to ensure that it has gone to completion. A solution of 100 mM EDTA (to scavenge the excess gadolinium ions) is added dropwise with stirring until the solution became clear.

Purification:

The crude product is purified by preparative HPLC (Kromasil C18, ammonium formate (50 mM)/ACN) and the purified product analyzed by LC-MS.

B. Synthesis of Compound ID 802.

See reaction scheme below. Peptide, SEQ ID 408 (0.061 mmol) labeled as 1 in synthesis scheme was dissolved in 15 mL of DMF. t-butyl protected DOTAGA-pentafluorophenylester, 2, (0.366 mmol) was added and DIEA added to adjust the pH to 7.5. After reaction at room temperature overnight, the solvent was removed under reduced pressure. The crude solid, 3, was dissolved in a 20 mL mixture of TFA:methane sulfonic acid:TIS:water:phenol (18:0.5:0.5:0.5:0.5) and stirred for 20 min at room temperature. The deprotected ligand, 4, was obtained after precipitation with ether. The solid was then taken up in 25 mL water and neutralized by addition of 1 M NaOH until the pH was 6.5. Solid $GdCl_3.6H_2O$ (75 mg, 0.20 mmol) was added at RT and the pH re-adjusted to 6.5. The solution was stirred overnight and the resultant solution was cloudy. $Na_2H_2EDTA$ solution (0.1 M) was added dropwise with stirring until the solution became clear. The resultant solution was purified by preparative HPLC (Kromasil C18, ammonium formate (50 mM)/ACN) and the product, 5, eluted at 45% ACN. The product was analyzed by LC-MS and gave the correct mass.

Reaction scheme for compound ID 802:
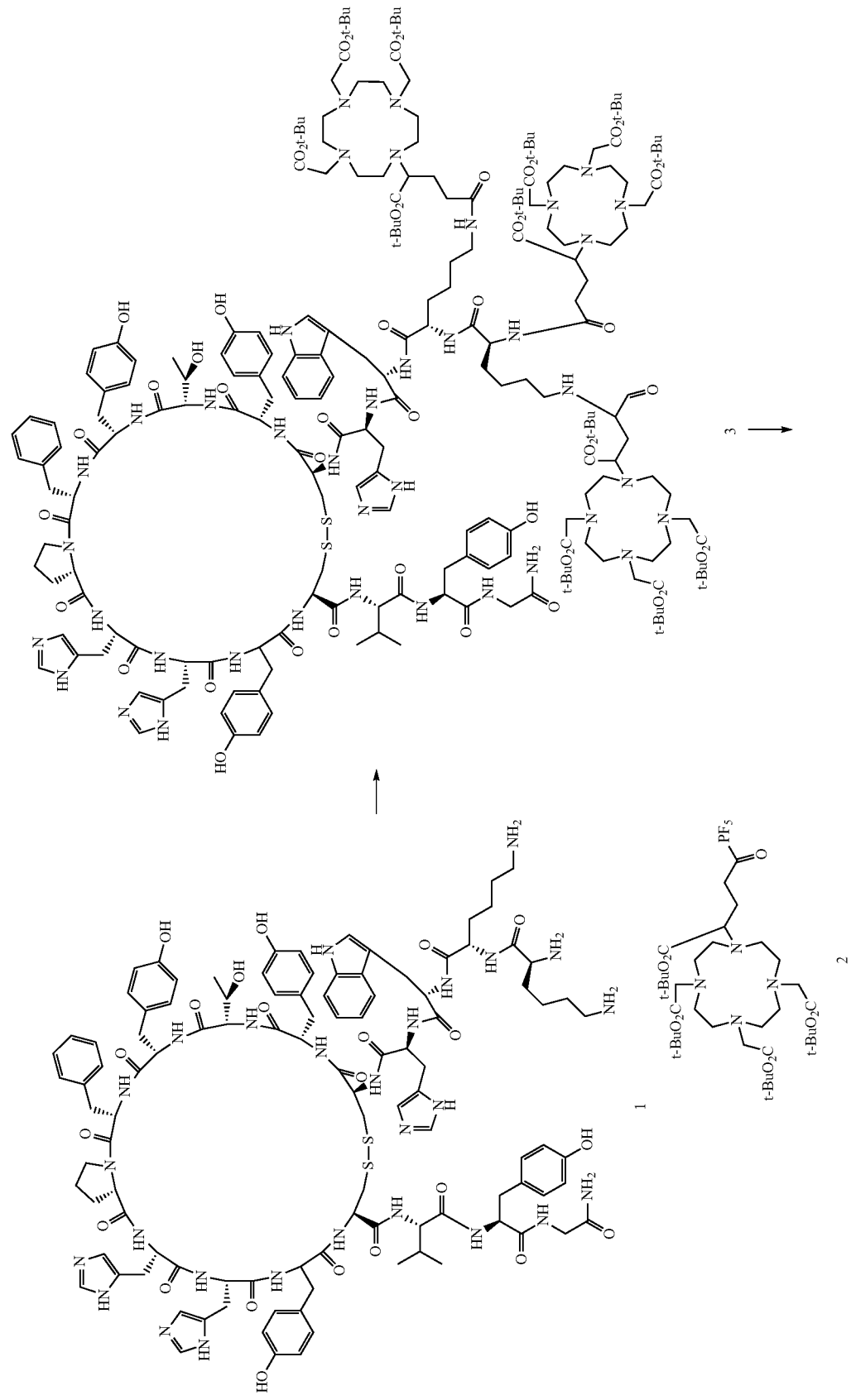

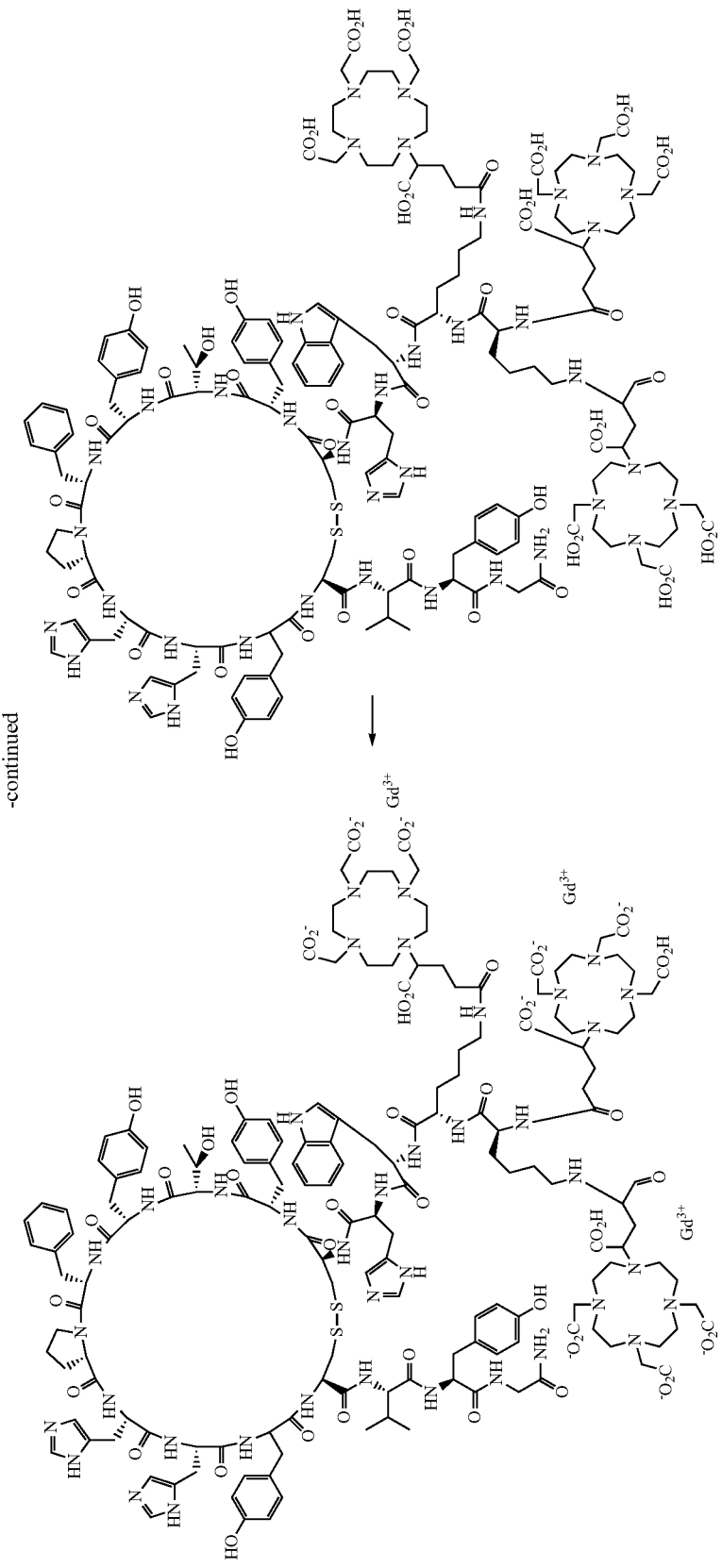

15. Synthesis of Compound ID 803

A Dual Peptide, Gadolinium Tetramer

A. Synthesis of bb-DTPE Tetramer Diacid.

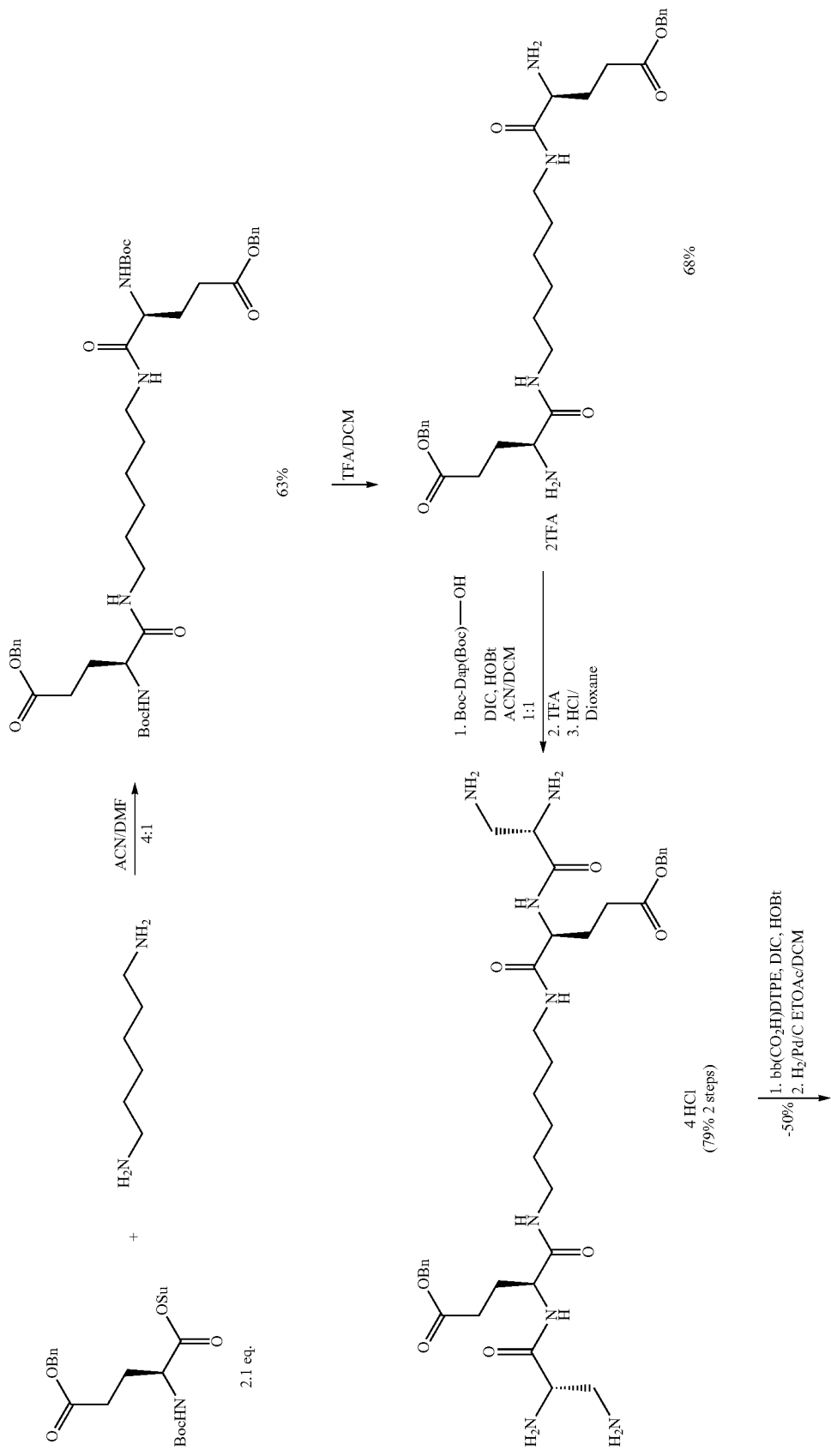

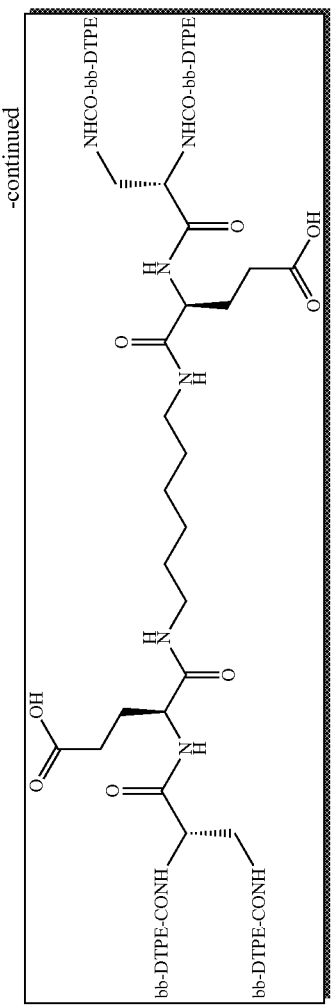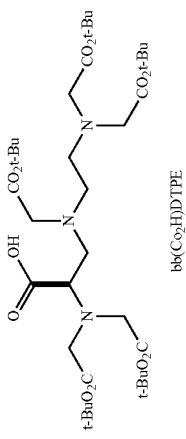

Synthesis of Bis-Amide 1,6 diaminohexane and hydroxysuccinimide ester of Boc-Glu(OBn)-OH were dissolved in dichloromethane and the mixture was stirred for 5 h at RT. The solvent was evaporated and the resulting solid was washed with EtOAc to give the desired bis-amide (M+1=755.5) in a 93% yield.

Deprotection of the Boc Groups

The di-Boc protected derivative was dissolved in 2:1 mixture of dichloromethane/TFA and the mixture was stirred for 2 h at RT. The mixture was concentrated to half of the initial volume and the diamine was precipitated with ether as a TFA salt in a 68% yield.

Coupling of Diamine with Di-Boc-Diaminopropanoic Acid.

Boc-dap-(Boc)-OH DHCA salt was suspended in 0.5 N $KHSO_4$ and the free acid was extracted with EtOAc. The combined organic fractions were dried over $Na_2SO_4$ and evaporated to dryness. The acid and the diamine were dissolved in dichloromethane and HOBt, $H_2O$, DIEA and DIC were successively added under argon at 0° C. The mixture was stirred for 20 hr between 0° C. and RT. The desired product was obtained as a white solid after filtration of the reaction mixture and several washes with 1:1 ether/dichloromethane and then with ether resulting in a 75% yield.

Deprotection of the Boc Groups.

Boc-protected tetramine was dissolved in a 1:2 TFA/dichloromethane and the solution was stirred for 1 h. The mixture was evaporated to dryness and the residue was triturated with 4 M HCl in dioxane and the mixture was concentrated under reduced pressure. The residue was triturated with 4 M HCl in dioxane and the mixture diluted with ether. The desired tetramine was obtained as a tetrahydrochloride salt in a 89% yield.

Coupling of Bb-DTPE to Tetramine.

Acid and tetramine were dissolved in a 1:1 mixture of acetonitrile/DMF and the pH was adjusted to 9 (wet pH paper test) with DIEA. DIC and HOBt were added and the pH was adjusted to 9 with DIEA. The reaction mixture was stirred overnight. The reaction mixture was diluted with water and extracted with EtOAc. The organic layers were combined and washed successively with saturated $NaHCO_3$, 0.1 N HCl solution and with brine and then dried over $Na_2SO_4$. The desired tetramer was obtained after purification by flash chromatography on silica gel using for eluent a gradient of Hexanes/1-PrOH/DIEA 20:1:0.1 to 15:1:0.1 in a 50% yield.

Deprotection of the Diacid

The di-benzyl ester was dissolved in a 1:1 mixture of EtOAC/dichloromethane. The mixture was shaken overnight in a Parr bottle under 45 psi $H_2$ in the presence of 10% Palladium on carbon (12.5% by weight). The desired acid was obtained after filtration of the catalyst and evaporation of the solvents (M+2=1674.6; M+3=1116.8; M+4=837.8).

Compound ID 803

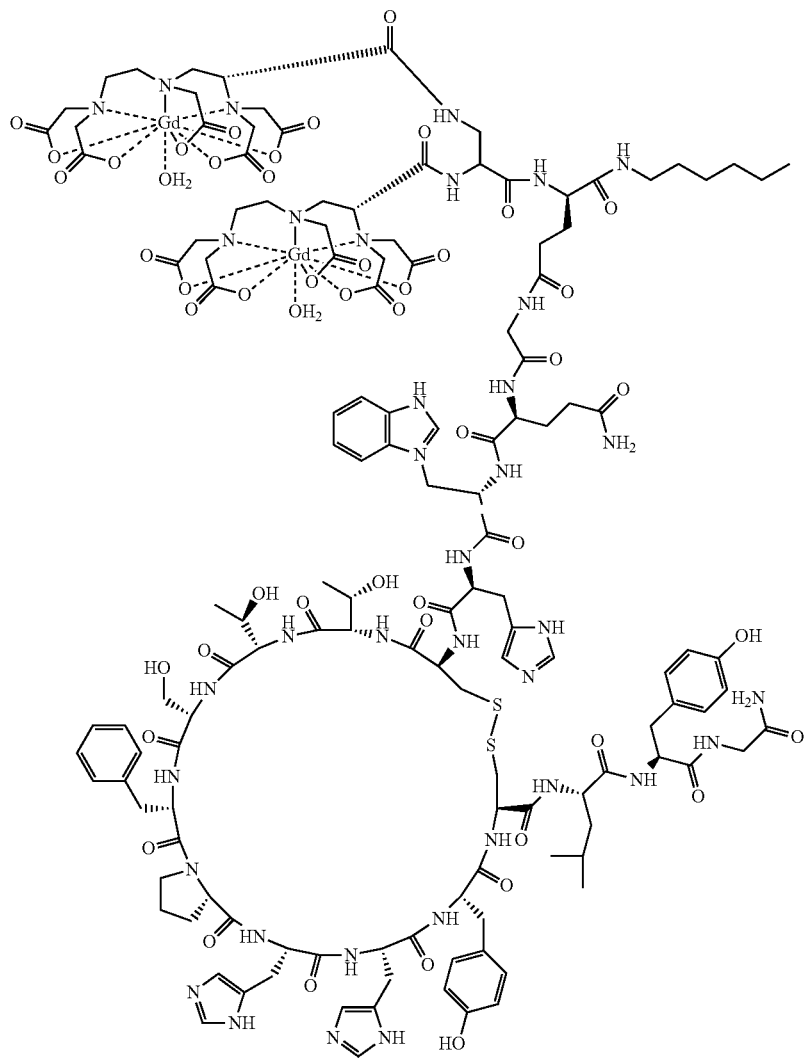

-continued
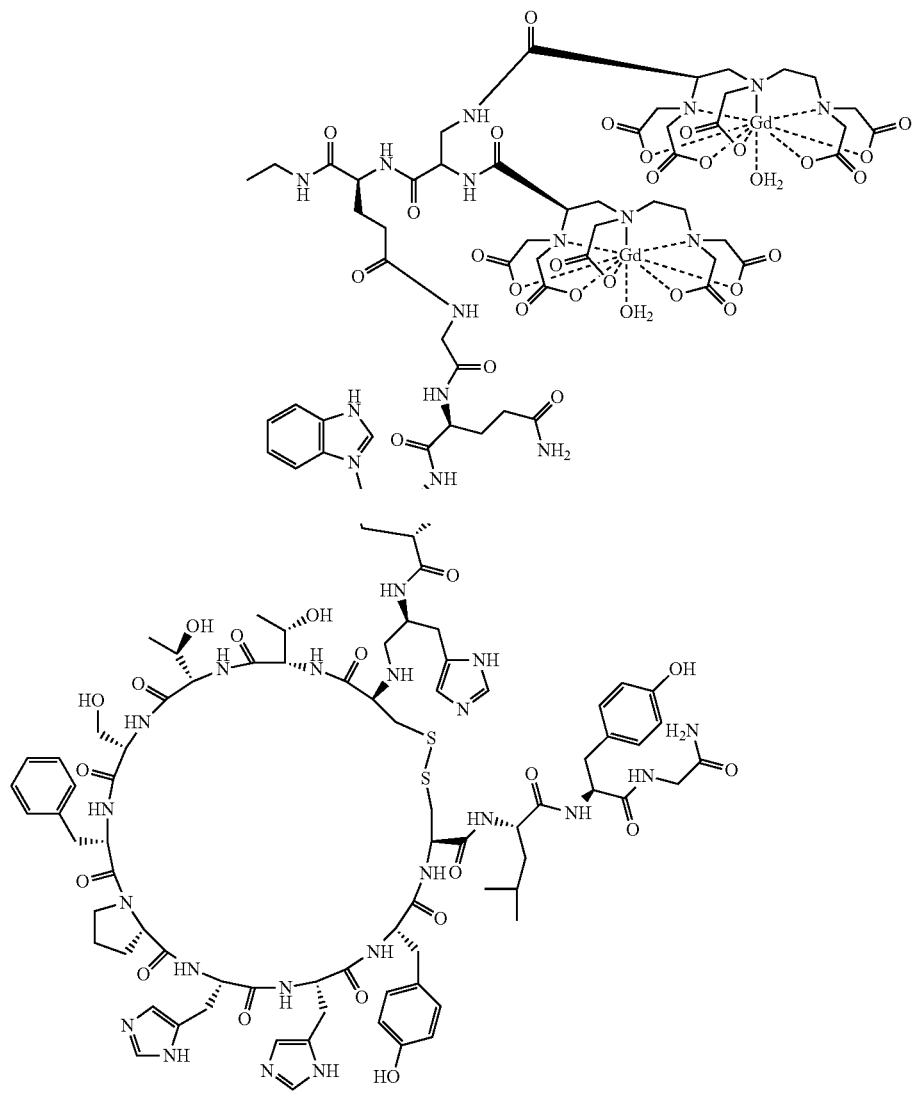
B. Synthesis of Protected Dual Peptide-Tetramer.
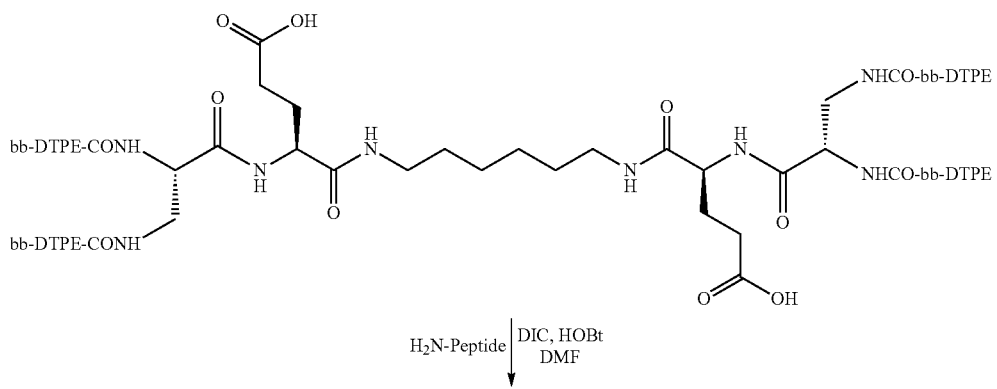

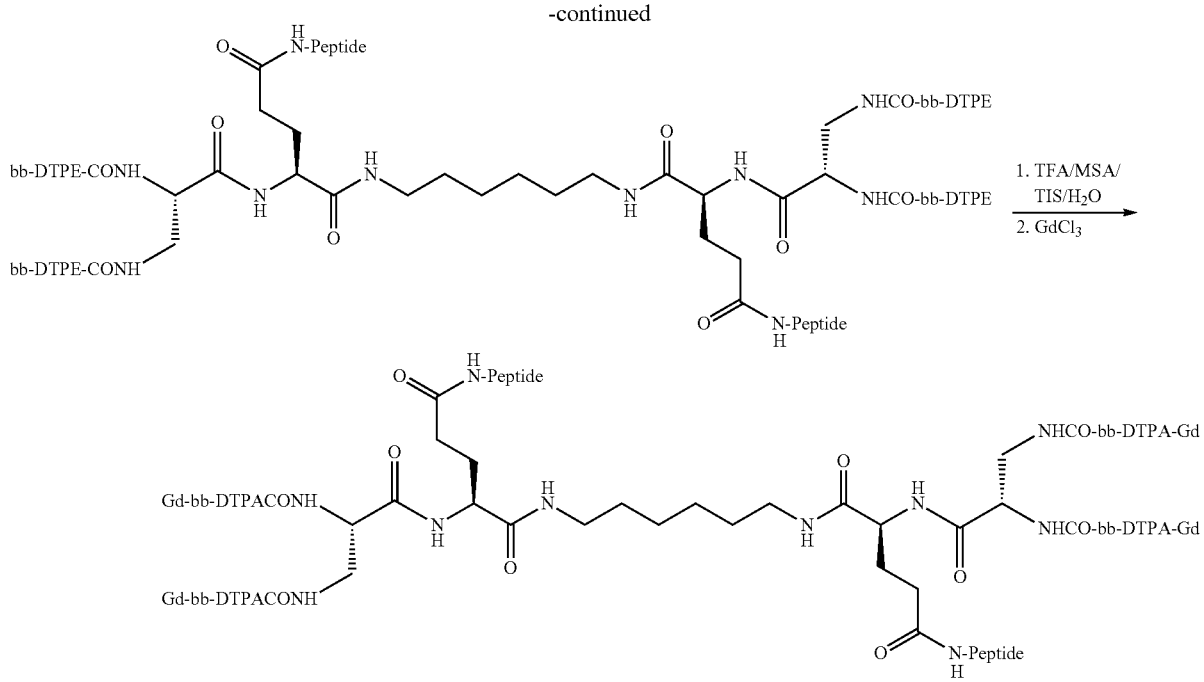

-continued

Coupling of the Diacid Tetramer to the N-Terminus of the Peptide.

The diacid, SEQ ID NO. 264 peptide (1.5 eq. per acid) and HOBt, 1H$_2$O were dissolved in DMF. DIC (1.1 eq. per acid) dissolved in DMF was added and the pH was adjusted to 7-8 with DIEA. The reaction was monitored by LC-MS. The protected tetramer was purified by HPLC with a C4 column using a gradient of 0.1% TFA in ACN/H$_2$O.

Deprotection of Dual Peptide-Tetramer

Protected tetramer-dual peptide was dissolved in the deprotection cocktail mixture (10 ml/80 mg of tetramer dual peptide) composed of TFA/methanesulfonic acid/TIS/H$_2$O 87.5:2.5:5:5 and the solution was stirred for 1.5 h at RT. The crude ligand was obtained after precipitation with ether and filtration.

Chelation and Purification of Compound ID 803.

The crude ligand was dissolved in H$_2$O and the pH was adjusted to 6 with 1 N NaOH. Solid GdCl$_3$.6H$_2$O (4.5 eq) was added at RT and the pH re-adjusted to 6.5. The solution was stirred for an hour and the resultant solution was cloudy. Na$_2$H$_2$EDTA solution (0.1 M) was added dropwise with stirring until the solution became clear. The resultant solution was purified by preparative HPLC (Kromasil C18, ammonium formate (50 mM)/ACN). The product was analyzed by LC-MS and gave the correct mass.

16. Langendorff Heart Model

A. General Langendorff Preparation

After deep anesthesia with pentobarbital (80 mg/kg ip), the chest cavity of a male Sprague Dawley rat (300 g) was opened, retracted and the heart was removed immediately and placed in an ice-cold normal Krebs-Henseleit (K-H) solution (NaCl, 118 mM; KCl, 4.7 mM; CaCl$_2$, 2.5 mM; MgSO$_4$, 1.2 mM; KH$_2$PO$_4$, 1.2 mM; NaHCO$_3$, 25 mM; glucose, 5.5 mM). A K-H buffer filled 20 Gauge needle was inserted into the apex of the heart penetrating into the bottom of the chamber. This was attached to a pressure transducer used to record and monitor heart function. Perfusion pressure (~60 mmHg) was monitored using a second transducer. The heart was perfused at a constant flow rate of 10-12 mL/min with 37° C. Krebs-Henseleit buffer saturated with a mixture of 95% O$_2$ and 5% CO$_2$ gas. The heart was paced at 300 beats/min.

B. Equilibrium Binding to Perfused Langendorff Rat Heart

The dual peptide gadolinium tetramer (Compound ID 803) was compared to GdDTPA. Compound ID 803 and GdDTPA were added to the K-H buffer solution to a total concentration of 3 μM. Also added to the K-H buffer was a radiotracer analog of Compound ID 803 or GdDTPA. For Compound ID 803, the radiotracer was an aliquot of the In-111 labeled compound. For GdDTPA, the tracer added was Tc-99m labeled DTPA. The amount of radioactivity added to the buffer solution was 1-5 μCi.

The heart was perfused for a period of 10 minutes and the perfusion solution was recycled through the heart. The total volume of K-H buffer used was 50-60 mL. After 10 min, the heart was removed from the apparatus and any connective tissue was removed. The heart was opened, fluid in the chambers drained, and the interior blotted dry with filter paper. The heart was then weighed and the radioactivity in the heart measured with a Packard Cobra 5003 Gamma Scintillation counter. An aliquot of the K-H buffer was also weighed and counted. Studies were performed at least in duplicate.

Results:

| Compound | N | Heart (nmol/g) | Buffer (μM) | Heart:Buffer |
|---|---|---|---|---|
| Comp ID 803 | 2 | 9.1 ± 1.8 | 3.0 | 3.02 ± 0.62 |
| GdDTPA | 3 | 1.4 ± 0.02 | 3.0 | 0.46 ± 0.05 |

Conclusion:

GdDTPA is a marker of extracellular space. It was used as a negative control. The amount of GdDTPA in the heart is representative of the buffer present in the heart. Compound ID 803, with good collagen binding, exhibits about 7 times more heart uptake than GdDTPA. This indicates specific heart uptake for the collagen binding compound.

C. Washout Kinetics of the Collagen Binding Compound (Compound ID NO: 803) from Perfused Langendorff Rat Heart A Langendorff rat heart preparation was perfused with K-H buffer at a rate of 10-12 mL/min. A one mL solution containing Compound ID NO:803 (300 μM), radiolabeled (In-111) Compound ID NO:803 (1-6 μCi), GdDTPA (300 μM), and radiolabeled (Tc-99m) DTPA (5-8 μCi) was infused into the heart at a rate of 1 mL/29639-0002002 min. After the infusion was finished, the heart was either removed or perfusion was allowed to continue for an additional 10 minutes and then the heart was removed. The perfusion buffer was not recirculated through the heart. After removal of any connective tissue, the heart was opened, fluid in the chambers drained, and the interior blotted dry with filter paper. The heart was then weighed and the radioactivity in the heart measured with a Packard Cobra 5003 Gamma Scintillation counter. The Tc-99m counts were measured in the window 128-165 keV; the 1-125 counts were measured in the window 15-75 keV with a 5% correction for spillover from the technetium. An aliquot of the K-H buffer was also weighed and counted. Concentration estimates were decay corrected. Studies were performed at least in duplicate.

Results:

| Compound | N | Time after infusion (min) | Heart (% ID/g) |
|---|---|---|---|
| Comp ID 803 | 3 | 0 | 2.03 ± 0.23 |
| GdDTPA | 3 | 0 | 2.53 ± 0.50 |
| Comp ID 803 | 3 | 10 | 1.09 ± 0.53 |
| GdDTPA | 2 | 10 | 0.056 ± 0.011 |

Conclusion:

The collagen binding compound (Compound ID No: 803) is significantly retained in the heart after perfusion with buffer for 10 minutes. At 10 minutes after infusion of the compounds, 54% of Compound ID No: 803 that was present at 0 minutes post infusion remains, compared to only 2.2% for GdDTPA. This indicates that the collagen binding compound (Compound ID NO: 803) binds to and is retained by the heart.

17. GdDTPA Substituted Peptides

A. N-Terminal Functionalized Peptide-Chelate Conjugates

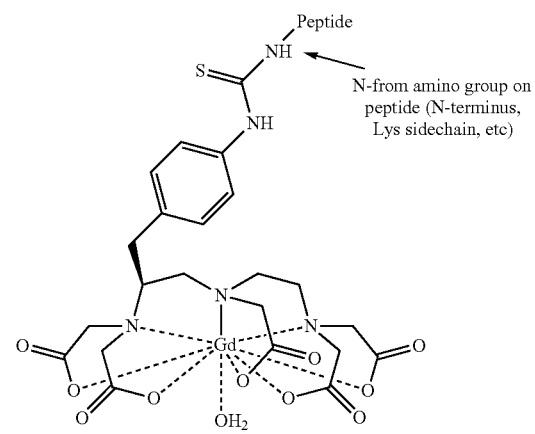

TABLE 42

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| Comp ID | SEQ ID NO | SEQ ID NO | Sequence | | | | | | | |
|---|---|---|---|---|---|---|---|---|---|---|
| 800 | 496 | 496 | $Gd^T$ | G | K(G.$Gd^T$) | W | H | C | T | T | K($Gd^T$) |
| 801 | 497 | 497 | $Gd^T$ | K($Gd^T$) | K($Gd^T$) | W | H | C | Y | T | Y |
| 802 | 498 | 498 | $Gd^T$ | DK($Gd^D$) | K($Gd^D$) | W | H | C | Y | T | Y |
| 807 | 499 | 499 | $Gd^T$ | G | Q | W | H | C | T | T | R |
| 808 | 500 | 500 | $Gd^T$ | G | Q | W | H | C | T | T | R |
| 813 | 501 | 501 | $Gd^T$ | G | Q | W | H | C | T | T | K($Gd^T$) |
| 815 | 502 | 502 | $Gd^T$ | G | Q | W | H | C | T | T | R |
| 816 | 503 | 503 | $Gd^T$ | G | Q | W | H | C | T | T | Y |
| 820 | 504 | 504 | $Gd^G$ | G | Q | W | T | C | S | G | D |
| 821 | 505 | 505 | $Gd^G$ | | D | W | T | C | S | r | D |
| 822 | 506 | 506 | $Gd^G$ | | D | W | T | C | R | G | D |
| 823 | 507 | 507 | $Gd^G$ | G | Q | W | T | C | S | G | D |
| 824 | 508 | 508 | $Gd^G$ | | P | W | T | C | S | G | D |
| 825 | 509 | 509 | $Gd^T$ | | D | W | T | C | Y(Bn,3-Cl) | G | D |
| 826 | 510 | 510 | $Gd^T$ | G | Q | W | T | C | Y | G | D |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 827 511 511 | $Gd^T$ | | D | W | T | C | F(4-tBu) | G | D |
| 828 512 512 | $Gd^T$ | | D | W | T | C | F(4-CO2H) | G | D |
| 829 513 513 | $Gd^T$ | | D | W | T | C | S | y | D |
| 830 514 514 | $Gd^T$ | G | A | W | T | C | S | G | D |
| 831 515 515 | $Gd^T$ | | D | W | T | C | S | G | D |
| 832 516 516 | $Gd^T$ | G | Q | W | T | C | S | G | D |
| 833 517 517 | $Gd^T$ | G | Q | W | T | C | S | G | D |
| 834 518 518 | $Gd^T$ | | D | W | T | C | S | G | D |
| 835 519 519 | $Gd^T$ | | D | W | T | C | S | a | D |
| 836 520 520 | $Gd^T$ | | D | W | T | C | S | s | D |
| 837 521 521 | $Gd^T$ | G | Q | W | T | C | S | G | D |
| 838 522 522 | $Gd^{GM}$ | G | Q | W | T | C | S | G | D |
| 839 523 523 | $Gd^T$ | G | Q | W | T | C | S | G | D |
| 840 524 524 | $Gd^T$ | G | Q | W | A | C | S | G | D |
| 841 525 525 | $Gd^T$ | G | Q | W | T | C | S | G | D |
| 842 526 526 | $Gd^T$ | | D | W | T | C | S | G | D |
| 843 527 527 | $Gd^T$ | | D | W | T | C | Y(3-NO2) | G | D |
| 844 528 528 | $Gd^T$ | | D | W | T | C | Y | G | D |
| 845 529 529 | $Gd^T$ | | D | W | T | C | S | G | D |
| 846 530 530 | $Gd^T$ | | D | W | T | C | S | G | D |
| 847 531 531 | $Gd^T$ | | D | W | T | C | S | d-leu | D |
| 848 532 532 | $Gd^T$ | | D | W | T | C | S | G | D |
| 849 533 533 | $Gd^T$ | | D | W | T | C | 4-Pal | G | D |
| 850 534 534 | $Gd^T$ | | D | W | T | C | S | G | D |
| 851 535 535 | $Gd^T$ | G | Q | W | H | C | T | T | D |
| 852 536 536 | $Gd^T$ | G | Q | W | H | C | T | T | S |
| 853 537 537 | $Gd^T$ | G | Q | W | H | C | T | T | A |
| 854 538 538 | $Gd^T$ | PP | Q | W | H | C | T | T | R |
| 855 539 539 | $Gd^T$ | G | Q | W | H | C | T | T | R |
| 856 540 540 | $Gd^T$ | PP | Q | W | H | C | T | T | R |
| 857 541 541 | $Gd^T$ | G | A | W | H | C | T | T | R |
| 858 542 542 | $Gd^T$ | G | Q | W | H | C | T | T | R |
| 859 543 543 | $Gd^T$ | G | Q | W | H | C | T | T | R |
| 860 544 544 | $Gd^T$ | G | Q | W | H | C | T | T | R |
| 861 545 545 | $Gd^T$ | G | Q | W | H | C | T | T | Y |
| 862 546 546 | $Gd^T$ | G | Q | W | H | C | T | T | L |
| 863 547 547 | $Gd^T$ | G | Q | W | H | C | T | T | L |
| 864 548 548 | $Gd^T$ | G | Q | W | H | C | T | T | R |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 865 | 549 | 549 | $Gd^T$ | G | Q | W | H | C | T | T | R |
| 866 | 550 | 550 | $Gd^T$ | G | q | W | H | C | T | T | R |
| 867 | 551 | 551 | $Gd^T$ | G | Q | W | H | C | T | T | R |
| 868 | 552 | 552 | $Gd^T$ | G | Q | thien-W | H | C | T | T | R |
| 869 | 553 | 553 | $Gd^T$ | G | Q | W | H | C | T | T | S |
| 870 | 554 | 554 | $Gd^T$ | G | Q | W | S | C | T | T | R |
| 871 | 555 | 555 | $Gd^T$ | G | Q | W | H | C | T | T | R |
| 872 | 556 | 556 | $Gd^T$ | G | Q | 2-Nal | H | C | T | T | R |
| 873 | 557 | 557 | $Gd^T$ | G | Q | W | H | C | T | T | R |
| 874 | 558 | 558 | | G | Q | W | H | C | T | T | Y |
| 875 | 559 | 559 | $Gd^T$ | GK(G.GdT) | Q | W | H | C | T | T | Y |
| 876 | 560 | 560 | $Gd^T$ | G | Q | W | A | C | T | T | R |
| 877 | 561 | 561 | $Gd^T$ | G | Q | W | H | C | A | T | R |
| 878 | 562 | 562 | $Gd^T$ | G | Q | W | H | C | T | T | R |
| 879 | 563 | 563 | $Gd^T$ | G | Q | W | H | C | T | t | R |
| 880 | 564 | 564 | $Gd^T$ | G | Q | W | H | C | T | T | R |
| 881 | 565 | 565 | $Gd^T$ | G | Q | W | H | C | T | T | R |
| 882 | 566 | 566 | $Gd^T$ | G | Q | W | H | C | T | T | D |
| 883 | 567 | 567 | $Gd^T$ | G | Q | W | H | C | T | T | D |
| 884 | 568 | 568 | $Gd^T$ | G | Q | W | H | C | T | T | D |
| 885 | 569 | 569 | $Gd^T$ | G | Q | W | H | C | T | T | D |
| 886 | 570 | 570 | $Gd^T$ | G | Q | W | H | C | T | T | D |
| 887 | 571 | 571 | $Gd^T$ | G | Q | W | H | C | T | T | D |
| 888 | 572 | 572 | $Gd^T$ | G | Q | W | H | C | T | T | D |
| 889 | 573 | 573 | $Gd^T$ | G | Q | W | H | C | T | T | D |
| 890 | 574 | 574 | $Gd^T$ | G | Q | W | H | C | T | T | D |
| 891 | 575 | 575 | $Gd^T$ | G | Q | W | H | C | T | T | D |
| 892 | 576 | 576 | $Gd^T$ | G | Q | W | H | C | T | T | D |
| 893 | 577 | 577 | $Gd^T$ | G | Q | W | H | C | T | T | D |
| 894 | 578 | 578 | $Gd^T$ | G | Q | W | H | C | T | T | D |
| 895 | 579 | 579 | $Gd^T$ | G | Q | W | H | C | T | T | D |
| 896 | 580 | 580 | $Gd^T$ | G | Q | W | H | Pen | T | T | R |
| 897 | 581 | 581 | $Gd^T$ | G | Q | W | H | C | T | n | R |
| 898 | 582 | 582 | $Gd^T$ | G | Q | W | H | C | T | s | R |
| 899 | 583 | 583 | $Gd^T$ | G | Q | W | H | C | T | y | R |
| 900 | 584 | 584 | $Gd^T$ | G | Q | W | H | C | T | r | R |
| 901 | 585 | 585 | $Gd^T$ | G | Q | W | H | C | T | T | R |
| 902 | 586 | 586 | $Gd^T$ | G | Q | W | H | C | T | T | R |
| 903 | 587 | 587 | $Gd^T$ | G | Q | W | H | C | T | T | R |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | | |
|---|---|---|---|---|---|---|---|---|---|---|
| 904 | 588 | 588 | $Gd^T$ | G | Q | W | H | C | T | T | R |
| 905 | 589 | 589 | $Gd^T$ | G | Q | W | H | C | T | T | R |
| 906 | 590 | 590 | $Gd^T$ | G | Q | W | H | C | T | T | R |
| 907 | 591 | 591 | $Gd^T$ | G | Q | W | H | C | T | T | L |
| 908 | 592 | 592 | $Gd^T$ | G | A | W | H | C | T | T | L |
| 909 | 593 | 593 | $Gd^T$ | | A | W | H | C | T | T | L |
| 910 | 594 | 594 | $Gd^T$ | G | D | W | H | C | T | T | L |
| 911 | 595 | 595 | $Gd^T$ | G | S | W | H | C | T | T | L |
| 912 | 596 | 596 | $Gd^T$ | P | P | W | H | C | T | T | L |
| 913 | 597 | 597 | $Gd^T$ | G | Q | W | H | C | T | T | L |
| 914 | 598 | 598 | $Gd^T$ | G | Q | W | H | C | T | T | Y |
| 915 | 599 | 599 | $Gd^T$ | G | A | W | H | C | T | T | Y |
| 916 | 600 | 600 | $Gd^T$ | G | Q | W | H | C | T | T | Y(3-Cl) |
| 917 | 601 | 601 | $Gd^T$ | G | Q | W | H | C | T | T | I |
| 918 | 602 | 602 | $Gd^T$ | G | Q | W | H | C | T | T | Cha |
| 919 | 603 | 603 | $Gd^G$ | G | Q | W | H | C | T | T | Y |
| 920 | 604 | 604 | $Gd^G$ | G | Q | W | H | C | Y | T | L |
| 921 | 605 | 605 | $Gd^T$ | G | Q | W | H | C | T | Y | L |
| 922 | 606 | 606 | $Gd^T$ | G | Q | W | N | C | T | T | L |
| 923 | 607 | 607 | $Gd^T$ | G | Q | W | H | C | T | T | L |
| 924 | 608 | 608 | $Gd^T$ | G | Q | W | H | C | T | T | L |
| 925 | 609 | 609 | | cbz-G | Q | W | H | C | T | T | R |
| 926 | 610 | 610 | | cbz-G | Q | W | H | C | T | T | K($Gd^T$) |
| 927 | 611 | 611 | $Gd^T$ | G | Q | W | H | C | T | T | L |
| 928 | 612 | 612 | $Gd^T$ | G | Q | W | H | C | T | T | L |
| 929 | 613 | 613 | $Gd^T$ | G | Q | W | H | C | T | T | F(4-F) |
| 930 | 614 | 614 | $Gd^T$ | G | K(G.$Gd^T$) | W | H | C | T | T | L |
| 931 | 615 | 615 | $Gd^T$ | G | Q | W | H | C | T | T | R |
| 932 | 616 | 616 | $Gd^T$ | G | Q | W | H | C | T | T | R |
| 933 | 617 | 617 | $Gd^T$ | G | Q | W | H | C | T | T | R |
| 934 | 618 | 618 | $Gd^T$ | G | Q | W | H | C | T | T | R |
| 935 | 619 | 619 | $Gd^T$ | G | Q | W | H | C | T | T | R |
| 936 | 620 | 620 | $Gd^T$ | G | Q | W | H | C | T | D | R |
| 937 | 621 | 621 | $Gd^T$ | | A | W | H | C | T | T | R |
| 938 | 622 | 622 | $Gd^T$ | G | Q | W | H | C | T | T | R |
| 939 | 623 | 623 | | cbz-G | Q | W | H | C | T | Dpr($Gd^T$) | R |
| 940 | 624 | 624 | | cbz-G | Q | W | H | C | T | K(GdT) | R |
| 941 | 625 | 625 | | cbz-G | Q | W | H | C | T | Orn($Gd^T$) | R |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 942 | 626 | 626 | $Gd^T$ | G | K(G.$Gd^T$) | W | H | C | T | T | Y |
| 943 | 627 | 627 | $Gd^T$ | G | K(G.$Gd^T$) | W | H | C | Y | T | Y |
| 944 | 628 | 628 | $Gd^T$ | G | K(G.$Gd^T$) | W | H | C | Y | T | Y |
| 945 | 629 | 629 | $Gd^T$ | G | K(G.$Gd^T$) | W | H | C | Y | T | Y |
| 946 | 630 | 630 | $Gd^T$ | G | K(G.$Gd^T$) | W | H | C | T | T | Y |
| 947 | 631 | 631 | $Gd^T$ | G | K(G.$Gd^T$) | W | H | C | T | T | Y |
| 948 | 632 | 632 | $Gd^T$ | G | K(G.$Gd^T$) | W | H | C | T | T | Y |
| 949 | 633 | 633 | $Gd^T$ | G | K(G.$Gd^T$) | W | H | C | T | T | Y |
| 950 | 634 | 634 | $Gd^T$ | G | K(G.$Gd^T$) | W | H | C | T | T | Y |
| 951 | 635 | 635 | $Gd^T$ | G | K(G.$Gd^T$) | W | H | C | T | T | Y |
| 952 | 636 | 636 | $Gd^T$ | G | K(G.$Gd^T$) | W | H | C | T | T | Y |
| 953 | 637 | 637 | $Gd^T$ | G | K(G.$Gd^T$) | W | H | C | T | T | Y |
| 954 | 638 | 638 | $Gd^T$ | G | Q | W | H | C | T | T | R |
| 955 | 639 | 639 | $Gd^T$ | G | Q | W | H | C | T | T | R |
| 956 | 640 | 640 | $Gd^T$ | G | Q | W | K($Gd^T$) | C | T | T | R |
| 957 | 641 | 641 | $Gd^T$ | G | Q | W | H | C | K($Gd^T$) | T | R |
| 958 | 642 | 642 | $Gd^T$ | G | Q | W | H | C | T | T | R |
| 959 | 643 | 643 | $Gd^T$ | G | Q | W | H | C | Y | T | L |
| 960 | 644 | 644 | $Gd^T$ | K($Gd^T$) | K(K($Gd^T$)$Gd^T$) | G.Q.W | H | C | T | T | Y |
| 961 | 645 | 645 | $Gd^D$ | GK(G.$Gd^D$) | Q | W | H | C | T | T | Y |
| 962 | 646 | 646 | $Gd^T$ | G | K(G.$Gd^T$) | W | H | C | T | T | Y |
| 963 | 647 | 647 | $Gd^T$ | G | K(G.$Gd^T$) | W | H | C | Y | T | Y |
| 964 | 648 | 648 | $Gd^T$ | G | K(G.$Gd^T$) | W | H | C | Y | T | Y |
| 965 | 649 | 649 | $Gd^T$ | G | K(G.$Gd^T$) | W | H | C | T | T | Y |
| 966 | 650 | 650 | $Gd^T$ | G | K(G.$Gd^T$) | W | H | C | T | T | L |
| 967 | 651 | 651 | $Gd^T$ | G | K(G.$Gd^T$) | W | H | C | T | T | Y |
| 968 | 652 | 652 | $Gd^T$ | G | K(G.$Gd^T$) | W | H | C | T | T | Y |
| 969 | 653 | 653 | $Gd^T$ | G | K(G.$Gd^T$) | W | H | C | T | T | Y |
| 970 | 654 | 654 | $Gd^T$ | G | K(G.$Gd^T$) | W | H | C | T | T | Y |
| 971 | 655 | 655 | $Gd^T$ | G | K(G.$Gd^T$) | W | H | C | T | T | Y |
| 972 | 656 | 656 | $Gd^T$ | G | K(G.$Gd^T$) | W | H | C | T | T | Y |
| 973 | 657 | 657 | $Gd^T$ | G | K(G.$Gd^T$) | W | H | C | Y(3-I) | T | Y |
| 974 | 658 | 658 | $Gd^T$ | G | K(G.$Gd^T$) | W | H | C | Y | T | Y |
| 975 | 659 | 659 | $Gd^T$ | G | K(G.$Gd^T$) | W | H | C | T | T | Y |
| 976 | 660 | 660 | $Gd^T$ | G | K(G.$Gd^T$) | W | H | C | T | T | Y |
| 977 | 661 | 661 | $Gd^T$ | G | K(G.$Gd^T$) | W | H | C | T | T | Y |
| 978 | 662 | 662 | $Gd^T$ | G | K(G.$Gd^T$) | W | H | C | Y | T | K($Gd^T$) |
| 979 | 663 | 663 | $Gd^T$ | G | K(G.$Gd^T$) | W | H | C | Y | T | K($Gd^T$) |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 980 664 664 | $Gd^T$ | G | K(G.$Gd^T$) | W | H | C | T | T | K($Gd^T$) |
| 981 665 665 | $Gd^T$ | G.Y | K(Y.G.$Gd^T$) | W | H | C | T | T | Y |
| 982 666 666 | $Gd^T$ | G.V | K(V.G.$Gd^T$) | W | H | C | T | T | Y |
| 983 667 667 | $Gd^T$ | G.F | K(F.G.$Gd^T$) | W | H | C | T | T | Y |
| 984 668 668 | $Gd^T$ | G.H | K(H.G.$Gd^T$) | W | H | C | T | T | Y |
| 985 669 669 | $Gd^T$ | G | K(G.$Gd^T$) | W | H | C | Y | T | Y |
| 986 670 670 | $Gd^T$ | G | K(G.$Gd^T$) | W | H | C | Y | T | Y |
| 987 671 671 | $Gd^T$ | G | K(G.$Gd^T$) | W | H | C | Y | T | Y |
| 988 672 672 | $Gd^T$ | G | K(G.$Gd^T$) | W | H | C | Y | T | Y |
| 989 673 673 | $Gd^T$ | G | K(G.$Gd^T$) | W | H | C | Y | T | Y |
| 990 674 674 | $Gd^T$ | G | K(G.$Gd^T$) | W | Y | C | T | T | Y |
| 991 675 675 | $Gd^T$ | G | K(G.$Gd^T$) | W | H | C | Y | K(GdT) | Y |
| 992 676 676 | $Gd^T$ | G | K(G.$Gd^T$) | W | H | C | Y | T | Y |
| 993 677 677 | $Gd^T$ | G | Q | W | H | C | Y | T | K($Gd^T$) |
| 994 678 678 | $Gd^T$ | G | Q | W | H | C | Y | T | Y |
| 995 679 679 | $Gd^T$ | G | K(G.$Gd^T$) | W | H | C | Y | T | K($Gd^T$) |
| 996 680 680 | $Gd^T$ | G | K(G.$Gd^T$) | W | H | C | Y | T | Y |
| 997 681 681 | $Gd^T$ | K($Gd^T$) | K(G.$Gd^T$) | W | H | C | Y | T | K($Gd^T$) |
| 998 682 682 | $Gd^T$ | G. | K(G.$Gd^T$) | W | H | C | Y | T | Y |
| 999 683 683 | $Gd^T$ | G. | K(G.$Gd^T$) | W | H | C | Y | T | Y |
| 1000 684 684 | $Gd^T$ | G | K(G.$Gd^T$) | W | H | C | Y | T | Y |
| 1001 685 685 | $Gd^D$ | G | K(G.$Gd^D$) | W | H | C | T | T | K($Gd^D$) |
| 1002 686 686 | $Gd^T$ | Dpr($Gd^T$) | Dpr(Dpr($Gd^T$)$Gd^T$) | W | H | C | Y | T | Y |
| 1003 687 687 | $Gd^T$ | K($Gd^T$) | K(K($Gd^T$)$Gd^T$) | W | H | C | Y | T | Y |
| 1004 688 688 | $Gd^T$ | G | K(G.$Gd^T$) | W | H | C | Y | T | K($Gd^T$) |
| 1005 689 689 | $Gd^T$ | G | K(G.$Gd^T$) | W | H | C | Y | T | Dab($Gd^T$) |
| 1006 690 690 | $Gd^T$ | G | K(G.$Gd^T$) | W | H | C | Y | T | Dpr($Gd^T$) |
| 1007 691 691 | $Gd^T$ | G | Dab(G.$Gd^T$) | W | H | C | Y | T | K($Gd^T$) |
| 1008 692 692 | $Gd^T$ | K($Gd^T$) | W | H | C | Y | T | K($Gd^T$) | F |
| 1009 693 693 | $Gd^T$ | G | K(G.$Gd^T$) | W | H | C | Y | T | K($Gd^T$) |
| 1010 694 694 | $Gd^T$ | G | K(G.$Gd^T$) | W | H | C | Y | T | K($Gd^T$) |
| 1011 695 695 | $Gd^T$ | G | K(G.$Gd^T$) | W | H | C | Y | T | K($Gd^T$) |
| 1012 696 696 | $Gd^T$ | G | K(G.$Gd^T$) | W | H | C | Y | T | K($Gd^T$) |
| 1013 697 697 | $Gd^T$ | G | K(G.$Gd^T$) | W | H | C | Y | T | K($Gd^T$) |
| 1014 698 698 | $Gd^T$ | K($Gd^D$) | K($Gd^D$) | W | H | C | Y | T | Y |
| 1015 699 699 | $Gd^D$ | K($Gd^D$) | K($Gd^D$) | G.W | H | C | Y | T | Y |
| 1016 700 700 | $Gd^D$ | K($Gd^D$) | K($Gd^D$) | A.W | H | C | Y | T | Y |
| 1017 701 701 | $Gd^D$ | K($Gd^D$) | K($Gd^D$) | L.W | H | C | Y | T | Y |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| Comp ID | SEQ ID NO | SEQ ID NO | | | | | | | | |
|---|---|---|---|---|---|---|---|---|---|---|
| 1018 | 702 | 702 | $Gd^D$ | K($Gd^D$) | K($Gd^D$) | Y.W | H | C | Y | T | Y |
| 1019 | 703 | 703 | $Gd^T$ | G | K(G.$Gd^T$) | W | H | C | Y | T | Y |

| Comp ID | SEQ ID NO | SEQ ID NO | Sequence | | | | | | | |
|---|---|---|---|---|---|---|---|---|---|---|
| 800 | 496 | 496 | F | P | H | H | Y | C | L | Y | Bip |
| 801 | 497 | 497 | F | P | H | H | Y | C | V | Y | G |
| 802 | 498 | 498 | F | P | H | H | Y | C | L | Y | G |
| 807 | 499 | 499 | F | P | H | H | Y | C | L | Y | G |
| 808 | 500 | 500 | F | P | H | H | Y | C | L | Y | G |
| 813 | 501 | 501 | F | P | H | H | Y | C | L | Y | G |
| 815 | 502 | 502 | F | P | H | H | Y | C | K($Gd^T$) | Y | G |
| 816 | 503 | 503 | F | P | H | H | Y | C | L | Y | G |
| 820 | 504 | 504 | A | Y | T | W | H | C | A | Y | E |
| 821 | 505 | 505 | E | Y | T | W | H | C | N | Y | E |
| 822 | 506 | 506 | E | Y | T | W | H | C | N | Y | E |
| 823 | 507 | 507 | E | Y | T | W | H | C | N | Y | |
| 824 | 508 | 508 | E | Y | A | W | H | C | N | Y | e |
| 825 | 509 | 509 | E | Y | T | W | H | C | N | Y | E |
| 826 | 510 | 510 | E | Y | T | W | Y | C | N | Y | E |
| 827 | 511 | 511 | E | Y | T | W | H | C | N | Y | E |
| 828 | 512 | 512 | E | Y | T | W | H | C | N | Y | E |
| 829 | 513 | 513 | E | Y | T | W | H | C | N | Y | E |
| 830 | 514 | 514 | E | Y | T | W | H | C | N | Y | E |
| 831 | 515 | 515 | E | Y | T | W | H | C | N | Y(3-I) | E |
| 832 | 516 | 516 | E | Y | A | W | H | C | N | Y | e |
| 833 | 517 | 517 | E | Y | T | W | A | C | N | Y | E |
| 834 | 518 | 518 | E | Y | Y | W | H | C | N | Y | E |
| 835 | 519 | 519 | E | Y | T | W | H | C | N | Y | E |
| 836 | 520 | 520 | E | Y | T | W | H | C | N | Y | E |
| 837 | 521 | 521 | E | Y | T | W | H | C | N | Y | E |
| 838 | 522 | 522 | A | Y | T | W | H | C | N | Y | E |
| 839 | 523 | 523 | E | Y | T | W | H | C | A | Y | E |
| 840 | 524 | 524 | E | Y | T | W | H | C | N | Y | E |
| 841 | 525 | 525 | E | Y | T | W | H | C | N | Y | A |
| 842 | 526 | 526 | E | Y | T | W | Y | C | N | Y | E |
| 843 | 527 | 527 | E | Y | T | W | H | C | N | Y | E |
| 844 | 528 | 528 | E | Y | T | W | H | C | N | Y | E |
| 845 | 529 | 529 | E | Y | R | W | H | C | N | Y | E |
| 846 | 530 | 530 | E | Y(3-I) | T | W | H | C | N | Y | E |

TABLE 42-continued

Examples of peptide-chelate conjugates. In this table, $Gd^I$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 847 | 531 | 531 | E | Y | T | W | H | C | N | Y | E |
| 848 | 532 | 532 | E | Y | T | W | H | C | N | Y | E |
| 849 | 533 | 533 | E | Y | T | W | H | C | N | Y | E |
| 850 | 534 | 534 | E | Y | T | W | H | C | N | Y | Aib |
| 851 | 535 | 535 | F | P | H | H | Y | C | L | Y | G |
| 852 | 536 | 536 | F | P | H | H | Y | C | L | Y | G |
| 853 | 537 | 537 | F | P | H | H | Y | C | L | Y | G |
| 854 | 538 | 538 | F | P | H | H | Y | C | L | Y | G |
| 855 | 539 | 539 | F | P | H | H | Y | C | A | Y | G |
| 856 | 540 | 540 | F | HyP | H | H | Y | C | L | Y | G |
| 857 | 541 | 541 | F | P | H | H | Y | C | L | Y | G |
| 858 | 542 | 542 | F | P | H | H | Y | C | L | Y | G |
| 859 | 543 | 543 | Y | P | H | H | Y | C | L | Y | G |
| 860 | 544 | 544 | 1-Nal | P | H | H | Y | C | L | Y | G |
| 861 | 545 | 545 | F | P | H | H | Y | C | L | Y | G |
| 862 | 546 | 546 | F | P | H | H | Y | C | L | Y | G |
| 863 | 547 | 547 | F | P | H | H | Y | C | L | Y | G |
| 864 | 548 | 548 | F | P | H | H | y | C | L | Y | G |
| 865 | 549 | 549 | F | P | A | H | Y | C | L | Y | G |
| 866 | 550 | 550 | F | P | H | H | Y | C | L | Y | G |
| 867 | 551 | 551 | F | P | H | H | 1-Nal | C | L | Y | G |
| 868 | 552 | 552 | F | P | H | H | Y | C | L | Y | G |
| 869 | 553 | 553 | F | P | H | H | Y | C | L | Y | G |
| 870 | 554 | 554 | F | P | H | H | Y | C | L | Y | G |
| 871 | 555 | 555 | F | P | H | H | Y | C | L | Y | G |
| 872 | 556 | 556 | F | P | H | H | Y | C | L | Y | G |
| 873 | 557 | 557 | F | P | H | H | Bip | C | L | Y | G |
| 874 | 558 | 558 | F | P | H | H | Y | C | L | Y | G |
| 875 | 559 | 559 | F | P | H | H | Y | C | L | Y | G |
| 876 | 560 | 560 | F | P | H | H | Y | C | L | Y | G |
| 877 | 561 | 561 | F | P | H | H | Y | C | L | Y | G |
| 878 | 562 | 562 | F | P | H | A | Y | C | L | Y | G |
| 879 | 563 | 563 | F | P | H | H | Y | C | L | Y | G |
| 880 | 564 | 564 | F | P | S | H | Y | C | L | Y | G |
| 881 | 565 | 565 | Bip | P | H | H | Y | C | L | Y | G |
| 882 | 566 | 566 | Bpa | P | H | H | Y | C | L | Y | G |
| 883 | 567 | 567 | F(4-CN) | P | H | H | Y | C | L | Y | G |
| 884 | 568 | 568 | F(4-NH2) | P | H | H | Y | C | L | Y | G |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 885 | 569 | 569 | F(4-NH2)(Gd$^T$) | P | H | H | Y | C | L | Y | G |
| 886 | 570 | 570 | F | P | H | Dpr | Y | C | L | Y | G |
| 887 | 571 | 571 | F | P | H | Dpr(Gd$^T$) | Y | C | L | Y | G |
| 888 | 572 | 572 | F | P | H | 2-Pal | Y | C | L | Y | G |
| 889 | 573 | 573 | F | P | H | H | Y | C | L | Bpa | G |
| 890 | 574 | 574 | F | P | H | H | Y | C | L | F | G |
| 891 | 575 | 575 | F | P | H | H | Y | C | L | 2-Nal | G |
| 892 | 576 | 576 | F | P | H | H | Y | C | L | Y(3-Cl) | G |
| 893 | 577 | 577 | F(3,4-OMe) | P | H | H | Y | C | L | Y | G |
| 894 | 578 | 578 | 2-Nal | P | H | H | Y | C | L | Y | G |
| 895 | 579 | 579 | Y(3-Cl) | P | H | H | Y | C | L | Y | G |
| 896 | 580 | 580 | F | P | H | H | Y | C | L | Y | G |
| 897 | 581 | 581 | F | P | H | H | Y | C | L | Y | G |
| 898 | 582 | 582 | F | P | H | H | Y | C | L | Y | G |
| 899 | 583 | 583 | F | P | H | H | Y | C | L | Y | G |
| 900 | 584 | 584 | F | P | H | H | Y | C | L | Y | G |
| 901 | 585 | 585 | F | P | H | H | if | C | L | Y | G |
| 902 | 586 | 586 | F | P | H | H | r | C | L | Y | G |
| 903 | 587 | 587 | F | P | H | H | bip | C | L | Y | G |
| 904 | 588 | 588 | F | P | H | H | 1-nal | C | L | Y | G |
| 905 | 589 | 589 | F | P | H | H | t | C | L | Y | G |
| 906 | 590 | 590 | F | P | H | H | Y | Pen | L | Y | G |
| 907 | 591 | 591 | F | P | H | H | y | C | L | Y | G |
| 908 | 592 | 592 | F | P | H | H | y | C | L | Y | G |
| 909 | 593 | 593 | F | P | H | H | y | C | L | Y | G |
| 910 | 594 | 594 | F | P | H | H | y | C | L | Y | G |
| 911 | 595 | 595 | F | P | H | H | y | C | L | Y | G |
| 912 | 596 | 596 | F | P | H | H | y | C | L | Y | G |
| 913 | 597 | 597 | F | P | H | H | 1-Nal | C | L | Y | G |
| 914 | 598 | 598 | F | P | H | H | y | C | L | Y | G |
| 915 | 599 | 599 | F | P | H | H | y | C | L | Y | G |
| 916 | 600 | 600 | F | P | H | H | y | C | L | Y | G |
| 917 | 601 | 601 | F | P | H | H | y | C | L | Y | G |
| 918 | 602 | 602 | F | P | H | H | y | C | L | Y | G |
| 919 | 603 | 603 | F | P | H | H | Y | C | L | Y | G |
| 920 | 604 | 604 | F | P | H | H | Y | C | L | Y | G |
| 921 | 605 | 605 | F | P | H | H | Y | C | L | Y | G |
| 922 | 606 | 606 | F | P | H | H | Y | C | L | Y | G |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 923 | 607 | 607 | F | P | N | H | Y | C | L | Y | G |
| 924 | 608 | 608 | F | P | H | N | Y | C | L | Y | G |
| 925 | 609 | 609 | F | P | H | H | Y | C | L | Y | G |
| 926 | 610 | 610 | F | P | H | H | Y | C | L | Y | G |
| 927 | 611 | 611 | F | P | H | H | Y | C | I | Y | G |
| 928 | 612 | 612 | F | P | H | H | Y | C | V | Y | G |
| 929 | 613 | 613 | F | P | H | H | Y | C | L | Y | G |
| 930 | 614 | 614 | F | P | H | H | Y | C | L | Y | G |
| 931 | 615 | 615 | F | P | H | H | Y | C | F | Y | G |
| 932 | 616 | 616 | F | P | H | H | Y | C | Hfe | Y | G |
| 933 | 617 | 617 | F | P | H | H | h-Tyr | C | L | Y | G |
| 934 | 618 | 618 | F | P | H | H | h-Tyr(Me) | C | L | Y | G |
| 935 | 619 | 619 | F | P | H | H | F(3-OMe) | C | L | Y | G |
| 936 | 620 | 620 | F | P | H | H | Y | C | L | Y | G |
| 937 | 621 | 621 | F | P | A | H | Y | C | L | Y | G |
| 938 | 622 | 622 | F | N-Me-A | H | H | Y | C | L | Y | G |
| 939 | 623 | 623 | F | P | H | H | Y | C | L | Y | G |
| 940 | 624 | 624 | F | P | H | H | Y | C | L | Y | G |
| 941 | 625 | 625 | F | P | H | H | Y | C | L | Y | G |
| 942 | 626 | 626 | F | P | H | H | Y | C | V | Y | G |
| 943 | 627 | 627 | F | P | H | H | Y | C | L | Y | G |
| 944 | 628 | 628 | F | P | H | H | Y | C | V | Y | G |
| 945 | 629 | 629 | F | P | H | H | Y | C | V | Y | Y |
| 946 | 630 | 630 | F | P | Y | H | Y | C | L | Y | G |
| 947 | 631 | 631 | F | P | H | Y | Y | C | L | Y | G |
| 948 | 632 | 632 | F | P | H | W | Y | C | L | Y | G |
| 949 | 633 | 633 | F | P | H | H | Y | C | L | Y | Y |
| 950 | 634 | 634 | F | P | H | H | Y | C | L | Y | Bip |
| 951 | 635 | 635 | F | P | H | H | Bip | C | L | Y | G |
| 952 | 636 | 636 | F | P | H | H | Y(3-Cl) | C | L | Y | G |
| 953 | 637 | 637 | F | P | H | H | Y(2,6-Me2) | C | L | Y | G |
| 954 | 638 | 638 | F | P | H | H | Y | C | L | Y | G |
| 955 | 639 | 639 | F | P | H | H | Y | C | L | Y | G |
| 956 | 640 | 640 | F | P | H | H | Y | C | L | Y | G |
| 957 | 641 | 641 | F | P | H | H | Y | C | L | Y | G |
| 958 | 642 | 642 | F | P | K(Gd$^T$) | H | Y | C | L | Y | G |
| 959 | 643 | 643 | F | P | H | H | Y | C | L | Y | G |
| 960 | 644 | 644 | F | P | H | H | Y | C | L | Y | G |
| 961 | 645 | 645 | F | P | H | H | Y | C | L | Y | G |

TABLE 42-continued

Examples of peptide-chelate conjugates. In this table, Gd$^T$ is GdDTPA-thiourea, Gd$^G$ is GdDTPA-glutamate (GluDTPA), Gd$^{GM}$ is GdDOTA-GlyMe, and Gd$^D$ is GdDOTAGA.

| | | | | | | | | | |
|---|---|---|---|---|---|---|---|---|---|
| 962 646 646 | F | P | T | H | Y | C | L | Y | G |
| 963 647 647 | F | P | Y | H | Y | C | V | Y | G |
| 964 648 648 | F | P | Y | H | Y | C | L | Y | G |
| 965 649 649 | F | P | H | H | V | C | L | Y | G |
| 966 650 650 | F | P | H | H | V | C | L | Y | G |
| 967 651 651 | F | P | H | H | Y | C | L | Bip | G |
| 968 652 652 | F | P | H | H | Bip | C | L | Y | G |
| 969 653 653 | F | P | H | H | Y | C | L | Y | F(4-NH2) |
| 970 654 654 | F | P | H | H | Y | C | L | F(4-NH2) | G |
| 971 655 655 | F | P | H | H | Y | C | L | F(4-NH2) (Gd$^T$) | G |
| 972 656 656 | F | P | H | H | F(4-NH2) | C | L | Y | G |
| 973 657 657 | F | P | H | H | Y | C | L | Y | G |
| 974 658 658 | F | P | H | H | Y | C | V | Y | G |
| 975 659 659 | F | P | H | H | Y | C | V | Y | Y |
| 976 660 660 | F | P | H | H | Y | C | L | Y | Y |
| 977 661 661 | F | P | H | H | Y | C | L | Y | Bip |
| 978 662 662 | F | P | H | H | Y | C | V | Y | G |
| 979 663 663 | F | P | H | H | Y | C | V | Y | Y |
| 980 664 664 | F | P | H | H | Y | C | L | Y | Y |
| 981 665 665 | F | P | H | H | Y | C | L | Y | G |
| 982 666 666 | F | P | H | H | Y | C | L | Y | G |
| 983 667 667 | F | P | H | H | Y | C | L | Y | G |
| 984 668 668 | F | P | H | H | Y | C | L | Y | G |
| 985 669 669 | F | P | H | H | Y | C | L | Y | F |
| 986 670 670 | F | P | H | H | Y | C | L | Y | Phg |
| 987 671 671 | F | P | H | H | Y | C | L | Y | Y |
| 988 672 672 | F | P | H | H | Y | C | L | Y | y |
| 989 673 673 | F | P | H | H | Y | C | L | Y | V |
| 990 674 674 | F | P | H | H | Y | C | L | Y | G |
| 991 675 675 | F | P | H | H | Y | C | L | Y | G |
| 992 676 676 | F | P | H | H | 1-Nal | C | L | Y | G |
| 993 677 677 | F | P | H | H | Y | C | L | Y | G |
| 994 678 678 | F | P | H | H | Y | C | L | Y | G |
| 995 679 679 | F | P | H | H | Y | C | L | Y | G |
| 996 680 680 | F | P | H | H | Y | C | L | Y | G |
| 997 681 681 | F | P | H | H | Y | C | L | Y | Bip |
| 998 682 682 | F | P | H | H | Y | C | V | Y | G |
| 999 683 683 | F | P | H | H | Y | C | V | Y | G |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | | | | | | | |
|---|---|---|---|---|---|---|---|---|---|
| 1000 | 684 | 684 | F | P | H | H | Y | C | V | Y | G |
| 1001 | 685 | 685 | F | P | H | H | Y | C | L | Y | Bip |
| 1002 | 686 | 686 | F | P | H | H | Y | C | V | Y | G |
| 1003 | 687 | 687 | F | P | H | H | Y | C | V | Y | G |
| 1004 | 688 | 688 | F | P | H | H | Y | C | V | Y | Bip |
| 1005 | 689 | 689 | F | P | H | H | Y | C | V | Y | Bip |
| 1006 | 690 | 690 | F | P | H | H | Y | C | V | Y | Bip |
| 1007 | 691 | 691 | F | P | H | H | Y | C | V | Y | Bip |
| 1008 | 692 | 692 | P | H | H | Y | C | V | Y | Bip | |
| 1009 | 693 | 693 | F | P | H | H | Y | C | V | Y | Bip |
| 1010 | 694 | 694 | F | P | H | H | Y | C | V | Y | Y |
| 1011 | 695 | 695 | F | P | Y | H | Y | C | V | Y | Y |
| 1012 | 696 | 696 | F | P | H | H | Y | C | K($Gd^T$) | Y | Bip |
| 1013 | 697 | 697 | F | P | H | H | Y | C | K($Gd^T$) | Y | Y |
| 1014 | 698 | 698 | F | P | H | H | Y | C | V | Y | G |
| 1015 | 699 | 699 | F | P | H | H | Y | C | T | Y | G |
| 1016 | 700 | 700 | F | P | H | H | Y | C | V | Y | G |
| 1017 | 701 | 701 | F | P | H | H | Y | C | V | Y | G |
| 1018 | 702 | 702 | F | P | H | H | Y | C | V | Y | G |
| 1019 | 703 | 703 | F | P | H | H | Y | C | V | Y | Bip |

| Comp ID | SEQ ID NO | SEQ ID NO | Sequence |
|---|---|---|---|
| 800 | 496 | 496 | |
| 801 | 497 | 497 | |
| 802 | 498 | 498 | |
| 807 | 499 | 499 | K($Gd^T$) |
| 808 | 500 | 500 | k($Gd^T$) |
| 813 | 501 | 501 | |
| 815 | 502 | 502 | |
| 816 | 503 | 503 | 1,4 AMB ($Gd^T$) |
| 820 | 504 | 504 | |
| 821 | 505 | 505 | |
| 822 | 506 | 506 | |
| 823 | 507 | 507 | |
| 824 | 508 | 508 | |
| 825 | 509 | 509 | |
| 826 | 510 | 510 | |
| 827 | 511 | 511 | |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | |
|---|---|---|---|
| 828 | 512 | 512 | |
| 829 | 513 | 513 | |
| 830 | 514 | 514 | |
| 831 | 515 | 515 | |
| 832 | 516 | 516 | |
| 833 | 517 | 517 | |
| 834 | 518 | 518 | |
| 835 | 519 | 519 | |
| 836 | 520 | 520 | |
| 837 | 521 | 521 | GTE |
| 838 | 522 | 522 | |
| 839 | 523 | 523 | |
| 840 | 524 | 524 | |
| 841 | 525 | 525 | |
| 842 | 526 | 526 | |
| 843 | 527 | 527 | |
| 844 | 528 | 528 | |
| 845 | 529 | 529 | |
| 846 | 530 | 530 | |
| 847 | 531 | 531 | |
| 848 | 532 | 532 | |
| 849 | 533 | 533 | |
| 850 | 534 | 534 | |
| 851 | 535 | 535 | |
| 852 | 536 | 536 | |
| 853 | 537 | 537 | |
| 854 | 538 | 538 | |
| 855 | 539 | 539 | |
| 856 | 540 | 540 | |
| 857 | 541 | 541 | |
| 858 | 542 | 542 | |
| 859 | 543 | 543 | |
| 860 | 544 | 544 | |
| 861 | 545 | 545 | |
| 862 | 546 | 546 | |
| 863 | 547 | 547 | |
| 864 | 548 | 548 | |
| 865 | 549 | 549 | |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | |
|---|---|---|---|
| 866 | 550 | 550 | |
| 867 | 551 | 551 | |
| 868 | 552 | 552 | |
| 869 | 553 | 553 | |
| 870 | 554 | 554 | |
| 871 | 555 | 555 | |
| 872 | 556 | 556 | |
| 873 | 557 | 557 | |
| 874 | 558 | 558 | PEG(GdG) |
| 875 | 559 | 559 | |
| 876 | 560 | 560 | |
| 877 | 561 | 561 | |
| 878 | 562 | 562 | |
| 879 | 563 | 563 | |
| 880 | 564 | 564 | |
| 881 | 565 | 565 | |
| 882 | 566 | 566 | |
| 883 | 567 | 567 | |
| 884 | 568 | 568 | |
| 885 | 569 | 569 | |
| 886 | 570 | 570 | |
| 887 | 571 | 571 | |
| 888 | 572 | 572 | |
| 889 | 573 | 573 | |
| 890 | 574 | 574 | |
| 891 | 575 | 575 | |
| 892 | 576 | 576 | |
| 893 | 577 | 577 | |
| 894 | 578 | 578 | |
| 895 | 579 | 579 | |
| 896 | 580 | 580 | |
| 897 | 581 | 581 | |
| 898 | 582 | 582 | |
| 899 | 583 | 583 | |
| 900 | 584 | 584 | |
| 901 | 585 | 585 | |
| 902 | 586 | 586 | |
| 903 | 587 | 587 | |
| 904 | 588 | 588 | |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | |
|---|---|---|---|
| 905 | 589 | 589 | |
| 906 | 590 | 590 | |
| 907 | 591 | 591 | |
| 908 | 592 | 592 | |
| 909 | 593 | 593 | |
| 910 | 594 | 594 | |
| 911 | 595 | 595 | |
| 912 | 596 | 596 | |
| 913 | 597 | 597 | |
| 914 | 598 | 598 | |
| 915 | 599 | 599 | |
| 916 | 600 | 600 | |
| 917 | 601 | 601 | |
| 918 | 602 | 602 | |
| 919 | 603 | 603 | |
| 920 | 604 | 604 | |
| 921 | 605 | 605 | |
| 922 | 606 | 606 | |
| 923 | 607 | 607 | |
| 924 | 608 | 608 | |
| 925 | 609 | 609 | $k(Gd^T)$ |
| 926 | 610 | 610 | |
| 927 | 611 | 611 | |
| 928 | 612 | 612 | |
| 929 | 613 | 613 | |
| 930 | 614 | 614 | |
| 931 | 615 | 615 | |
| 932 | 616 | 616 | |
| 933 | 617 | 617 | |
| 934 | 618 | 618 | |
| 935 | 619 | 619 | |
| 936 | 620 | 620 | |
| 937 | 621 | 621 | |
| 938 | 622 | 622 | |
| 939 | 623 | 623 | |
| 940 | 624 | 624 | |
| 941 | 625 | 625 | |
| 942 | 626 | 626 | |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | |
|---|---|---|---|
| 943 | 627 | 627 | |
| 944 | 628 | 628 | |
| 945 | 629 | 629 | |
| 946 | 630 | 630 | |
| 947 | 631 | 631 | |
| 948 | 632 | 632 | |
| 949 | 633 | 633 | |
| 950 | 634 | 634 | |
| 951 | 635 | 635 | |
| 952 | 636 | 636 | |
| 953 | 637 | 637 | |
| 954 | 638 | 638 | PEG($Gd^T$) |
| 955 | 639 | 639 | K(K($Gd^T$)$Gd^T$) |
| 956 | 640 | 640 | |
| 957 | 641 | 641 | |
| 958 | 642 | 642 | |
| 959 | 643 | 643 | |
| 960 | 644 | 644 | |
| 961 | 645 | 645 | |
| 962 | 646 | 646 | |
| 963 | 647 | 647 | |
| 964 | 648 | 648 | |
| 965 | 649 | 649 | |
| 966 | 650 | 650 | |
| 967 | 651 | 651 | |
| 968 | 652 | 652 | |
| 969 | 653 | 653 | |
| 970 | 654 | 654 | |
| 971 | 655 | 655 | |
| 972 | 656 | 656 | |
| 973 | 657 | 657 | |
| 974 | 658 | 658 | K(GdT) |
| 975 | 659 | 659 | K(GdT) |
| 976 | 660 | 660 | K(GdT) |
| 977 | 661 | 661 | K(GdT) |
| 978 | 662 | 662 | |
| 979 | 663 | 663 | |
| 980 | 664 | 664 | |

TABLE 42-continued

Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.

| | | | |
|---|---|---|---|
| 981 | 665 | 665 | |
| 982 | 666 | 666 | |
| 983 | 667 | 667 | |
| 984 | 668 | 668 | |
| 985 | 669 | 669 | K(GdT) |
| 986 | 670 | 670 | K(GdT) |
| 987 | 671 | 671 | K(GdT) |
| 988 | 672 | 672 | K(GdT) |
| 989 | 673 | 673 | K(GdT) |
| 990 | 674 | 674 | |
| 991 | 675 | 675 | |
| 992 | 676 | 676 | |
| 993 | 677 | 677 | K($Gd^T$) |
| 994 | 678 | 678 | K($Gd^T$) |
| 995 | 679 | 679 | K($Gd^T$) |
| 996 | 680 | 680 | K($Gd^T$) |
| 997 | 681 | 681 | |
| 998 | 682 | 682 | PEG($Gd^T$) |
| 999 | 683 | 683 | 1,6-Hex ($Gd^T$) |
| 1000 | 684 | 684 | 1,4 AMB ($Gd^T$) |
| 1001 | 685 | 685 | |
| 1002 | 686 | 686 | |
| 1003 | 687 | 687 | |
| 1004 | 688 | 688 | |
| 1005 | 689 | 689 | |
| 1006 | 690 | 690 | |
| 1007 | 691 | 691 | |
| 1008 | 692 | 692 | |
| 1009 | 693 | 693 | R |
| 1010 | 694 | 694 | Y |
| 1011 | 695 | 695 | |
| 1012 | 696 | 696 | |
| 1013 | 697 | 697 | |
| 1014 | 698 | 698 | |
| 1015 | 699 | 699 | |
| 1016 | 700 | 700 | |
| 1017 | 701 | 701 | |

TABLE 42-continued
Examples of peptide-chelate conjugates. In this table, $Gd^T$ is GdDTPA-thiourea, $Gd^G$ is GdDTPA-glutamate (GluDTPA), $Gd^{GM}$ is GdDOTA-GlyMe, and $Gd^D$ is GdDOTAGA.
| | | |
|---|---|---|
| 1018 | 702 | 702 |
| 1019 | 703 | 703 |
B. Examples of N- and C-Terminal GdDTPA Substituted Peptides Linked Via a Thiourea Containing Linkage.
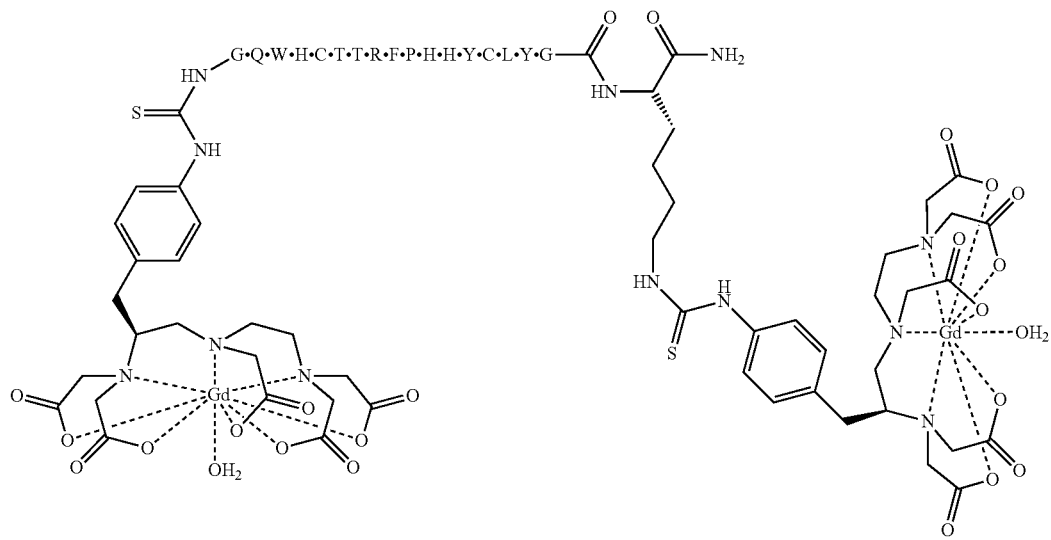
Compound ID 807
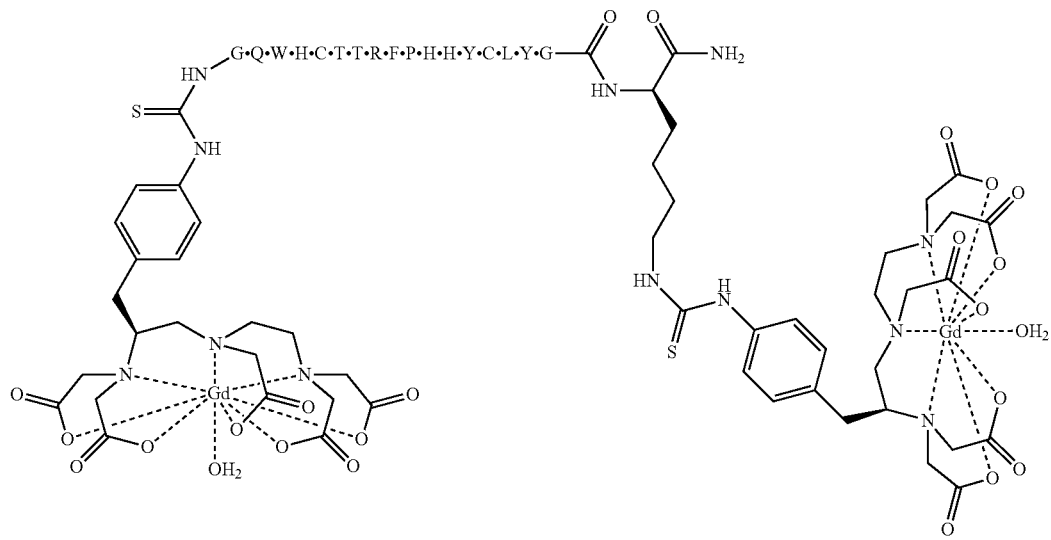
Compound ID 808

-continued
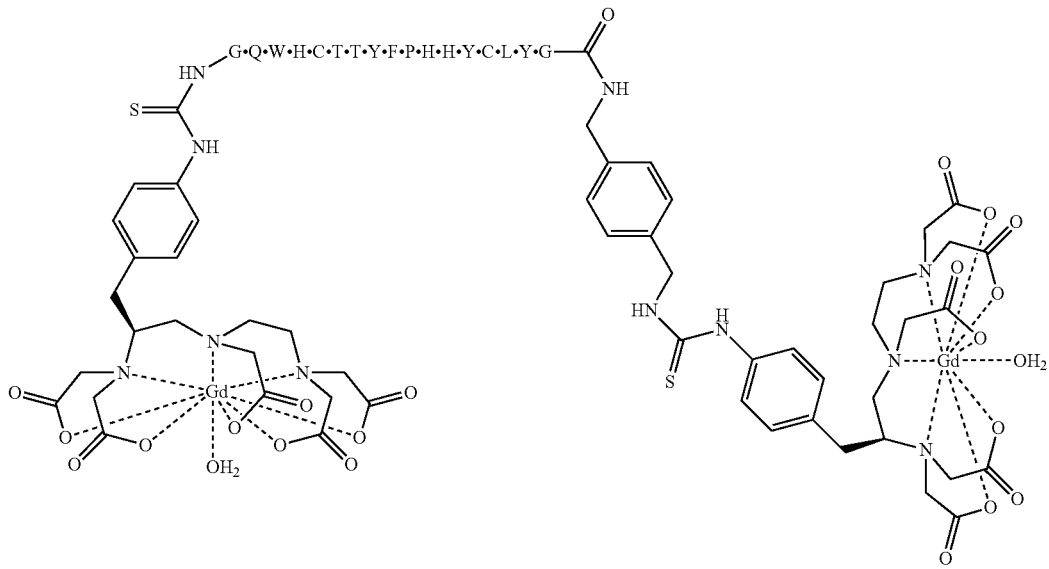
Compound ID 816
C. Examples of Agents Having Chelates Linked to a Peptide Side Chain
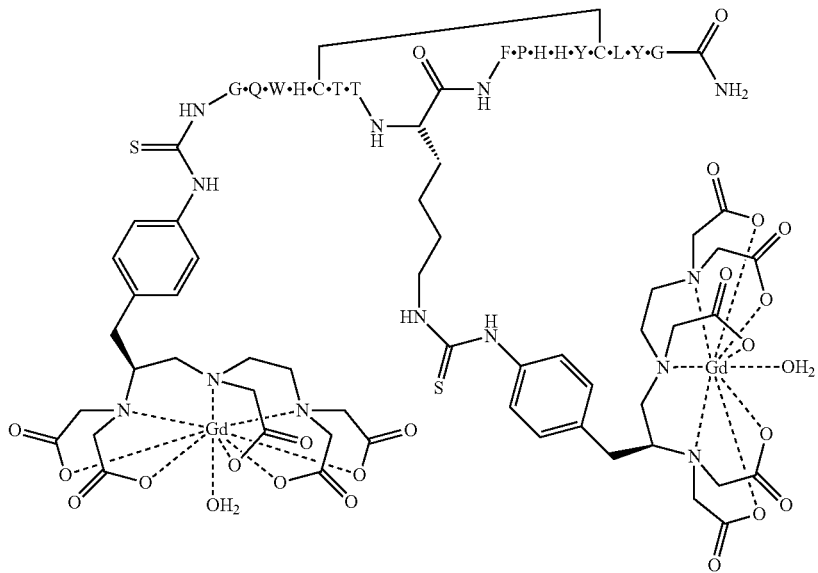
Comp ID 813

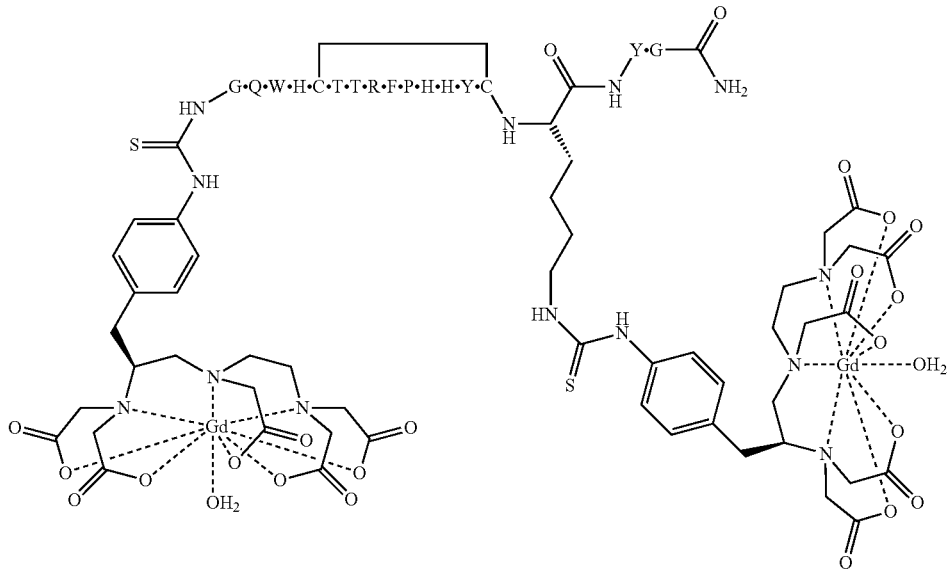

Comp ID 815

18. Collagen Binding of Peptides and Peptide-Chelate Conjugates

A. Preparation of Human Collagen:

Acid soluble human collagen extracted from placenta (Sigma, cat#C7774, lot#083K375) is dissolved in 15 mM HCl (3.5 mg/ml) by vortexing and gently shaking for 3-4 hours at 4° C. The acid soluble collagen is dissolved against PBS, pH 7.4 (three buffer exchanges are used). The $NaH_2PO_4$ protein concentration is determined by the BCA method (Pierce, Cat #23225) using bovine collagen (Vitrogen, cat #FXP-019) as a reference standard. Percent gelation (fibril formation) of the collagen is determined by incubating 10 μM collagen (3.3 mg/ml) at 37° C. for 6 hours. A typical percent gelation is 60%.

B. Preparation of Rat Collagen:

Rat collagen (acid soluble, type I, rat tail, Upstate USA, Inc, cat#08-115) is dialyzed against 10 mM Phosphate ($NaH_2PO_4$), pH 4.2 with three changes of the dialysis buffer. For the final assay, a 1:10 volume of 10×PBS (100 mM $NaH_2PO_4$, 1.5 M NaCl pH 7.4) is added to the collagen solution (final 1×PBS) and incubated at 37° C. for 2 hours. The gelation is typically 90%.

C. Preparation of Microliter Plate:

Collagen solutions are gelled and dried down in the wells of a 96 well microtiter plate (non-binding polystyrene, VWR, cat#29445-142) or polypropylene plate (Coaster, cat #29444-100, code 3364). 75 μl of 10 μM human collagen is aliquoted into each well and the plate is incubated at 37° C. for 6 hours to form a gel. The collagen gels are evaporated overnight to dryness at 37° C. Ungelled collagen is removed by washing the collagen films with 200 μl PBS (four times, 15 min per wash). The thin collagen fibril film remains, coating the bottom of each well. The final well content of gelled collagen is 150 μg. After washing by PBS the plate is again dried at 37° C. for 2 hours and is stored at −20° C.

D. Binding Assay:

600 μl of 5 μM peptide solution is prepared in PBS, pH 7.4. 90 μl of the 5 μM peptide solution is added to two collagen containing wells, and in addition, an empty well to control for nonspecific plastic binding. 90 μl is also reserved in a HPLC glass vial as a sample to measure the total concentration. The plate is then incubated on a shaker table (300 rpm) for 2 hours at room temperature to allow the compound to bind. After 2 hours the supernatant from each well (with or without collagen) is transferred to an HPLC glass vial. The relative amount of free, unbound compound in the sample supernatants and the amount of compound in the reserved (total) sample are determined either by HPLC (Agilent, 1100 series) or for the metal containing compounds by ICP-MS (Agilent 7500). For HPLC analysis, the compounds are chromatographed on a Kromasil C-4 column (AKZONOBEL, cat #E 22840), and eluted use a two buffer system (buffer A, 1% TFA in distilled water, buffer B 1% TFA in Acetonitrile). Each sample (30 μA) is injected onto the column and the compound (peptide or other compound) is eluted by a 10-40% gradient of buffer B (3 min, 5 ml/min). The peak area of the compound in each sample is determined by integration using the ChemStation software. For ICP-MS analysis the gadolinium concentration is determined directly. Values for the supernatant samples ([Free]) after incubation with collagen and the total sample are averaged. The percent bound, % B, is calculated from the formula: % B=([Total]−[Free])/[Total].

TABLE 43

Collagen binding of Gd-peptide conjugates to human and rat collagen at 5 μM compound and 5 μM collagen, 37° C., pH 7.4

| Comp ID NO. | Human binding | Rat binding |
|---|---|---|
| 800 | 85% | 88% |
| 801 | 81% | 77% |
| 802 | 57% | 45% |
| 807 | 48% | 45% |
| 808 | 25% | 19% |
| 813 | 65% | 55% |
| 815 | 66% | 59% |
| 816 | 48% | 48% |
| 820 | 60% | 29% |
| 821 | 56% | 29% |
| 822 | 47% | 20% |
| 823 | 53% | 28% |
| 824 | 12% | 0% |
| 825 | 61% | 63% |
| 826 | 87% | 71% |
| 827 | 41% | 20% |
| 828 | 52% | 20% |
| 829 | 20% | 21% |
| 830 | 26% | 11% |
| 831 | 50% | 21% |
| 832 | 12% | 4% |
| 833 | 13% | 4% |
| 834 | 22% | 9% |
| 835 | 17% | 9% |
| 836 | 13% | 8% |
| 837 | 22% | 10% |
| 838 | 70% | 61% |
| 839 | 30% | 11% |
| 840 | 15% | 3% |
| 841 | 51% | 28% |
| 842 | 23% | 9% |
| 843 | 55% | 36% |
| 844 | 68% | 48% |
| 845 | 36% | 10% |
| 846 | 31% | 9% |
| 847 | 16% | 7% |
| 848 | 35% | 9% |
| 849 | 64% | 42% |
| 850 | 75% | 67% |
| 851 | 50% | 41% |
| 852 | 65% | 57% |
| 853 | 66% | 57% |
| 854 | 64% | 56% |
| 855 | 27% | 15% |
| 856 | 52% | 42% |
| 857 | 67% | 69% |
| 858 | 64% | 46% |
| 859 | 47% | 38% |
| 860 | 60% | 45% |
| 861 | 73% | 79% |
| 862 | 77% | 76% |
| 863 | 67% | 57% |
| 864 | 64% | 50% |
| 865 | 30% | 17% |
| 866 | 60% | 38% |
| 867 | 55% | 48% |
| 868 | 36% | 40% |
| 869 | 46% | 37% |
| 870 | 30% | 28% |
| 871 | 68% | 54% |
| 872 | 41% | 35% |
| 873 | 38% | 33% |
| 874 | 45% | 28% |
| 875 | 64% | 60% |
| 876 | 48% | 26% |
| 877 | 58% | 41% |
| 878 | 8% | 9% |
| 879 | 33% | 0% |
| 880 | 30% | 0% |
| 881 | 19% | 28% |
| 882 | 0% | 13% |
| 883 | 8% | 2% |
| 884 | 24% | 15% |
| 885 | 16% | 9% |
| 886 | 8% | 13% |
| 887 | 0% | 16% |
| 888 | 38% | 30% |
| 889 | 38% | 19% |
| 890 | 38% | 15% |
| 891 | 79% | 70% |
| 892 | 63% | 56% |
| 893 | 4% | 2% |
| 894 | 20% | 15% |
| 895 | 7% | 0% |
| 896 | 50% | 41% |
| 897 | 4% | 1% |
| 898 | 5% | 3% |
| 899 | 20% | 14% |
| 900 | 4% | 1% |
| 901 | 2% | 2% |
| 902 | 7% | 2% |
| 903 | 3% | 5% |
| 904 | 0% | 3% |
| 905 | 6% | 2% |
| 906 | 13% | 5% |
| 907 | 6% | 1% |
| 908 | 20% | 0% |
| 909 | 14% | 0% |
| 910 | 13% | 0% |
| 911 | 15% | 0% |
| 912 | 20% | 0% |
| 913 | 78% | 64% |
| 914 | 19% | 0% |
| 915 | 15% | 0% |
| 916 | 23% | 0% |
| 917 | 12% | 0% |
| 918 | 19% | 0% |
| 919 | 93% | 93% |
| 920 | 67% | 91% |
| 921 | 68% | 35% |
| 922 | 68% | 58% |
| 923 | 28% | 10% |
| 924 | 24% | 1% |
| 925 | 64% | 62% |
| 926 | 81% | 87% |
| 927 | 64% | 63% |
| 928 | 73% | 80% |
| 929 | 27% | 34% |
| 930 | 31% | 42% |
| 931 | 70% | 83% |
| 932 | 59% | 79% |
| 933 | 36% | 24% |
| 934 | 21% | 14% |
| 935 | 59% | 39% |
| 936 | 9% | 5% |
| 937 | 11% | 14% |
| 938 | 16% | 13% |
| 939 | 4% | 5% |
| 940 | 9% | 8% |
| 941 | 8% | 5% |
| 942 | 78% | 67% |
| 943 | 55% | 72% |
| 944 | 91% | 84% |
| 945 | 83% | 82% |
| 946 | 71% | 68% |
| 947 | 64% | 57% |
| 948 | 25% | 17% |
| 949 | 72% | 79% |
| 950 | 78% | 79% |
| 951 | 45% | 32% |
| 952 | 52% | 72% |
| 953 | 50% | 50% |
| 954 | 31% | 22% |
| 955 | 51% | 36% |
| 956 | 39% | 15% |
| 957 | 42% | 39% |
| 958 | 45% | 33% |
| 959 | 58% | 68% |

TABLE 43-continued

Collagen binding of Gd-peptide conjugates to human and rat collagen at 5 µM compound and 5 µM collagen, 37° C., pH 7.4

| Comp ID NO. | Human binding | Rat binding |
|---|---|---|
| 960 | 30% | 34% |
| 961 | 54% | 55% |
| 962 | 20% | 10% |
| 963 | 82% | 91% |
| 964 | 88% | 86% |
| 965 | 26% | 11% |
| 966 | 14% | 8% |
| 967 | 11% | 4% |
| 968 | 77% | 64% |
| 970 | 53% | 54% |
| 971 | 21% | 25% |
| 972 | 3% | 0% |
| 973 | 85% | 92% |
| 974 | 71% | 69% |
| 975 | 70% | 64% |
| 976 | 62% | 57% |
| 977 | 40% | 43% |
| 978 | 64% | 66% |
| 979 | 87% | 86% |
| 980 | 85% | 80% |
| 981 | 73% | 81% |
| 982 | 40% | 47% |
| 983 | 58% | 59% |
| 984 | 67% | 69% |
| 985 | 56% | 68% |
| 986 | 60% | 67% |
| 987 | 62% | 68% |
| 988 | 69% | 71% |
| 989 | 67% | 74% |
| 990 | 59% | 62% |
| 991 | 23% | 11% |
| 992 | 75% | 64% |
| 993 | 75% | 70% |
| 994 | 86% | 84% |
| 995 | 51% | 42% |
| 996 | 76% | 67% |
| 997 | 53% | 55% |
| 998 | 71% | 75% |
| 999 | 65% | 66% |
| 1000 | 75% | 68% |
| 1001 | 83% | 81% |
| 1002 | 44% | 45% |
| 1003 | 48% | 47% |
| 1004 | 91% | 90% |
| 1005 | 90% | 95% |
| 1006 | 89% | 87% |
| 1007 | 87% | 92% |
| 1008 | 94% | 93% |
| 1009 | 93% | 96% |
| 1010 | 92% | 89% |
| 1011 | 94% | 93% |
| 1012 | 91% | 92% |
| 1013 | 81% | 88% |
| 1014 | 72% | 61% |
| 1015 | 29% | 30% |
| 1016 | 48% | 50% |
| 1017 | 25% | 18% |
| 1018 | 53% | 55% |
| 1019 | 14% | 6% |

Binding Constant.

The binding of Compound ID No. 800 to mouse collagen (5 µM) was measured over the concentration range 1-300 µM of Comp ID No:800. The binding data was fit to a model on N binding sites with equal affinity. This yielded a dissociation constant of 1.8 µM and 8 equivalent binding sites.

19. Binding of Comp ID No 1014 to Other Collagens

Compound ID No 1014 was assayed for binding to type I collagen of different species using the dried collagen assay described above. Under the conditions 6 µM Comp ID No 1014, 5 µM collagen, 37° C., pH 7.4, Comp ID No 1014 was 81.3% bound to human collagen, 73% bound to pig collagen, 68.9% bound to rabbit collagen, 62.9% bound to rat collagen, 47.7% bound to mouse collagen.

This shows that Comp ID No 1014 has affinity for type I collagen from a number of species.

Additional competition studies were carried out. The dried collagen assay was modified to include a soluble competitor protein. In this experiment there was 5 µM insoluble type I human or rat collagen, 5 µM Comp ID No 1014, and 1.6 µM of a competitor protein.

| Competitor protein | % bound to insoluble human collagen | % bound to insoluble rat collagen |
|---|---|---|
| None | 70.1 | 58.6 |
| Type I human collagen | 60.5 | 21.0 |
| Type II human collagen | 68.8 | 54.2 |
| Type III human collagen | 66.6 | 46.9 |
| Type IV human collagen | 59.9 | 28.1 |

There was significant inhibition of binding from soluble type I human collagen and soluble type IV human collagen indicating strong binding of Comp ID No 1014 to these collagens. There was weaker inhibition with soluble type III human collagen and weaker still with type II human collagen. However both of these collagens still inhibited binding and indicated that there is some affinity of Comp ID No 1014 for type III and type II human collagen.

20. $^{111}$In Radiolabeling of Comp ID 726

Peptide-chelate conjugate Compound ID 726 (11.0 mg, 2.41 µmol) was dissolved in 200 µL of nanopure water in a glass vial equipped with a Teflon-coated magnetic stir bar. A solution of $^{111}$InCl$_3$ in 1M HCl (Perkin Elmer, 8.2 µL, 328 µCi) was then added followed by 100 µL of water. The pH of the resulting solution was checked with pH paper and 1M HCl was added to reach pH 4. The resulting solution was heated at 45° C. and stirred for 1 hour. The solution was removed from the hot plate and left to cool to room temperature. A 2 µL aliquot was taken and added to about 100 of 50 mM HEPES buffer (pH≈7) for analysis by HPLC using a γ detector (C4 column; eluent A: 50 mM ammonium formate, 0.1 mM EDTA in water; eluent B: acetonitrile; gradient of 2 to 45% B in 13 minutes; any unreacted In-111 elutes in the void). Radiochemical purity was >99%. When the reaction was complete, the pH was readjusted to ~7 by addition of a 1M solution of sodium hydroxide.

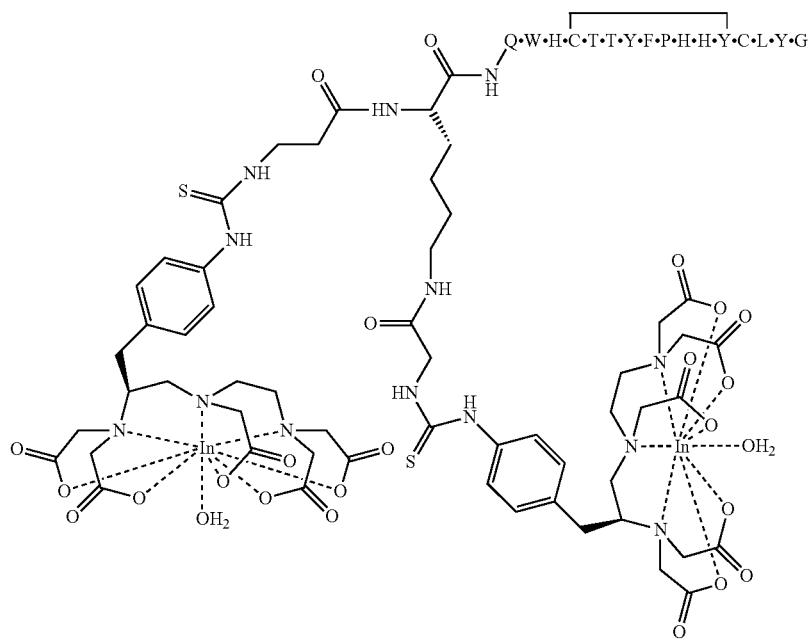

21. Additional Synthesized Peptides

Additional peptides were synthesized following the general protocol described in Example 2. Peptide sequences are shown in Tables 44 and 45. Note that a lower-case letter indicates the D-form of the amino acid.

TABLE 44 all peptides are cyclic and cyclized through a disulfide bond between the two cysteines:

| SEQ ID NO. | Sequence | | | | | | | | | | | | | |
|---|---|---|---|---|---|---|---|---|---|---|---|---|---|---|
| 704 | K(H.G) | W H C | T | T Y F P H H | Y | C L | Y | G | |
| 705 | GQ | W H C | T | T Y F P H H | Y | C L | Y | G | |
| 706 | Q | W H C | T | T Y F P H H | Y | C L | Y | G | |
| 707 | K(G) | W H C | Y | T Y F P H H | Y | C V | Y | G | 1,4 AMB |
| 708 | K(G) | W H C | Y | T Y F P Y H | Y | C V | Y | G | |
| 709 | K(G) | W H C | Y | T Y F P Y H | Y | C V | Y | G | |
| 710 | K(G) | W H C | T | T Y F P H H | V | C L | Y | G | |
| 711 | K(G) | W H C | T | T L F P H H | V | C L | Y | G | |
| 712 | K(G) | W H C | T | T Y F P H H | Y | C L | Dip | G | |
| 713 | K(G) | W H C | T | T Y F P H H | Dip | C L | Y | G | |
| 714 | K(G) | W H C | T | T Y F P H H | Dip | C L | Y | G | |
| 715 | K(G) | W H C | T | T Y F P H H | Y | C L | Y | F(4-NH2) | |
| 716 | K(G) | W H C | T | T Y F P H H | Y | C L F(4-NH2) | | G | |
| 717 | K(G) | W H C | T | T Y F P H H | Y | C L F(4-NH2) | | G | |
| 718 | K(G) | W H C | T | T Y F P H H F(4-NH2) | | C L | Y | G | |
| 719 | K(G) | W H C Y(3-I) | T Y F P H H | | Y | C L | Y | G | |

TABLE 44-continued all peptides are cyclic and cyclized through a disulfide bond between the two cysteines:

| SEQ ID NO. | | | | Sequence | | | | | | |
|---|---|---|---|---|---|---|---|---|---|---|
| 720 | K(G) | W H C | Y(3-I) | T Y F P H H | Y | C L | Y | G | |
| 721 | K(G) | W H C | Y | T Y F P H H | Y | C V | Y | G | K |
| 722 | K(G) | W H C | Y | T Y F P H H | Y | C V | Y | Y | K |
| 723 | K(G) | W H C | Y | T Y F P H H | Y | C V | Y | Y | K |
| 724 | K(G) | W H C | T | T Y F P H H | Y | C L | Y | Y | K |
| 725 | K(G) | W H C | T | T Y F P H H | Y | C L | Y | Bip | K |
| 726 | K(G) | W H C | Y | T K F P H H | Y | C V | Y | G | |
| 727 | K(G) | W H C | Y | T K F P H H | Y | C V | Y | Y | |
| 728 | K(G) | W H C | T | T K F P H H | Y | C L | Y | Y | |
| 729 | K(G) | W H C | T | T K F P H H | Y | C L | Y | Bip | |
| 730 | K(Y.G) | W H C | T | T Y F P H H | Y | C L | Y | G | |
| 731 | K(V.G) | W H C | T | T Y F P H H | Y | C L | Y | G | |
| 732 | K(F.G) | W H C | T | T Y F P H H | Y | C L | Y | G | |
| 733 | K(H.G) | W H C | T | T Y F P H H | Y | C L | Y | G | |
| 734 | K | W H C | Y | T Y F P H H | Y | C V | Y | G | |
| 735 | K(F.G) | W H C | T | T Y F P H H | Y | C L | Y | G | |
| 736 | K(V.G) | W H C | T | T Y F P H H | Y | C L | Y | G | |
| 737 | K(Y.G) | W H C | T | T Y F P H H | Y | C L | Y | G | |
| 738 | K(G) | W H C | T | T K F P H H | Y | C L | Y | Bip | |
| 739 | K(G) | W H C | T | T K F P H H | Y | C L | Y | Y | |
| 740 | K(G) | W H C | Y | T K F P H H | Y | C V | Y | Y | |
| 741 | K(G) | W H C | Y | T K F P H H | Y | C V | Y | G | |
| 742 | K(G) | W H C | T | T Y F P H H | Y | C L | Y | Bip | K |
| 743 | K(G) | W H C | T | T Y F P H H | Y | C L | Y | Y | K |

TABLE 45 all peptides are cyclic and cyclized through a disulfide bond between the two cysteines:

| SEQ ID NO: | | | Sequence | | | | | | |
|---|---|---|---|---|---|---|---|---|---|
| 744 | K(G) | W H C T T | K | F P H H | Y | C L Y | Bip | |
| 745 | K(G) | W H C Y T | Y | F P H H | Y | C L Y | F | K |
| 746 | K(G) | W H C Y T | Y | F P H H | Y | C L Y | F | K |
| 747 | K(G) | W H C Y T | Y | F P H H | Y | C L Y | Y | K |
| 748 | K(G) | W H C Y T | Y | F P H H | Y | C L Y | Y | K |
| 749 | K(G) | W H C Y T | Y | F P H H | Y | C L Y | y | K |
| 750 | K(G) | W H C T T | Y | F P H H | Y | C L Y | V | K |

TABLE 45-continued all peptides are cyclic and cyclized through a disulfide bond between the two cysteines:

| SEQ ID NO: | | | | Sequence | | | | | |
|---|---|---|---|---|---|---|---|---|---|
| 751 | K(G) | W Y C Y K | Y | F P H H | Y | C L Y | G | | |
| 752 | K(G) | W H C Y K | Y | F P H H | Y | C L Y | G | | |
| 753 | K(G) | W H C Y T | Y | F P H H | Y | C L Y | G | | |
| 754 | K(G) | W H C Y T | Y | F P H H | 1-Nal | C L Y | G | | |
| 755 | Q | W H C Y T | K | F P H H | Y | C L Y | G | K | |
| 756 | Q | W H C Y T | Y | F P H H | Y | C L Y | G | K | |
| 757 | Q | W H C Y T | Y | F P H H | Y | C L Y | G | K | |
| 758 | K(G) | W H C T T | Y | F P H H | Y | C L Y | Y | K | |
| 759 | K(G) | W H C Y T | Y | F P H H | Y | C L Y | V | K | |
| 760 | KK(K) | W H C Y T | Y | F P H H | Y | C V Y | G | | |
| 761 | Dpr(Dpr) | W H C Y T | Y | F P H H | Y | C V Y | G | | |
| 762 | K(G) | W H C Y T | Y | F P H H | Y | C L Y | G | K | |
| 763 | K(G) | W H C Y T | Y | F P H H | Y | C L Y | F | K | |
| 764 | K(G) | W H C Y T | Y | F P H H | Y | C L Y | Phg | K | |
| 765 | K(G) | W H C Y T | Y | F P H H | Y | C L Y | Y | K | |
| 766 | K(G) | W H C Y T | Y | F P H H | Y | C L Y | y | K | |
| 767 | K(G) | W H C Y T | Y | F P H H | Y | C L Y | V | K | |
| 768 | K(G) | W Y C T T | Y | F P H H | Y | C L Y | G | | |
| 769 | K(G) | W Y C Y K | Y | F P H H | Y | C L Y | G | | |
| 770 | K(G) | W Y C Y T | Y | F P H H | 1-Nal | C L Y | G | | |
| 771 | Q | W K C Y T | K | F P H H | Y | C L Y | G | K | |
| 772 | Q | W Y C Y T | Y | F P H H | Y | C L Y | G | K | |
| 773 | K(G) | W K C Y T | K | F P H H | Y | C L Y | G | K | |
| 774 | K(G) | W Y C Y T | Y | F P H H | Y | C L Y | G | K | |
| 775 | K(G) | W H C T T | Y | F P T H | Y | C L Y | G | | |
| 776 | K(G) | W H C Y T | Y | F P Y H | Y | C L Y | G | | |
| 777 | K | W H C T T | K | F P H H | Y | C L Y | Bip | | |
| 778 | K | W H C T T | K | F P H H | Y | C L Y | Bip | | |
| 779 | K(G) | W H C Y T | Y | F P H H | Y | C V Y | G | 1,6-Hex | |
| 780 | K(G) | W H C Y T | Y | F P H H | Y | C V Y | G | PEG | |
| 781 | K | W H C Y T | Y | F P H H | Y | C V Y | G | | |
| 782 | K(G) | W H C Y T | Y | F P H H | Y | C V Y | G | PEG | |
| 783 | K(G) | W H C Y T | Y | F P H H | Y | C V Y | G | 1,6-Hex | |
| 784 | K(G) | W H C Y T | Y | F P H H | Y | C V Y | G | 1,4 AMB | |
| 785 | K(G) | W H C T T | K | F P H H | Y | C L Y | Bip | | |
| 786 | Dpr(Dpr) | W H C Y T | Y | F P H H | Y | C V Y | G | | |
| 787 | KK(K) | W H C Y T | Y | F P H H | Y | C V Y | G | | |

TABLE 45-continued all peptides are cyclic and cyclized through a disulfide bond between the two cysteines:

| SEQ ID NO: | | | | | Sequence | | | | | | |
|---|---|---|---|---|---|---|---|---|---|---|---|
| 788 | K(G) | W H C Y T | K | F P H H | Y | C V Y | Bip | |
| 789 | K(G) | W H C Y T | Dab | F P H H | Y | C L Y | Bip | |
| 790 | K(G) | W H C Y T | Dpr | F P H H | Y | C V Y | Bip | |
| 791 | Dab(G) | W H C Y T | K | F P H H | Y | C V Y | Bip | |
| 792 | K | W H C Y T | K | F P H H | Y | C V Y | Bip | |
| 793 | K(G) | W H C Y T | K | F P H H | Y | C V Y | Bip | R |
| 794 | K(G) | W H C Y T | K | F P H H | Y | C V Y | Y | |
| 795 | K(G) | W H C Y T | K | F P Y H | Y | C V Y | Y | |
| 796 | K(G) | W H C Y T | K | F P H H | Y | C K Y | Bip | |
| 797 | K(G) | W H C Y T | K | F P H H | Y | C K Y | Y | |
| 798 | | W H C Y T | Y | F P H H | Y | C V Y | G | |
| 799 | K | W H C Y T | Y | F P H H | Y | C L Y | G | |
| 800 | G | W H C Y T | Y | F P H H | Y | C T Y | G | |
| 801 | A | W H C Y T | Y | F P H H | Y | C V Y | G | |
| 802 | L | W H C Y T | Y | F P H H | Y | C V Y | G | |
| 803 | Y | W H C Y T | Y | F P H H | Y | C V Y | G | |
| 804 | K(G) | W H c T T | K | F P H H | Y | C L Y | Bip | |
| 805 | K(G) | W H c T T | K | F P H H | Y | C L Y | Bip | |

22. Synthesis of Compound ID No. 1014

Synthesis of Peptide.

The peptide (SEQ ID No. 408) was synthesized on an automated peptide synthesizer "Symphony" (Rainin Inc.) using 1 to 12 batch reactors loaded with 0.1 mmol of commercially available Rink amide resin (~0.20 mmol/g). A double coupling cycle is used for each Fmoc protected amino acid and a 5-fold excess of each amino acid is used per coupling to synthesize the peptide on the resin. Standard Fmoc chemistry is used to elongate the peptide on the resin. The Fmoc is removed with a solution of 20% piperidine in dimethylformamide. Each amino acid dissolved in a 0.2 M solution of 1-hydroxybenzotriazole in NMP is coupled to the peptide using a 0.2 M solution of diisopropylcarbodiimide in NMP. After each deprotection or coupling step the resin is washed alternatively three times with DMF and MeOH. The completed peptide/resin is washed with $CH_2Cl_2$ and dried under nitrogen.

After the synthesis of the peptide on the resin is complete, the peptide is cleaved from the resin using the following cleavage cocktail: TFA/Anisole/TIS/$H_2O$ 88:4:4:4 (10 mL per 100 μmoles of peptide). The solution of fully deprotected peptide is then precipitated with cold ether (40 mL). The peptide solid is isolated after centrifugation and then re-dissolved in a 1:1 mixture of DMSO/40 mM pH 5 Acetate buffer (3 mL per 25 mg of peptide). The cyclization is monitored by LC-MS (12 to 48 h). The cyclic peptide is purified by reverse phase preparative HPLC with UV (280 nm) detection using a mixture of 0.1% trifluoroacetic acid (TFA) and 10% (0.1% TFA in acetonitrile (ACN)) for 5 minutes and then rising from 25 to 40% (0.1% TFA in ACN) over 14 min (20 mL/min, Kromasil C18, 250×20 mm, 10 mm particle size, 100 Å pore size). The fractions of pure peptide are pooled and lyophilized to give the final peptide moiety.

Synthesis of ITC-$Gd_3$

Synthesis of (S)—N1-(2-aminoethyl)-3-(4-nitrophenyl)propane-1,2-diamine tri-hydrochloride salt

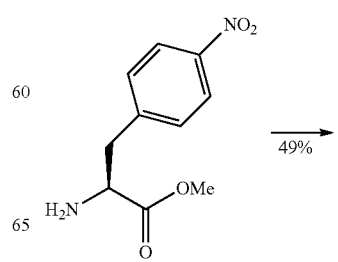

-continued

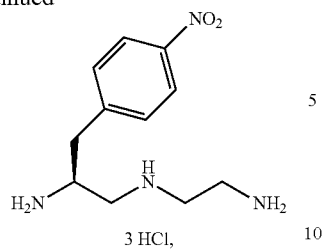

The (S)—N1-(2-aminoethyl)-3-(4-nitrophenyl)propane-1,2-diamine tri-hydrochloride salt was synthesized following the procedures of Brechbiel and Meares (Brechbiel, M. W. et al. *Inorg. Chem.* 1986, 25, 2772; Meares, C. F. *Bioconjugate Chem.* 2000, 11, 292.). The HCl salt of the methyl ester of para-nitrobenzylalanine (p-NO$_2$Bn-Ala-OMe, HCl salt, 13.03 g, 50 mmoles, 1 eq.) was dissolved in methanol (30 mL) and triethylamine (10.5 mL, 75 mmoles, 1.5 eq.) was added. The reaction mixture was stirred for 15 minutes at RT and ether (225 mL) was added. The reaction mixture was cooled to 0° C. with an ice-bath and the precipitate was filtered off and rinsed with ether (20 mL). The filtrate was concentrated to an orange oil which was re-dissolved in methanol (10 mL) and the solution of free amine was added at RT to ethylenediamine (100 mL, 1500 mmoles, 30 eq.) via a syringe pump over 4 h under argon. The mixture was stirred for 11 h and the ethylenediamine and the methanol were evaporated under high vacuum to give the desired crude amide (13.16 g, 104%) as a brown oil which was used directly in the next step without any further purification.

The crude amide was dissolved in anhydrous THF (250 mL) and 1M Borane-THF complex (200 mL, 200 mmoles, 12 eq.) was added dropwise in 3 portions (100 mL, 50 mL and 50 mL) at 0° C. over 4 days. The reaction was stirred at RT between the additions. The reaction was refluxed at 65° C. for 5 h and cooled to 10° C. with an ice-bath. The reaction was quenched with a very slow addition of methanol (10 mL) at 10° C. Another portion of methanol (140 mL) was added more rapidly and the temperature was slowly raised to RT. The solvents were evaporated and the residue was re-dissolved in methanol (50 mL) and the solvent was evaporated and the last 2 operations repeated a second time. The last traces of ethylenediamine were removed under high vacuum overnight. The residue was dissolved in absolute alcohol (200 mL) and 4M HCl in dioxane (50 mL) was added at 0° C. and a gum formed. The mixture was refluxed for 3.5 h and a fine powder formed over time. The reaction was stirred overnight at RT and then cooled to 5° C. in the refrigerator. The precipitate was filtered and rinsed with ether to give 8.53 g of the desired triamine tri-hydrochloride salt (49%) as a slightly yellow solid.

MS: 239 (M+1).

Coupling of DOTAGA to Triamine.

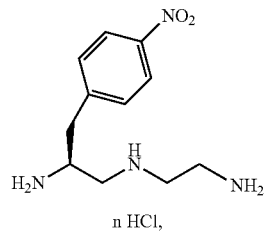

+

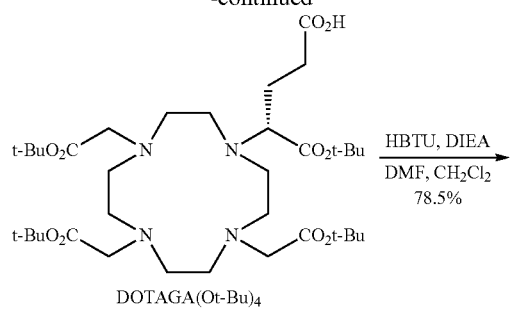

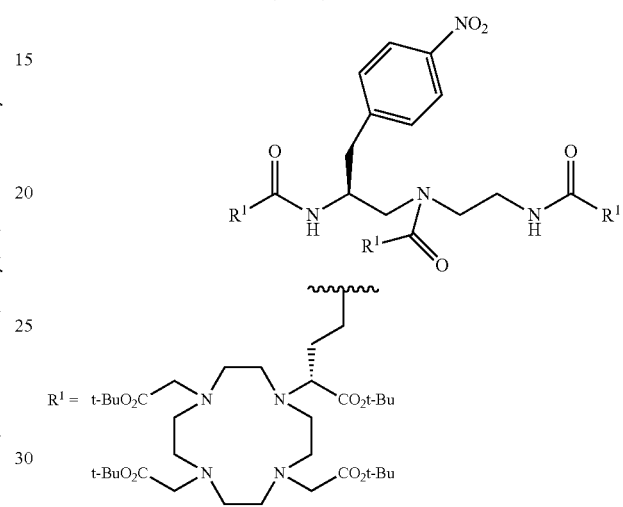

Triamine hydrochloride (n≤3) (2.07 g, ≤5.95 mmoles) purified by prep-HPLC was dissolved in DMF (60 mL) and CH$_2$Cl$_2$ (20 mL). DOTAGA(O-t-Bu)$_4$ (13.76 g, 19.6 mmoles, 3 eq.) and DIEA (62 mL, 35.7 mmoles, 5.5 eq.) were added at once. HBTU (7.45 g, 19.6 mmoles, 3 eq.) was added portionwise at 0° C. under argon and the brown solution was stirred for 24 h at RT. Excess DOTAGA was scavenged with a tris-amine resin (10.0 mmoles). HBTU (1.90 g, 5 mmoles) and DIEA (2 mL, 11.5 mmoles) were added and the mixture stirred for 8 h. The resin was filtered and the solvent was evaporated under high vacuum. The residue was dissolved in EtOAc and washed successively with saturated NaHCO$_3$ and brine. The organic layer was dried over Na$_2$SO$_4$ and the solvent was evaporated. The residue was purified by flash chromatography on silica gel (CH$_2$Cl$_2$/MeOH: 99.5:0.5 to 98:2) to give a pure fraction (0.46 g, 70%) and a lesser pure fraction (1.28 g, 8.5%). MS: (M+3/3) 763.3; (M+2/2) 1144.1.

Reduction of Nitro Group.

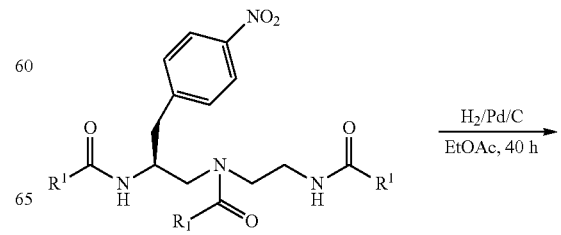

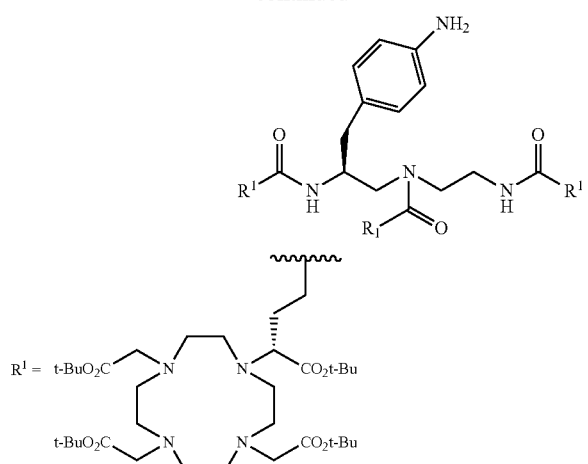

p-NO₂Bn tris-DOTAGA amide (16.52 g, 7.22 mmoles, 1 eq.) was dissolved in EtOAc (100 mL) and 10% Palladium on carbon (4.0 g) was added under argon. The mixture was shaken under 45 psi Hydrogen. Fresh catalyst was added (2 g after 16 h and 2 g after 23.5 h). The catalyst was filtered after 40 h and the solvent was evaporated to give 16.61 g of crude aniline derivative which was purified by flash chromatography on silica gel (CH₂Cl₂/MeOH: 99:1 to 98:2) to give 14.32 g (88%) of the desired product. MS: (M+3/3) 753.1; (M+2/2) 1129.1.

Deprotection of Ligand.

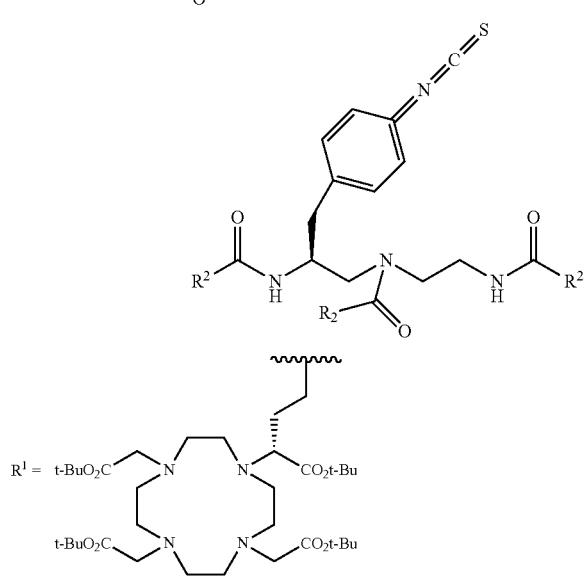

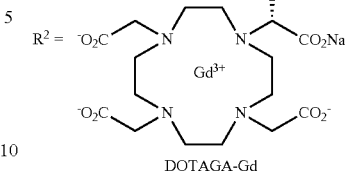

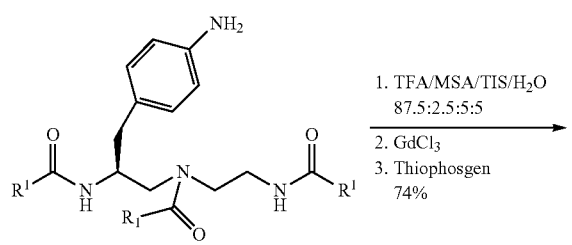

Deprotection of Ligand.

A mixture of TFA (280 mL), TIS (16 mL) and H₂O (16 mL) was added at 10° C. to the p-NH₂Bn tris-DOTAGA amide (16.67 g, 7.4 mmoles, 1 eq.) and the solution was stirred for 10 minutes at 10° C. Methanesulfonic acid (8 mL) was added dropwise over 2 minutes and the solution was stirred at RT for 2 h. The reaction mixture was poured into ether (1.5 L) cooled at 10° C. and the mixture was kept overnight in the refrigerator. The ligand was filtered quickly under argon, rinsed with ether (4×100 mL). The hygroscopic solid was transferred to a round bottom flask and was dried under high vacuum to give the desired ligand (17.26 g, 104% crude yield) as an off-white solid as a methanesulfonate salt. MS: 528.3 (M+3/3); 792.7 (M+2)/2; (M+1) 1584.9.

Chelation of Ligand

Ligand p-NH₂-Bn-tris-DOTAGA (17.21 g, max 7.4 mmoles) was dissolved in 25 mL of nanopure water. The solution was stirred at room temperature. The pH was adjusted to 6.5 (pH-meter) by slow addition of first a 4M then a 1M aqueous solution of sodium hydroxide.

The temperature was then increased to about 50° C. Solid gadolinium chloride hexahydrate was added in portions (11.1 mmoles; 3.69 mmoles; 3.69 mmoles then 1.845 mmoles). After each addition, as the solid dissolved over time, the pH decreased as a result of chelation. It was adjusted back to 6.5 by addition of a 1M aqueous solution of sodium hydroxide. The reaction was monitored by HPLC-MS and more GdCl₃ was added until only the tris-chelate could be detected. The total amount of salt added at that point was 20.325 mmoles, amounting to 6.775 mmoles tris-chelate.

A 100 mM aqueous solution of EDTA (10 mL) was added and the pH was adjusted back to 6.5. The solution was checked by HPLC-MS and used as is for the next step.

MS: 1025.2 (M+2)/2; 683.5 (M+3)/3 (complex isotopic pattern due to Gd isotopes)

Conversion of Anilino Group to Isothiocyanto Group with Thiophosgene to Give ITC-Gd₃.

To an aqueous solution of p-NH₂Bn-tris-Gd-DOTAGA amide (6.77 mmoles by ICP) was added CHCl₃ (50 mL) and thiophosgene (0.65 mL, 8.47 mmoles, 1.25 eq.) and the heterogeneous mixture was stirred vigorously for 16 h. The reaction was monitored by HPLC. The organic layer was decanted and the last traces of solvent and excess thiophosgen were evaporated (excess thiophosgen was quenched with ethylenediamine before disposal). The aqueous solution was decanted and the grey solid was filtered through a paper filter to give a 27.8 mM solution of desired isothiocyanate chelate (196 ml, 5.45 mmoles, 74% 3 steps). The concentration was determined by ICP. MS: 697.0 (M+3/3); 1045.0 (M+2)/2.

Coupling of the Peptide to ITC-Gd₃
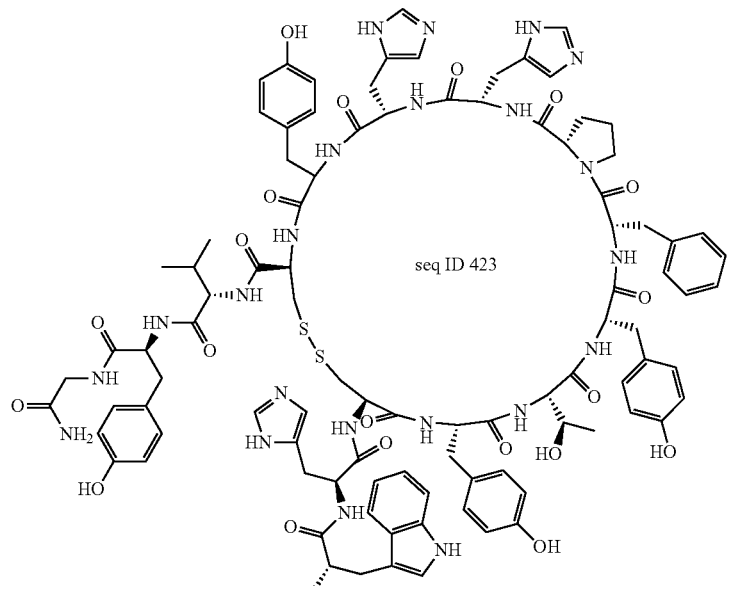
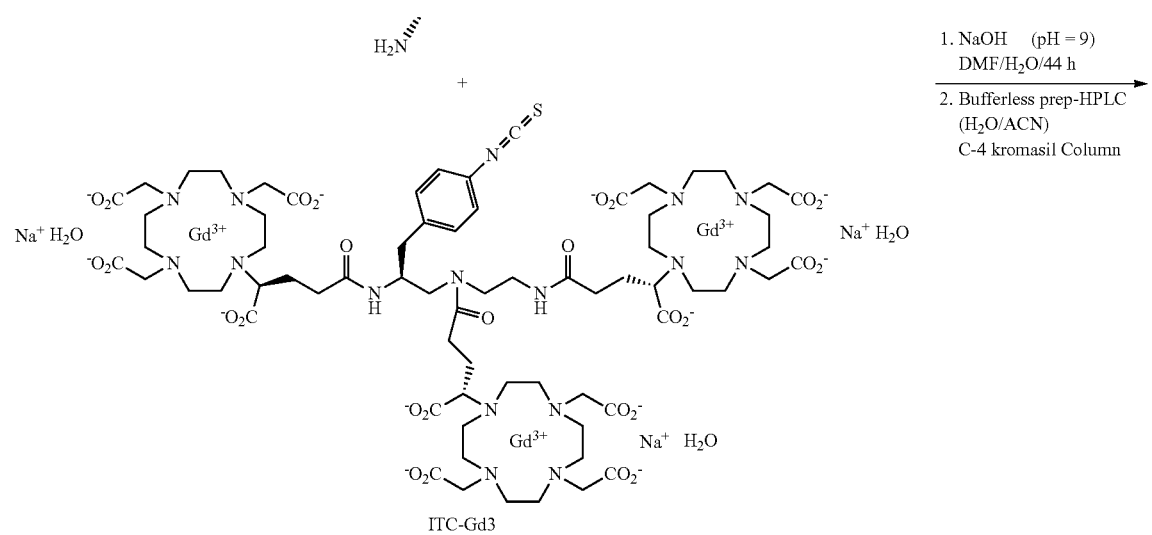

-continued

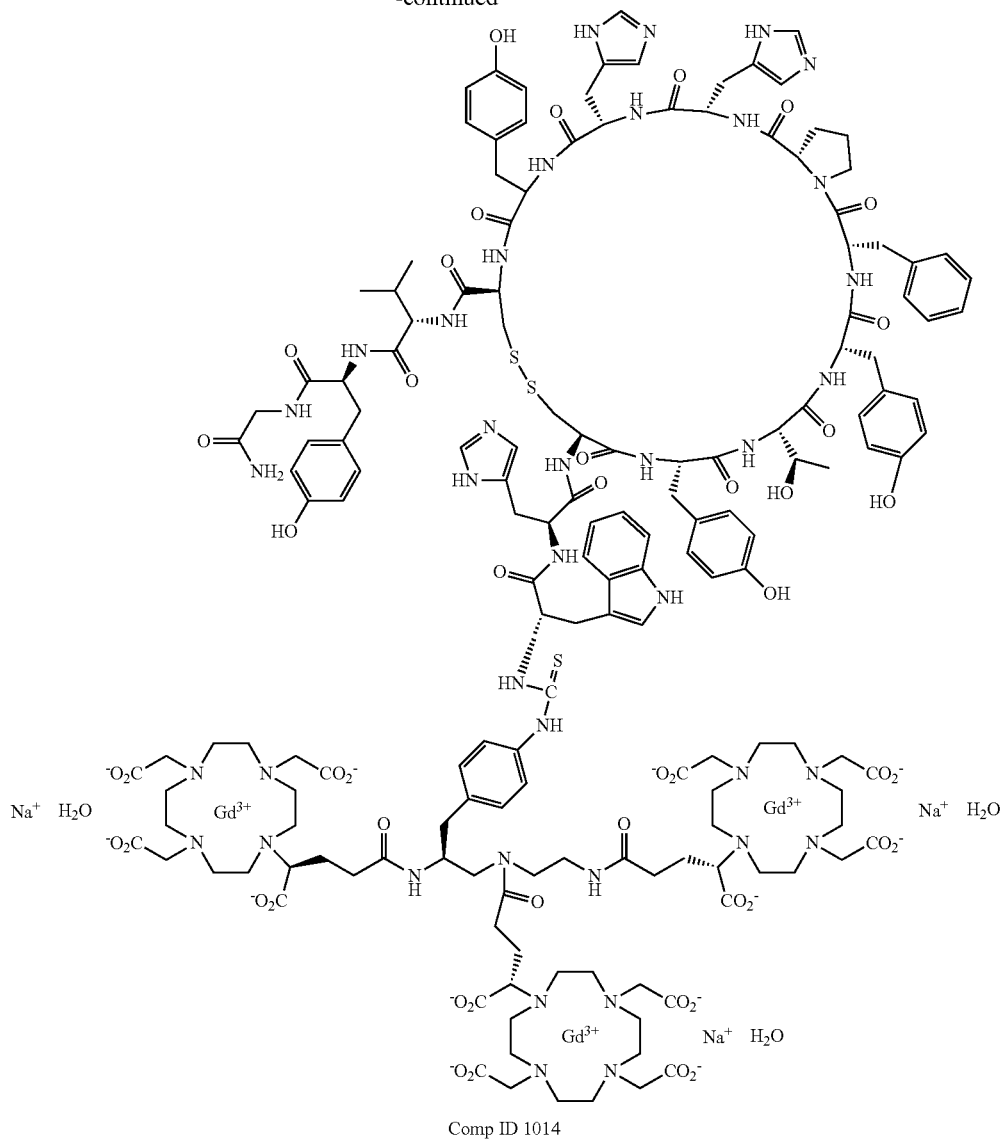

Comp ID 1014

The pH of a 38.6 mM solution of ITC-Gd$_3$ (16.0 mL, 0.61 mmole, 1.2 eq.) was adjusted to 6 with 1N NaOH and the peptide (SEQ ID NO: 408) (1.014 g, calculated as 100% purity and 100% potency) was added portionwise. The pH was progressively adjusted to pH=9 with 1N NaOH and the insoluble peptide was continuously re-dissolved with DMF (amine free, 20 mL). The reaction was monitored by HPLC using a neutral pH method (Phosphate pH=7 buffer/ACN) and a C-18 column. After 18 h excess ITC-Gd3 was added (2 ml, 0.15 eq.) was added and the solution was stirred for 23 h. The crude peptide conjugate of Compound ID NO. 1014 was purified by prep-HPLC on 2 inch C-4 column using bufferless conditions (ACN/H$_2$O 2% for 5 min 2 to 23 over 5 min and 23 to 30% over 15 min) to give the desired product (0.87 g calculated as 100% purity and 100% potency, 38% yield). MS 1354.8 (M+3/3); 1016.2 (M+4)/4; 813.2 (M+5)/5.

23. Mouse Model of Chonic Infarction

Myocardial infarction was induced in C57BL/6 mice by occlusion of the left anterior descending coronary artery followed by reperfusion. The mice were anesthetized with an intraperitoneal (i.p.) injection of 100 µg pentobarbital sodium per gram body weight and a thorocotamy was performed. The pericardium was removed and the left anterior artery was sutured with a 7.0 silk suture for 60 minutes after which reperfusion was established.

Imaging was performed on separate animals at 7 days, 40 days, or 210 days following infarction. Imaging was performed using on a Varian 4.7 T MRI system Mice were anesthetized with isoflurane (1 vol. % in oxygen). Three pediatric electrocardiogram (ECG) leads were attached to shaved limbs and a rectal temperature probe was placed. ECG and core body temperature were monitored with a SAII Model 1025 monitoring and gating system (Small Animal Instruments, Inc., Stony Brook, N.Y., USA). Temperature was maintained at 37.0±0.5° C. using circulating hot water. Imaging was performed prior to, and serially (every 5 minutes) post intravenous (tail vein) injection of 25 µmol/kg Compound ID NO. 800. 6-8 short-axis inversion-recovery slices covering the whole heart from base to apex were acquired with TI=430 ms, TR=1000 ms, RE=4.3 ms and 2 averages. All images had a slice thickness of 1 mm with an in-plane resolution of 100×100 µm after zero-filling.

Figure 5:
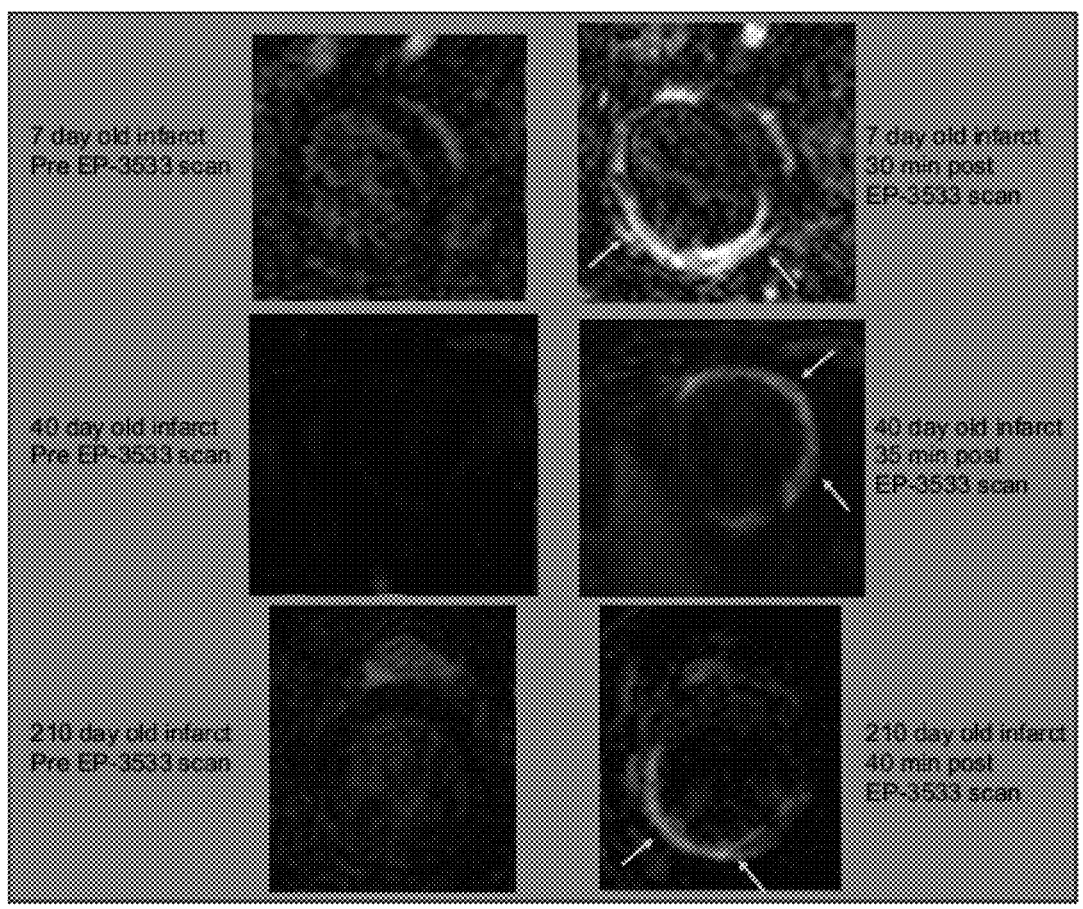
FIG. 5 shows a panel of pre- and post compound ID 800 images for mice with 7 day, 40 day, or 210 day infarcts. The images show that compound ID 800 enhances the myocardium relative to the pre-contrast image. The compound ID 800 enhanced images show the infarct zone as hyperintense relative to the normal, viable myocardium. These images demonstrate that the collagen targeted contrast agent can be used to demonstrate viability in infarctions of different ages from relatively acute to chronic.

FIG. 5 shows a panel of pre- and post Compound ID NO. 800 images for mice with 7 day, 40 day, or 210 day infarcts. The images show that Compound ID NO. 800 enhances the myocardium relative to the pre-contrast image. The Compound ID NO. 800 enhanced images show the infarct zone as hyperintense relative to the normal, viable myocardium. These images demonstrate that the collagen targeted contrast agent can be used to demonstrate viability in infarctions of different ages from relatively acute to chronic.

Figure 6:
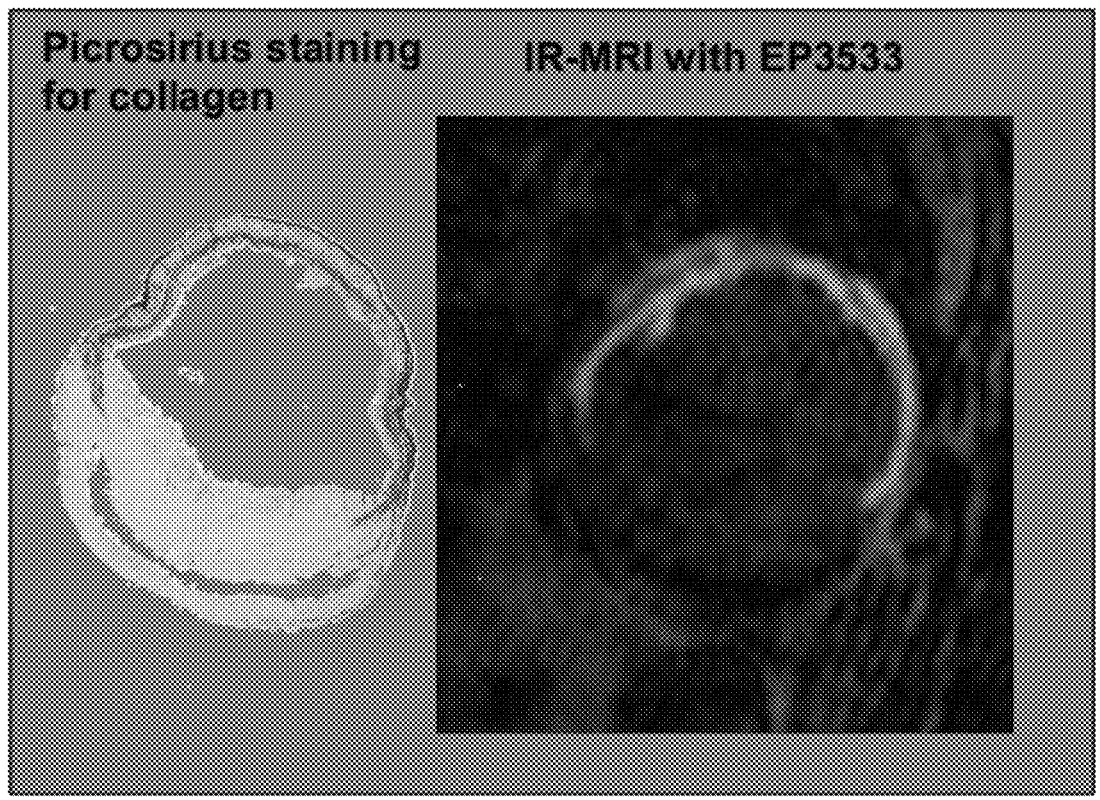
FIG. 6 shows that the picrosirius stained myocardium correlates very well with the MR image. The collagen rich scar stained darkly by picrosirius red appears hyperenhanced (bright) on the MR image.

A heart with a 40 day old infarct was explanted, thoroughly washed in saline solution and fixed in a 3% by volume isotonic solution of formaldehyde for 12 hrs at 3° C. They were washed in PBS and stored in 70% ETOH before embedding in paraffin. The heart was sectioned at 10 µm thick intervals from base to apex and stained with picrosirius red which stains positive for collagen. FIG. 6 shows that the picrosirius stained myocardium correlates very well with the MR image. The collagen rich scar stained darkly by picrosirius red appears hyperenhanced (bright) on the MR image.

For two mice that had 40 day old infarcts, the hearts were explanted 50 min post-injection of Compound ID NO. 800, thoroughly washed in saline solution and grossly divided in two sections, scar versus non-scar, by visually detecting the white epicardium associated with scar. Each sample was assessed for tissue gadolinium concentration by inductively coupled plasma mass spectrometry. Blood samples were also taken at 50 min post-injection and analyzed for gadolinium. In the two animals, respectively, there was 137 and 122 nmol Gd/g scar; 56.6 and 40.4 nmol Gd/g viable myocardium; and 27.8 and 14.6 nmol Gd/g blood. These results quantitatively confirm the imaging and histology data. These data show that: 1) the collagen targeted agent localizes preferentially in the collagen rich scar; and 2) binding to collagen in the both the viable myocardium and in the infarct zone results in retention of the agent and higher gadolinium levels than in the blood.

24. Pig Model of Perfusion Imaging

Domestic swine (50 kg) were premedicated with 0.5 ml intramuscular atropine, 0.2 ml intramuscular azaperone/kg bodyweight, and 0.1 ml ketamine/kg bodyweight. An aqueous solution of pentobarbital (1:3) was administered intravenously via an ear vein as needed to maintain anesthesia. The animals were intubated, and mechanical ventilation was maintained throughout the entire study.

A critical coronary artery stenosis was created by advancing a 3 mm Smash balloon catheter into the proximal left anterior descending (LAD) artery. After baseline MRI scanning, the balloon was inflated under X-ray guidance. X-ray angiography indicated reduced flow distal to the balloon but the absence of a complete occlusion. Lanthanum labeled microspheres (BioPAL Inc.) were administered into the left ventricle as a marker of blood flow at this point. The pig was placed in the MR scanner and an adenosine infusion (0.25 mg/kg/min) was started. After 8 minutes of adenosine, another microsphere injection was made with ytterbium labeled microspheres (BioPAL Inc.). After 10 minutes of adenosine infusion, a 25 mL bolus of Compound ID NO. 1014 (13 µmol/kg) in 80 mM sucrose solution was administered via an ear vein. The adenosine infusion was maintained for an additional 5 minutes. Steady state imaging was performed at 5, 20, 40, and 60 min post Compound ID NO. 1014. Additional X-ray angiography was performed at 30 minutes post Compound ID NO. 1014 injection to demonstrate that the LAD was still patent. The animal was sacrificed at ca. 70 minutes post Compound ID NO. 1014 and the heart removed and sectioned according to American Heart Association guidelines (M D Cerqueira et al, Circulation, 2002, 105:539-42) and assayed for Gd and microsphere content. TTC staining was applied to rule out infarction of the myocardium.

Imaging was performed on 1.5-T Gyroscan Intera whole body MR system. A radiofrequency spoiled 3D gradient echo sequence was used for the steady state imaging. Five 10 mm slices were acquired in short-axis orientation. Scan parameters were TR=5.0 ms; TE=1.5 ms; flip angle=30°; FOV=260×260 mm; 256×256 matrix.

Figure 7:
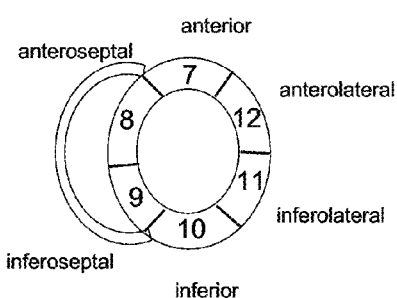
FIG. 7 illustrates example images from the mid-cavity of the heart. Prior to compound ID 1014 injection, the myocardium and ventricles are both dark. Five minutes after injection (A) the ventricles are hyperintense because of contrast agent in the blood and the myocardium shows a dark, ischemic zone in anterior and anteroseptal segments 7 and 8 whereas the inferior and lateral wall is much more enhanced. At 20 minutes (B), the signal in the blood has decreased but the myocardium remains dark in segments 7 and 8 and brighter in segments 9-12. Microsphere measurements (C) comparing flow in each segment to the remote myocardium (basal segments) indicated that regional perfusion was significantly reduced in the LAD territory (anteroseptal segments 7, 8). Microsphere measurements comparing blood flow at adenosine stress to flow at rest (D) showed flow was significantly reduced in ateroseptal segments 7 and 8 during stress.
Figure 7:
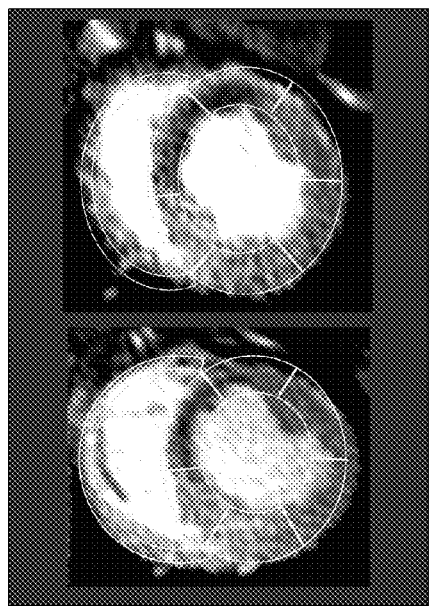
Figure 7:
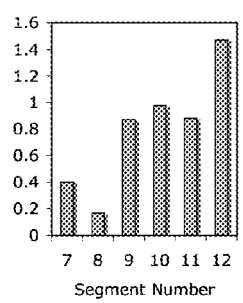
Figure 7:
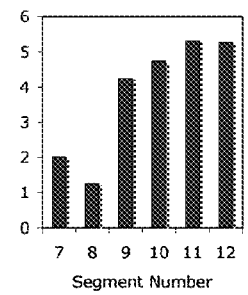

Example short-axis images from the mid-cavity of the heart are shown in FIG. 7. Prior to Compound ID NO. 1014 injection, the myocardium and ventricles are both dark. Five minutes after injection the ventricles are hyperintense because of contrast agent in the blood and the myocardium shows a dark, ischemic zone in anterior and anteroseptal segments 7 and 8 whereas the inferior and lateral wall is much more enhanced. At 20 minutes, the signal in the blood has decreased but the myocardium remains dark in segments 7 and 8 and brighter in segments 9-12. Microsphere data are expressed in two ways. First blood flow during adenosine stress for the mid-cavity of the heart (segments 7-12) is compared to blood flow at rest, prior to adenosine. Note that perfusion increases significantly by 4-5 fold in segments 9-12, but there is little flow increase in segments 7 and 8. The relative flow in the mid-cavity at stress was also compared to the mean flow in the basal segments of the heart. The base of the heart is proximal to the LAD occlusion and does not suffer from a perfusion deficit. The mean flow in the base was taken as "normal" perfusion at stress. Again, segments 9-12 show flow that is equivalent to flow in the basal segments, i.e. normal. However flow is significantly reduced in segments 7 and 8.

These data demonstrate that the MR images are reflective of perfusion in the myocardium as measured by microspheres. The collagen targeted contrast agent provides positive image contrast in the normally perfused myocardium, whereas the ischemic part of the myocardium is hypointense (dark).

25. Pig Model of Perfusion and Viability Imaging

A Domestic swine (50 kg) was premedicated with 0.5 ml intramuscular atropine, 0.2 ml intramuscular azaperone/kg bodyweight, and 0.1 ml ketamine/kg bodyweight. An aqueous solution of pentobarbital (1:3) was administered intravenously via an ear vein as needed to maintain anesthesia. The animal was intubated, and mechanical ventilation was maintained throughout the entire study.

A critical coronary artery stenosis was created by advancing a 3 mm Smash balloon catheter into the proximal left anterior descending (LAD) artery. After baseline MRI scanning, the balloon was inflated under X-ray guidance. X-ray angiography indicated reduced flow distal to the balloon but the absence of a complete occlusion. Lanthanum labeled microspheres (BioPAL Inc.) were administered into the left ventricle as a marker of blood flow at this point. The pig was placed in the MR scanner and an adenosine infusion (0.25 mg/kg/min) was started. After 8 minutes of adenosine, another microsphere injection was made with gold labeled microspheres (BioPAL Inc.). After 10 minutes of adenosine infusion, a 25 mL bolus of Compound ID NO. 1014 (13 µmol/kg) in 80 mM sucrose solution was administered via an ear vein. The adenosine infusion was maintained for an additional 5 minutes. Steady state imaging was performed at 5, 20, 40, and 60 min post Compound ID NO. 1014. Additional X-ray angiography was performed at 30 minutes post Compound ID NO. 1014 injection to demonstrate that the LAD was still patent. The animal was sacrificed at ca. 70 minutes post Compound ID NO. 1014 and the heart removed and sectioned according to American Heart Association guidelines (MD Cerqueira et al, Circulation, 2002, 105:539-42) and assayed for Gd and microsphere content. TTC staining was applied to identify regions of infarction of the myocardium.

Imaging was performed on 1.5-T Gyroscan Intera whole body MR system. A radiofrequency spoiled 3D gradient echo sequence was used for the steady state imaging. Five 10 mm slices were acquired in short-axis orientation. Scan parameters were TR=5.0 ms; TE=1.5 ms; flip angle=30°; FOV=260×260 mm; 256×256 matrix.

Figure 8:
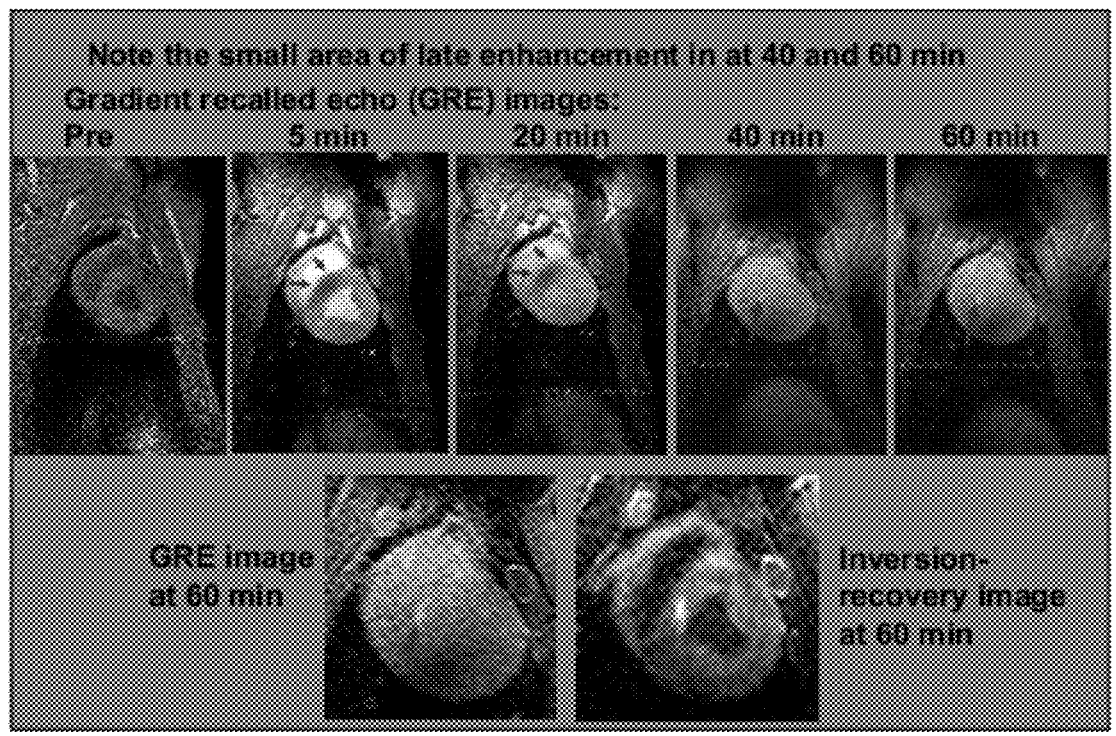
FIG. 8 shows example images from the mid-cavity of the heart.

Example short-axis images from the mid-cavity of the heart are shown in FIG. 8. Prior to Compound ID NO. 1014 injection, the myocardium and ventricles are both dark. Five minutes after injection the ventricles are hyperintense because of contrast agent in the blood and the myocardium shows a dark, ischemic zone in anterior and anteroseptal segments whereas the inferior and lateral wall is much more enhanced. At 20 minutes, the signal in the blood has decreased but the myocardium remains dark in segments anteroseptal area and brighter in the inferior and lateral wall. At 40 and 60 minutes, redistribution has occurred and the whole myocardium is of near uniform intensity with a small exception. In the septum, there is a region of hyperenhancement present at 40 min and increasing in intensity at 60 min (arrow). An inversion recovery image obtained at 60 minutes clearly highlights this hyperintense region. Upon autopsy and TTC staining, it was confirmed that there is a small infarction (6×4 mm on TTC staining) in the septum.

These data demonstrate that the collagen targeted contrast agent can provide MR images are reflective of perfusion in the myocardium. The collagen targeted contrast agent provides positive image contrast in the normally perfused myocardium, whereas the ischemic part of the myocardium is hypointense (dark). The collagen targeted agent also provides information on viability. Infarcted tissue appears hyperintense relative to viable and ischemic myocardium on these delayed scans. This is apparent on gradient echo and inversion recovery T1-weighted images.

26. Comparison of Collagen Binding Constant and Heart Uptake with Collagen Binding Contrast Agent and Non-Binding Analog The affinity to collagen of two similar compounds (Compound ID No. 800 and Compound ID No. 1019) was assessed over the concentration range 1-300 μM compound at a fixed collagen concentration of 5 μM using the dried collagen assay. Compound ID No. 800 and Compound ID No. 1019 differ only in the chirality of one cysteine. Compound ID No. 1019 has a D-cysteine whereas Compound ID No. 800 has an L-Cys in this position. The binding data was fit to a model on N binding sites with equal affinity. This yielded a dissociation constant, Kd, of 1.8 μM and 8 equivalent binding sites for Compound ID No. 800, whereas the affinity of Compound ID No. 1019 for type I collagen was much lower (Kd=400 μM). This demonstrates the specificity of Compound ID No. 800 for binding to collagen.

In vivo heart uptake of these two compounds were also compared. Compound (either Compound ID 800 or Compound ID No. 1019), at a dose of 10 μmol/kg, was injected into the tail vein of conscious male BALB/c mice (N=4 per compound). The animals were sacrificed at 15 minutes post-injection. The organs were immediately removed and rinsed in saline, and then blotted dry. Organs were digested with nitric acid and gadolinium content determined by ICP-MS. Gadolinium concentrations in the heart were 25.5±2.0, 14.7±1.0, and in the blood 14.3±2.3, 13.3±0.3 nmol Gd/g tissue for Compound ID 800 and Compound ID No. 1019, respectively. These data show that the collagen binder Compound ID 800 is preferentially taken up in a collagen rich organ like the heart, whereas Compound ID No. 1019 is poorly taken up by the heart. Both compounds have similar concentrations in the blood.

27. Relaxivity of Compound ID NO. 1014

The relaxivity of Compound ID NO. 1014 was determined in pig plasma at 37° C. using a Bruker mq60 spectrometer operating at 60 MHz (1.4 tesla). Compound ID NO. 1014 in pig plasma ranged from 0-200 μM. Samples were equilibrated for at least 30 minutes at 37° C. $T_1$ was measured using an inversion recovery sequence. 10 delay times were used and $T_1$ was estimated from the monoexponential change in signal intensity with delay time. Recycle delays were set to at least $5T_1$. $T_2$ was determined using a CPMG sequence with phase cycling. Typically 400 echoes were collected and $T_2$ estimated from the monoexponential decay in signal. Relaxivities were calculated by subtracting the relaxation rate of the plasma with Gd from the relaxation rate of the plasma sample with Gd and then dividing the result by the concentration of Compound ID NO. 1014. The relaxivities determined this way were $r_1$=63.8±5.6 mM$^{-1}$ s$^-$; $r_2$=115.6±10.7 mM$^{-1}$ s$^{-1}$.

A number of embodiments have been described. Nevertheless, it will be understood that various modifications may be made without departing from the spirit and scope of the invention. Accordingly, other embodiments are within the scope of the following claims.

What is claimed is:

1. A collagen binding peptide, wherein the collagen binding peptide comprises a cyclic peptide comprising the amino acid sequence:

```
                                        (SEQ ID NO: 74)
        Q-W-H-C-T-T-R-F-P-H-H-Y-C-L-Y-G;
``` wherein the peptide has a total length of 16 to 20 amino acids, and wherein one or more of the amino acids in the peptide is derivatized with a non-metallic radionuclide selected from the group consisting of $^{18}F$, $^{123}I$, $^{125}I$, and $^{131}I$.

2. A collagen binding peptide, wherein the collagen binding peptide comprises a cyclic peptide comprising the amino acid sequence:

```
                                    (SEQ ID NO: 828)
        C*-X1-X2-X3-X4-X5-X6-X7-X8-C*,
``` wherein:
C* is C or Pen in D or L form;
X1=T, A, K, V, I, S, Y, G, R, P, L, 3-NO2 Y, 4-Pal, 4-CO2H-F, 4-tBu-F, F(4-NH2), Y(Bn, 3-Cl), b-h-S, Y(3-I), or Aib, in D or L form;
X2=T, A, N, S, Y, R, V, I, K, D, G, b-h-G, Orn, or Dpr, in D or L form;
X3=R, A, S, L, Y, D, K, G, P, Aib, Y(3-Cl), I, Cha, Abu, F(4-F), Dopa, Tle, Cit, b-h-D, or K(Boc), in D or L form;
X4=F, Bip, F(4-CF3), 4-Pal, 1-Nal, F(4-NO2), Hfe, Bpa, F(4-CN), F(4-NH2), F(3,4-OMe), 2-Nal, Y(3-Cl), Aib, or b-h-E, in D or L form;
X5=P, P(3-OH), APro, Pip, N-Me-A, P(3-OH), Y(3-I), b-h-Y, or Aib, in D or L form;
X6=H, A, S, K, N, Y, T, D, R, W, P, Aib, or b-h-T, in D or L form;
X7=H, A, S, N, D, Y, W, Aib, Dpr, 2-Pal, 1-Nal, thien-W, W(5-OH), or b-h-W, in D or L form; and
X8=Y, A, R, T, V, H, D, S, P, 1-Nal, Bip, DOPA, H-Tyr, H-Tyr(Me), F(3-OMe), Y(3-Cl), Y(2,6-Me2), Dip, F(4-NH2), or Aib, in D or L form; and
wherein the peptide has a length of 10 to 20 amino acids, and wherein one or more of the amino acids in the peptide is derivatized with a non-metallic radionuclide selected from the group consisting of $^{18}F$, $^{123}I$, $^{125}I$, and $^{131}I$.

3. The collagen binding peptide of claim 2, wherein the cyclic peptide comprises the amino acid sequence:

| | |
|---|---|
| C-T-T-S-F-P-H-H-Y-C, | (SEQ ID NO: 817) |
| C-T-T-K-F-P-H-H-Y-C, | (SEQ ID NO: 818) |
| C-Y-T-Y-F-P-H-H-Y-C, | (SEQ ID NO: 819) |
| C-T-T-R-F-P-H-H-Y-C, or | (SEQ ID NO: 820) |
| C-S-G-D-E-Y-T-W-H-C. | (SEQ ID NO: 821) |

4. The collagen binding peptide of claim 2, wherein the cyclic peptide comprises the amino acid sequence:

```
                                            (SEQ ID NO: 829)
        C*-X1-X2-X3-X4-X5-X6-X7-X8-C*-X9-X10-X11,
``` wherein:
X9, X10, and X11 are any amino acid; and
wherein the peptide has a length of 13 to 20 amino acids.

5. The collagen binding peptide of claim 4, wherein:
X9=L, A, I, K, V, F, N, Y, P, Aib, Hse, Hfe, Bpa, 2-Nal, Y(3-Cl), Dip, or F(4-NH2), in D or L form;
X10=Y, A, F, E, Bpa, 2-Nal, Y(3-Cl), Dip, F(4-NH2), or Y(3-I), in D or L form; and
X11=G, E, Y, F, V, Bip, F(4-NH2), or Aib, in D or L form.

6. The collagen binding peptide of claim 4, wherein the cyclic peptide comprises the amino acid sequence:

```
                                          (SEQ ID NO: 832)
C*-X1-X2-X3-X4-X5-X6-X7-X8-C*-X9-X10-X11-X12,
``` wherein:
X11 is any amino acid;
X12 is any one or two amino acids; and
wherein the peptide has a length of 14 to 20 amino acids.

7. The collagen binding peptide of claim 6, wherein:
X11=G, E, Y, F, V, Bip, F(4-NH2), or Aib, in D or L form; and
X12=K, KK, Peg K, PEG(1×O), 1,4-AMB, 1,3-AMB, 1,6-Hex, PEG, or GTE, in D or L form.

8. The collagen binding peptide of claim 2, wherein the collagen binding peptide comprises a cyclic peptide comprising the amino acid sequence:

```
                              (SEQ ID NO: 830)
X14-X13-C*-X1-X2-X3-X4-X5-X6-X7-X8-C*,
``` wherein:
X13 and X14 are any amino acid;
C* is C or Pen, in D or L form; and
wherein the peptide has a length of 12 to 20 amino acids.

9. The collagen binding peptide of claim 8, wherein:
X13=H, A, S, K, N, D, Y, T, P, or Aib, in D or L form; and
X14=W, A, Y, 1-Nal, 2-Nal, thien-W, Tic, or W(5-OH), in D or L form.

10. The collagen binding peptide of claim 8, wherein the collagen binding peptide comprises a cyclic peptide comprising the amino acid sequence:

```
                                      (SEQ ID NO: 834)
X16-X15-X14-X13-C*-X1-X2-X3-X4-X5-X6-X7-X8-C*,
``` wherein:
X15 and X16 comprise one to three amino acids; and
wherein the peptide has a length of 14 to 20 amino acids.

11. The collagen binding peptide of claim 10, wherein:
X15=Q, G, A, D, S, P, K, GQ, K(G), K(Y.G), K(V.G), K(F.G), K(H.H), KK(K), Dpr, or Aib, in D or L form; and
X16=G, K, PP, GY, GV, GF, GH, GK(G), KK(K), Dpr, EAG, or PPG, in D or L form.

12. The collagen binding peptide of claim 11, wherein:
X15=Q, D, or K(G); and
X16=G.

13. A collagen binding peptide, wherein the collagen binding peptide comprises a cyclic peptide comprising the amino acid sequence:

```
                                    (SEQ ID NO: 831)
X1-X2-X3-C*-X4-T-X5-X6-P*-X7-H-X8-C-X9-X10-X11
``` wherein:
X1=any amino acid in L form;
X2=W or W*;
X3=H, A, K, or S;
X4=T, Y, G, K, or Y*;
X5=any amino acid in L form;
X6=F, Y, Y*;
X7=H, A, or Y;
X8=Y or Y*;
X9=L, V, L*, or Y*;
X10=Y, F, or Y*; and
X11=G, Y, Bip, or Y*;
wherein:
W* is 1-Nal, 2-Nal, Bpa, thien-W, W(5-OH), 7-aza-Trp, 1-methyl-Trp, 5-bromo-Tryp, 5-chloro-Tryp, 5-fluor-Trp, 7-methyl-trp, 6-methyl-Trp, 6-flouro-Trp, or 6-hydroxy-trp;
Y* is F(4-NH2), F(3,4-OMe2), F(3-OMe), F(4-CF3), F(4-CN), F(4-NO2), F(4-F), F(4-NO2), Hfe, 4-tBu-F, 4-CO2H-F, h-Tyr, h-Tyr(Me), Y(2,6-Me2), Y(3-Cl), Y(3-I), Y(Bn, 3-Cl), 2-substituted L-Tyr, 2,3-substituted-L-Tyr, 2,3,5-substituted-L-tyr, 2,5-substituted-L-Tyr, 2,6-substituted-L-Tyr, 2,3,5,6-substituted-L-Tyr, 3-substituted-L-Tyr, 3,5-substituted-L-Tyr, 2-substituted L-Phe, 2,3-substituted-L-Phe, 2,3,5-substituted-L-Phe, 2,5-substituted-L-Phe, 2,6-substituted-L-Phe, 2,3,5,6-substituted-L-Phe, 3-substituted-L-Phe, 3,5-substituted-L-Phe, L-2-pyridylalanine, L-3-pyridylalanine, or L-4-pyridylalanine;
L* is I, V, A, L, G, Tle, L-norvaline, L-norleucine, L-dehydroleucine, L-abu (2-aminobutyric acid), L-tert-leucine, beta-cyclohexyl-L-alanine, L-homoleucine, or L-homo-cyclohexylalanine;
C* is C or Pen;
P* is P, L-hydroxyproline, piperidine-2-carboxylic acid, or 4-hydroxypiperidine-2-carboxylic acid; and
wherein the peptide has a length of 16 to 20 amino acids, and wherein one or more of the amino acids in the peptide is derivatized with a non-metallic radionuclide selected from the group consisting of $^{18}$F, $^{123}$I, $^{125}$I, and $^{131}$I.

14. The collagen binding peptide of claim 13, wherein:
X1=Q or K(G); and
X5=R, Y, L, D, or K.

15. The collagen binding peptide of any one of claims 1, 2, and 13, wherein the non-metallic radionuclide is $^{18}$F.

16. The collagen binding peptide of any one of claims 1, 2, and 13, wherein at least one of the one or more derivatized amino acids is a derivatized tyrosine.

17. The collagen binding peptide of claim 16, wherein the derivatized tyrosine is iodinated with $^{123}$I, $^{125}$I, or $^{131}$I.

18. The collagen binding peptide of any one of claims 1, 2, and 13, wherein the one or more amino acids are derivatized with a non-metallic radionuclide at the N-terminus, the C-terminus or at an amino acid side chain.

\* \* \* \* \*

SEQUENCE LISTING

<160> NUMBER OF SEQ ID NOS: 836

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Tyr His Ala Cys Tyr Gln Ala Gly Cys Trp Ile Trp 1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Gly Trp Cys Glu Trp Ala Gln Asn Asn Cys Trp Asn Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Trp Trp Cys His Glu Met Pro Ser Met Cys Phe Gly Phe
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Trp Met Cys Val Asp Pro Pro Leu Trp Arg Cys Trp Val Gln
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Trp Lys Cys Trp Gly Val Val Lys Trp Glu Cys Ile Trp Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Trp Gln Cys Ser Gly Asn Gln Lys Trp Ser Cys Glu Trp Phe
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 7

Asn Trp Tyr Cys Thr Gly Thr Lys Ser Trp Glu Cys Phe Trp Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Trp Gln Cys Phe Gly Ala Ser Asp Trp His Cys Thr Trp Val
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Trp Asn Cys Tyr Gly Val Thr Glu Trp His Cys Tyr Met Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Thr Val Cys His Pro Pro Tyr Tyr Gly Arg Cys Asn Phe Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Leu Val Cys His Pro Pro Tyr Ser Gly Ser Cys Ser Leu His
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Met Ile Cys His Ala Pro Tyr Val Gly Lys Cys Asn Phe Leu
1               5                   10                  15

<210> SEQ ID NO 13
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Trp Thr Cys Ser Gly Asp Glu Tyr Thr Trp His Cys Asn Tyr Glu
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Trp Thr Cys Arg Gly Asp Glu Tyr Thr Trp His Cys Asn Tyr Glu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Trp Thr Cys Tyr Gly Asp Glu Tyr Thr Trp His Cys Asn Tyr Glu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Trp Thr Cys Ser Gly Asp Glu Tyr Tyr Trp His Cys Asn Tyr Glu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Trp Thr Cys Ser Gly Asp Glu Tyr Thr Trp His Cys Asn Tyr Glu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Asp Trp Thr Cys Ser Gly Asp Glu Tyr Thr Trp Cys Asn Tyr Glu
1               5                   10                  15
```

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Asp Trp Thr Cys Ser Gly Asp Glu Tyr Arg Trp His Cys Asn Tyr Glu
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Pro Trp Tyr Cys Ser Gly Asp His Leu Asp Trp Lys Cys Ile Tyr Gln
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Asp Trp Thr Cys Val Gly Asp His Lys Thr Trp Lys Cys Asn Phe His
1               5                   10                  15
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Asp Trp Glu Cys His Gly Asn Glu Phe Glu Trp Asn Cys Leu Met Arg
1               5                   10                  15
```

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Ala Trp Asp Cys Ser Gly Asn Ile Pro Thr Trp Tyr Cys Arg Arg Leu
1               5                   10                  15
```

<210> SEQ ID NO 24
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 24

Glu Trp Leu Cys Val Gly Asp Ser Leu Lys Trp Tyr Cys Lys His Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Trp Leu Cys Thr Gly Gly Ala Ala Thr Trp Asn Cys Lys Phe Asp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Arg Cys Asp Gly Asp Ala His Asp Trp His Cys Asp Trp Phe
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Trp His Cys Phe Gly Asp Asn Glu Asn Trp Met Cys Asn Leu Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Trp Ile Cys Thr Gly Asp Asn Ile Asp Trp Asn Cys Arg Phe Ala
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Trp Ile Cys His Gly Asp Phe Asp Thr Trp Lys Cys Asp Leu Gln
1               5                   10                  15
```

```
<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Trp Asp Cys Gln Gly Thr Asp Asn Ile Trp Glu Cys Val Arg Lys
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Trp Val Cys Gly Gly Asp His Thr Thr Trp Glu Cys His Leu Gln
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Trp Val Cys Ser Gly Asp His Ala Asp Trp Ser Cys Ala Leu Ile
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Trp Thr Cys Val Gly Gly Glu Lys Thr Trp Gly Cys Val Trp Asn
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Trp Asp Cys Thr Gly Asn Ser Ala Glu Trp Arg Cys Glu Met Gln
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Tyr Trp Val Cys Gly Gly Asp His Gln Ser Trp His Cys Ser His Pro
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Trp Ser Cys Gly Gly Asp His Asn Ala Trp Lys Cys Gln Tyr Ser
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Trp Asn Cys His Gly Thr Asp Ala Asn Trp Lys Cys Val Leu Asn
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Trp Ser Cys His Gly Asp Ala Ala Asp Trp Pro Cys Gln Trp Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Trp Gln Cys Ser Gly Asp Ala Ser Val Trp Asn Cys Asp Trp Ile
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Trp Arg Cys Arg Gly Asp Ser Ser Ser Trp Leu Cys Asp Tyr Thr
1               5                   10                  15

<210> SEQ ID NO 41
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Val Trp Ala Cys Arg Gly Gly Thr Thr Asn Trp His Cys Asp Leu
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Trp Arg Cys Asp Gln Phe Lys Gly Lys Trp Val Cys Arg Gly Gly
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Trp Gln Cys Tyr Ser Asp Lys Thr Ser Trp Val Cys Asn Leu Tyr
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Trp Asn Cys Tyr Glu Tyr Asp Ser Gln Trp Ile Cys Asp His Leu
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Trp Gln Cys Thr Gln Tyr Ala Asn Gln Trp Asn Cys Lys Tyr Asn
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Trp Val Cys Leu Gln Lys Gly Pro Lys Trp Val Cys Asp Trp Asp
1               5                   10                  15
```

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Trp Thr Cys Arg Met Thr Glu Asn Thr Trp Val Cys Asp Leu Asn
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Trp Ser Cys Trp Ile Val Glu Gly Arg Trp Asn Cys Ser Asp Ile
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Trp Phe Cys Ser Gln Lys Asn Arg Leu Trp Ser Cys Gly Glu Thr
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Trp Phe Cys Glu Leu Met Gln Asp Gln Trp Gln Cys Gly Ser Lys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Trp Phe Cys Glu Leu Met His Asp Gln Trp Gln Cys Gly Ser Lys
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 52

Arg Trp Ser Cys Trp Leu Asp Glu Asn Gly Trp Lys Cys Asp Gly Thr
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Trp Phe Cys Lys Leu Val Asp Gly Asn Trp Glu Cys Ser Thr Lys
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Trp Asn Cys Thr Met Thr Lys Ser Gly Trp Arg Cys Phe Glu Lys
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Trp Asn Cys His Trp Arg Asn Gln Gly Trp Leu Cys Ser Gly Gly
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Trp Asn Cys His Met Ile Arg Asn Glu Trp Arg Cys Thr Gly His
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Trp Thr Cys Asp Leu Gln Arg Gly Asp Trp Gln Cys Ser Thr Ile
1               5                   10                  15

<210> SEQ ID NO 58
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 58

Gly Trp Val Cys Met Met Arg Glu Thr Asp Trp Asn Cys Ser Ile
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Trp Gln Cys Arg Leu Thr Asp Tyr Gly Trp Asn Cys Asp Glu Arg
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Trp His Cys Val Leu Asn Asp Phe Arg Trp Thr Cys Gly Gly Asp
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Trp Ser Cys Tyr Met Val Asp His Gln Trp Tyr Cys Arg Glu Phe
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Trp Ser Cys Tyr Leu Gly Asp Asn Gly Trp Asn Cys His Asp Arg
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Trp Tyr Cys Ser Gln Ala Leu Asp Asn Trp Ser Cys Lys Leu Arg
1               5                   10                  15
```

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Trp Ile Cys Ser His Asn Asp Lys Gly Trp Thr Cys Gly Asp Gln
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Trp Glu Cys Val His Thr Lys Gly Glu Trp Tyr Cys Glu Thr Lys
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Trp Ser Cys Val Leu Asp Ala Asp Gly Trp Val Cys Ser Asp Asn
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Trp Ser Cys His Ser Met Asp Met Gln Trp His Cys Asp Phe Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Trp His Cys Phe Leu Glu Asn His His Trp Met Cys Ser Asp His
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 69

His Trp Gln Cys Gly Glu Lys Met Ser Phe Trp Ser Cys Glu Leu Val
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Trp Arg Cys Ala Leu Leu Asp Gly His Trp Gln Cys Thr Asp His
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Trp His Cys Ala Leu Met Gly Ser Arg Trp Val Cys Gly Gln Asn
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Trp His Cys Val Phe Ile Gln Gly Asp Trp Leu Cys Asn Ser Gly
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Trp His Cys Ala Leu Val Glu Asn Ser Trp Gln Cys Ser Glu Ala
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Trp His Cys Thr Thr Arg Phe Pro His His Tyr Cys Leu Tyr Gly
1               5                   10                  15

<210> SEQ ID NO 75
<211> LENGTH: 16
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Arg Asn Cys Val Leu Asn Asp Phe Arg Trp Thr Cys Gly Gly Asp
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Gly Ala Cys Asp Ile Phe Pro Thr Phe His Thr Cys Pro Gly Val
1               5                   10                  15

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Trp Gln Cys Gln Gly Thr Asp Ser Leu Asp Trp Lys Cys Leu Tyr
1               5                   10                  15
Met

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Trp Ala Cys Asp Leu Asp Glu Tyr Gly Gly Trp Gln Cys Tyr Thr
1               5                   10                  15
Gly

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Trp Thr Cys Glu Leu Asp Phe Arg Gln Ser Trp Tyr Cys Tyr Asp
1               5                   10                  15
Lys

<210> SEQ ID NO 80
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 80

Ser Trp Tyr Cys Asn Asn Gly Ser Tyr Gly Gln Trp His Cys Glu His
1               5                   10                  15
Arg

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Trp Phe Cys Glu Met Asp Glu Tyr Gly Lys Trp Asn Cys Gly Met
1               5                   10                  15
Met

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Trp Thr Cys Ser Met Asp Arg Asn Tyr Asp Trp Val Cys Gly Glu
1               5                   10                  15
Lys

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Trp Ala Cys Asn Thr Thr Ser Lys Gly Asp Trp Glu Cys Thr Asn
1               5                   10                  15
Leu

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Trp Ser Cys Asp Leu Ala Met Asp Asn Glu Trp Phe Cys Ser Thr
1               5                   10                  15
Lys

<210> SEQ ID NO 85
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 85

Gly Trp Thr Cys Ser Gln Pro Gly Ala Asn Val Trp Asn Cys Thr Met
1               5                   10                  15

Gln

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Trp Tyr Cys Asp Trp Asp Asp Arg Lys Gly Trp Met Cys Gly Ser
1               5                   10                  15

Asp

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Trp Thr Cys Asp Gln Ala Lys Gly Gly Ala Trp Ser Cys Ser Ser
1               5                   10                  15

Thr

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Trp Thr Cys Met Arg Asp Gln Val Gly Glu Trp His Cys Gly Thr
1               5                   10                  15

Glu

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Trp His Cys Glu Leu Asp Ser His Met Glu Trp Ser Cys Ser Gly
1               5                   10                  15

His

<210> SEQ ID NO 90
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 90

Thr Trp Ala Cys Gly Trp Thr Thr Thr Gly Trp Asp Asn Cys Arg Trp
1               5                   10                  15

Ile

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Trp Ala Cys Gly Trp Thr Thr Ala Gly Trp Asp Asn Cys Arg Trp
1               5                   10                  15

Ile

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Trp Ala Cys Gly Trp Thr Thr Thr Gly Trp Asp Asn Cys Arg Trp
1               5                   10                  15

Ile

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Trp Ala Cys Gln Lys Gly Gln His Asp Trp Glu Lys Cys His Trp
1               5                   10                  15

Leu

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Thr Asp Cys Gln Trp Met Asp Glu Gln Leu Trp Thr Cys Arg Trp
1               5                   10                  15

Asp

<210> SEQ ID NO 95
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Thr Asp Cys Gln Trp Met Asp Glu Gln Ile Trp Thr Cys Arg Trp
1               5                   10                  15

Asp

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Trp Gln Leu Cys Ser Ser Arg Asn Asp His Val Ala Tyr Cys Phe Val
1               5                   10                  15

Ser

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Ile Ser Cys Glu Ser Ser Glu Glu Lys Ile Ser Tyr Cys Trp Arg
1               5                   10                  15

Ala

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Gln Val Cys Ala Asp Ser Pro Gly Val Ile Thr Tyr Cys Tyr Thr
1               5                   10                  15

Tyr

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Lys Lys Cys Trp Tyr Asn Asp Gly Gly His Leu Arg Cys Arg Thr
1               5                   10                  15

Leu

<210> SEQ ID NO 100
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Trp Gly Cys Arg Gln Gly Thr Gly Glu His Trp Ser His Cys Met
1               5                   10                  15

Trp Phe

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Trp Trp Thr Cys His Met Thr Trp Ser Gly Gln Trp Asp Ser Cys Lys
1               5                   10                  15

Trp His

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Ala Tyr Cys Met Thr Asp Pro Ser Gly Lys Tyr Arg Tyr Cys Gln
1               5                   10                  15

Asn Trp

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Pro Ala Cys Asp Asp Gln Thr His Leu Trp Asn Leu Ala Cys Trp
1               5                   10                  15

Pro Ala

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: N-methyl-Gly

<400> SEQUENCE: 104

Tyr His Ala Cys Tyr Gln Ala Gly Cys Trp Ile Trp
1               5                   10
```

```
<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: N-methyl-Ala

<400> SEQUENCE: 105

Tyr His Ala Cys Tyr Gln Ala Gly Cys Trp Ile Trp
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr His Ala Cys Tyr Gln Ala Gly Cys Trp Ile Tyr
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr His Ala Cys Tyr Gln Ala Gly Cys Tyr Ile Trp
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr His Ala Cys Tyr Gln Ala Gly Cys Tyr Ile Tyr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Ser Ala Cys Tyr Gln Ala Gly Cys Trp Ile Trp
1               5                   10

<210> SEQ ID NO 110
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 110

Tyr Ser Ala Cys Tyr Gln Ala Gly Cys Tyr Ile Tyr
1               5                  10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr His Ala Ser Tyr Gln Ala Gly Ser Trp Ile Trp
1               5                  10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Lys Ala Cys Ser Val His Asp Glu Phe Gly Cys Leu Ile Ser
1               5                  10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Phe Ser Glu Cys Val Trp Val Asn Ala Tyr Gln Cys Glu Tyr Phe
1               5                  10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Thr Cys Ser Gly Asp Glu Tyr Thr Trp His Cys Asn Tyr Glu
1               5                  10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Trp Thr Cys Ser Gly Asp Pro Tyr Thr Trp His Cys Asn Tyr Glu
1               5                  10                  15
```

```
<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Trp Thr Cys Ser Gly Asp His Leu Thr Trp His Cys Asn Tyr Gly
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Trp Thr Cys Ser Gly Asp His Leu Thr Trp Lys Cys Asn Tyr Gly
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Trp Thr Cys Ser Gly Asn His Leu Thr Trp Tyr Cys Asn Tyr Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Trp Thr Cys Ser Gly Asp Glu Phe Thr Trp His Cys Asn Tyr Glu
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 120

Asp Trp Thr Cys Ser Gly Asp Glu Tyr Ala Trp His Cys Asn Tyr Glu
1               5                   10                  15

<210> SEQ ID NO 121
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 121

Pro Trp Thr Cys Ser Gly Asp Glu Tyr Ala Trp His Cys Asn Tyr Glu
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Trp Thr Cys Ser Gly Asp Glu Tyr Thr Trp His Cys Asn Tyr Glu
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Trp Thr Cys Ser Gly Asp Glu Tyr Thr Trp His Cys Asn Tyr
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: D-Ala
<220> FEATURE:
<221> NAME/KEY: MOD_RES
<222> LOCATION: (16)
<223> OTHER INFORMATION: D-Glu

<400> SEQUENCE: 124

Gln Trp Thr Cys Ser Gly Asp Glu Tyr Ala Trp His Cys Asn Ala Glu
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 125
```

```
Gln Trp Thr Cys Ser Gly Asp Glu Tyr Ser Trp His Cys Asn Tyr Glu
1               5                   10                  15
```

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 126

```
Gln Trp Thr Cys Ser Gly Asp Glu Tyr Ala Trp His Cys Asn Tyr Glu
1               5                   10                  15
```

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Gln Trp Thr Cys Ser Gly Asp Glu Tyr Thr Trp Ser Cys Asn Tyr Glu
1               5                   10                  15
```

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Gln Trp Thr Cys Ser Gly Asp Ala Tyr Thr Trp His Cys Ala Tyr Glu
1               5                   10                  15
```

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Ala Trp Thr Cys Ser Gly Asp Glu Tyr Thr Trp His Cys Asn Tyr Glu
1               5                   10                  15
```

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Trp Trp Ala Cys Gln Lys Gly Arg His Asp Trp Glu Lys Cys Arg Trp
1               5                   10                  15

Leu
```

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala His Ala Cys Tyr Gln Ala Gly Cys Trp Ile Trp
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Ala Ala Cys Tyr Gln Ala Gly Cys Trp Ile Trp
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Tyr His Ala Cys Ala Gln Ala Gly Cys Trp Ile Trp
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr His Ala Cys Tyr Ala Ala Gly Cys Trp Ile Trp
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr His Ala Cys Tyr Gln Ala Ala Cys Trp Ile Trp
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 136

Tyr His Ala Cys Tyr Gln Ala Gly Cys Ala Ile Trp
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr His Ala Cys Tyr Gln Ala Gly Cys Trp Ala Trp
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Tyr His Ala Cys Tyr Gln Ala Gly Cys Trp Ile Ala
1               5                   10

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Ala Thr Cys Ser Gly Asp Glu Tyr Thr Trp His Cys Asn Tyr Glu
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Trp Ala Cys Ser Gly Asp Glu Tyr Thr Trp His Cys Asn Tyr Glu
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Trp Thr Cys Ala Gly Asp Glu Tyr Thr Trp His Cys Asn Tyr Glu
1               5                   10                  15

<210> SEQ ID NO 142
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 142

Gln Trp Thr Cys Ser Ala Asp Glu Tyr Thr Trp His Cys Asn Tyr Glu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Trp Thr Cys Ser Gly Ala Glu Tyr Thr Trp His Cys Asn Tyr Glu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Trp Thr Cys Ser Gly Asp Ala Tyr Thr Trp His Cys Asn Tyr Glu
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Trp Thr Cys Ser Gly Asp Glu Ala Thr Trp His Cys Asn Tyr Glu
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Trp Thr Cys Ser Gly Asp Glu Tyr Ala Trp His Cys Asn Tyr Glu
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Trp Thr Cys Ser Gly Asp Glu Tyr Thr Ala His Cys Asn Tyr Glu
1               5                   10                  15
```

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Trp Thr Cys Ser Gly Asp Glu Tyr Thr Trp Ala Cys Asn Tyr Glu
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Trp Thr Cys Ser Gly Asp Glu Tyr Thr Trp His Cys Ala Tyr Glu
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Trp Thr Cys Ser Gly Asp Glu Tyr Thr Trp His Cys Asn Ala Glu
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Trp Thr Cys Ser Gly Asp Glu Tyr Thr Trp His Cys Asn Tyr Ala
1               5                   10                  15

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Tyr

<400> SEQUENCE: 152

Tyr His Ala Cys Tyr Gln Ala Gly Cys Trp Ile Trp
1               5                   10

<210> SEQ ID NO 153
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-His

<400> SEQUENCE: 153

Tyr His Ala Cys Tyr Gln Ala Gly Cys Trp Ile Trp
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: D-Ala

<400> SEQUENCE: 154

Tyr His Ala Cys Tyr Gln Ala Gly Cys Trp Ile Trp
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: D-Cys

<400> SEQUENCE: 155

Tyr His Ala Cys Tyr Gln Ala Gly Cys Trp Ile Trp
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: D-Tyr

<400> SEQUENCE: 156

Tyr His Ala Cys Tyr Gln Ala Gly Cys Trp Ile Trp
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
```

<223> OTHER INFORMATION: D-Gln

<400> SEQUENCE: 157

Tyr His Ala Cys Tyr Gln Ala Gly Cys Trp Ile Trp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Ala

<400> SEQUENCE: 158

Tyr His Ala Cys Tyr Gln Ala Gly Cys Trp Ile Trp
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: D-Cys

<400> SEQUENCE: 159

Tyr His Ala Cys Tyr Gln Ala Gly Cys Trp Ile Trp
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: D-Trp

<400> SEQUENCE: 160

Tyr His Ala Cys Tyr Gln Ala Gly Cys Trp Ile Trp
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: D-Ile

<400> SEQUENCE: 161

Tyr His Ala Cys Tyr Gln Ala Gly Cys Trp Ile Trp
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: D-Trp

<400> SEQUENCE: 162

Tyr His Ala Cys Tyr Gln Ala Gly Cys Trp Ile Trp
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Tyr
<220> FEATURE:
<221> NAME/KEY: MOD_RES
<222> LOCATION: (2)
<223> OTHER INFORMATION: D-His
<220> FEATURE:
<221> NAME/KEY: MOD_RES
<222> LOCATION: (3)
<223> OTHER INFORMATION: D-Ala
<220> FEATURE:
<221> NAME/KEY: MOD_RES
<222> LOCATION: (4)
<223> OTHER INFORMATION: D-Cys
<220> FEATURE:
<221> NAME/KEY: MOD_RES
<222> LOCATION: (5)
<223> OTHER INFORMATION: D-Tyr
<220> FEATURE:
<221> NAME/KEY: MOD_RES
<222> LOCATION: (6)
<223> OTHER INFORMATION: D-Gln
<220> FEATURE:
<221> NAME/KEY: MOD_RES
<222> LOCATION: (7)
<223> OTHER INFORMATION: D-Ala
<220> FEATURE:
<221> NAME/KEY: MOD_RES
<222> LOCATION: (9)
<223> OTHER INFORMATION: D-Cys
<220> FEATURE:
<221> NAME/KEY: MOD_RES
<222> LOCATION: (10)
<223> OTHER INFORMATION: D-Trp
<220> FEATURE:
<221> NAME/KEY: MOD_RES
<222> LOCATION: (11)
<223> OTHER INFORMATION: D-Ile
<220> FEATURE:
<221> NAME/KEY: MOD_RES
<222> LOCATION: (12)
<223> OTHER INFORMATION: D-Trp

<400> SEQUENCE: 163

Tyr His Ala Cys Tyr Gln Ala Gly Cys Trp Ile Trp
1               5                   10

<210> SEQ ID NO 164
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Gln

<400> SEQUENCE: 164

Gln Trp Thr Cys Ser Gly Asp Glu Tyr Thr Trp His Cys Asn Tyr Glu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Trp

<400> SEQUENCE: 165

Gln Trp Thr Cys Ser Gly Asp Glu Tyr Thr Trp His Cys Asn Tyr Glu
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: D-Thr

<400> SEQUENCE: 166

Gln Trp Thr Cys Ser Gly Asp Glu Tyr Thr Trp His Cys Asn Tyr Glu
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: D-Cys

<400> SEQUENCE: 167

Gln Trp Thr Cys Ser Gly Asp Glu Tyr Thr Trp His Cys Asn Tyr Glu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)
<223> OTHER INFORMATION: D-Ser

<400> SEQUENCE: 168

Gln Trp Thr Cys Ser Gly Asp Glu Tyr Thr Trp His Cys Asn Tyr Glu
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Asp

<400> SEQUENCE: 169

Gln Trp Thr Cys Ser Gly Asp Glu Tyr Thr Trp His Cys Asn Tyr Glu
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: D-Glu

<400> SEQUENCE: 170

Gln Trp Thr Cys Ser Gly Asp Glu Tyr Thr Trp His Cys Asn Tyr Glu
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: D-Tyr

<400> SEQUENCE: 171

Gln Trp Thr Cys Ser Gly Asp Glu Tyr Thr Trp His Cys Asn Tyr Glu
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: D-Thr

<400> SEQUENCE: 172

Gln Trp Thr Cys Ser Gly Asp Glu Tyr Thr Trp His Cys Asn Tyr Glu
1               5                   10                  15
```

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: D-Trp

<400> SEQUENCE: 173

Gln Trp Thr Cys Ser Gly Asp Glu Tyr Thr Trp His Cys Asn Tyr Glu
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: D-His

<400> SEQUENCE: 174

Gln Trp Thr Cys Ser Gly Asp Glu Tyr Thr Trp His Cys Asn Tyr Glu
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Cys

<400> SEQUENCE: 175

Gln Trp Thr Cys Ser Gly Asp Glu Tyr Thr Trp His Cys Asn Tyr Glu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: D-Asn

<400> SEQUENCE: 176

Gln Trp Thr Cys Ser Gly Asp Glu Tyr Thr Trp His Cys Asn Tyr Glu
1               5                   10                  15

<210> SEQ ID NO 177
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: D-Tyr

<400> SEQUENCE: 177

Gln Trp Thr Cys Ser Gly Asp Glu Tyr Thr Trp His Cys Asn Tyr Glu
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 178

Gln Trp Thr Cys Ser Gly Asp Glu Tyr Thr Trp His Cys Asn Tyr Glu
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Ala

<400> SEQUENCE: 179

Asp Trp Thr Cys Ser Ala Asp Glu Tyr Thr Trp His Cys Asn Tyr Glu
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Ser

<400> SEQUENCE: 180

Asp Trp Thr Cys Ser Ser Asp Glu Tyr Thr Trp His Cys Asn Tyr Glu
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Arg
```

```
<400> SEQUENCE: 181

Asp Trp Thr Cys Ser Arg Asp Glu Tyr Thr Trp His Cys Asn Tyr Glu
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Tyr

<400> SEQUENCE: 182

Asp Trp Thr Cys Ser Tyr Asp Glu Tyr Thr Trp His Cys Asn Tyr Glu
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Leu

<400> SEQUENCE: 183

Asp Trp Thr Cys Ser Leu Asp Glu Tyr Thr Trp His Cys Asn Tyr Glu
1               5                   10                  15

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Trp Thr Cys His Met Thr Trp Ser Gly Gln Trp Asp Ser Cys Lys
1               5                   10                  15

Trp His

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Gln Trp Thr Cys Ser Gly Asp Glu Tyr Thr Trp His Cys Asn Tyr
1               5                   10                  15

Glu

<210> SEQ ID NO 186
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 186

Gly Gln Trp His Cys Thr Thr Arg Phe Pro His His Tyr Cys Leu Tyr
1               5                   10                  15

Gly

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Gly Asp Trp Thr Cys Val Gly Asp His Lys Thr Trp Lys Cys Asn
1               5                   10                  15

Phe His

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Pro Pro Gln Trp His Cys Thr Thr Arg Phe Pro His His Tyr Cys Leu
1               5                   10                  15

Tyr Gly

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Gly Thr Trp Arg Cys Asp Gln Phe Lys Gly Lys Trp Val Cys Arg
1               5                   10                  15

Gly Gly

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)
<223> OTHER INFORMATION: D-Glu

<400> SEQUENCE: 190

Gly Gln Trp Thr Cys Ser Gly Asp Glu Tyr Thr Trp His Cys Asn Tyr
1               5                   10                  15

Glu
```

```
<210> SEQ ID NO 191
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Pro Pro Gln Trp Thr Cys Ser Gly Asp Glu Tyr Thr Trp His Cys Asn
1               5                   10                  15

Tyr Glu Pro Pro Glu
            20

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Gln Trp His Cys Thr Thr Arg Phe Pro His His Tyr Cys Leu Tyr
1               5                   10                  15

Gly

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Gln Trp Thr Cys Ser Gly Asp Glu Tyr Thr Trp His Cys Asn Tyr
1               5                   10                  15

Glu

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Asp Trp Thr Cys Val Gly Asp His Lys Thr Trp Lys Cys Asn Phe
1               5                   10                  15

His

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Trp Gly Cys Arg Gln Gly Thr Gly Glu His Trp Ser His Cys Met
1               5                   10                  15

Trp Phe
```

<210> SEQ ID NO 196
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Trp Trp Thr Cys His Met Thr Trp Ser Gly Gln Trp Asp Ser Cys Lys
1               5                   10                  15

Trp His

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Ala Trp His Cys Thr Thr Arg Phe Pro His His Tyr Cys Leu Tyr
1               5                   10                  15

Gly

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Gln Ala His Cys Thr Thr Arg Phe Pro His His Tyr Cys Leu Tyr
1               5                   10                  15

Gly

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Gln Trp Ala Cys Thr Thr Arg Phe Pro His His Tyr Cys Leu Tyr
1               5                   10                  15

Gly

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Gln Trp His Cys Ala Thr Arg Phe Pro His His Tyr Cys Leu Tyr
1               5                   10                  15

Gly

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gln Trp His Cys Thr Ala Arg Phe Pro His His Tyr Cys Leu Tyr
1               5                   10                  15

Gly

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gln Trp His Cys Thr Thr Ala Phe Pro His His Tyr Cys Leu Tyr
1               5                   10                  15

Gly

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gln Trp His Cys Thr Thr Arg Ala Pro His His Tyr Cys Leu Tyr
1               5                   10                  15

Gly

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Gln Trp His Cys Thr Thr Arg Phe Ala His His Tyr Cys Leu Tyr
1               5                   10                  15

Gly

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gln Trp His Cys Thr Thr Arg Phe Pro Ala His Tyr Cys Leu Tyr
1               5                   10                  15

Gly

```
<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206
```

Gly Gln Trp His Cys Thr Thr Arg Phe Pro His Ala Tyr Cys Leu Tyr
1               5                   10                  15

Gly

```
<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207
```

Gly Gln Trp His Cys Thr Thr Arg Phe Pro His His Ala Cys Leu Tyr
1               5                   10                  15

Gly

```
<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208
```

Gly Gln Trp His Cys Thr Thr Arg Phe Pro His His Tyr Cys Ala Tyr
1               5                   10                  15

Gly

```
<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209
```

Gly Gln Trp His Cys Thr Thr Arg Phe Pro His His Tyr Cys Leu Ala
1               5                   10                  15

Gly

```
<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Gln
```

<400> SEQUENCE: 210

Gly Gln Trp His Cys Thr Thr Arg Phe Pro His His Tyr Cys Leu Tyr
1               5                   10                  15

Gly

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: D-Trp

<400> SEQUENCE: 211

Gly Gln Trp His Cys Thr Thr Arg Phe Pro His His Tyr Cys Leu Tyr
1               5                   10                  15

Gly

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: D-His

<400> SEQUENCE: 212

Gly Gln Trp His Cys Thr Thr Arg Phe Pro His His Tyr Cys Leu Tyr
1               5                   10                  15

Gly

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: D-Cys

<400> SEQUENCE: 213

Gly Gln Trp His Cys Thr Thr Arg Phe Pro His His Tyr Cys Leu Tyr
1               5                   10                  15

Gly

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)

<223> OTHER INFORMATION: D-Thr

<400> SEQUENCE: 214

Gly Gln Trp His Cys Thr Thr Arg Phe Pro His His Tyr Cys Leu Tyr
1               5                   10                  15

Gly

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Thr

<400> SEQUENCE: 215

Gly Gln Trp His Cys Thr Thr Arg Phe Pro His His Tyr Cys Leu Tyr
1               5                   10                  15

Gly

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: D-Arg

<400> SEQUENCE: 216

Gly Gln Trp His Cys Thr Thr Arg Phe Pro His His Tyr Cys Leu Tyr
1               5                   10                  15

Gly

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: D-Phe

<400> SEQUENCE: 217

Gly Gln Trp His Cys Thr Thr Arg Phe Pro His His Tyr Cys Leu Tyr
1               5                   10                  15

Gly

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (10)
<223> OTHER INFORMATION: D-Pro

<400> SEQUENCE: 218

Gly Gln Trp His Cys Thr Thr Arg Phe Pro His His Tyr Cys Leu Tyr
1               5                   10                  15

Gly

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: D-His

<400> SEQUENCE: 219

Gly Gln Trp His Cys Thr Thr Arg Phe Pro His His Tyr Cys Leu Tyr
1               5                   10                  15

Gly

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: D-His

<400> SEQUENCE: 220

Gly Gln Trp His Cys Thr Thr Arg Phe Pro His His Tyr Cys Leu Tyr
1               5                   10                  15

Gly

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 221

Gly Gln Trp His Cys Thr Thr Arg Phe Pro His His Tyr Cys Leu Tyr
1               5                   10                  15

Gly

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (14)
<223> OTHER INFORMATION: D-Cys

<400> SEQUENCE: 222

Gly Gln Trp His Cys Thr Thr Arg Phe Pro His His Tyr Cys Leu Tyr
1               5                   10                  15

Gly

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: D-Leu

<400> SEQUENCE: 223

Gly Gln Trp His Cys Thr Thr Arg Phe Pro His His Tyr Cys Leu Tyr
1               5                   10                  15

Gly

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Gln
<220> FEATURE:
<221> NAME/KEY: MOD_RES
<222> LOCATION: (3)
<223> OTHER INFORMATION: D-Trp
<220> FEATURE:
<221> NAME/KEY: MOD_RES
<222> LOCATION: (4)
<223> OTHER INFORMATION: D-His
<220> FEATURE:
<221> NAME/KEY: MOD_RES
<222> LOCATION: (5)
<223> OTHER INFORMATION: D-Cys
<220> FEATURE:
<221> NAME/KEY: MOD_RES
<222> LOCATION: (6)
<223> OTHER INFORMATION: D-Thr
<220> FEATURE:
<221> NAME/KEY: MOD_RES
<222> LOCATION: (7)
<223> OTHER INFORMATION: D-Thr
<220> FEATURE:
<221> NAME/KEY: MOD_RES
<222> LOCATION: (8)
<223> OTHER INFORMATION: D-Arg
<220> FEATURE:
<221> NAME/KEY: MOD_RES
<222> LOCATION: (9)
<223> OTHER INFORMATION: D-Phe
<220> FEATURE:
<221> NAME/KEY: MOD_RES
<222> LOCATION: (10)
<223> OTHER INFORMATION: D-Pro
<220> FEATURE:
<221> NAME/KEY: MOD_RES
<222> LOCATION: (11)
<223> OTHER INFORMATION: D-His
```

```
<220> FEATURE:
<221> NAME/KEY: MOD_RES
<222> LOCATION: (12)
<223> OTHER INFORMATION: D-His
<220> FEATURE:
<221> NAME/KEY: MOD_RES
<222> LOCATION: (13)
<223> OTHER INFORMATION: D-Tyr
<220> FEATURE:
<221> NAME/KEY: MOD_RES
<222> LOCATION: (14)
<223> OTHER INFORMATION: D-Cys
<220> FEATURE:
<221> NAME/KEY: MOD_RES
<222> LOCATION: (15)
<223> OTHER INFORMATION: D-Leu
<220> FEATURE:
<221> NAME/KEY: MOD_RES
<222> LOCATION: (16)
<223> OTHER INFORMATION: D-Tyr

<400> SEQUENCE: 224

Gly Gln Trp His Cys Thr Thr Arg Phe Pro His His Tyr Cys Leu Tyr
1               5                   10                  15
Gly

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Tyr

<400> SEQUENCE: 225

Gly Gln Trp His Cys Thr Thr Arg Phe Pro His His Tyr Cys Leu Tyr
1               5                   10                  15
Gly

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 1-Nal

<400> SEQUENCE: 226

Gly Gln Xaa His Cys Thr Thr Arg Phe Pro His His Tyr Cys Leu Tyr
1               5                   10                  15
Gly

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
```

<223> OTHER INFORMATION: 2-Nal

<400> SEQUENCE: 227

Gly Gln Xaa His Cys Thr Thr Arg Phe Pro His His Tyr Cys Leu Tyr
1               5                   10                  15

Gly

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: thien-W

<400> SEQUENCE: 228

Gly Gln Xaa His Cys Thr Thr Arg Phe Pro His His Tyr Cys Leu Tyr
1               5                   10                  15

Gly

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Gln Tyr His Cys Thr Thr Arg Phe Pro His His Tyr Cys Leu Tyr
1               5                   10                  15

Gly

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Tic

<400> SEQUENCE: 230

Gly Xaa His Cys Thr Thr Arg Phe Pro His His Tyr Cys Leu Tyr Gly
1               5                   10                  15

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Trp(5-OH)

<400> SEQUENCE: 231

Gly Gln Trp His Cys Thr Thr Ser Phe Pro His His Tyr Cys Leu Tyr

```
                1               5                   10                  15

Gly

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Gln Trp Ser Cys Thr Thr Arg Phe Pro His His Tyr Cys Leu Tyr
1               5                   10                  15

Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Aib

<400> SEQUENCE: 233

Gly Gln Trp Xaa Cys Thr Thr Arg Phe Pro His His Tyr Cys Leu Tyr
1               5                   10                  15

Gly

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 234

Gly Gln Trp Lys Cys Thr Thr Arg Phe Pro His His Tyr Cys Leu Tyr
1               5                   10                  15

Gly

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 235

Gly Gln Trp Ser Cys Thr Thr Arg Phe Pro His His Tyr Cys Leu Tyr
1               5                   10                  15

Gly
```

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Gln Trp Asn Cys Thr Thr Leu Phe Pro His His Tyr Cys Leu Tyr
1               5                   10                  15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gln Trp Asp Cys Thr Thr Leu Phe Pro His His Tyr Cys Leu Tyr
1               5                   10                  15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 238

Gly Lys Trp Tyr Cys Thr Thr Tyr Phe Pro His His Tyr Cys Leu Tyr
1               5                   10                  15

Gly

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Aib

<400> SEQUENCE: 239

Gly Gln Trp His Cys Xaa Thr Arg Phe Pro His His Tyr Cys Leu Tyr
1               5                   10                  15

Gly

<210> SEQ ID NO 240
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 240

Gly Gln Trp His Cys Lys Thr Arg Phe Pro His His Tyr Cys Leu Tyr
1               5                   10                  15
Gly

<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Aib

<400> SEQUENCE: 241

Gly Gln Trp His Cys Xaa Thr Arg Phe Pro His His Tyr Cys Leu Tyr
1               5                   10                  15
Gly

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gln Trp His Cys Val Thr Leu Phe Pro His His Tyr Cys Leu Tyr
1               5                   10                  15
Gly

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gln Trp His Cys Ile Thr Leu Phe Pro His His Tyr Cys Leu Tyr
1               5                   10                  15
Gly

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Gln Trp His Cys Ser Thr Leu Phe Pro His His Tyr Cys Leu Tyr
1               5                   10                  15

Gly

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Gln Trp His Cys Tyr Thr Leu Phe Pro His His Tyr Cys Leu Tyr
1               5                   10                  15

Gly

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gln Trp His Cys Gly Thr Leu Phe Pro His His Tyr Cys Leu Tyr
1               5                   10                  15

Gly

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (6)
<223> OTHER INFORMATION: Tyr(3-I)

<400> SEQUENCE: 247

Gly Lys Trp His Cys Tyr Thr Tyr Phe Pro His His Tyr Cys Leu Tyr
1               5                   10                  15

Gly

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Asn

<400> SEQUENCE: 248

Gly Gln Trp His Cys Thr Asn Arg Phe Pro His His Tyr Cys Leu Tyr
1               5                   10                  15

Gly

```
<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Ser

<400> SEQUENCE: 249

Gly Gln Trp His Cys Thr Ser Arg Phe Pro His His Tyr Cys Leu Tyr
1               5                   10                  15

Gly

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Tyr

<400> SEQUENCE: 250

Gly Gln Trp His Cys Thr Tyr Arg Phe Pro His His Tyr Cys Leu Tyr
1               5                   10                  15

Gly

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Arg

<400> SEQUENCE: 251

Gly Gln Trp His Cys Thr Arg Arg Phe Pro His His Tyr Cys Leu Tyr
1               5                   10                  15

Gly

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Gln Trp His Cys Thr Val Leu Phe Pro His His Tyr Cys Leu Tyr
1               5                   10                  15

Gly

<210> SEQ ID NO 253
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Gln Trp His Cys Thr Ile Leu Phe Pro His His Tyr Cys Leu Tyr
1               5                   10                  15
Gly

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Gln Trp His Cys Thr Asn Leu Phe Pro His His Tyr Cys Leu Tyr
1               5                   10                  15
Gly

<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Gln Trp His Cys Thr Tyr Leu Phe Pro His His Tyr Cys Leu Tyr
1               5                   10                  15
Gly

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (7)
<223> OTHER INFORMATION: Dpr

<400> SEQUENCE: 256

Gly Gln Trp His Cys Thr Xaa Arg Phe Pro His His Tyr Cys Leu Tyr
1               5                   10                  15
Gly

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (7)
<223> OTHER INFORMATION: Dpr

<400> SEQUENCE: 257

Gly Gln Trp His Cys Thr Xaa Arg Phe Pro His His Tyr Cys Leu Tyr
1               5                   10                  15
Gly

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 258

Gly Gln Trp His Cys Thr Lys Arg Phe Pro His His Tyr Cys Leu Tyr
1               5                   10                  15
Gly

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Gln Trp His Cys Thr Lys Arg Phe Pro His His Tyr Cys Leu Tyr
1               5                   10                  15
Gly

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (7)
<223> OTHER INFORMATION: Orn

<400> SEQUENCE: 260

Gly Gln Trp His Cys Thr Xaa Arg Phe Pro His His Tyr Cys Leu Tyr
1               5                   10                  15
Gly

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (7)
<223> OTHER INFORMATION: Orn

<400> SEQUENCE: 261

Gly Gln Trp His Cys Thr Xaa Arg Phe Pro His His Tyr Cys Leu Tyr
1               5                   10                  15
Gly

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Gln Trp His Cys Thr Asp Arg Phe Pro His His Tyr Cys Leu Tyr
1               5                   10                  15
Gly

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 263

Gly Lys Trp His Cys Tyr Lys Tyr Phe Pro His His Tyr Cys Leu Tyr
1               5                   10                  15
Gly

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Gln Trp His Cys Thr Thr Ser Phe Pro His His Tyr Cys Leu Tyr
1               5                   10                  15
Gly

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gln Trp His Cys Thr Thr Asp Phe Pro His His Tyr Cys Leu Tyr
1               5                   10                  15
Gly
```

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Gly Gln Trp His Cys Thr Thr Leu Phe Pro His His Tyr Cys Leu Tyr
1               5                   10                  15

Gly

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Gly Gln Trp His Cys Thr Thr Tyr Phe Pro His His Tyr Cys Leu Tyr
1               5                   10                  15

Gly

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: cbz-Gly

<400> SEQUENCE: 268

Gly Gln Trp His Cys Thr Thr Lys Phe Pro His His Tyr Cys Leu Tyr
1               5                   10                  15

Gly

<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)
<223> OTHER INFORMATION: Aib

<400> SEQUENCE: 269

Gly Gln Trp His Cys Thr Thr Xaa Phe Pro His His Tyr Cys Leu Tyr
1               5                   10                  15

Gly

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (8)
<223> OTHER INFORMATION: Tyr(3-Cl)
<220> FEATURE:
<221> NAME/KEY: MOD_RES
<222> LOCATION: (13)
<223> OTHER INFORMATION: D-Tyr

<400> SEQUENCE: 270

Gly Gln Trp His Cys Thr Thr Tyr Phe Pro His His Tyr Cys Leu Tyr
1               5                   10                  15

Gly

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 271

Gly Gln Trp His Cys Thr Thr Ile Phe Pro His His Tyr Cys Leu Tyr
1               5                   10                  15

Gly

<210> SEQ ID NO 272
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Cha
<220> FEATURE:
<221> NAME/KEY: MOD_RES
<222> LOCATION: (13)
<223> OTHER INFORMATION: D-Tyr

<400> SEQUENCE: 272

Gly Gln Trp His Cys Thr Thr Xaa Phe Pro His His Tyr Cys Leu Tyr
1               5                   10                  15

Gly

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Abu

<400> SEQUENCE: 273

Gly Gln Trp His Cys Thr Thr Xaa Phe Pro His His Tyr Cys Leu Tyr
1               5                   10                  15
```

Gly

```
<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Phe(4-F)

<400> SEQUENCE: 274
```

Gly Gln Trp His Cys Thr Thr Phe Phe Pro His His Tyr Cys Leu Tyr
1               5                   10                  15

Gly

```
<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Dopa

<400> SEQUENCE: 275
```

Gly Gln Trp His Cys Thr Thr Xaa Phe Pro His His Tyr Cys Leu Tyr
1               5                   10                  15

Gly

```
<210> SEQ ID NO 276
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tle

<400> SEQUENCE: 276
```

Gly Gln Trp His Cys Thr Thr Xaa Phe Pro His His Tyr Cys Leu Tyr
1               5                   10                  15

Gly

```
<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Cit

<400> SEQUENCE: 277
```

Gly Gln Trp His Cys Thr Thr Xaa Phe Pro His His Tyr Cys Leu Tyr
1               5                   10                  15

Gly

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Gln Trp His Cys Thr Thr Arg Tyr Pro His His Tyr Cys Leu Tyr
1               5                   10                  15

Gly

<210> SEQ ID NO 279
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Bip

<400> SEQUENCE: 279

Gly Gln Trp His Cys Thr Thr Arg Xaa Pro His His Tyr Cys Leu Tyr
1               5                   10                  15

Gly

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-CF3)

<400> SEQUENCE: 280

Gly Gln Trp His Cys Thr Thr Arg Phe Pro His His Tyr Cys Leu Tyr
1               5                   10                  15

Gly

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 4-Pal

<400> SEQUENCE: 281

Gly Gln Trp His Cys Thr Thr Arg Xaa Pro His His Tyr Cys Leu Tyr
1               5                   10                  15

Gly

```
<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal

<400> SEQUENCE: 282

Gly Gln Trp His Cys Thr Thr Arg Xaa Pro His His Tyr Cys Leu Tyr
1               5                   10                  15

Gly

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-NO2)

<400> SEQUENCE: 283

Gly Gln Trp His Cys Thr Thr Arg Phe Pro His His Tyr Cys Leu Tyr
1               5                   10                  15

Gly

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Hfe

<400> SEQUENCE: 284

Gly Gln Trp His Cys Thr Thr Arg Xaa Pro His His Tyr Cys Leu Tyr
1               5                   10                  15

Gly

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Bpa

<400> SEQUENCE: 285

Gly Gln Trp His Cys Thr Thr Asp Xaa Pro His His Tyr Cys Leu Tyr
1               5                   10                  15

Gly
```

```
<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-CN)

<400> SEQUENCE: 286

Gly Gln Trp His Cys Thr Thr Asp Phe Pro His His Tyr Cys Leu Tyr
1               5                   10                  15

Gly

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-NH2)

<400> SEQUENCE: 287

Gly Gln Trp His Cys Thr Thr Asp Phe Pro His His Tyr Cys Leu Tyr
1               5                   10                  15

Gly

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(3,4-OMe)

<400> SEQUENCE: 288

Gly Gln Trp His Cys Thr Thr Asp Phe Pro His His Tyr Cys Leu Tyr
1               5                   10                  15

Gly

<210> SEQ ID NO 289
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal

<400> SEQUENCE: 289

Gly Gln Trp His Cys Thr Thr Asp Xaa Pro His His Tyr Cys Leu Tyr
1               5                   10                  15
```

Gly

<210> SEQ ID NO 290
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Tyr(3-Cl)

<400> SEQUENCE: 290

Gly Gln Trp His Cys Thr Thr Asp Tyr Pro His His Tyr Cys Leu Tyr
1               5                   10                  15

Gly

<210> SEQ ID NO 291
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Pro(3-OH)

<400> SEQUENCE: 291

Pro Pro Gln Trp His Cys Thr Thr Arg Phe Pro His His Tyr Cys Leu
1               5                   10                  15

Tyr Gly

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Delta-Pro

<400> SEQUENCE: 292

Gly Gln Trp His Cys Thr Thr Ser Phe Pro His His Tyr Cys Leu Tyr
1               5                   10                  15

Gly

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Pip

<400> SEQUENCE: 293

Gly Gln Trp His Cys Thr Thr Ser Phe Xaa His His Tyr Cys Leu Tyr
1               5                   10                  15

Gly

<210> SEQ ID NO 294
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: N-Methyl-Ala

<400> SEQUENCE: 294

Gly Gln Trp His Cys Thr Thr Arg Phe Ala His His Tyr Cys Leu Tyr
1               5                   10                  15

Gly

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Pro(3-OH)

<400> SEQUENCE: 295

Asp Trp Ser Cys Thr Thr Asp Tyr Pro Ala His Tyr Cys Leu Tyr Gly
1               5                   10                  15

<210> SEQ ID NO 296
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gly Gln Trp His Cys Thr Thr Arg Phe Pro Ser His Tyr Cys Leu Tyr
1               5                   10                  15

Gly

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 297

Gly Gln Trp His Cys Thr Thr Arg Phe Pro Lys His Tyr Cys Leu Tyr
1               5                   10                  15

Gly

<210> SEQ ID NO 298

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Aib

<400> SEQUENCE: 298

Gly Gln Trp His Cys Thr Thr Arg Phe Pro Xaa His Tyr Cys Leu Tyr
1               5                   10                  15

Gly

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Gln Trp His Cys Thr Thr Leu Phe Pro Asn His Tyr Cys Leu Tyr
1               5                   10                  15

Gly

<210> SEQ ID NO 300
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ala Trp His Cys Thr Thr Arg Phe Pro Ala His Tyr Cys Leu Tyr Gly
1               5                   10                  15

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 301

Gly Lys Trp His Cys Thr Thr Tyr Phe Pro Tyr His Tyr Cys Leu Tyr
1               5                   10                  15

Gly

<210> SEQ ID NO 302
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302
```

```
Gly Gln Trp His Cys Thr Thr Arg Phe Pro His Ser Tyr Cys Leu Tyr
1               5                   10                  15

Gly

<210> SEQ ID NO 303
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Aib

<400> SEQUENCE: 303

Gly Gln Trp His Cys Thr Thr Arg Phe Pro His Xaa Tyr Cys Leu Tyr
1               5                   10                  15

Gly

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Dpr

<400> SEQUENCE: 304

Gly Gln Trp His Cys Thr Thr Asp Phe Pro His Xaa Tyr Cys Leu Tyr
1               5                   10                  15

Gly

<210> SEQ ID NO 305
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 2-Pal

<400> SEQUENCE: 305

Gly Gln Trp His Cys Thr Thr Asp Phe Pro His Xaa Tyr Cys Leu Tyr
1               5                   10                  15

Gly

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gly Gln Trp His Cys Thr Thr Leu Phe Pro His Asn Tyr Cys Leu Tyr
1               5                   10                  15
```

Gly

<210> SEQ ID NO 307
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Gln Trp His Cys Thr Thr Leu Phe Pro His Asp Tyr Cys Leu Tyr
1               5                   10                  15

Gly

<210> SEQ ID NO 308
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 308

Gly Lys Trp His Cys Thr Thr Tyr Phe Pro His Tyr Tyr Cys Leu Tyr
1               5                   10                  15

Gly

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 309

Gly Lys Trp His Cys Thr Thr Tyr Phe Pro His Trp Tyr Cys Leu Tyr
1               5                   10                  15

Gly

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 310

Gly Gln Trp His Cys Thr Thr Arg Phe Pro His His Xaa Cys Leu Tyr
1               5                   10                  15

Gly

```
<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Bip

<400> SEQUENCE: 311

Gly Gln Trp His Cys Thr Thr Arg Phe Pro His His Xaa Cys Leu Tyr
1               5                   10                  15

Gly

<210> SEQ ID NO 312
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Arg

<400> SEQUENCE: 312

Gly Gln Trp His Cys Thr Thr Arg Phe Pro His His Arg Cys Leu Tyr
1               5                   10                  15

Gly

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Bip

<400> SEQUENCE: 313

Gly Gln Trp His Cys Thr Thr Arg Phe Pro His His Xaa Cys Leu Tyr
1               5                   10                  15

Gly

<210> SEQ ID NO 314
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-1-Nal

<400> SEQUENCE: 314

Gly Gln Trp His Cys Thr Thr Arg Phe Pro His His Xaa Cys Leu Tyr
1               5                   10                  15

Gly
```

```
<210> SEQ ID NO 315
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Thr

<400> SEQUENCE: 315

Gly Gln Trp His Cys Thr Thr Arg Phe Pro His His Thr Cys Leu Tyr
1               5                   10                  15

Gly

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 316

Gly Gln Trp His Cys Thr Thr Leu Phe Pro His His Xaa Cys Leu Tyr
1               5                   10                  15

Gly

<210> SEQ ID NO 317
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Dopa

<400> SEQUENCE: 317

Gly Gln Trp His Cys Thr Thr Ser Phe Pro His His Xaa Cys Leu Tyr
1               5                   10                  15

Gly

<210> SEQ ID NO 318
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: h-Tyr

<400> SEQUENCE: 318

Gly Gln Trp His Cys Thr Thr Arg Phe Pro His His Tyr Cys Leu Tyr
1               5                   10                  15

Gly
```

```
<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: h-Tyr(Me)

<400> SEQUENCE: 319

Gly Gln Trp His Cys Thr Thr Arg Phe Pro His His Tyr Cys Leu Tyr
1               5                   10                  15

Gly

<210> SEQ ID NO 320
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Phe(3-OMe)

<400> SEQUENCE: 320

Gly Gln Trp His Cys Thr Thr Arg Phe Pro His His Phe Cys Leu Tyr
1               5                   10                  15

Gly

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (13)
<223> OTHER INFORMATION: Bip

<400> SEQUENCE: 321

Gly Lys Trp His Cys Thr Thr Tyr Phe Pro His His Xaa Cys Leu Tyr
1               5                   10                  15

Gly

<210> SEQ ID NO 322
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
```

```
<222> LOCATION: (13)
<223> OTHER INFORMATION: Tyr(3-Cl)

<400> SEQUENCE: 322

Gly Lys Trp His Cys Thr Thr Tyr Phe Pro His His Tyr Cys Leu Tyr
1               5                   10                  15

Gly

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (13)
<223> OTHER INFORMATION: Tyr(2,6-Me2)

<400> SEQUENCE: 323

Gly Lys Trp His Cys Thr Thr Tyr Phe Pro His His Tyr Cys Leu Tyr
1               5                   10                  15

Gly

<210> SEQ ID NO 324
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 324

Gly Lys Trp His Cys Thr Thr Tyr Phe Pro His His Val Cys Leu Tyr
1               5                   10                  15

Gly

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 325

Gly Lys Trp His Cys Thr Thr Leu Phe Pro His His Val Cys Leu Tyr
1               5                   10                  15

Gly

<210> SEQ ID NO 326
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (13)
<223> OTHER INFORMATION: Dip

<400> SEQUENCE: 326

Gly Lys Trp His Cys Thr Thr Tyr Phe Pro His His Xaa Cys Leu Tyr
1               5                   10                  15

Gly

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (13)
<223> OTHER INFORMATION: Dip

<400> SEQUENCE: 327

Gly Lys Trp His Cys Thr Thr Tyr Phe Pro His His Xaa Cys Leu Tyr
1               5                   10                  15

Gly

<210> SEQ ID NO 328
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (13)
<223> OTHER INFORMATION: Phe(4-NH2)

<400> SEQUENCE: 328

Gly Lys Trp His Cys Thr Thr Tyr Phe Pro His His Phe Cys Leu Tyr
1               5                   10                  15

Gly

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
```

```
<220> FEATURE:
<221> NAME/KEY: MOD_RES
<222> LOCATION: (13)
<223> OTHER INFORMATION: 1-Nal

<400> SEQUENCE: 329

Gly Lys Trp His Cys Tyr Thr Tyr Phe Pro His His Xaa Cys Leu Tyr
1               5                   10                  15

Gly

<210> SEQ ID NO 330
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Pen

<400> SEQUENCE: 330

Gly Gln Trp His Xaa Thr Thr Arg Phe Pro His His Tyr Cys Leu Tyr
1               5                   10                  15

Gly

<210> SEQ ID NO 331
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Pen

<400> SEQUENCE: 331

Gly Gln Trp His Cys Thr Thr Arg Phe Pro His His Tyr Xaa Leu Tyr
1               5                   10                  15

Gly

<210> SEQ ID NO 332
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Pen
<220> FEATURE:
<221> NAME/KEY: MOD_RES
<222> LOCATION: (14)
<223> OTHER INFORMATION: Pen

<400> SEQUENCE: 332

Gly Gln Trp His Xaa Thr Thr Arg Phe Pro His His Tyr Xaa Leu Tyr
1               5                   10                  15

Gly

<210> SEQ ID NO 333
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 333

Gly Gln Trp His Cys Thr Thr Arg Phe Pro His His Tyr Cys Lys Tyr
1               5                   10                  15

Gly

<210> SEQ ID NO 334
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Aib

<400> SEQUENCE: 334

Gly Gln Trp His Cys Thr Thr Arg Phe Pro His His Tyr Cys Xaa Tyr
1               5                   10                  15

Gly

<210> SEQ ID NO 335
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Gln Trp His Cys Thr Thr Leu Phe Pro His His Tyr Cys Ile Tyr
1               5                   10                  15

Gly

<210> SEQ ID NO 336
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Gln Trp His Cys Thr Thr Leu Phe Pro His His Tyr Cys Val Tyr
1               5                   10                  15

Gly

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (15)
<223> OTHER INFORMATION: Hse

<400> SEQUENCE: 337

Gly Gln Trp His Cys Thr Thr Leu Phe Pro His His Tyr Cys Xaa Tyr
1               5                   10                  15

Gly

<210> SEQ ID NO 338
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Gln Trp His Cys Thr Thr Arg Phe Pro His His Tyr Cys Phe Tyr
1               5                   10                  15

Gly

<210> SEQ ID NO 339
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Hfe

<400> SEQUENCE: 339

Gly Gln Trp His Cys Thr Thr Arg Phe Pro His His Tyr Cys Xaa Tyr
1               5                   10                  15

Gly

<210> SEQ ID NO 340
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Bpa

<400> SEQUENCE: 340

Gly Gln Trp His Cys Thr Thr Asp Phe Pro His His Tyr Cys Leu Xaa
1               5                   10                  15

Gly

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gly Gln Trp His Cys Thr Thr Asp Phe Pro His His Tyr Cys Leu Phe
1               5                   10                  15
```

Gly

<210> SEQ ID NO 342
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: 2-Nal

<400> SEQUENCE: 342

Gly Gln Trp His Cys Thr Thr Asp Phe Pro His His Tyr Cys Leu Xaa
1               5                   10                  15

Gly

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Tyr(3-Cl)

<400> SEQUENCE: 343

Gly Gln Trp His Cys Thr Thr Asp Phe Pro His His Tyr Cys Leu Tyr
1               5                   10                  15

Gly

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: 2-Nal

<400> SEQUENCE: 344

Gly Gln Trp His Cys Thr Thr Leu Phe Pro His His Tyr Cys Leu Xaa
1               5                   10                  15

Gly

<210> SEQ ID NO 345
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (16)
<223> OTHER INFORMATION: Dip -continued

<400> SEQUENCE: 345

Gly Lys Trp His Cys Thr Thr Tyr Phe Pro His His Tyr Cys Leu Xaa
1               5                   10                  15

Gly

<210> SEQ ID NO 346
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (16)
<223> OTHER INFORMATION: Phe(4-NH2)

<400> SEQUENCE: 346

Gly Lys Trp His Cys Thr Thr Tyr Phe Pro His His Tyr Cys Leu Phe
1               5                   10                  15

Gly

<210> SEQ ID NO 347
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Gln Tyr Thr Cys Ser Gly Asp Glu Tyr Thr Trp His Cys Asn Tyr
1               5                   10                  15

Glu

<210> SEQ ID NO 348
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 1-Nal

<400> SEQUENCE: 348

Gly Gln Xaa Thr Cys Ser Gly Asp Glu Tyr Thr Trp His Cys Asn Tyr
1               5                   10                  15

Glu

<210> SEQ ID NO 349
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)

<223> OTHER INFORMATION: thien-W

<400> SEQUENCE: 349

Asp Xaa Thr Cys Ser Gly Asp Glu Tyr Thr Trp His Cys Asn Tyr Glu
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Trp(5-OH)

<400> SEQUENCE: 350

Asp Trp Thr Cys Ser Gly Asp Glu Tyr Thr Trp His Cys Asn Tyr Glu
1               5                   10                  15

<210> SEQ ID NO 351
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gly Gln Trp Thr Cys Ser Gly Asp Glu Tyr Tyr His Cys Asn Tyr
1               5                   10                  15

Glu

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal

<400> SEQUENCE: 352

Gly Gln Trp Thr Cys Ser Gly Asp Glu Tyr Thr Xaa His Cys Asn Tyr
1               5                   10                  15

Glu

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: thein-W

<400> SEQUENCE: 353

Asp Trp Thr Cys Ser Gly Asp Glu Tyr Thr Xaa His Cys Asn Tyr Glu
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Trp(5-OH)

<400> SEQUENCE: 354

Asp Trp Thr Cys Ser Gly Asp Glu Tyr Thr Trp His Cys Asn Tyr Glu
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: b-h-Trp

<400> SEQUENCE: 355

Asp Trp Thr Cys Ser Gly Asp Glu Tyr Thr Trp His Cys Asn Tyr Glu
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Trp Thr Cys Ser Gly Asp Glu Tyr Thr His His Cys Asn Tyr Glu
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Asp Trp Thr Cys Arg Gly Asp Glu Tyr Thr Trp His Cys Asn Tyr Glu
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: D-Tyr

<400> SEQUENCE: 358

Asp Trp Thr Cys Tyr Gly Asp Glu Tyr Thr Trp His Cys Asn Tyr Glu
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Asp Trp Thr Cys Pro Gly Asp Glu Tyr Thr Trp His Cys Asn Tyr Glu
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asp Trp Thr Cys Tyr Gly Asp Glu Tyr Thr Trp His Cys Asn Tyr Glu
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: b-h-Ser

<400> SEQUENCE: 361

Asp Trp Thr Cys Ser Gly Asp Glu Tyr Thr Trp His Cys Asn Tyr Glu
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asp Trp Thr Cys Leu Gly Asp Glu Tyr Thr Trp His Cys Asn Tyr Glu
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 3-NO2 Tyr

<400> SEQUENCE: 363

Asp Trp Thr Cys Tyr Gly Asp Glu Tyr Thr Trp His Cys Asn Tyr Glu

<210> SEQ ID NO 364
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 3-NO2 Tyr

<400> SEQUENCE: 364

Asp Trp Thr Cys Tyr Gly Asp Glu Tyr Thr Trp His Cys Asn Tyr Glu
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 4-Pal

<400> SEQUENCE: 365

Asp Trp Thr Cys Xaa Gly Asp Glu Tyr Thr Trp His Cys Asn Tyr Glu
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 4-CO2H-Phe

<400> SEQUENCE: 366

Asp Trp Thr Cys Phe Gly Asp Glu Tyr Thr Trp His Cys Asn Tyr Glu
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: 4-tBu-Phe

<400> SEQUENCE: 367

Asp Trp Thr Cys Phe Gly Asp Glu Tyr Thr Trp His Cys Asn Tyr Glu
1               5                   10                  15

<210> SEQ ID NO 368
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Phe(4-NH2)

<400> SEQUENCE: 368

Asp Trp Thr Cys Phe Gly Asp Glu Tyr Thr Trp His Cys Asn Tyr Glu
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Tyr(Bn,3-Cl)

<400> SEQUENCE: 369

Asp Trp Thr Cys Tyr Gly Asp Glu Tyr Thr Trp His Cys Asn Tyr Glu
1               5                   10                  15

<210> SEQ ID NO 370
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Gln Trp Thr Cys Tyr Gly Asp Glu Tyr Thr Trp Tyr Cys Asn Tyr
1               5                   10                  15

Glu

<210> SEQ ID NO 371
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Aib

<400> SEQUENCE: 371

Asp Trp Thr Cys Xaa Gly Asp Glu Tyr Thr Trp His Cys Asn Tyr Glu
1               5                   10                  15

<210> SEQ ID NO 372
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Pro Pro Gln Trp His Cys Thr Thr Arg Phe Pro His His Tyr Cys Leu
1               5                   10                  15
```

Tyr Gly

<210> SEQ ID NO 373
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Gln Trp His Cys Thr Thr Arg Phe Tyr Thr Trp His Cys Asn Tyr
1               5                   10                  15

Glu

<210> SEQ ID NO 374
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gly Gln Trp His Cys Thr Thr Arg Phe Pro His His Tyr Cys Leu Tyr
1               5                   10                  15

Gly

<210> SEQ ID NO 375
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Gln Trp His Cys Thr Thr Arg Phe Pro His His Tyr Cys Leu Tyr
1               5                   10                  15

Gly

<210> SEQ ID NO 376
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Trp His Cys Thr Thr Arg Phe Pro His His Tyr Cys Leu Tyr Gly
1               5                   10                  15

<210> SEQ ID NO 377
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 377

```
Gly Lys Gln Trp His Cys Thr Thr Tyr Phe Pro His His Tyr Cys Leu
1               5                   10                  15

Tyr Gly
```

<210> SEQ ID NO 378
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 378

```
Gly Gln Trp His Cys Thr Thr Leu Phe Pro His His Tyr Cys Leu Tyr
1               5                   10                  15

Gly
```

<210> SEQ ID NO 379
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 379

```
Gly Ala Trp His Cys Thr Thr Leu Phe Pro His His Tyr Cys Leu Tyr
1               5                   10                  15

Gly
```

<210> SEQ ID NO 380
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: D-Tyr

<400> SEQUENCE: 380

```
Ala Trp His Cys Thr Thr Leu Phe Pro His His Tyr Cys Leu Tyr Gly
1               5                   10                  15
```

<210> SEQ ID NO 381
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 381

```
Gly Asp Trp His Cys Thr Thr Leu Phe Pro His His Tyr Cys Leu Tyr
```

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 382

Gly Ser Trp His Cys Thr Thr Leu Phe Pro His His Tyr Cys Leu Tyr
1               5                   10                  15

Gly

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 383

Pro Pro Trp His Cys Thr Thr Leu Phe Pro His His Tyr Cys Leu Tyr
1               5                   10                  15

Gly

<210> SEQ ID NO 384
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 384

Gly Gln Trp His Cys Thr Thr Tyr Phe Pro His His Tyr Cys Leu Tyr
1               5                   10                  15

Gly

<210> SEQ ID NO 385
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 385

Gly Ala Trp His Cys Thr Thr Tyr Phe Pro His His Tyr Cys Leu Tyr
1               5                   10                  15

Gly

<210> SEQ ID NO 386
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 386

Gly Lys Trp His Cys Thr Thr Leu Phe Pro His His Tyr Cys Leu Tyr
1               5                   10                  15

Gly

<210> SEQ ID NO 387
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Abu

<400> SEQUENCE: 387

Gly Xaa Trp His Cys Thr Thr Ser Phe Pro His His Tyr Cys Leu Tyr
1               5                   10                  15

Gly

<210> SEQ ID NO 388
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Cit

<400> SEQUENCE: 388

Gly Xaa Trp His Cys Thr Thr Ser Phe Pro His His Tyr Cys Leu Tyr
1               5                   10                  15

Gly

<210> SEQ ID NO 389
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 389

```
Gly Lys Trp His Cys Thr Thr Tyr Phe Pro His His Tyr Cys Val Tyr
1               5                   10                  15

Gly

<210> SEQ ID NO 390
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 390

Gly Lys Trp His Cys Tyr Thr Tyr Phe Pro His His Tyr Cys Leu Tyr
1               5                   10                  15

Gly

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 391

Gly Lys Trp His Cys Tyr Thr Tyr Phe Pro His His Tyr Cys Val Tyr
1               5                   10                  15

Gly

<210> SEQ ID NO 392
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 392

Gly Lys Trp His Cys Tyr Thr Tyr Phe Pro His His Tyr Cys Val Tyr
1               5                   10                  15

Tyr

<210> SEQ ID NO 393
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
```

```
<400> SEQUENCE: 393

Gly Lys Trp His Cys Thr Thr Tyr Phe Pro His His Tyr Cys Leu Tyr
1               5                   10                  15

Tyr

<210> SEQ ID NO 394
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (17)
<223> OTHER INFORMATION: Bip

<400> SEQUENCE: 394

Gly Lys Trp His Cys Thr Thr Tyr Phe Pro His His Tyr Cys Leu Tyr
1               5                   10                  15

Xaa

<210> SEQ ID NO 395
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Lys)

<400> SEQUENCE: 395

Lys Lys Gly Gln Trp His Cys Thr Thr Tyr Phe Pro His His Tyr Cys
1               5                   10                  15

Leu Tyr Gly

<210> SEQ ID NO 396
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 396

Gly Lys Trp His Cys Thr Thr Tyr Phe Pro Thr His Tyr Cys Leu Tyr
1               5                   10                  15

Gly

<210> SEQ ID NO 397
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)
<223> OTHER INFORMATION: Lys(Gly)

<400> SEQUENCE: 397

Gly Lys Trp His Cys Tyr Thr Tyr Phe Pro Tyr His Tyr Cys Val Tyr
1               5                   10                  15

Gly

<210> SEQ ID NO 398
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 398

Gly Lys Trp His Cys Tyr Thr Tyr Phe Pro Tyr His Tyr Cys Leu Tyr
1               5                   10                  15

Gly

<210> SEQ ID NO 399
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (17)
<223> OTHER INFORMATION: Phe(4-NH2)

<400> SEQUENCE: 399

Gly Lys Trp His Cys Thr Thr Tyr Phe Pro His His Tyr Cys Leu Tyr
1               5                   10                  15

Phe

<210> SEQ ID NO 400
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (17)
<223> OTHER INFORMATION: Bip

<400> SEQUENCE: 400

Gly Lys Trp His Cys Thr Thr Lys Phe Pro His His Tyr Cys Leu Tyr
1               5                   10                  15

Xaa
```

```
<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 401

Gly Lys Trp His Cys Tyr Thr Lys Phe Pro His His Tyr Cys Val Tyr
1               5                   10                  15

Gly

<210> SEQ ID NO 402
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 402

Gly Lys Trp His Cys Tyr Thr Lys Phe Pro His His Tyr Cys Val Tyr
1               5                   10                  15

Tyr

<210> SEQ ID NO 403
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 403

Gly Lys Trp His Cys Thr Thr Lys Phe Pro His His Tyr Cys Leu Tyr
1               5                   10                  15

Tyr

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Tyr-Gly)

<400> SEQUENCE: 404

Gly Tyr Lys Trp His Cys Thr Thr Tyr Phe Pro His His Tyr Cys Leu
1               5                   10                  15
```

Tyr Gly

<210> SEQ ID NO 405
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Val-Gly)

<400> SEQUENCE: 405

Gly Val Lys Trp His Cys Thr Thr Tyr Phe Pro His His Tyr Cys Leu
1               5                   10                  15

Tyr Gly

<210> SEQ ID NO 406
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Phe-Gly)

<400> SEQUENCE: 406

Gly Phe Lys Trp His Cys Thr Thr Tyr Phe Pro His His Tyr Cys Leu
1               5                   10                  15

Tyr Gly

<210> SEQ ID NO 407
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(His-Gly)

<400> SEQUENCE: 407

Gly His Lys Trp His Cys Thr Thr Tyr Phe Pro His His Tyr Cys Leu
1               5                   10                  15

Tyr Gly

<210> SEQ ID NO 408
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Lys Lys Trp His Cys Tyr Thr Tyr Phe Pro His His Tyr Cys Val Tyr
1               5                   10                  15

Gly

```
<210> SEQ ID NO 409
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dpr
<220> FEATURE:
<221> NAME/KEY: MOD_RES
<222> LOCATION: (2)
<223> OTHER INFORMATION: Dpr(Dpr)

<400> SEQUENCE: 409

Xaa Xaa Trp His Cys Tyr Thr Tyr Phe Pro His His Tyr Cys Val Tyr
1               5                   10                  15

Gly

<210> SEQ ID NO 410
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Lys)

<400> SEQUENCE: 410

Lys Lys Trp His Cys Tyr Thr Tyr Phe Pro His His Tyr Cys Val Tyr
1               5                   10                  15

Gly

<210> SEQ ID NO 411
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gln Trp Thr Cys Ser Gly Asp Glu Pro His His Tyr Cys Leu Tyr
1               5                   10                  15

Gly

<210> SEQ ID NO 412
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gln Trp Thr Cys Ser Gly Asp Phe Pro His His Tyr Cys Leu Tyr
1               5                   10                  15

Gly

<210> SEQ ID NO 413
<211> LENGTH: 17
<212> TYPE: PRT
```

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Gly Gln Trp Thr Cys Ser Gly Asp Phe Pro His His Tyr Cys Leu Tyr
1               5                   10                  15

Gly

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 414

Gly Gln Trp Thr Cys Ser Gly Arg Phe Pro His His Tyr Cys Leu Tyr
1               5                   10                  15

Gly

<210> SEQ ID NO 415
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: cbz-Gly

<400> SEQUENCE: 415

Gly Gln Trp His Cys Thr Thr Arg Phe Pro His His Tyr Cys Leu Tyr
1               5                   10                  15

Gly Lys

<210> SEQ ID NO 416
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (18)
<223> OTHER INFORMATION: D-Lys

<400> SEQUENCE: 416

Gly Gln Trp His Cys Thr Thr Arg Phe Pro His His Tyr Cys Leu Tyr
1               5                   10                  15

Gly Lys

<210> SEQ ID NO 417
<211> LENGTH: 17
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (1)
<223> OTHER INFORMATION: cbz-Gly

<400> SEQUENCE: 417

Gly Gln Trp His Cys Thr Thr Arg Phe Pro His His Tyr Cys Leu Tyr
1               5                   10                  15

Gly

<210> SEQ ID NO 418
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly

<400> SEQUENCE: 418

Gly Gln Trp His Cys Thr Thr Arg Phe Pro His His Tyr Cys Leu Tyr
1               5                   10                  15

Gly Lys Lys

<210> SEQ ID NO 419
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Gln Trp His Cys Thr Thr Tyr Phe Pro His His Tyr Cys Leu Tyr
1               5                   10                  15

Gly

<210> SEQ ID NO 420
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gly Gln Trp His Cys Tyr Thr Leu Phe Pro His His Tyr Cys Leu Tyr
1               5                   10                  15

Gly

<210> SEQ ID NO 421
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Gln Trp His Cys Tyr Thr Leu Phe Pro His His Tyr Cys Leu Tyr
1               5                   10                  15
```

```
Gly

<210> SEQ ID NO 422
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Gln Trp His Cys Tyr Thr Leu Phe Pro His His Tyr Cys Leu Tyr
1               5                   10                  15

Gly

<210> SEQ ID NO 423
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Gln Trp His Cys Thr Thr Tyr Phe Pro His His Tyr Cys Leu Tyr
1               5                   10                  15

Gly

<210> SEQ ID NO 424
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gly Gln Trp His Cys Thr Thr Tyr Phe Pro His His Tyr Cys Leu Tyr
1               5                   10                  15

Gly

<210> SEQ ID NO 425
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Gly Gln Trp His Cys Thr Thr Tyr Phe Pro His His Tyr Cys Leu Tyr
1               5                   10                  15

Gly

<210> SEQ ID NO 426
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
```

```
<400> SEQUENCE: 426

Gly Lys Trp His Cys Tyr Thr Tyr Phe Pro His His Tyr Cys Val Tyr
1               5                   10                  15

Gly Lys

<210> SEQ ID NO 427
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 427

Gly Lys Trp His Cys Tyr Thr Tyr Phe Pro His His Tyr Cys Val Tyr
1               5                   10                  15

Tyr Lys

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 428

Gly Lys Trp His Cys Thr Thr Tyr Phe Pro His His Tyr Cys Leu Tyr
1               5                   10                  15

Tyr Lys

<210> SEQ ID NO 429
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 429

Gly Lys Trp His Cys Thr Thr Tyr Phe Pro His His Tyr Cys Leu Tyr
1               5                   10                  15

Tyr Lys

<210> SEQ ID NO 430
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
```

```
<220> FEATURE:
<221> NAME/KEY: MOD_RES
<222> LOCATION: (17)
<223> OTHER INFORMATION: Bip

<400> SEQUENCE: 430

Gly Lys Trp His Cys Thr Thr Tyr Phe Pro His His Tyr Cys Leu Tyr
1               5                   10                  15

Xaa Lys

<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 431

Gly Lys Trp His Cys Tyr Thr Tyr Phe Pro His His Tyr Cys Val Tyr
1               5                   10                  15

Gly

<210> SEQ ID NO 432
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 432

Gly Lys Trp His Cys Tyr Thr Tyr Phe Pro His His Tyr Cys Leu Tyr
1               5                   10                  15

Phe Lys

<210> SEQ ID NO 433
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 433

Gly Lys Trp His Cys Tyr Thr Tyr Phe Pro His His Tyr Cys Leu Tyr
1               5                   10                  15

Tyr Lys

<210> SEQ ID NO 434
<211> LENGTH: 18
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<221> NAME/KEY: MOD_RES
<222> LOCATION: (2)
<223> OTHER INFORMATION: Lys(Gly)

<400> SEQUENCE: 434

Gly Lys Trp His Cys Tyr Thr Tyr Phe Pro His His Tyr Cys Leu Tyr
1               5                   10                  15

Tyr Lys

<210> SEQ ID NO 435
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)
<220> FEATURE:
<221> NAME/KEY: MOD_RES
<222> LOCATION: (17)
<223> OTHER INFORMATION: D-Tyr

<400> SEQUENCE: 435

Gly Lys Trp His Cys Tyr Thr Tyr Phe Pro His His Tyr Cys Leu Tyr
1               5                   10                  15

Tyr Lys

<210> SEQ ID NO 436
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 436

Gly Lys Trp His Cys Tyr Thr Tyr Phe Pro His His Tyr Cys Leu Tyr
1               5                   10                  15

Val Lys

<210> SEQ ID NO 437
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 437

Gly Lys Trp His Cys Tyr Thr Tyr Phe Pro His His Tyr Cys Leu Tyr
1               5                   10                  15

Val Lys

<210> SEQ ID NO 438
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Gln Trp His Cys Tyr Thr Lys Phe Pro His His Tyr Cys Leu Tyr
1               5                   10                  15

Gly Lys

<210> SEQ ID NO 439
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Gly Gln Trp His Cys Tyr Thr Tyr Phe Pro His His Tyr Cys Leu Tyr
1               5                   10                  15

Gly Lys

<210> SEQ ID NO 440
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 440

Gly Lys Trp His Cys Tyr Thr Tyr Phe Pro His His Tyr Cys Leu Tyr
1               5                   10                  15

Gly Lys

<210> SEQ ID NO 441
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly)

<400> SEQUENCE: 441

Gly Lys Trp His Cys Tyr Thr Tyr Phe Pro His His Tyr Cys Val Tyr
1               5                   10                  15

Gly

<210> SEQ ID NO 442
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)
<223> OTHER INFORMATION: Lys(Gly)

<400> SEQUENCE: 442

Gly Lys Trp His Cys Tyr Thr Tyr Phe Pro His His Tyr Cys Val Tyr
1               5                   10                  15

Gly

<210> SEQ ID NO 443
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Asp Trp Thr Cys Ser Gly Pro Glu Tyr Thr Trp His Cys Asn Tyr Glu
1               5                   10                  15

<210> SEQ ID NO 444
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: b-h-Asp

<400> SEQUENCE: 444

Asp Trp Thr Cys Ser Gly Asp Glu Tyr Thr Trp His Cys Asn Tyr Glu
1               5                   10                  15

<210> SEQ ID NO 445
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Asp Trp Thr Cys Ser Gly Leu Glu Tyr Thr Trp His Cys Asn Tyr Glu
1               5                   10                  15

<210> SEQ ID NO 446
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Lys(Boc)

<400> SEQUENCE: 446

Gly Gln Trp Thr Cys Ser Gly Lys Glu Tyr Thr Trp His Cys Asn Tyr
1               5                   10                  15

Glu

<210> SEQ ID NO 447
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Aib

<400> SEQUENCE: 447

Asp Trp Thr Cys Ser Gly Xaa Glu Tyr Thr Trp His Cys Asn Tyr Glu
1               5                   10                  15

<210> SEQ ID NO 448
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Asp Trp Thr Cys Ser Gly Asp Glu Asp Thr Trp His Cys Asn Tyr Glu
1               5                   10                  15

<210> SEQ ID NO 449
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Asp Trp Thr Cys Ser Gly Asp Glu Arg Thr Trp His Cys Asn Tyr Glu
1               5                   10                  15

<210> SEQ ID NO 450
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Asp Trp Thr Cys Ser Gly Asp Glu Pro Thr Trp His Cys Asn Tyr Glu
1               5                   10                  15

<210> SEQ ID NO 451
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Tyr(3-I)

<400> SEQUENCE: 451

Asp Trp Thr Cys Ser Gly Asp Glu Tyr Thr Trp His Cys Asn Tyr Glu
1               5                   10                  15

<210> SEQ ID NO 452
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: b-h-Tyr

<400> SEQUENCE: 452

Asp Trp Thr Cys Ser Gly Asp Glu Tyr Thr Trp His Cys Asn Tyr Glu
1               5                   10                  15

<210> SEQ ID NO 453
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Aib

<400> SEQUENCE: 453

Asp Trp Thr Cys Ser Gly Asp Glu Xaa Thr Trp His Cys Asn Tyr Glu
1               5                   10                  15

<210> SEQ ID NO 454
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Tyr(3-I)

<400> SEQUENCE: 454

Asp Trp Thr Cys Ser Gly Asp Glu Tyr Thr Trp His Cys Asn Tyr Glu
1               5                   10                  15

<210> SEQ ID NO 455
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Glu Ala Gly Gln Trp Thr Cys Ser Gly Asp Glu Tyr Thr Trp His Cys
1               5                   10                  15

Asn Tyr Glu

<210> SEQ ID NO 456
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Gln Trp Thr Cys Ser Gly Asp Glu Tyr Thr Trp His Cys Asn Tyr
```

-continued

```
                  1               5                  10                  15

Glu

<210> SEQ ID NO 457
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Glu Ala Gly Gln Trp Thr Cys Ser Gly Asp Glu Tyr Thr Trp His Cys
  1               5                  10                  15

Asn Tyr Glu

<210> SEQ ID NO 458
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)
<223> OTHER INFORMATION: D-Glu

<400> SEQUENCE: 458

Gly Gln Trp Thr Cys Ser Gly Asp Glu Tyr Thr Trp His Cys Asn Tyr
  1               5                  10                  15

Glu

<210> SEQ ID NO 459
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)
<223> OTHER INFORMATION: D-Glu

<400> SEQUENCE: 459

Gly Gln Trp Thr Cys Ser Gly Asp Glu Tyr Thr Trp His Cys Asn Tyr
  1               5                  10                  15

Glu Lys

<210> SEQ ID NO 460
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: D-Glu

<400> SEQUENCE: 460

Pro Pro Gly Gln Trp Thr Cys Ser Gly Asp Glu Tyr Thr Trp His Cys
  1               5                  10                  15

Asn Tyr Glu Lys
```

<210> SEQ ID NO 461
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: D-Glu

<400> SEQUENCE: 461

Pro Pro Gly Gln Trp Thr Cys Ser Gly Asp Glu Tyr Thr Trp His Cys
1               5                   10                  15

Asn Tyr Glu

<210> SEQ ID NO 462
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Asp Trp Thr Cys Ser Gly Asp Tyr Tyr Thr Trp His Cys Asn Tyr Glu
1               5                   10                  15

<210> SEQ ID NO 463
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Gln
<220> FEATURE:
<221> NAME/KEY: MOD_RES
<222> LOCATION: (3)
<223> OTHER INFORMATION: D-Trp
<220> FEATURE:
<221> NAME/KEY: MOD_RES
<222> LOCATION: (4)
<223> OTHER INFORMATION: D-Thr
<220> FEATURE:
<221> NAME/KEY: MOD_RES
<222> LOCATION: (5)
<223> OTHER INFORMATION: D-Cys
<220> FEATURE:
<221> NAME/KEY: MOD_RES
<222> LOCATION: (6)
<223> OTHER INFORMATION: D-Ser
<220> FEATURE:
<221> NAME/KEY: MOD_RES
<222> LOCATION: (8)
<223> OTHER INFORMATION: D-Asp
<220> FEATURE:
<221> NAME/KEY: MOD_RES
<222> LOCATION: (9)
<223> OTHER INFORMATION: D-Glu
<220> FEATURE:
<221> NAME/KEY: MOD_RES
<222> LOCATION: (10)
<223> OTHER INFORMATION: D-Tyr
<220> FEATURE:
<221> NAME/KEY: MOD_RES
<222> LOCATION: (11)

```
<223> OTHER INFORMATION: D-Thr
<220> FEATURE:
<221> NAME/KEY: MOD_RES
<222> LOCATION: (12)
<223> OTHER INFORMATION: D-Trp
<220> FEATURE:
<221> NAME/KEY: MOD_RES
<222> LOCATION: (13)
<223> OTHER INFORMATION: D-His
<220> FEATURE:
<221> NAME/KEY: MOD_RES
<222> LOCATION: (14)
<223> OTHER INFORMATION: D-Cys
<220> FEATURE:
<221> NAME/KEY: MOD_RES
<222> LOCATION: (15)
<223> OTHER INFORMATION: D-Asn
<220> FEATURE:
<221> NAME/KEY: MOD_RES
<222> LOCATION: (16)
<223> OTHER INFORMATION: D-Tyr
<220> FEATURE:
<221> NAME/KEY: MOD_RES
<222> LOCATION: (17)
<223> OTHER INFORMATION: D-Glu

<400> SEQUENCE: 463

Gly Gln Trp Thr Cys Ser Gly Asp Glu Tyr Thr Trp His Cys Asn Tyr
1               5                   10                  15
Glu

<210> SEQ ID NO 464
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Asp Trp Thr Cys Ser Gly Asp Glu Tyr Asp Trp His Cys Asn Tyr Glu
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Asp Trp Thr Cys Ser Gly Asp Glu Tyr Arg Trp His Cys Asn Tyr Glu
1               5                   10                  15

<210> SEQ ID NO 466
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Asp Trp Thr Cys Ser Gly Asp Arg Tyr Thr Trp His Cys Asn Tyr Glu
1               5                   10                  15

<210> SEQ ID NO 467
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 467

Asp Trp Thr Cys Ser Gly Asp Leu Tyr Thr Trp His Cys Asn Tyr Glu
1               5                   10                  15

<210> SEQ ID NO 468
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gly Gln Trp Thr Cys Ser Gly Asp Glu Tyr Thr Trp His Cys Asn
1               5                   10                  15

<210> SEQ ID NO 469
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gly Gln Trp Thr Cys Ser Gly Asp Glu Tyr Thr Trp His Cys
1               5                   10

<210> SEQ ID NO 470
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gly Gln Trp Thr Cys Ser Gly Asp Tyr Thr Trp His Cys Asn Tyr Glu
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Asp Trp Thr Cys Ser Gly Asp Glu Tyr Pro Trp His Cys Asn Tyr Glu
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Asp Trp Thr Cys Ser Gly Asp Glu Tyr Tyr Trp His Cys Asn Tyr Glu
1               5                   10                  15
```

```
<210> SEQ ID NO 473
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Asp Trp Thr Cys Ser Gly Asp Glu Tyr Thr Trp Asp Cys Asn Tyr Glu
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Asp Trp Thr Cys Ser Gly Asp Glu Tyr Thr Trp Tyr Cys Asn Tyr Glu
1               5                   10                  15

<210> SEQ ID NO 475
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Pro Pro Gln Trp Thr Cys Ser Gly Asp Glu Tyr Thr Trp His Cys Ala
1               5                   10                  15

Tyr Glu

<210> SEQ ID NO 476
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Pro Pro Gln Trp Thr Cys Ser Gly Asp Ala Tyr Thr Trp His Cys Ala
1               5                   10                  15

Tyr Glu

<210> SEQ ID NO 477
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gly Gln Trp Thr Cys Ser Gly Asp Ala Tyr Thr Trp Ser Cys Asn Tyr
1               5                   10                  15

Glu

<210> SEQ ID NO 478
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Asp Trp Thr Cys Ser Gly Asp Glu Tyr Thr Trp Pro Cys Asn Tyr Glu
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Asp Trp Thr Cys Ser Gly Asp Glu Tyr Thr Trp His Cys Pro Tyr Glu
1               5                   10                  15

<210> SEQ ID NO 480
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Asp Trp Thr Cys Ser Gly Asp Glu Tyr Thr Trp His Cys Asn Tyr Glu
1               5                   10                  15

<210> SEQ ID NO 481
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Asp Trp Thr Cys Ser Gly Asp Glu Tyr Leu Trp His Cys Asn Tyr Glu
1               5                   10                  15

<210> SEQ ID NO 482
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gly Gln Trp Thr Cys Ser Gly Asp Ala Tyr Thr Trp Ser Cys Asn Tyr
1               5                   10                  15

Glu

<210> SEQ ID NO 483
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 483

Asp Trp Pro Cys Ser Gly Asp Glu Tyr Thr Trp His Cys Asn Tyr Glu
1               5                   10                  15

<210> SEQ ID NO 484
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Aib

<400> SEQUENCE: 484

Asp Trp Thr Cys Ser Gly Asp Xaa Tyr Thr Trp His Cys Asn Tyr Glu
1               5                   10                  15

<210> SEQ ID NO 485
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Lys

<400> SEQUENCE: 485

Gly Gln Trp Thr Cys Ser Lys Asp Glu Tyr Thr Trp His Cys Asn Tyr
1               5                   10                  15

Glu

<210> SEQ ID NO 486
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aib

<400> SEQUENCE: 486

Xaa Trp Thr Cys Ser Gly Asp Glu Tyr Thr Trp His Cys Asn Tyr Glu
1               5                   10                  15

<210> SEQ ID NO 487
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Aib

<400> SEQUENCE: 487

Asp Trp Xaa Cys Ser Gly Asp Glu Tyr Thr Trp His Cys Asn Tyr Glu
1               5                   10                  15
```

<210> SEQ ID NO 488
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Aib

<400> SEQUENCE: 488

Asp Trp Thr Cys Ser Gly Asp Glu Xaa Thr Trp His Cys Asn Tyr Glu
1               5                   10                  15

<210> SEQ ID NO 489
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Aib

<400> SEQUENCE: 489

Asp Trp Thr Cys Ser Gly Asp Glu Tyr Xaa Trp His Cys Asn Tyr Glu
1               5                   10                  15

<210> SEQ ID NO 490
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Aib

<400> SEQUENCE: 490

Asp Trp Thr Cys Ser Gly Asp Glu Tyr Thr Trp Xaa Cys Asn Tyr Glu
1               5                   10                  15

<210> SEQ ID NO 491
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Aib

<400> SEQUENCE: 491

Asp Trp Thr Cys Ser Gly Asp Glu Tyr Thr Trp His Cys Asn Tyr Xaa
1               5                   10                  15

<210> SEQ ID NO 492
<211> LENGTH: 16
<212> TYPE: PRT
<213> ORGANISM: Artificial Sequence
<220> FEATURE:
<223> OTHER INFORMATION: Description of Artificial Sequence: Synthetic

```
           peptide
<220> FEATURE:
<221> NAME/KEY: MOD_RES
<222> LOCATION: (6)
<223> OTHER INFORMATION: b-h-Gly

<400> SEQUENCE: 492

Asp Trp Thr Cys Ser Gly Asp Glu Tyr Thr Trp His Cys Asn Tyr Glu
1               5                   10                  15

<210> SEQ ID NO 493
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: b-h-Glu

<400> SEQUENCE: 493

Asp Trp Thr Cys Ser Gly Asp Glu Tyr Thr Trp His Cys Asn Tyr Glu
1               5                   10                  15

<210> SEQ ID NO 494
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: b-h-Tyr

<400> SEQUENCE: 494

Asp Trp Thr Cys Ser Gly Asp Glu Tyr Thr Trp His Cys Asn Tyr Glu
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: b-h-Thr

<400> SEQUENCE: 495

Asp Trp Thr Cys Ser Gly Asp Glu Tyr Thr Trp His Cys Asn Tyr Glu
1               5                   10                  15

<210> SEQ ID NO 496
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
```

```
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 496

Gly Lys Trp His Cys Thr Thr Lys Phe Pro His His Tyr Cys Leu Tyr
1               5                   10                  15
Xaa

<210> SEQ ID NO 497
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdT)

<400> SEQUENCE: 497

Lys Lys Trp His Cys Tyr Thr Tyr Phe Pro His His Tyr Cys Val Tyr
1               5                   10                  15
Gly

<210> SEQ ID NO 498
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 498

Lys Lys Trp His Cys Tyr Thr Tyr Phe Pro His His Tyr Cys Leu Tyr
1               5                   10                  15
Gly

<210> SEQ ID NO 499
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: Lys(GdT)

<400> SEQUENCE: 499

Gly Gln Trp His Cys Thr Thr Arg Phe Pro His His Tyr Cys Leu Tyr
1               5                   10                  15
Gly Lys

<210> SEQ ID NO 500
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: D-Lys(GdT)

<400> SEQUENCE: 500

Gly Gln Trp His Cys Thr Thr Arg Phe Pro His His Tyr Cys Leu Tyr
1               5                  10                  15
Gly Lys

<210> SEQ ID NO 501
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Lys(GdT)

<400> SEQUENCE: 501

Gly Gln Trp His Cys Thr Thr Lys Phe Pro His His Tyr Cys Leu Tyr
1               5                  10                  15
Gly

<210> SEQ ID NO 502
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Lys(GdT)

<400> SEQUENCE: 502

Gly Gln Trp His Cys Thr Thr Arg Phe Pro His His Tyr Cys Lys Tyr
1               5                  10                  15
Gly

<210> SEQ ID NO 503
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Gly Gln Trp His Cys Thr Thr Tyr Phe Pro His His Tyr Cys Leu Tyr
1               5                  10                  15
Gly

<210> SEQ ID NO 504
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 504

Gly Gln Trp Thr Cys Ser Gly Asp Ala Tyr Thr Trp His Cys Ala Tyr
1               5                   10                  15

Glu

<210> SEQ ID NO 505
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Arg

<400> SEQUENCE: 505

Asp Trp Thr Cys Ser Arg Asp Glu Tyr Thr Trp His Cys Asn Tyr Glu
1               5                   10                  15

<210> SEQ ID NO 506
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Asp Trp Thr Cys Arg Gly Asp Glu Tyr Thr Trp His Cys Asn Tyr Glu
1               5                   10                  15

<210> SEQ ID NO 507
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Gly Gln Trp Thr Cys Ser Gly Asp Glu Tyr Thr Trp His Cys Asn Tyr
1               5                   10                  15

<210> SEQ ID NO 508
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: D-Glu

<400> SEQUENCE: 508

Pro Trp Thr Cys Ser Gly Asp Glu Tyr Ala Trp His Cys Asn Tyr Glu
1               5                   10                  15

<210> SEQ ID NO 509
<211> LENGTH: 16
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (5)
<223> OTHER INFORMATION: Tyr(Bn,3-Cl)

<400> SEQUENCE: 509

Asp Trp Thr Cys Tyr Gly Asp Glu Tyr Thr Trp His Cys Asn Tyr Glu
1               5                   10                  15

<210> SEQ ID NO 510
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gly Gln Trp Thr Cys Tyr Gly Asp Glu Tyr Thr Trp Tyr Cys Asn Tyr
1               5                   10                  15

Glu

<210> SEQ ID NO 511
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Phe(4-tBu)

<400> SEQUENCE: 511

Asp Trp Thr Cys Phe Gly Asp Glu Tyr Thr Trp His Cys Asn Tyr Glu
1               5                   10                  15

<210> SEQ ID NO 512
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Phe(4-CO2H)

<400> SEQUENCE: 512

Asp Trp Thr Cys Phe Gly Asp Glu Tyr Thr Trp His Cys Asn Tyr Glu
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Asp Trp Thr Cys Ser Tyr Asp Glu Tyr Thr Trp His Cys Asn Tyr Glu
1               5                   10                  15

<210> SEQ ID NO 514
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gly Ala Trp Thr Cys Ser Gly Asp Glu Tyr Thr Trp His Cys Asn Tyr
1               5                   10                  15

Glu

<210> SEQ ID NO 515
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Tyr(3-I)

<400> SEQUENCE: 515

Asp Trp Thr Cys Ser Gly Asp Glu Tyr Thr Trp His Cys Asn Tyr Glu
1               5                   10                  15

<210> SEQ ID NO 516
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)
<223> OTHER INFORMATION: D-Glu

<400> SEQUENCE: 516

Gly Gln Trp Thr Cys Ser Gly Asp Glu Tyr Ala Trp His Cys Asn Tyr
1               5                   10                  15

Glu

<210> SEQ ID NO 517
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Gln Trp Thr Cys Ser Gly Asp Glu Tyr Thr Trp Ala Cys Asn Tyr
1               5                   10                  15

Glu

<210> SEQ ID NO 518
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518
```

```
Asp Trp Thr Cys Ser Gly Asp Glu Tyr Tyr Trp His Cys Asn Tyr Glu
1               5                   10                  15
```

<210> SEQ ID NO 519
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Ala

<400> SEQUENCE: 519

```
Asp Trp Thr Cys Ser Ala Asp Glu Tyr Thr Trp His Cys Asn Tyr Glu
1               5                   10                  15
```

<210> SEQ ID NO 520
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Ser

<400> SEQUENCE: 520

```
Asp Trp Thr Cys Ser Ser Asp Glu Tyr Thr Trp His Cys Asn Tyr Glu
1               5                   10                  15
```

<210> SEQ ID NO 521
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

```
Gly Gln Trp Thr Cys Ser Gly Asp Glu Tyr Thr Trp His Cys Asn Tyr
1               5                   10                  15

Glu
```

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

```
Gly Gln Trp Thr Cys Ser Gly Asp Ala Tyr Thr Trp His Cys Asn Tyr
1               5                   10                  15

Glu
```

<210> SEQ ID NO 523
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Gly Gln Trp Thr Cys Ser Gly Asp Glu Tyr Thr Trp His Cys Ala Tyr
1               5                   10                  15
Glu

<210> SEQ ID NO 524
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Gly Gln Trp Ala Cys Ser Gly Asp Glu Tyr Thr Trp His Cys Asn Tyr
1               5                   10                  15
Glu

<210> SEQ ID NO 525
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gly Gln Trp Thr Cys Ser Gly Asp Glu Tyr Thr Trp His Cys Asn Tyr
1               5                   10                  15
Ala

<210> SEQ ID NO 526
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Asp Trp Thr Cys Ser Gly Asp Glu Tyr Thr Trp Tyr Cys Asn Tyr Glu
1               5                   10                  15

<210> SEQ ID NO 527
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Tyr(3-NO2)

<400> SEQUENCE: 527

Asp Trp Thr Cys Tyr Gly Asp Glu Tyr Thr Trp His Cys Asn Tyr Glu
1               5                   10                  15

<210> SEQ ID NO 528
<211> LENGTH: 16
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 528

Asp Trp Thr Cys Tyr Gly Asp Glu Tyr Thr Trp His Cys Asn Tyr Glu
1               5                   10                  15

<210> SEQ ID NO 529
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Asp Trp Thr Cys Ser Gly Asp Glu Tyr Arg Trp His Cys Asn Tyr Glu
1               5                   10                  15

<210> SEQ ID NO 530
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Tyr(3-I)

<400> SEQUENCE: 530

Asp Trp Thr Cys Ser Gly Asp Glu Tyr Thr Trp His Cys Asn Tyr Glu
1               5                   10                  15

<210> SEQ ID NO 531
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Leu

<400> SEQUENCE: 531

Asp Trp Thr Cys Ser Leu Asp Glu Tyr Thr Trp His Cys Asn Tyr Glu
1               5                   10                  15

<210> SEQ ID NO 532
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Asp Trp Thr Cys Ser Gly Asp Glu Tyr Thr Trp His Cys Asn Tyr Glu
1               5                   10                  15

<210> SEQ ID NO 533
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)
<223> OTHER INFORMATION: 4-Pal

<400> SEQUENCE: 533

Asp Trp Thr Cys Xaa Gly Asp Glu Tyr Thr Trp His Cys Asn Tyr Glu
1               5                   10                  15

<210> SEQ ID NO 534
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Aib

<400> SEQUENCE: 534

Asp Trp Thr Cys Ser Gly Asp Glu Tyr Thr Trp His Cys Asn Tyr Xaa
1               5                   10                  15

<210> SEQ ID NO 535
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gly Gln Trp His Cys Thr Thr Asp Phe Pro His His Tyr Cys Leu Tyr
1               5                   10                  15
Gly

<210> SEQ ID NO 536
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Gly Gln Trp His Cys Thr Thr Ser Phe Pro His His Tyr Cys Leu Tyr
1               5                   10                  15
Gly

<210> SEQ ID NO 537
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Gly Gln Trp His Cys Thr Thr Ala Phe Pro His His Tyr Cys Leu Tyr
1               5                   10                  15
Gly

<210> SEQ ID NO 538
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Pro Pro Gln Trp His Cys Thr Thr Arg Phe Pro His His Tyr Cys Leu
1               5                   10                  15

Tyr Gly

<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Gly Gln Trp His Cys Thr Thr Arg Phe Pro His His Tyr Cys Ala Tyr
1               5                   10                  15

Gly

<210> SEQ ID NO 540
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: HyP

<400> SEQUENCE: 540

Pro Pro Gln Trp His Cys Thr Thr Arg Phe Xaa His His Tyr Cys Leu
1               5                   10                  15

Tyr Gly

<210> SEQ ID NO 541
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Gly Ala Trp His Cys Thr Thr Arg Phe Pro His His Tyr Cys Leu Tyr
1               5                   10                  15

Gly

<210> SEQ ID NO 542
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gly Gln Trp His Cys Thr Thr Arg Phe Pro His His Tyr Cys Leu Tyr
1               5                   10                  15
```

Gly

<210> SEQ ID NO 543
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Gly Gln Trp His Cys Thr Thr Arg Tyr Pro His His Tyr Cys Leu Tyr
1               5                   10                  15

Gly

<210> SEQ ID NO 544
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal

<400> SEQUENCE: 544

Gly Gln Trp His Cys Thr Thr Arg Xaa Pro His His Tyr Cys Leu Tyr
1               5                   10                  15

Gly

<210> SEQ ID NO 545
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gly Gln Trp His Cys Thr Thr Tyr Phe Pro His His Tyr Cys Leu Tyr
1               5                   10                  15

Gly

<210> SEQ ID NO 546
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gly Gln Trp His Cys Thr Thr Leu Phe Pro His His Tyr Cys Leu Tyr
1               5                   10                  15

Gly

<210> SEQ ID NO 547
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 547

Gly Gln Trp His Cys Thr Thr Leu Phe Pro His His Tyr Cys Leu Tyr
1               5                   10                  15

Gly

<210> SEQ ID NO 548
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gly Gln Trp His Cys Thr Thr Arg Phe Pro His His Tyr Cys Leu Tyr
1               5                   10                  15

Gly

<210> SEQ ID NO 549
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gly Gln Trp His Cys Thr Thr Arg Phe Pro Ala His Tyr Cys Leu Tyr
1               5                   10                  15

Gly

<210> SEQ ID NO 550
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Gly Gln Trp His Cys Thr Thr Arg Phe Pro His His Tyr Cys Leu Tyr
1               5                   10                  15

Gly

<210> SEQ ID NO 551
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 551

Gly Gln Trp His Cys Thr Thr Arg Phe Pro His His Xaa Cys Leu Tyr
1               5                   10                  15

Gly

<210> SEQ ID NO 552
<211> LENGTH: 17
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: thien-W

<400> SEQUENCE: 552

Gly Gln Xaa His Cys Thr Thr Arg Phe Pro His His Tyr Cys Leu Tyr
1               5                   10                  15

Gly

<210> SEQ ID NO 553
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Gly Gln Trp His Cys Thr Thr Ser Phe Pro His His Tyr Cys Leu Tyr
1               5                   10                  15

Gly

<210> SEQ ID NO 554
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gly Gln Trp Ser Cys Thr Thr Arg Phe Pro His His Tyr Cys Leu Tyr
1               5                   10                  15

Gly

<210> SEQ ID NO 555
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Gly Gln Trp His Cys Thr Thr Arg Phe Pro His His Tyr Cys Leu Tyr
1               5                   10                  15

Gly

<210> SEQ ID NO 556
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 2-Nal

<400> SEQUENCE: 556

Gly Gln Xaa His Cys Thr Thr Arg Phe Pro His His Tyr Cys Leu Tyr
1               5                   10                  15

Gly

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Bip

<400> SEQUENCE: 557

Gly Gln Trp His Cys Thr Thr Arg Phe Pro His His Xaa Cys Leu Tyr
1               5                   10                  15

Gly

<210> SEQ ID NO 558
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gly Gln Trp His Cys Thr Thr Tyr Phe Pro His His Tyr Cys Leu Tyr
1               5                   10                  15

Gly

<210> SEQ ID NO 559
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 559

Gly Lys Gln Trp His Cys Thr Thr Tyr Phe Pro His His Tyr Cys Leu
1               5                   10                  15

Tyr Gly

<210> SEQ ID NO 560
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gly Gln Trp Ala Cys Thr Thr Arg Phe Pro His His Tyr Cys Leu Tyr
1               5                   10                  15

Gly

<210> SEQ ID NO 561

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Gly Gln Trp His Cys Ala Thr Arg Phe Pro His His Tyr Cys Leu Tyr
1               5                   10                  15

Gly

<210> SEQ ID NO 562
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gly Gln Trp His Cys Thr Thr Arg Phe Pro His Ala Tyr Cys Leu Tyr
1               5                   10                  15

Gly

<210> SEQ ID NO 563
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Thr

<400> SEQUENCE: 563

Gly Gln Trp His Cys Thr Thr Arg Phe Pro His His Tyr Cys Leu Tyr
1               5                   10                  15

Gly

<210> SEQ ID NO 564
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gly Gln Trp His Cys Thr Thr Arg Phe Pro Ser His Tyr Cys Leu Tyr
1               5                   10                  15

Gly

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Bip
```

-continued

```
<400> SEQUENCE: 565

Gly Gln Trp His Cys Thr Thr Arg Xaa Pro His His Tyr Cys Leu Tyr
1               5                   10                  15
Gly

<210> SEQ ID NO 566
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Bpa

<400> SEQUENCE: 566

Gly Gln Trp His Cys Thr Thr Asp Xaa Pro His His Tyr Cys Leu Tyr
1               5                   10                  15
Gly

<210> SEQ ID NO 567
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-CN)

<400> SEQUENCE: 567

Gly Gln Trp His Cys Thr Thr Asp Phe Pro His His Tyr Cys Leu Tyr
1               5                   10                  15
Gly

<210> SEQ ID NO 568
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-NH2)

<400> SEQUENCE: 568

Gly Gln Trp His Cys Thr Thr Asp Phe Pro His His Tyr Cys Leu Tyr
1               5                   10                  15
Gly

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(4-NH2)(GdT)
```

```
<400> SEQUENCE: 569

Gly Gln Trp His Cys Thr Thr Asp Phe Pro His His Tyr Cys Leu Tyr
1               5                   10                  15

Gly

<210> SEQ ID NO 570
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Dpr

<400> SEQUENCE: 570

Gly Gln Trp His Cys Thr Thr Asp Phe Pro His Xaa Tyr Cys Leu Tyr
1               5                   10                  15

Gly

<210> SEQ ID NO 571
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Dpr(GdT)

<400> SEQUENCE: 571

Gly Gln Trp His Cys Thr Thr Asp Phe Pro His Xaa Tyr Cys Leu Tyr
1               5                   10                  15

Gly

<210> SEQ ID NO 572
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 2-Pal

<400> SEQUENCE: 572

Gly Gln Trp His Cys Thr Thr Asp Phe Pro His Xaa Tyr Cys Leu Tyr
1               5                   10                  15

Gly

<210> SEQ ID NO 573
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
```

<223> OTHER INFORMATION: Bpa

<400> SEQUENCE: 573

Gly Gln Trp His Cys Thr Thr Asp Phe Pro His His Tyr Cys Leu Xaa
1               5                   10                  15

Gly

<210> SEQ ID NO 574
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Gln Trp His Cys Thr Thr Asp Phe Pro His His Tyr Cys Leu Phe
1               5                   10                  15

Gly

<210> SEQ ID NO 575
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: 2-Nal

<400> SEQUENCE: 575

Gly Gln Trp His Cys Thr Thr Asp Phe Pro His His Tyr Cys Leu Xaa
1               5                   10                  15

Gly

<210> SEQ ID NO 576
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Tyr(3-Cl)

<400> SEQUENCE: 576

Gly Gln Trp His Cys Thr Thr Asp Phe Pro His His Tyr Cys Leu Tyr
1               5                   10                  15

Gly

<210> SEQ ID NO 577
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Phe(3,4-OMe)

<400> SEQUENCE: 577

```
Gly Gln Trp His Cys Thr Thr Asp Phe Pro His His Tyr Cys Leu Tyr
1               5                   10                  15

Gly

<210> SEQ ID NO 578
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal

<400> SEQUENCE: 578

Gly Gln Trp His Cys Thr Thr Asp Xaa Pro His His Tyr Cys Leu Tyr
1               5                   10                  15

Gly

<210> SEQ ID NO 579
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Tyr(3-Cl)

<400> SEQUENCE: 579

Gly Gln Trp His Cys Thr Thr Asp Tyr Pro His His Tyr Cys Leu Tyr
1               5                   10                  15

Gly

<210> SEQ ID NO 580
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Pen

<400> SEQUENCE: 580

Gly Gln Trp His Xaa Thr Thr Arg Phe Pro His His Tyr Cys Leu Tyr
1               5                   10                  15

Gly

<210> SEQ ID NO 581
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Asn
```

```
<400> SEQUENCE: 581

Gly Gln Trp His Cys Thr Asn Arg Phe Pro His His Tyr Cys Leu Tyr
1               5                   10                  15

Gly

<210> SEQ ID NO 582
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Ser

<400> SEQUENCE: 582

Gly Gln Trp His Cys Thr Ser Arg Phe Pro His His Tyr Cys Leu Tyr
1               5                   10                  15

Gly

<210> SEQ ID NO 583
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Tyr

<400> SEQUENCE: 583

Gly Gln Trp His Cys Thr Tyr Arg Phe Pro His His Tyr Cys Leu Tyr
1               5                   10                  15

Gly

<210> SEQ ID NO 584
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Arg

<400> SEQUENCE: 584

Gly Gln Trp His Cys Thr Arg Arg Phe Pro His His Tyr Cys Leu Tyr
1               5                   10                  15

Gly

<210> SEQ ID NO 585
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Phe
```

```
<400> SEQUENCE: 585

Gly Gln Trp His Cys Thr Thr Arg Phe Pro His His Phe Cys Leu Tyr
1               5                   10                  15

Gly

<210> SEQ ID NO 586
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Arg

<400> SEQUENCE: 586

Gly Gln Trp His Cys Thr Thr Arg Phe Pro His His Arg Cys Leu Tyr
1               5                   10                  15

Gly

<210> SEQ ID NO 587
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Bip

<400> SEQUENCE: 587

Gly Gln Trp His Cys Thr Thr Arg Phe Pro His His Xaa Cys Leu Tyr
1               5                   10                  15

Gly

<210> SEQ ID NO 588
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-1-Nal

<400> SEQUENCE: 588

Gly Gln Trp His Cys Thr Thr Arg Phe Pro His His Xaa Cys Leu Tyr
1               5                   10                  15

Gly

<210> SEQ ID NO 589
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
```

<223> OTHER INFORMATION: D-Thr

<400> SEQUENCE: 589

Gly Gln Trp His Cys Thr Thr Arg Phe Pro His His Thr Cys Leu Tyr
1               5                   10                  15
Gly

<210> SEQ ID NO 590
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Pen

<400> SEQUENCE: 590

Gly Gln Trp His Cys Thr Thr Arg Phe Pro His His Tyr Xaa Leu Tyr
1               5                   10                  15
Gly

<210> SEQ ID NO 591
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 591

Gly Gln Trp His Cys Thr Thr Leu Phe Pro His His Tyr Cys Leu Tyr
1               5                   10                  15
Gly

<210> SEQ ID NO 592
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 592

Gly Ala Trp His Cys Thr Thr Leu Phe Pro His His Tyr Cys Leu Tyr
1               5                   10                  15
Gly

<210> SEQ ID NO 593
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (12)
<223> OTHER INFORMATION: D-Tyr

<400> SEQUENCE: 593

Ala Trp His Cys Thr Thr Leu Phe Pro His His Tyr Cys Leu Tyr Gly
 1               5                  10                  15

<210> SEQ ID NO 594
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 594

Gly Asp Trp His Cys Thr Thr Leu Phe Pro His His Tyr Cys Leu Tyr
 1               5                  10                  15

Gly

<210> SEQ ID NO 595
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 595

Gly Ser Trp His Cys Thr Thr Leu Phe Pro His His Tyr Cys Leu Tyr
 1               5                  10                  15

Gly

<210> SEQ ID NO 596
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 596

Pro Pro Trp His Cys Thr Thr Leu Phe Pro His His Tyr Cys Leu Tyr
 1               5                  10                  15

Gly

<210> SEQ ID NO 597
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
```

<223> OTHER INFORMATION: 1-Nal

<400> SEQUENCE: 597

Gly Gln Trp His Cys Thr Thr Leu Phe Pro His His Xaa Cys Leu Tyr
1               5                   10                  15

Gly

<210> SEQ ID NO 598
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 598

Gly Gln Trp His Cys Thr Thr Tyr Phe Pro His His Tyr Cys Leu Tyr
1               5                   10                  15

Gly

<210> SEQ ID NO 599
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 599

Gly Ala Trp His Cys Thr Thr Tyr Phe Pro His His Tyr Cys Leu Tyr
1               5                   10                  15

Gly

<210> SEQ ID NO 600
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Tyr(3-Cl)
<220> FEATURE:
<221> NAME/KEY: MOD_RES
<222> LOCATION: (13)
<223> OTHER INFORMATION: D-Tyr

<400> SEQUENCE: 600

Gly Gln Trp His Cys Thr Thr Tyr Phe Pro His His Tyr Cys Leu Tyr
1               5                   10                  15

Gly

<210> SEQ ID NO 601
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: D-Tyr

<400> SEQUENCE: 601
```

Gly Gln Trp His Cys Thr Thr Ile Phe Pro His His Tyr Cys Leu Tyr
1               5                   10                  15

Gly

```
<210> SEQ ID NO 602
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Cha
<220> FEATURE:
<221> NAME/KEY: MOD_RES
<222> LOCATION: (13)
<223> OTHER INFORMATION: D-Tyr

<400> SEQUENCE: 602
```

Gly Gln Trp His Cys Thr Thr Xaa Phe Pro His His Tyr Cys Leu Tyr
1               5                   10                  15

Gly

```
<210> SEQ ID NO 603
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603
```

Gly Gln Trp His Cys Thr Thr Tyr Phe Pro His His Tyr Cys Leu Tyr
1               5                   10                  15

Gly

```
<210> SEQ ID NO 604
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604
```

Gly Gln Trp His Cys Tyr Thr Leu Phe Pro His His Tyr Cys Leu Tyr
1               5                   10                  15

Gly

```
<210> SEQ ID NO 605
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 605

Gly Gln Trp His Cys Thr Tyr Leu Phe Pro His His Tyr Cys Leu Tyr
1               5                   10                  15

Gly

<210> SEQ ID NO 606
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gly Gln Trp Asn Cys Thr Thr Leu Phe Pro His His Tyr Cys Leu Tyr
1               5                   10                  15

Gly

<210> SEQ ID NO 607
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Gly Gln Trp His Cys Thr Thr Leu Phe Pro Asn His Tyr Cys Leu Tyr
1               5                   10                  15

Gly

<210> SEQ ID NO 608
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Gly Gln Trp His Cys Thr Thr Leu Phe Pro His Asn Tyr Cys Leu Tyr
1               5                   10                  15

Gly

<210> SEQ ID NO 609
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (18)
<223> OTHER INFORMATION: Lys(GdT)

<400> SEQUENCE: 609

Gly Gln Trp His Cys Thr Thr Arg Phe Pro His His Tyr Cys Leu Tyr
1               5                   10                  15

Gly Lys
```

```
<210> SEQ ID NO 610
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (8)
<223> OTHER INFORMATION: Lys(GdT)

<400> SEQUENCE: 610

Gly Gln Trp His Cys Thr Thr Lys Phe Pro His His Tyr Cys Leu Tyr
1               5                   10                  15

Gly

<210> SEQ ID NO 611
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Gly Gln Trp His Cys Thr Thr Leu Phe Pro His His Tyr Cys Ile Tyr
1               5                   10                  15

Gly

<210> SEQ ID NO 612
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Gly Gln Trp His Cys Thr Thr Leu Phe Pro His His Tyr Cys Val Tyr
1               5                   10                  15

Gly

<210> SEQ ID NO 613
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Phe(4-F)

<400> SEQUENCE: 613

Gly Gln Trp His Cys Thr Thr Phe Phe Pro His His Tyr Cys Leu Tyr
1               5                   10                  15

Gly

<210> SEQ ID NO 614
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 614

Gly Lys Trp His Cys Thr Thr Leu Phe Pro His His Tyr Cys Leu Tyr
1               5                   10                  15

Gly

<210> SEQ ID NO 615
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Gly Gln Trp His Cys Thr Thr Arg Phe Pro His His Tyr Cys Phe Tyr
1               5                   10                  15

Gly

<210> SEQ ID NO 616
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Hfe

<400> SEQUENCE: 616

Gly Gln Trp His Cys Thr Thr Arg Phe Pro His His Tyr Cys Xaa Tyr
1               5                   10                  15

Gly

<210> SEQ ID NO 617
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: h-Tyr

<400> SEQUENCE: 617

Gly Gln Trp His Cys Thr Thr Arg Phe Pro His His Tyr Cys Leu Tyr
1               5                   10                  15

Gly

<210> SEQ ID NO 618
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: h-Tyr(Me)

<400> SEQUENCE: 618

Gly Gln Trp His Cys Thr Thr Arg Phe Pro His His Tyr Cys Leu Tyr
1               5                   10                  15

Gly

<210> SEQ ID NO 619
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: Phe(3-OMe)

<400> SEQUENCE: 619

Gly Gln Trp His Cys Thr Thr Arg Phe Pro His His Phe Cys Leu Tyr
1               5                   10                  15

Gly

<210> SEQ ID NO 620
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Gly Gln Trp His Cys Thr Asp Arg Phe Pro His His Tyr Cys Leu Tyr
1               5                   10                  15

Gly

<210> SEQ ID NO 621
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Ala Trp His Cys Thr Thr Arg Phe Pro Ala His Tyr Cys Leu Tyr Gly
1               5                   10                  15

<210> SEQ ID NO 622
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: N-Me-Ala

<400> SEQUENCE: 622

```
Gly Gln Trp His Cys Thr Thr Arg Phe Ala His His Tyr Cys Leu Tyr
1               5                   10                  15

Gly

<210> SEQ ID NO 623
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (7)
<223> OTHER INFORMATION: Dpr(GdT)

<400> SEQUENCE: 623

Gly Gln Trp His Cys Thr Xaa Arg Phe Pro His His Tyr Cys Leu Tyr
1               5                   10                  15

Gly

<210> SEQ ID NO 624
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (7)
<223> OTHER INFORMATION: Lys(GdT)

<400> SEQUENCE: 624

Gly Gln Trp His Cys Thr Lys Arg Phe Pro His His Tyr Cys Leu Tyr
1               5                   10                  15

Gly

<210> SEQ ID NO 625
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: cbz-Gly
<220> FEATURE:
<221> NAME/KEY: MOD_RES
<222> LOCATION: (7)
<223> OTHER INFORMATION: Orn(GdT)

<400> SEQUENCE: 625

Gly Gln Trp His Cys Thr Xaa Arg Phe Pro His His Tyr Cys Leu Tyr
1               5                   10                  15

Gly

<210> SEQ ID NO 626
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 626

Gly Lys Trp His Cys Thr Thr Tyr Phe Pro His His Tyr Cys Val Tyr
1               5                   10                  15
Gly

<210> SEQ ID NO 627
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 627

Gly Lys Trp His Cys Tyr Thr Tyr Phe Pro His His Tyr Cys Leu Tyr
1               5                   10                  15
Gly

<210> SEQ ID NO 628
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 628

Gly Lys Trp His Cys Tyr Thr Tyr Phe Pro His His Tyr Cys Val Tyr
1               5                   10                  15
Gly

<210> SEQ ID NO 629
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 629

Gly Lys Trp His Cys Tyr Thr Tyr Phe Pro His His Tyr Cys Val Tyr
1               5                   10                  15
Tyr
```

```
<210> SEQ ID NO 630
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 630

Gly Lys Trp His Cys Thr Thr Tyr Phe Pro Tyr His Tyr Cys Leu Tyr
1               5                   10                  15
Gly

<210> SEQ ID NO 631
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 631

Gly Lys Trp His Cys Thr Thr Tyr Phe Pro His Tyr Tyr Cys Leu Tyr
1               5                   10                  15
Gly

<210> SEQ ID NO 632
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 632

Gly Lys Trp His Cys Thr Thr Tyr Phe Pro His Trp Tyr Cys Leu Tyr
1               5                   10                  15
Gly

<210> SEQ ID NO 633
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 633

Gly Lys Trp His Cys Thr Thr Tyr Phe Pro His His Tyr Cys Leu Tyr
1               5                   10                  15
Tyr
```

<210> SEQ ID NO 634
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (17)
<223> OTHER INFORMATION: Bip

<400> SEQUENCE: 634

Gly Lys Trp His Cys Thr Thr Tyr Phe Pro His His Tyr Cys Leu Tyr
1               5                   10                  15
Xaa

<210> SEQ ID NO 635
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: Bip

<400> SEQUENCE: 635

Gly Lys Trp His Cys Thr Thr Tyr Phe Pro His His Xaa Cys Leu Tyr
1               5                   10                  15
Gly

<210> SEQ ID NO 636
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: Tyr(3-Cl)

<400> SEQUENCE: 636

Gly Lys Trp His Cys Thr Thr Tyr Phe Pro His His Tyr Cys Leu Tyr
1               5                   10                  15
Gly

<210> SEQ ID NO 637
<211> LENGTH: 17
<212> TYPE: PRT
<213> ORGANISM: Artificial Sequence
<220> FEATURE:
<223> OTHER INFORMATION: Description of Artificial Sequence: Synthetic

```
                            peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: Tyr(2,6-Me2)

<400> SEQUENCE: 637

Gly Lys Trp His Cys Thr Thr Tyr Phe Pro His His Tyr Cys Leu Tyr
1               5                  10                  15

Gly

<210> SEQ ID NO 638
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Gly Gln Trp His Cys Thr Thr Arg Phe Pro His His Tyr Cys Leu Tyr
1               5                  10                  15

Gly

<210> SEQ ID NO 639
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: Lys(Lys(GdT)GdT)

<400> SEQUENCE: 639

Gly Gln Trp His Cys Thr Thr Arg Phe Pro His His Tyr Cys Leu Tyr
1               5                  10                  15

Gly Lys

<210> SEQ ID NO 640
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Lys(GdT)

<400> SEQUENCE: 640

Gly Gln Trp Lys Cys Thr Thr Arg Phe Pro His His Tyr Cys Leu Tyr
1               5                  10                  15

Gly

<210> SEQ ID NO 641
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Lys(GdT)

<400> SEQUENCE: 641

Gly Gln Trp His Cys Lys Thr Arg Phe Pro His His Tyr Cys Leu Tyr
1               5                   10                  15

Gly

<210> SEQ ID NO 642
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Lys(GdT)

<400> SEQUENCE: 642

Gly Gln Trp His Cys Thr Thr Arg Phe Pro Lys His Tyr Cys Leu Tyr
1               5                   10                  15

Gly

<210> SEQ ID NO 643
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Gly Gln Trp His Cys Tyr Thr Leu Phe Pro His His Tyr Cys Leu Tyr
1               5                   10                  15

Gly

<210> SEQ ID NO 644
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(GdT)
<220> FEATURE:
<221> NAME/KEY: MOD_RES
<222> LOCATION: (2)
<223> OTHER INFORMATION: Lys(Lys((GdT)GdT)

<400> SEQUENCE: 644

Lys Lys Gly Gln Trp His Cys Thr Thr Tyr Phe Pro His His Tyr Cys
1               5                   10                  15

Leu Tyr Gly

<210> SEQ ID NO 645
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdD)

<400> SEQUENCE: 645

Gly Lys Gln Trp His Cys Thr Thr Tyr Phe Pro His His Tyr Cys Leu
1               5                   10                  15

Tyr Gly

<210> SEQ ID NO 646
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 646

Gly Lys Trp His Cys Thr Thr Tyr Phe Pro Thr His Tyr Cys Leu Tyr
1               5                   10                  15

Gly

<210> SEQ ID NO 647
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 647

Gly Lys Trp His Cys Tyr Thr Tyr Phe Pro Tyr His Tyr Cys Val Tyr
1               5                   10                  15

Gly

<210> SEQ ID NO 648
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 648

Gly Lys Trp His Cys Tyr Thr Tyr Phe Pro Tyr His Tyr Cys Leu Tyr
1               5                   10                  15

Gly

<210> SEQ ID NO 649
<211> LENGTH: 17
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 649

Gly Lys Trp His Cys Thr Thr Tyr Phe Pro His His Val Cys Leu Tyr
1               5                   10                  15

Gly

<210> SEQ ID NO 650
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 650

Gly Lys Trp His Cys Thr Thr Leu Phe Pro His His Val Cys Leu Tyr
1               5                   10                  15

Gly

<210> SEQ ID NO 651
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (16)
<223> OTHER INFORMATION: Dip

<400> SEQUENCE: 651

Gly Lys Trp His Cys Thr Thr Tyr Phe Pro His His Tyr Cys Leu Xaa
1               5                   10                  15

Gly

<210> SEQ ID NO 652
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: Dip

<400> SEQUENCE: 652
```

Gly Lys Trp His Cys Thr Thr Tyr Phe Pro His His Xaa Cys Leu Tyr
1               5                   10                  15

Gly

<210> SEQ ID NO 653
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (17)
<223> OTHER INFORMATION: Phe(4-NH2)

<400> SEQUENCE: 653

Gly Lys Trp His Cys Thr Thr Tyr Phe Pro His His Tyr Cys Leu Tyr
1               5                   10                  15

Phe

<210> SEQ ID NO 654
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (16)
<223> OTHER INFORMATION: Phe(4-NH2)

<400> SEQUENCE: 654

Gly Lys Trp His Cys Thr Thr Tyr Phe Pro His His Tyr Cys Leu Phe
1               5                   10                  15

Gly

<210> SEQ ID NO 655
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (16)
<223> OTHER INFORMATION: Phe(4-NH2)(GdT)

<400> SEQUENCE: 655

Gly Lys Trp His Cys Thr Thr Tyr Phe Pro His His Tyr Cys Leu Phe
1               5                   10                  15

Gly

<210> SEQ ID NO 656

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: Phe(4-NH2)

<400> SEQUENCE: 656

Gly Lys Trp His Cys Thr Thr Tyr Phe Pro His His Phe Cys Leu Tyr
1               5                   10                  15

Gly

<210> SEQ ID NO 657
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (6)
<223> OTHER INFORMATION: Tyr(3-I)

<400> SEQUENCE: 657

Gly Lys Trp His Cys Tyr Thr Tyr Phe Pro His His Tyr Cys Leu Tyr
1               5                   10                  15

Gly

<210> SEQ ID NO 658
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 658

Gly Lys Trp His Cys Tyr Thr Tyr Phe Pro His His Tyr Cys Val Tyr
1               5                   10                  15

Gly Lys

<210> SEQ ID NO 659
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 659

Gly Lys Trp His Cys Tyr Thr Tyr Phe Pro His His Tyr Cys Val Tyr
1               5                   10                  15

Tyr Lys

<210> SEQ ID NO 660
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 660

Gly Lys Trp His Cys Thr Thr Tyr Phe Pro His His Tyr Cys Leu Tyr
1               5                   10                  15

Tyr Lys

<210> SEQ ID NO 661
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (17)
<223> OTHER INFORMATION: Bip
<220> FEATURE:
<221> NAME/KEY: MOD_RES
<222> LOCATION: (18)
<223> OTHER INFORMATION: Lys(GdT)

<400> SEQUENCE: 661

Gly Lys Trp His Cys Thr Thr Tyr Phe Pro His His Tyr Cys Leu Tyr
1               5                   10                  15

Xaa Lys

<210> SEQ ID NO 662
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
```

```
<220> FEATURE:
<221> NAME/KEY: MOD_RES
<222> LOCATION: (8)
<223> OTHER INFORMATION: Lys(GdT)

<400> SEQUENCE: 662

Gly Lys Trp His Cys Tyr Thr Lys Phe Pro His His Tyr Cys Val Tyr
1               5                   10                  15

Gly

<210> SEQ ID NO 663
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)

<400> SEQUENCE: 663

Gly Lys Trp His Cys Tyr Thr Lys Phe Pro His His Tyr Cys Val Tyr
1               5                   10                  15

Tyr

<210> SEQ ID NO 664
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)

<400> SEQUENCE: 664

Gly Lys Trp His Cys Thr Thr Lys Phe Pro His His Tyr Cys Leu Tyr
1               5                   10                  15

Tyr

<210> SEQ ID NO 665
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Tyr-Gly-GdT)

<400> SEQUENCE: 665

Gly Tyr Lys Trp His Cys Thr Thr Tyr Phe Pro His His Tyr Cys Leu
1               5                   10                  15

Tyr Gly
```

```
<210> SEQ ID NO 666
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Val-Gly-GdT)

<400> SEQUENCE: 666

Gly Val Lys Trp His Cys Thr Thr Tyr Phe Pro His His Tyr Cys Leu
1               5                   10                  15

Tyr Gly

<210> SEQ ID NO 667
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(Phe-Gly-GdT)

<400> SEQUENCE: 667

Gly Phe Lys Trp His Cys Thr Thr Tyr Phe Pro His His Tyr Cys Leu
1               5                   10                  15

Tyr Gly

<210> SEQ ID NO 668
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Lys(His-Gly-GdT)

<400> SEQUENCE: 668

Gly His Lys Trp His Cys Thr Thr Tyr Phe Pro His His Tyr Cys Leu
1               5                   10                  15

Tyr Gly

<210> SEQ ID NO 669
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 669
```

```
Gly Lys Trp His Cys Tyr Thr Tyr Phe Pro His His Tyr Cys Leu Tyr
1               5                   10                  15

Phe Lys

<210> SEQ ID NO 670
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (17)
<223> OTHER INFORMATION: Phg
<220> FEATURE:
<221> NAME/KEY: MOD_RES
<222> LOCATION: (18)
<223> OTHER INFORMATION: Lys(GdT)

<400> SEQUENCE: 670

Gly Lys Trp His Cys Tyr Thr Tyr Phe Pro His His Tyr Cys Leu Tyr
1               5                   10                  15

Xaa Lys

<210> SEQ ID NO 671
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 671

Gly Lys Trp His Cys Tyr Thr Tyr Phe Pro His His Tyr Cys Leu Tyr
1               5                   10                  15

Tyr Lys

<210> SEQ ID NO 672
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 672

Gly Lys Trp His Cys Tyr Thr Tyr Phe Pro His His Tyr Cys Leu Tyr
1               5                   10                  15
```

Tyr Lys

<210> SEQ ID NO 673
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 673

Gly Lys Trp His Cys Tyr Thr Tyr Phe Pro His His Tyr Cys Leu Tyr
1               5                   10                  15

Val Lys

<210> SEQ ID NO 674
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 674

Gly Lys Trp Tyr Cys Thr Thr Tyr Phe Pro His His Tyr Cys Leu Tyr
1               5                   10                  15

Gly

<210> SEQ ID NO 675
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (7)
<223> OTHER INFORMATION: Lys(GdT)

<400> SEQUENCE: 675

Gly Lys Trp His Cys Tyr Lys Tyr Phe Pro His His Tyr Cys Leu Tyr
1               5                   10                  15

Gly

<210> SEQ ID NO 676
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (13)
<223> OTHER INFORMATION: 1-Nal

<400> SEQUENCE: 676

Gly Lys Trp His Cys Tyr Thr Tyr Phe Pro His His Xaa Cys Leu Tyr
1               5                   10                  15

Gly

<210> SEQ ID NO 677
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (18)
<223> OTHER INFORMATION: Lys(GdT)

<400> SEQUENCE: 677

Gly Gln Trp His Cys Tyr Thr Lys Phe Pro His His Tyr Cys Leu Tyr
1               5                   10                  15

Gly Lys

<210> SEQ ID NO 678
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: Lys(GdT)

<400> SEQUENCE: 678

Gly Gln Trp His Cys Tyr Thr Tyr Phe Pro His His Tyr Cys Leu Tyr
1               5                   10                  15

Gly Lys

<210> SEQ ID NO 679
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (18)
```

```
<223> OTHER INFORMATION: Lys(GdT)

<400> SEQUENCE: 679

Gly Lys Trp His Cys Tyr Thr Lys Phe Pro His His Tyr Cys Leu Tyr
1               5                   10                  15

Gly Lys

<210> SEQ ID NO 680
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (18)
<223> OTHER INFORMATION: Lys(GdT)

<400> SEQUENCE: 680

Gly Lys Trp His Cys Tyr Thr Tyr Phe Pro His His Tyr Cys Leu Tyr
1               5                   10                  15

Gly Lys

<210> SEQ ID NO 681
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 681

Lys Lys Trp His Cys Thr Thr Lys Phe Pro His His Tyr Cys Leu Tyr
1               5                   10                  15

Xaa

<210> SEQ ID NO 682
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 682

Gly Lys Trp His Cys Tyr Thr Tyr Phe Pro His His Tyr Cys Val Tyr
1               5                   10                  15
```

Gly

<210> SEQ ID NO 683
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 683

Gly Lys Trp His Cys Tyr Thr Tyr Phe Pro His His Tyr Cys Val Tyr
1               5                   10                  15

Gly

<210> SEQ ID NO 684
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)

<400> SEQUENCE: 684

Gly Lys Trp His Cys Tyr Thr Tyr Phe Pro His His Tyr Cys Val Tyr
1               5                   10                  15

Gly

<210> SEQ ID NO 685
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdD)
<220> FEATURE:
<221> NAME/KEY: MOD_RES
<222> LOCATION: (8)
<223> OTHER INFORMATION: Lys(GdD)
<220> FEATURE:
<221> NAME/KEY: MOD_RES
<222> LOCATION: (17)
<223> OTHER INFORMATION: Bip

<400> SEQUENCE: 685

Gly Lys Trp His Cys Thr Thr Lys Phe Pro His His Tyr Cys Leu Tyr
1               5                   10                  15

Xaa

<210> SEQ ID NO 686
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)
<223> OTHER INFORMATION: Dpr(GdT)
<220> FEATURE:
<221> NAME/KEY: MOD_RES
<222> LOCATION: (2)
<223> OTHER INFORMATION: Dpr(Dpr(GdT)GdT)

<400> SEQUENCE: 686

Xaa Xaa Trp His Cys Tyr Thr Tyr Phe Pro His His Tyr Cys Val Tyr
1               5                   10                  15

Gly

<210> SEQ ID NO 687
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(GdT)
<220> FEATURE:
<221> NAME/KEY: MOD_RES
<222> LOCATION: (2)
<223> OTHER INFORMATION: Lys(Lys(GdT)GdT)

<400> SEQUENCE: 687

Lys Lys Trp His Cys Tyr Thr Tyr Phe Pro His His Tyr Cys Val Tyr
1               5                   10                  15

Gly

<210> SEQ ID NO 688
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 688

Gly Lys Trp His Cys Tyr Thr Lys Phe Pro His His Tyr Cys Val Tyr
1               5                   10                  15

Xaa

<210> SEQ ID NO 689
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
```

```
<220> FEATURE:
<221> NAME/KEY: MOD_RES
<222> LOCATION: (8)
<223> OTHER INFORMATION: Dab(GdT)
<220> FEATURE:
<221> NAME/KEY: MOD_RES
<222> LOCATION: (17)
<223> OTHER INFORMATION: Bip

<400> SEQUENCE: 689

Gly Lys Trp His Cys Tyr Thr Xaa Phe Pro His His Tyr Cys Val Tyr
1               5                   10                  15

Xaa

<210> SEQ ID NO 690
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Dpr(GdT)
<220> FEATURE:
<221> NAME/KEY: MOD_RES
<222> LOCATION: (17)
<223> OTHER INFORMATION: Bip

<400> SEQUENCE: 690

Gly Lys Trp His Cys Tyr Thr Xaa Phe Pro His His Tyr Cys Val Tyr
1               5                   10                  15

Xaa

<210> SEQ ID NO 691
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dab(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 691

Gly Xaa Trp His Cys Tyr Thr Lys Phe Pro His His Tyr Cys Val Tyr
1               5                   10                  15

Xaa

<210> SEQ ID NO 692
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (1)
<223> OTHER INFORMATION: Lys(GdT)
<220> FEATURE:
<221> NAME/KEY: MOD_RES
<222> LOCATION: (7)
<223> OTHER INFORMATION: Lys(GdT)
<220> FEATURE:
<221> NAME/KEY: MOD_RES
<222> LOCATION: (16)
<223> OTHER INFORMATION: Bip

<400> SEQUENCE: 692

Lys Trp His Cys Tyr Thr Lys Phe Pro His His Tyr Cys Val Tyr Xaa
1               5                   10                  15

<210> SEQ ID NO 693
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 693

Gly Lys Trp His Cys Tyr Thr Lys Phe Pro His His Tyr Cys Val Tyr
1               5                   10                  15

Xaa Arg

<210> SEQ ID NO 694
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)

<400> SEQUENCE: 694

Gly Lys Trp His Cys Tyr Thr Lys Phe Pro His His Tyr Cys Val Tyr
1               5                   10                  15

Tyr Tyr

<210> SEQ ID NO 695
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)

<400> SEQUENCE: 695

Gly Lys Trp His Cys Tyr Thr Lys Phe Pro Tyr His Tyr Cys Val Tyr
 1               5                  10                  15

Tyr

<210> SEQ ID NO 696
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (15)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 696

Gly Lys Trp His Cys Tyr Thr Lys Phe Pro His His Tyr Cys Lys Tyr
 1               5                  10                  15

Xaa

<210> SEQ ID NO 697
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (15)
<223> OTHER INFORMATION: Lys(GdT)

<400> SEQUENCE: 697

Gly Lys Trp His Cys Tyr Thr Lys Phe Pro His His Tyr Cys Lys Tyr
 1               5                  10                  15

Tyr

<210> SEQ ID NO 698
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 698

Lys Lys Trp His Cys Tyr Thr Tyr Phe Pro His His Tyr Cys Val Tyr
1               5                   10                  15

Gly

<210> SEQ ID NO 699
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 699

Lys Lys Gly Trp His Cys Tyr Thr Tyr Phe Pro His His Tyr Cys Thr
1               5                   10                  15

Tyr Gly

<210> SEQ ID NO 700
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 700

Lys Lys Ala Trp His Cys Tyr Thr Tyr Phe Pro His His Tyr Cys Val
1               5                   10                  15

Tyr Gly

<210> SEQ ID NO 701
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 701

Lys Lys Leu Trp His Cys Tyr Thr Tyr Phe Pro His His Tyr Cys Val
1               5                   10                  15

Tyr Gly

<210> SEQ ID NO 702
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(GdD)

<400> SEQUENCE: 702

Lys Lys Tyr Trp His Cys Tyr Thr Tyr Phe Pro His His Tyr Cys Val
1               5                   10                  15

Tyr Gly

<210> SEQ ID NO 703
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Gly-GdT)
<220> FEATURE:
<221> NAME/KEY: MOD_RES
<222> LOCATION: (5)
<223> OTHER INFORMATION: D-Cys
<220> FEATURE:
<221> NAME/KEY: MOD_RES
<222> LOCATION: (8)
<223> OTHER INFORMATION: Lys(GdT)
<220> FEATURE:
<221> NAME/KEY: MOD_RES
<222> LOCATION: (17)
<223> OTHER INFORMATION: Bip

<400> SEQUENCE: 703

Gly Lys Trp His Cys Thr Thr Lys Phe Pro His His Tyr Cys Leu Tyr
1               5                   10                  15

Xaa

<210> SEQ ID NO 704
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(His-Gly)

<400> SEQUENCE: 704

Lys Trp His Cys Thr Thr Tyr Phe Pro His His Tyr Cys Leu Tyr Gly
1               5                   10                  15

<210> SEQ ID NO 705
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705
```

```
Gly Gln Trp His Cys Thr Thr Tyr Phe Pro His His Tyr Cys Leu Tyr
1               5                   10                  15

Gly

<210> SEQ ID NO 706
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Gln Trp His Cys Thr Thr Tyr Phe Pro His His Tyr Cys Leu Tyr Gly
1               5                   10                  15

<210> SEQ ID NO 707
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 707

Lys Trp His Cys Tyr Thr Tyr Phe Pro His His Tyr Cys Val Tyr Gly
1               5                   10                  15

<210> SEQ ID NO 708
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 708

Lys Trp His Cys Tyr Thr Tyr Phe Pro Tyr His Tyr Cys Val Tyr Gly
1               5                   10                  15

<210> SEQ ID NO 709
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 709

Lys Trp His Cys Tyr Thr Tyr Phe Pro Tyr His Tyr Cys Val Tyr Gly
1               5                   10                  15

<210> SEQ ID NO 710
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 710

Lys Trp His Cys Thr Thr Tyr Phe Pro His His Val Cys Leu Tyr Gly
1               5                   10                  15

<210> SEQ ID NO 711
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 711

Lys Trp His Cys Thr Thr Leu Phe Pro His His Val Cys Leu Tyr Gly
1               5                   10                  15

<210> SEQ ID NO 712
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (15)
<223> OTHER INFORMATION: Dip

<400> SEQUENCE: 712

Lys Trp His Cys Thr Thr Tyr Phe Pro His His Tyr Cys Leu Xaa Gly
1               5                   10                  15

<210> SEQ ID NO 713
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (12)
<223> OTHER INFORMATION: Dip

<400> SEQUENCE: 713

Lys Trp His Cys Thr Thr Tyr Phe Pro His His Xaa Cys Leu Tyr Gly
1               5                   10                  15

<210> SEQ ID NO 714
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (12)
<223> OTHER INFORMATION: Dip

<400> SEQUENCE: 714

Lys Trp His Cys Thr Thr Tyr Phe Pro His His Xaa Cys Leu Tyr Gly
1               5                   10                  15

<210> SEQ ID NO 715
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Phe(4-NH2)

<400> SEQUENCE: 715

Lys Trp His Cys Thr Thr Tyr Phe Pro His His Tyr Cys Leu Tyr Phe
1               5                   10                  15

<210> SEQ ID NO 716
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (15)
<223> OTHER INFORMATION: Phe(4-NH2)

<400> SEQUENCE: 716

Lys Trp His Cys Thr Thr Tyr Phe Pro His His Tyr Cys Leu Phe Gly
1               5                   10                  15

<210> SEQ ID NO 717
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (15)
<223> OTHER INFORMATION: Phe(4-NH2)

<400> SEQUENCE: 717
```

```
Lys Trp His Cys Thr Thr Tyr Phe Pro His His Tyr Cys Leu Phe Gly
1               5                   10                  15

<210> SEQ ID NO 718
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (12)
<223> OTHER INFORMATION: Phe(4-NH2)

<400> SEQUENCE: 718

Lys Trp His Cys Thr Thr Tyr Phe Pro His His Phe Cys Leu Tyr Gly
1               5                   10                  15

<210> SEQ ID NO 719
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (5)
<223> OTHER INFORMATION: Tyr(3-I)

<400> SEQUENCE: 719

Lys Trp His Cys Tyr Thr Tyr Phe Pro His His Tyr Cys Leu Tyr Gly
1               5                   10                  15

<210> SEQ ID NO 720
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (5)
<223> OTHER INFORMATION: Tyr(3-I)

<400> SEQUENCE: 720

Lys Trp His Cys Tyr Thr Tyr Phe Pro His His Tyr Cys Leu Tyr Gly
1               5                   10                  15

<210> SEQ ID NO 721
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Lys(Gly)

<400> SEQUENCE: 721

Lys Trp His Cys Tyr Thr Tyr Phe Pro His His Tyr Cys Val Tyr Gly
1               5                   10                  15

Lys

<210> SEQ ID NO 722
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 722

Lys Trp His Cys Tyr Thr Tyr Phe Pro His His Tyr Cys Val Tyr Tyr
1               5                   10                  15

Lys

<210> SEQ ID NO 723
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 723

Lys Trp His Cys Tyr Thr Tyr Phe Pro His His Tyr Cys Val Tyr Tyr
1               5                   10                  15

Lys

<210> SEQ ID NO 724
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 724

Lys Trp His Cys Thr Thr Tyr Phe Pro His His Tyr Cys Leu Tyr Tyr
1               5                   10                  15

Lys

<210> SEQ ID NO 725
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 725

Lys Trp His Cys Thr Thr Tyr Phe Pro His His Tyr Cys Leu Tyr Xaa
1               5                   10                  15

Lys

<210> SEQ ID NO 726
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 726

Lys Trp His Cys Tyr Thr Lys Phe Pro His His Tyr Cys Val Tyr Gly
1               5                   10                  15

<210> SEQ ID NO 727
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 727

Lys Trp His Cys Tyr Thr Lys Phe Pro His His Tyr Cys Val Tyr Tyr
1               5                   10                  15

<210> SEQ ID NO 728
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 728

Lys Trp His Cys Thr Thr Lys Phe Pro His His Tyr Cys Leu Tyr Tyr
1               5                   10                  15

<210> SEQ ID NO 729
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 729

Lys Trp His Cys Thr Thr Lys Phe Pro His His Tyr Cys Leu Tyr Xaa
1               5                   10                  15

<210> SEQ ID NO 730
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Tyr-Gly)

<400> SEQUENCE: 730

Lys Trp His Cys Thr Thr Tyr Phe Pro His His Tyr Cys Leu Tyr Gly
1               5                   10                  15

<210> SEQ ID NO 731
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Val-Gly)

<400> SEQUENCE: 731

Lys Trp His Cys Thr Thr Tyr Phe Pro His His Tyr Cys Leu Tyr Gly
1               5                   10                  15

<210> SEQ ID NO 732
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Phe-Gly)

<400> SEQUENCE: 732

Lys Trp His Cys Thr Thr Tyr Phe Pro His His Tyr Cys Leu Tyr Gly
1               5                   10                  15

<210> SEQ ID NO 733
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(His-Gly)
```

```
<400> SEQUENCE: 733

Lys Trp His Cys Thr Thr Tyr Phe Pro His His Tyr Cys Leu Tyr Gly
1               5                   10                  15

<210> SEQ ID NO 734
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Lys Trp His Cys Tyr Thr Tyr Phe Pro His His Tyr Cys Val Tyr Gly
1               5                   10                  15

<210> SEQ ID NO 735
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Phe-Gly)

<400> SEQUENCE: 735

Lys Trp His Cys Thr Thr Tyr Phe Pro His His Tyr Cys Leu Tyr Gly
1               5                   10                  15

<210> SEQ ID NO 736
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Val-Gly)

<400> SEQUENCE: 736

Lys Trp His Cys Thr Thr Tyr Phe Pro His His Tyr Cys Leu Tyr Gly
1               5                   10                  15

<210> SEQ ID NO 737
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Tyr-Gly)

<400> SEQUENCE: 737

Lys Trp His Cys Thr Thr Tyr Phe Pro His His Tyr Cys Leu Tyr Gly
1               5                   10                  15

<210> SEQ ID NO 738
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 738

Lys Trp His Cys Thr Thr Lys Phe Pro His His Tyr Cys Leu Tyr Xaa
1               5                   10                  15

<210> SEQ ID NO 739
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 739

Lys Trp His Cys Thr Thr Lys Phe Pro His His Tyr Cys Leu Tyr Tyr
1               5                   10                  15

<210> SEQ ID NO 740
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 740

Lys Trp His Cys Tyr Thr Lys Phe Pro His His Tyr Cys Val Tyr Tyr
1               5                   10                  15

<210> SEQ ID NO 741
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 741

Lys Trp His Cys Tyr Thr Lys Phe Pro His His Tyr Cys Val Tyr Gly
1               5                   10                  15

<210> SEQ ID NO 742
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 742

Lys Trp His Cys Thr Thr Tyr Phe Pro His His Tyr Cys Leu Tyr Xaa
1               5                   10                  15
Lys

<210> SEQ ID NO 743
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 743

Lys Trp His Cys Thr Thr Tyr Phe Pro His His Tyr Cys Leu Tyr Tyr
1               5                   10                  15
Lys

<210> SEQ ID NO 744
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 744

Lys Trp His Cys Thr Thr Lys Phe Pro His His Tyr Cys Leu Tyr Xaa
1               5                   10                  15

<210> SEQ ID NO 745
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 745

Lys Trp His Cys Tyr Thr Tyr Phe Pro His His Tyr Cys Leu Tyr Phe
1               5                   10                  15
Lys
```

```
<210> SEQ ID NO 746
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 746

Lys Trp His Cys Tyr Thr Tyr Phe Pro His His Tyr Cys Leu Tyr Phe
1               5                   10                  15

Lys

<210> SEQ ID NO 747
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 747

Lys Trp His Cys Tyr Thr Tyr Phe Pro His His Tyr Cys Leu Tyr Tyr
1               5                   10                  15

Lys

<210> SEQ ID NO 748
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 748

Lys Trp His Cys Tyr Thr Tyr Phe Pro His His Tyr Cys Leu Tyr Tyr
1               5                   10                  15

Lys

<210> SEQ ID NO 749
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: D-Tyr

<400> SEQUENCE: 749

Lys Trp His Cys Tyr Thr Tyr Phe Pro His His Tyr Cys Leu Tyr Tyr
```

-continued

```
1               5                   10                  15
Lys

<210> SEQ ID NO 750
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 750

Lys Trp His Cys Tyr Thr Tyr Phe Pro His His Tyr Cys Leu Tyr Val
1               5                   10                  15
Lys

<210> SEQ ID NO 751
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 751

Lys Trp Tyr Cys Thr Thr Tyr Phe Pro His His Tyr Cys Leu Tyr Gly
1               5                   10                  15

<210> SEQ ID NO 752
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 752

Lys Trp His Cys Tyr Lys Tyr Phe Pro His His Tyr Cys Leu Tyr Gly
1               5                   10                  15

<210> SEQ ID NO 753
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 753

Lys Trp His Cys Tyr Lys Tyr Phe Pro His His Tyr Cys Leu Tyr Gly
1               5                   10                  15
```

```
<210> SEQ ID NO 754
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (12)
<223> OTHER INFORMATION: 1-Nal

<400> SEQUENCE: 754

Lys Trp His Cys Tyr Thr Tyr Phe Pro His His Xaa Cys Leu Tyr Gly
1               5                   10                  15

<210> SEQ ID NO 755
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Gln Trp His Cys Tyr Thr Lys Phe Pro His His Tyr Cys Leu Tyr Gly
1               5                   10                  15

Lys

<210> SEQ ID NO 756
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Gln Trp His Cys Tyr Thr Tyr Phe Pro His His Tyr Cys Leu Tyr Gly
1               5                   10                  15

Lys

<210> SEQ ID NO 757
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Gln Trp His Cys Tyr Thr Tyr Phe Pro His His Tyr Cys Leu Tyr Gly
1               5                   10                  15

Lys

<210> SEQ ID NO 758
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)
<223> OTHER INFORMATION: Lys(Gly)

<400> SEQUENCE: 758

Lys Trp His Cys Thr Thr Tyr Phe Pro His His Tyr Cys Leu Tyr Tyr
1               5                   10                  15
Lys

<210> SEQ ID NO 759
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 759

Lys Trp His Cys Tyr Thr Tyr Phe Pro His His Tyr Cys Leu Tyr Val
1               5                   10                  15
Lys

<210> SEQ ID NO 760
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Lys)

<400> SEQUENCE: 760

Lys Lys Trp His Cys Tyr Thr Tyr Phe Pro His His Tyr Cys Val Tyr
1               5                   10                  15
Gly

<210> SEQ ID NO 761
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dpr(Dpr)

<400> SEQUENCE: 761

Xaa Trp His Cys Tyr Thr Tyr Phe Pro His His Tyr Cys Val Tyr Gly
1               5                   10                  15

<210> SEQ ID NO 762
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

<223> OTHER INFORMATION: Lys(Gly)

<400> SEQUENCE: 762

Lys Trp His Cys Tyr Thr Tyr Phe Pro His His Tyr Cys Leu Tyr Gly
1               5                   10                  15
Lys

<210> SEQ ID NO 763
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 763

Lys Trp His Cys Tyr Thr Tyr Phe Pro His His Tyr Cys Leu Tyr Phe
1               5                   10                  15
Lys

<210> SEQ ID NO 764
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Phg

<400> SEQUENCE: 764

Lys Trp His Cys Tyr Thr Tyr Phe Pro His His Tyr Cys Leu Tyr Xaa
1               5                   10                  15
Lys

<210> SEQ ID NO 765
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 765

Lys Trp His Cys Tyr Thr Tyr Phe Pro His His Tyr Cys Leu Tyr Tyr
1               5                   10                  15
Lys

<210> SEQ ID NO 766
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 766

Lys Trp His Cys Tyr Thr Tyr Phe Pro His His Tyr Cys Leu Tyr Tyr
1               5                   10                  15

Lys

<210> SEQ ID NO 767
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 767

Lys Trp His Cys Tyr Thr Tyr Phe Pro His His Tyr Cys Leu Tyr Val
1               5                   10                  15

Lys

<210> SEQ ID NO 768
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 768

Lys Trp Tyr Cys Thr Thr Tyr Phe Pro His His Tyr Cys Leu Tyr Gly
1               5                   10                  15

<210> SEQ ID NO 769
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 769

Lys Trp His Cys Tyr Lys Tyr Phe Pro His His Tyr Cys Leu Tyr Gly
1               5                   10                  15

<210> SEQ ID NO 770
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (12)
<223> OTHER INFORMATION: 1-Nal

<400> SEQUENCE: 770

Lys Trp His Cys Tyr Thr Tyr Phe Pro His His Xaa Cys Leu Tyr Gly
1               5                   10                  15

<210> SEQ ID NO 771
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Gln Trp His Cys Tyr Thr Lys Phe Pro His His Tyr Cys Leu Tyr Gly
1               5                   10                  15

Lys

<210> SEQ ID NO 772
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Gln Trp His Cys Tyr Thr Tyr Phe Pro His His Tyr Cys Leu Tyr Gly
1               5                   10                  15

Lys

<210> SEQ ID NO 773
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 773

Lys Trp His Cys Tyr Thr Lys Phe Pro His His Tyr Cys Leu Tyr Gly
1               5                   10                  15

Lys

<210> SEQ ID NO 774
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 774
```

```
Lys Trp His Cys Tyr Thr Tyr Phe Pro His His Tyr Cys Leu Tyr Gly
1               5                   10                  15

Lys

<210> SEQ ID NO 775
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 775

Lys Trp His Cys Thr Thr Tyr Phe Pro Thr His Tyr Cys Leu Tyr Gly
1               5                   10                  15

<210> SEQ ID NO 776
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 776

Lys Trp His Cys Tyr Thr Tyr Phe Pro Tyr His Tyr Cys Leu Tyr Gly
1               5                   10                  15

<210> SEQ ID NO 777
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Bip

<400> SEQUENCE: 777

Lys Trp His Cys Thr Thr Lys Phe Pro His His Tyr Cys Leu Tyr Xaa
1               5                   10                  15

<210> SEQ ID NO 778
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Bip

<400> SEQUENCE: 778

Lys Trp His Cys Thr Thr Lys Phe Pro His His Tyr Cys Leu Tyr Xaa
1               5                   10                  15
```

```
<210> SEQ ID NO 779
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 779

Lys Trp His Cys Tyr Thr Tyr Phe Pro His His Tyr Cys Val Tyr Gly
1               5                   10                  15

<210> SEQ ID NO 780
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 780

Lys Trp His Cys Tyr Thr Tyr Phe Pro His His Tyr Cys Val Tyr Gly
1               5                   10                  15

<210> SEQ ID NO 781
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Lys Trp His Cys Tyr Thr Tyr Phe Pro His His Tyr Cys Val Tyr Gly
1               5                   10                  15

<210> SEQ ID NO 782
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 782

Lys Trp His Cys Tyr Thr Tyr Phe Pro His His Tyr Cys Val Tyr Gly
1               5                   10                  15

<210> SEQ ID NO 783
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
```

<400> SEQUENCE: 783

Lys Trp His Cys Tyr Thr Tyr Phe Pro His His Tyr Cys Val Tyr Gly
1               5                   10                  15

<210> SEQ ID NO 784
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 784

Lys Trp His Cys Tyr Thr Tyr Phe Pro His His Tyr Cys Val Tyr Gly
1               5                   10                  15

<210> SEQ ID NO 785
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 785

Lys Trp His Cys Thr Thr Lys Phe Pro His His Tyr Cys Leu Tyr Xaa
1               5                   10                  15

<210> SEQ ID NO 786
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dpr(Dpr)

<400> SEQUENCE: 786

Xaa Trp His Cys Tyr Thr Tyr Phe Pro His His Tyr Cys Val Tyr Gly
1               5                   10                  15

<210> SEQ ID NO 787
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(Lys)

<400> SEQUENCE: 787

```
Lys Lys Trp His Cys Tyr Thr Tyr Phe Pro His His Tyr Cys Val Tyr
1               5                   10                  15

Gly

<210> SEQ ID NO 788
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 788

Lys Trp His Cys Tyr Thr Lys Phe Pro His His Tyr Cys Val Tyr Xaa
1               5                   10                  15

<210> SEQ ID NO 789
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (7)
<223> OTHER INFORMATION: Dap
<220> FEATURE:
<221> NAME/KEY: MOD_RES
<222> LOCATION: (16)
<223> OTHER INFORMATION: Bip

<400> SEQUENCE: 789

Lys Trp His Cys Tyr Thr Xaa Phe Pro His His Tyr Cys Val Tyr Xaa
1               5                   10                  15

<210> SEQ ID NO 790
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (7)
<223> OTHER INFORMATION: Dpr
<220> FEATURE:
<221> NAME/KEY: MOD_RES
<222> LOCATION: (16)
<223> OTHER INFORMATION: Bip

<400> SEQUENCE: 790

Lys Trp His Cys Tyr Thr Xaa Phe Pro His His Tyr Cys Val Tyr Xaa
1               5                   10                  15
```

```
<210> SEQ ID NO 791
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dap(Gly)
<220> FEATURE:
<221> NAME/KEY: MOD_RES
<222> LOCATION: (16)
<223> OTHER INFORMATION: Bip

<400> SEQUENCE: 791

Xaa Trp His Cys Tyr Thr Lys Phe Pro His His Tyr Cys Val Tyr Xaa
1               5                   10                  15

<210> SEQ ID NO 792
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: Bip

<400> SEQUENCE: 792

Lys Trp His Cys Tyr Thr Lys Phe Pro His His Tyr Cys Val Tyr Xaa
1               5                   10                  15

<210> SEQ ID NO 793
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 793

Lys Trp His Cys Tyr Thr Lys Phe Pro His His Tyr Cys Val Tyr Xaa
1               5                   10                  15
Arg

<210> SEQ ID NO 794
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 794
```

```
Lys Trp His Cys Tyr Thr Lys Phe Pro His His Tyr Cys Val Tyr Tyr
1               5                   10                  15

Tyr

<210> SEQ ID NO 795
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 795

Lys Trp His Cys Tyr Thr Lys Phe Pro Tyr His Tyr Cys Val Tyr Tyr
1               5                   10                  15

<210> SEQ ID NO 796
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (16)
<223> OTHER INFORMATION: Bip

<400> SEQUENCE: 796

Lys Trp His Cys Tyr Thr Lys Phe Pro His His Tyr Cys Lys Tyr Xaa
1               5                   10                  15

<210> SEQ ID NO 797
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)

<400> SEQUENCE: 797

Lys Trp His Cys Tyr Thr Lys Phe Pro His His Tyr Cys Lys Tyr Tyr
1               5                   10                  15

<210> SEQ ID NO 798
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Trp His Cys Tyr Thr Tyr Phe Pro His His Tyr Cys Val Tyr Gly
1               5                   10                  15

<210> SEQ ID NO 799
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Lys Trp His Cys Tyr Thr Tyr Phe Pro His His Tyr Cys Leu Tyr Gly
1               5                   10                  15

<210> SEQ ID NO 800
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Gly Trp His Cys Tyr Thr Tyr Phe Pro His His Tyr Cys Thr Tyr Gly
1               5                   10                  15

<210> SEQ ID NO 801
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Ala Trp His Cys Tyr Thr Tyr Phe Pro His His Tyr Cys Val Tyr Gly
1               5                   10                  15

<210> SEQ ID NO 802
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Leu Trp His Cys Tyr Thr Tyr Phe Pro His His Tyr Cys Val Tyr Gly
1               5                   10                  15

<210> SEQ ID NO 803
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Tyr Trp His Cys Tyr Thr Tyr Phe Pro His His Tyr Cys Val Tyr Gly
1               5                   10                  15

<210> SEQ ID NO 804
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

```
<223> OTHER INFORMATION: Lys(Gly)
<220> FEATURE:
<221> NAME/KEY: MOD_RES
<222> LOCATION: (4)
<223> OTHER INFORMATION: D-Cys
<220> FEATURE:
<221> NAME/KEY: MOD_RES
<222> LOCATION: (16)
<223> OTHER INFORMATION: Bip

<400> SEQUENCE: 804

Lys Trp His Cys Thr Thr Lys Phe Pro His His Tyr Cys Leu Tyr Xaa
1               5                   10                  15

<210> SEQ ID NO 805
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(Gly)
<220> FEATURE:
<221> NAME/KEY: MOD_RES
<222> LOCATION: (4)
<223> OTHER INFORMATION: D-Cys
<220> FEATURE:
<221> NAME/KEY: MOD_RES
<222> LOCATION: (16)
<223> OTHER INFORMATION: Bip

<400> SEQUENCE: 805

Lys Trp His Cys Thr Thr Lys Phe Pro His His Tyr Cys Leu Tyr Xaa
1               5                   10                  15

<210> SEQ ID NO 806
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)..(10)
<223> OTHER INFORMATION: Variable amino acid and this region may
      encompass 5 to 7 residues
<220> FEATURE:
<221> NAME/KEY: MOD_RES
<222> LOCATION: (12)
<223> OTHER INFORMATION: Variable amino acid
<220> FEATURE:
<223> OTHER INFORMATION: see specification as filed for detailed
      description of substitutions and preferred embodiments

<400> SEQUENCE: 806

Trp Xaa Cys Xaa Xaa Xaa Xaa Xaa Xaa Xaa Trp Xaa Cys
1               5                   10

<210> SEQ ID NO 807
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Ser, Val, Thr, His, Arg, Tyr or Asp
<220> FEATURE:
<221> NAME/KEY: MOD_RES
<222> LOCATION: (5)
<223> OTHER INFORMATION: Gly or any amino acid in the D form
<220> FEATURE:
<221> NAME/KEY: MOD_RES
<222> LOCATION: (6)
<223> OTHER INFORMATION: Asp or Asn
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (9)
<223> OTHER INFORMATION: Thr, Lys, His, Asp, Ala, Arg, Tyr or Glu
<220> FEATURE:
<221> NAME/KEY: MOD_RES
<222> LOCATION: (11)
<223> OTHER INFORMATION: Tyr, Lys, His, Val, Ser, Met or Asn
<220> FEATURE:
<223> OTHER INFORMATION: see specification as filed for detailed
      description of substitutions and preferred embodiments

<400> SEQUENCE: 807

Trp Xaa Cys Xaa Xaa Xaa Xaa Xaa Xaa Trp Xaa Cys
1               5                   10

<210> SEQ ID NO 808
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Ser, Val, Thr, His, Arg, Tyr or Asp
<220> FEATURE:
<221> NAME/KEY: MOD_RES
<222> LOCATION: (5)
<223> OTHER INFORMATION: Gly or any amino acid in the D form
<220> FEATURE:
<221> NAME/KEY: MOD_RES
<222> LOCATION: (6)
<223> OTHER INFORMATION: Asp or Asn
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (9)
<223> OTHER INFORMATION: Thr, Lys, His, Asp, Ala, Arg, Tyr or Glu
<220> FEATURE:
<221> NAME/KEY: MOD_RES
<222> LOCATION: (11)
<223> OTHER INFORMATION: Tyr, Lys, His, Val, Ser, Met or Asn
<220> FEATURE:
<221> NAME/KEY: MOD_RES
<222> LOCATION: (13)
<223> OTHER INFORMATION: Asn, Leu, Ile, Arg, Lys or Ala
<220> FEATURE:
<221> NAME/KEY: MOD_RES
```

```
<222> LOCATION: (14)
<223> OTHER INFORMATION: Tyr, Phe, Met, Arg or His
<220> FEATURE:
<223> OTHER INFORMATION: see specification as filed for detailed
      description of substitutions and preferred embodiments

<400> SEQUENCE: 808

Trp Xaa Cys Xaa Xaa Xaa Xaa Xaa Xaa Trp Xaa Cys Xaa Xaa
1               5                   10

<210> SEQ ID NO 809
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Trp Thr Cys Ser Gly Asp Glu Tyr Thr Trp His Cys
1               5                   10

<210> SEQ ID NO 810
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Trp Thr Cys Val Gly Asp His Lys Thr Trp Lys Cys
1               5                   10

<210> SEQ ID NO 811
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Trp Tyr Cys Ser Gly Asp His Leu Asp Trp Lys Cys
1               5                   10

<210> SEQ ID NO 812
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Trp Glu Cys His Gly Asn Glu Phe Glu Trp Asn Cys
1               5                   10

<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Variable amino acid
```

```
<220> FEATURE:
<221> NAME/KEY: MOD_RES
<222> LOCATION: (8)
<223> OTHER INFORMATION: Variable amino acid
<220> FEATURE:
<223> OTHER INFORMATION: see specification as filed for detailed
      description of substitutions and preferred embodiments

<400> SEQUENCE: 813

Cys Tyr Gln Xaa Xaa Cys Trp Xaa Trp
1               5

<210> SEQ ID NO 814
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Cys Tyr Gln Ala Gly Cys Trp Ile Trp
1               5

<210> SEQ ID NO 815
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (11)
<223> OTHER INFORMATION: Ile, Gly, Leu, Val, Phe or Pro
<220> FEATURE:
<223> OTHER INFORMATION: see specification as filed for detailed
      description of substitutions and preferred embodiments

<400> SEQUENCE: 815

Tyr Xaa Xaa Cys Tyr Gln Xaa Xaa Cys Trp Xaa Trp
1               5                   10

<210> SEQ ID NO 816
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or Pen
<220> FEATURE:
<221> NAME/KEY: MOD_RES
<222> LOCATION: (2)..(9)
<223> OTHER INFORMATION: Variable amino acid
<220> FEATURE:
<221> NAME/KEY: MOD_RES
<222> LOCATION: (10)
<223> OTHER INFORMATION: Cys or Pen
<220> FEATURE:
<223> OTHER INFORMATION: see specification as filed for detailed
      description of substitutions and preferred embodiments
```

```
<400> SEQUENCE: 816

Xaa Xaa Xaa Xaa Xaa Xaa Xaa Xaa Xaa Xaa
1               5                   10

<210> SEQ ID NO 817
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Cys Thr Thr Ser Phe Pro His His Tyr Cys
1               5                   10

<210> SEQ ID NO 818
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Cys Thr Thr Lys Phe Pro His His Tyr Cys
1               5                   10

<210> SEQ ID NO 819
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Cys Tyr Thr Tyr Phe Pro His His Tyr Cys
1               5                   10

<210> SEQ ID NO 820
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Cys Thr Thr Arg Phe Pro His His Tyr Cys
1               5                   10

<210> SEQ ID NO 821
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Cys Ser Gly Asp Glu Tyr Thr Trp His Cys
1               5                   10

<210> SEQ ID NO 822
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or Pen
<220> FEATURE:
<221> NAME/KEY: MOD_RES
<222> LOCATION: (2)..(9)
<223> OTHER INFORMATION: Variable amino acid
<220> FEATURE:
<221> NAME/KEY: MOD_RES
<222> LOCATION: (10)
<223> OTHER INFORMATION: Cys or Pen
<220> FEATURE:
<221> NAME/KEY: MOD_RES
<222> LOCATION: (11)..(13)
<223> OTHER INFORMATION: Variable amino acid
<220> FEATURE:
<223> OTHER INFORMATION: see specification as filed for detailed
      description of substitutions and preferred embodiments

<400> SEQUENCE: 822

Xaa Xaa Xaa Xaa Xaa Xaa Xaa Xaa Xaa Xaa Xaa Xaa Xaa
1               5                   10

<210> SEQ ID NO 823
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or Pen
<220> FEATURE:
<221> NAME/KEY: MOD_RES
<222> LOCATION: (2)..(9)
<223> OTHER INFORMATION: Variable amino acid
<220> FEATURE:
<221> NAME/KEY: MOD_RES
<222> LOCATION: (10)
<223> OTHER INFORMATION: Cys or Pen
<220> FEATURE:
<221> NAME/KEY: MOD_RES
<222> LOCATION: (11)..(13)
<223> OTHER INFORMATION: Variable amino acid
<220> FEATURE:
<221> NAME/KEY: MOD_RES
<222> LOCATION: (14)..(15)
<223> OTHER INFORMATION: Variable amino acid and this region may
      encompass 1 or 2 residues
<220> FEATURE:
<223> OTHER INFORMATION: see specification as filed for detailed
      description of substitutions and preferred embodiments

<400> SEQUENCE: 823

Xaa Xaa Xaa Xaa Xaa Xaa Xaa Xaa Xaa Xaa Xaa Xaa Xaa Xaa Xaa
1               5                   10                  15

<210> SEQ ID NO 824
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
```

<223> OTHER INFORMATION: Variable amino acid
<220> FEATURE:
<221> NAME/KEY: MOD_RES
<222> LOCATION: (3)
<223> OTHER INFORMATION: Cys or Pen
<220> FEATURE:
<221> NAME/KEY: MOD_RES
<222> LOCATION: (4)..(11)
<223> OTHER INFORMATION: Variable amino acid
<220> FEATURE:
<221> NAME/KEY: MOD_RES
<222> LOCATION: (12)
<223> OTHER INFORMATION: Cys or Pen
<220> FEATURE:
<223> OTHER INFORMATION: see specification as filed for detailed
      description of substitutions and preferred embodiments

<400> SEQUENCE: 824

Xaa Xaa Xaa Xaa Xaa Xaa Xaa Xaa Xaa Xaa Xaa Xaa
1               5                   10

<210> SEQ ID NO 825
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Variable amino acid and this region may
      encompass 1 to 3 residues
<220> FEATURE:
<221> NAME/KEY: MOD_RES
<222> LOCATION: (4)..(6)
<223> OTHER INFORMATION: Variable amino acid and this region may
      encompass 1 to 3 residues
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (9)
<223> OTHER INFORMATION: Cys or Pen
<220> FEATURE:
<221> NAME/KEY: MOD_RES
<222> LOCATION: (10)..(17)
<223> OTHER INFORMATION: Variable amino acid
<220> FEATURE:
<221> NAME/KEY: MOD_RES
<222> LOCATION: (18)
<223> OTHER INFORMATION: Cys or Pen
<220> FEATURE:
<223> OTHER INFORMATION: see specification as filed for detailed
      description of substitutions and preferred embodiments

<400> SEQUENCE: 825

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 826
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Variable amino acid

```
<220> FEATURE:
<221> NAME/KEY: MOD_RES
<222> LOCATION: (4)
<223> OTHER INFORMATION: Cys or Pen
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (9)
<223> OTHER INFORMATION: Pro, L-hydroxyproline, piperidine-2-carboxylic
      acid, or 4-hydroxypiperidine-2-carboxylic acid
<220> FEATURE:
<221> NAME/KEY: MOD_RES
<222> LOCATION: (10)
<223> OTHER INFORMATION: Variable amino acid
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<223> OTHER INFORMATION: see specification as filed for detailed
      description of substitutions and preferred embodiments

<400> SEQUENCE: 826

Xaa Xaa Xaa Xaa Xaa Thr Xaa Xaa Xaa Xaa His Xaa Cys Xaa Xaa Xaa
1               5                   10                  15

<210> SEQ ID NO 827
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(10)
<223> OTHER INFORMATION: Variable amino acid
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<223> OTHER INFORMATION: see specification as filed for detailed
      description of substitutions and preferred embodiments

<400> SEQUENCE: 827

Xaa Xaa Xaa Cys Xaa Xaa Asp Xaa Xaa Xaa Trp Xaa Cys Xaa Xaa Xaa
1               5                   10                  15

<210> SEQ ID NO 828
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or Pen, in D or L form
<220> FEATURE:
<221> NAME/KEY: MOD_RES
<222> LOCATION: (2)
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3
      -I), or Aib, in D or L form
<220> FEATURE:
<221> NAME/KEY: MOD_RES
<222> LOCATION: (3)
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: (4)
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D
      or L form
<220> FEATURE:
<221> NAME/KEY: MOD_RES
<222> LOCATION: (5)
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: (6)
<223> OTHER INFORMATION: P, P(3-OH), (delta)Pro, Pip, N-Me-A, P(3-OH),
      Y(3-I), b-h-Y, or Aib, in D or L form
<220> FEATURE:
<221> NAME/KEY: MOD_RES
<222> LOCATION: (7)
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: (8)
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: (9)
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: (10)
<223> OTHER INFORMATION: Cys or Pen, in D or L form

<400> SEQUENCE: 828

Xaa Xaa Xaa Xaa Xaa Xaa Xaa Xaa Xaa Xaa
1               5                   10

<210> SEQ ID NO 829
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or Pen, in D or L form
<220> FEATURE:
<221> NAME/KEY: MOD_RES
<222> LOCATION: (2)
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
```

```
         or Aib, in D or L form
<220> FEATURE:
<221> NAME/KEY: MOD_RES
<222> LOCATION: (3)
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: (4)
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: (5)
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: (6)
<223> OTHER INFORMATION: P, P(3-OH), (delta)Pro, Pip, N-Me-A, P(3-OH),
      Y(3-I), b-h-Y, or Aib, in D or L form
<220> FEATURE:
<221> NAME/KEY: MOD_RES
<222> LOCATION: (7)
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: (8)
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: (9)
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: (10)
<223> OTHER INFORMATION: Cys or Pen, in D or L form
<220> FEATURE:
<221> NAME/KEY: MOD_RES
<222> LOCATION: (11)..(13)
<223> OTHER INFORMATION: any amino acid

<400> SEQUENCE: 829

Xaa Xaa Xaa Xaa Xaa Xaa Xaa Xaa Xaa Xaa Xaa Xaa Xaa
1               5                   10

<210> SEQ ID NO 830
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)
<223> OTHER INFORMATION: Cys or Pen, in D or L form
<220> FEATURE:
<221> NAME/KEY: MOD_RES
<222> LOCATION: (4)
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L form
<220> FEATURE:
<221> NAME/KEY: MOD_RES
<222> LOCATION: (5)
<223> OTHER INFORMATION: T, A, N, S, Y, R, V, I, K, D, G, b-h-G, Orn,
      or Dpr, in D or L form
```

```
<220> FEATURE:
<221> NAME/KEY: MOD_RES
<222> LOCATION: (6)
<223> OTHER INFORMATION: = R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: (7)
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: (8)
<223> OTHER INFORMATION: P, P(3-OH), (delta)Pro, Pip, N-Me-A, P(3-OH),
      Y(3-I), b-h-Y, or Aib, in D or L form
<220> FEATURE:
<221> NAME/KEY: MOD_RES
<222> LOCATION: (9)
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: (10)
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: (11)
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: (12)
<223> OTHER INFORMATION: Cys or Pen, in D or L form

<400> SEQUENCE: 830

Xaa Xaa Xaa Xaa Xaa Xaa Xaa Xaa Xaa Xaa Xaa Xaa
1               5                   10

<210> SEQ ID NO 831
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: any amino acid in L form
<220> FEATURE:
<221> NAME/KEY: MOD_RES
<222> LOCATION: (2)
<223> OTHER INFORMATION: W, 1-Nal, 2-Nal, Bpa, thien-W, W(5-OH),
      7-aza-Trp, 1-methyl-Trp, 5-bromo-Tryp, 5-chloro-Tryp, 5-fluor-Trp,
      7-methyl-trp, 6-methyl-Trp, 6-flouro-Trp, or 6-hydroxy-trp
<220> FEATURE:
<221> NAME/KEY: MOD_RES
<222> LOCATION: (3)
<223> OTHER INFORMATION: H, A, K, or S
<220> FEATURE:
<221> NAME/KEY: MOD_RES
<222> LOCATION: (4)
<223> OTHER INFORMATION: Cys or Pen
<220> FEATURE:
<221> NAME/KEY: MOD_RES
<222> LOCATION: (5)
<223> OTHER INFORMATION: T, Y, G, K, F(4-NH2), F(3,4-OMe2), F(3-OMe),
      F(4-CF3), F(4-CN), F(4-NO2), F(4-F), F(4-NO2), Hfe, 4-tBu-F,
      4-CO2H-F, h-Tyr, h-Tyr(Me), Y(2,6-Me2), Y(3-Cl), Y(3-I), Y(Bn,
      3-Cl), 2-substituted L-Tyr, 2,3-substituted-L-Tyr, 2,3,5-
      substituted-L-tyr, 2,5-substituted-L-Tyr, 2,6-substituted-L-Tyr,
      2,3,5,6-substituted-L-Tyr, 3-substituted-L-Tyr, 3,5-substituted-
      L-Tyr, 2-substituted L-Phe, 2,3-substituted-L-Phe, 2,3,5-
      substituted-L- Phe, 2,5-substituted-L- Phe, 2,6-substituted-L-
```

```
      Phe, 2,3,5,6-substituted-L- Phe, 3-substituted-L- Phe, 3,5-
      substituted-L-L-2-pyridylalanine, L-3-pyridylalanine, or L-4-
      pyridylalanine
<220> FEATURE:
<221> NAME/KEY: MOD_RES
<222> LOCATION: (7)
<223> OTHER INFORMATION: any amino acid in L form
<220> FEATURE:
<221> NAME/KEY: MOD_RES
<222> LOCATION: (8)
<223> OTHER INFORMATION: F, Y, F(4-NH2), F(3,4-OMe2), F(3-OMe),
      F(4-CF3), F(4-CN), F(4-NO2), F(4-F), F(4-NO2), Hfe, 4-tBu-F,
      4-CO2H-F, h-Tyr, h-Tyr(Me), Y(2,6-Me2), Y(3-Cl), Y(3-I), Y(Bn,
      3-Cl), 2-substituted L-Tyr, 2,3-substituted-L-Tyr, 2,3,5-
      substituted-L-tyr, 2,5-substituted-L-Tyr, 2,6-substituted-L-Tyr,
      2,3,5,6-substituted-L-Tyr, 3-substituted-L-Tyr, 3,5-substituted-L-
      Tyr, 2-substituted L-Phe, 2,3-substituted-L-Phe, 2,3,5-
      substituted-L- Phe, 2,5-substituted-L- Phe, 2,6-substituted-L-
      Phe, 2,3,5,6-substituted-L- Phe, 3-substituted-L- Phe, 3,5-
      substituted-L-L-2-pyridylalanine, L-3-pyridylalanine, or L-4-
      pyridylalanine
<220> FEATURE:
<221> NAME/KEY: MOD_RES
<222> LOCATION: (9)
<223> OTHER INFORMATION: Pro, L-hydroxyproline, piperidine-2-carboxylic
      acid, or 4-hydroxypiperidine-2-carboxylic acid
<220> FEATURE:
<221> NAME/KEY: MOD_RES
<222> LOCATION: (10)
<223> OTHER INFORMATION: H, A, or Y
<220> FEATURE:
<221> NAME/KEY: MOD_RES
<222> LOCATION: (12)
<223> OTHER INFORMATION: Y, F(4-NH2), F(3,4-OMe2), F(3-OMe), F(4-CF3),
      F(4-CN), F(4-NO2), F(4-F), F(4-NO2), Hfe, 4-tBu-F, 4-CO2H-F,
      h-Tyr, h-Tyr(Me), Y(2,6-Me2), Y(3-Cl), Y(3-I), Y(Bn, 3-Cl),
      2-substituted L-Tyr, 2,3-substituted-L-Tyr, 2,3,5-substituted-L-
      tyr, 2,5-substituted-L-Tyr, 2,6-substituted-L-Tyr, 2,3,5,6-
      substituted-L-Tyr, 3-substituted-L-Tyr, 3,5-substituted-L-Tyr,
      2-substituted L-Phe, 2,3-substituted-L-Phe, 2,3,5-substituted-L-
      Phe, 2,5-substituted-L- Phe, 2,6-substituted-L- Phe, 2,3,5,6-
      substituted-L- Phe, 3-substituted-L- Phe, 3,5-substituted-L- Phe,
      L-2-pyridylalanine, L-3-pyridylalanine, or L-4-pyridylalanine
<220> FEATURE:
<221> NAME/KEY: MOD_RES
<222> LOCATION: (13)
<223> OTHER INFORMATION: Cys or Pen
<220> FEATURE:
<221> NAME/KEY: MOD_RES
<222> LOCATION: (14)
<223> OTHER INFORMATION: L, V, L I, V, A, L, G, Tle, L-norvaline, L-
      norleucine, L-dehydroleucine, L-abu (2-aminobutyric acid),
      L-tert-leucine, beta-cyclohexyl-L-alanine, L-homoleucine, or L-
      homo-cyclohexylalanine, or F(4-NH2), F(3,4-OMe2), F(3-OMe),
      F(4-CF3), F(4-CN), F(4-NO2), F(4-F), F(4-NO2), Hfe, 4-tBu-F,
      4-CO2H-F, h-Tyr, h-Tyr(Me), Y(2,6-Me2), Y(3-Cl), Y(3-I),
      Y(Bn, 3-Cl), 2-substituted L-Tyr, 2,3-substituted-L-Tyr, 2,3,5-
      substituted-L-tyr, 2,5-substituted-L-Tyr, 2,6-substituted-L-Tyr,
      2,3,5,6-substituted-L-Tyr, 3-substituted-L-Tyr, 3,5-substituted-
      L-Tyr, 2-substituted L-Phe, 2,3-substituted-L-Phe, 2,3,5-
      substituted-L- Phe, 2,5-substituted-L- Phe, 2,6-substituted-L-
      Phe, 2,3,5,6-substituted-L- Phe, 3-substituted-L- Phe, 3,5-
      substituted-L-L-2-pyridylalanine, L-3-pyridylalanine, or L-4-
      pyridylalanine
<220> FEATURE:
<221> NAME/KEY: MOD_RES
<222> LOCATION: (15)
<223> OTHER INFORMATION: Y, F, F(4-NH2), F(3,4-OMe2), F(3-OMe),
      F(4-CF3), F(4-CN), F(4-NO2), F(4-F), F(4-NO2), Hfe, 4-tBu-F,
      4-CO2H-F, h-Tyr, h-Tyr(Me), Y(2,6-Me2), Y(3-Cl), Y(3-I), Y(Bn,
      3-Cl), 2-subs 2,3-substituted-L-Tyr, 2,3,5-substituted-L-tyr,
      2,5-substituted-L-Tyr, 2,6-substituted-L-Tyr, 2,3,5,6-substituted-
      L-Tyr, 3-substituted-L-Tyr, 3,5-substituted-L-Tyr, 2-substituted
      L-Phe, 2,3-substituted-L-Phe, 2,3,5-substituted-L-Phe, 2,5-
      substituted-L- Phe, 2,6-substituted-L- Phe, 2,3,5,6-substituted-L-
      Phe, 3-substituted-L- Phe, 3,5-substituted-L- Phe, L-2-
      pyridylalanine, L-3-pyridylalanine, or L-4-pyridylalanine
<220> FEATURE:
<221> NAME/KEY: MOD_RES
```

```
<222> LOCATION: (16)
<223> OTHER INFORMATION: G, Y, Bip, or F(4-NH2), F(3,4-OMe2), F(3-OMe),
      F(4-CF3), F(4-CN), F(4-NO2), F(4-F), F(4-NO2), Hfe, 4-tBu-F, 4-
      CO2H-F, h-Tyr, h-Tyr(Me), Y(2,6-Me2), Y(3-Cl), Y(3-I), Y(Bn,
      3-Cl), 2-substituted L-Tyr, 2,3-substituted-L-Tyr, 2,3,5-
      substituted-L-tyr, 2,5-substituted-L-Tyr, 2,6-substituted-L-Tyr,
      2,3,5,6-substituted-L-Tyr, 3-substituted-L-Tyr, 3,5-substituted-
      L-Tyr, 2-substituted L-Phe, 2,3-substituted-L-Phe, 2,3,5-
      substituted-L- P 2,5-substituted-L- Phe, 2,6-substituted-L- Phe,
      2,3,5,6-substituted-L- Phe, 3-substituted-L- Phe, 3,5-substituted-
      L- Phe, L-2-pyridylalanine, L-3-pyridylalanine, or L-4-
      pyridylalanine

<400> SEQUENCE: 831

Xaa Xaa Xaa Xaa Xaa Thr Xaa Xaa Xaa Xaa His Xaa Cys Xaa Xaa Xaa
1               5                   10                  15

<210> SEQ ID NO 832
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: C* is C or Pen in D or L form
<220> FEATURE:
<221> NAME/KEY: MOD_RES
<222> LOCATION: 2
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L form
<220> FEATURE:
<221> NAME/KEY: MOD_RES
<222> LOCATION: 3
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: 4
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: 5
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: 6
<223> OTHER INFORMATION: P, P(3-OH), ?Pro, Pip, N-Me-A, P(3-OH), Y(3-I),
      b-h-Y, or Aib, in D or L form
<220> FEATURE:
<221> NAME/KEY: MOD_RES
<222> LOCATION: 7
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: 8
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: 9
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: 10
<223> OTHER INFORMATION: C* is C or Pen in D or L form
<220> FEATURE:
<221> NAME/KEY: MOD_RES
<222> LOCATION: 11
```

-continued

```
<223> OTHER INFORMATION: any amino acid
<220> FEATURE:
<221> NAME/KEY: MOD_RES
<222> LOCATION: 12
<223> OTHER INFORMATION: any amino acid
<220> FEATURE:
<221> NAME/KEY: MOD_RES
<222> LOCATION: 13
<223> OTHER INFORMATION: any amino acid
<220> FEATURE:
<221> NAME/KEY: MOD_RES
<222> LOCATION: 14
<223> OTHER INFORMATION: any one or two amino acids; wherein the peptide
      has a length of 14 to 20 amino acids

<400> SEQUENCE: 832

Xaa Xaa Xaa Xaa Xaa Xaa Xaa Xaa Xaa Xaa Xaa Xaa Xaa Xaa
1               5                   10

<210> SEQ ID NO 833
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: C* is C or Pen in D or L form
<220> FEATURE:
<221> NAME/KEY: MOD_RES
<222> LOCATION: 2
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L formm
<220> FEATURE:
<221> NAME/KEY: MOD_RES
<222> LOCATION: 3
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: 4
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: 5
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: 6
<223> OTHER INFORMATION: P, P(3-OH), ?Pro, Pip, N-Me-A, P(3-OH), Y(3-I),
      b-h-Y, or Aib, in D or L form
<220> FEATURE:
<221> NAME/KEY: MOD_RES
<222> LOCATION: 7
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: 8
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: 9
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: 10
<223> OTHER INFORMATION: C* is C or Pen in D or L form
<220> FEATURE:
```

```
<221> NAME/KEY: MOD_RES
<222> LOCATION: 11
<223> OTHER INFORMATION: any amino acid
<220> FEATURE:
<221> NAME/KEY: MOD_RES
<222> LOCATION: 12
<223> OTHER INFORMATION: any amino acid
<220> FEATURE:
<221> NAME/KEY: MOD_RES
<222> LOCATION: 13
<223> OTHER INFORMATION: G, E, Y, F, V, Bip, F(4-NH2), or Aib, in D or
      L form; and is any amino acid
<220> FEATURE:
<221> NAME/KEY: MOD_RES
<222> LOCATION: 14
<223> OTHER INFORMATION: K, KK, Peg K, PEG(1xO), 1,4-AMB, 1,3-AMB,
      1,6-Hex, PEG, or GTE, in D or L form; wherein the peptide has a
      length of 14 to 20 amino acids

<400> SEQUENCE: 833

Xaa Xaa Xaa Xaa Xaa Xaa Xaa Xaa Xaa Xaa Xaa Xaa Xaa Xaa
1               5                   10

<210> SEQ ID NO 834
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: one to three amino acids; and wherein the
      peptide has a length of 14 to 20 amino acids
<220> FEATURE:
<221> NAME/KEY: MOD_RES
<222> LOCATION: 2
<223> OTHER INFORMATION: one to three amino acids; and wherein the
      peptide has a length of 14 to 20 amino acids
<220> FEATURE:
<221> NAME/KEY: MOD_RES
<222> LOCATION: 3
<223> OTHER INFORMATION: any amino acid
<220> FEATURE:
<221> NAME/KEY: MOD_RES
<222> LOCATION: 4
<223> OTHER INFORMATION: any amino acid
<220> FEATURE:
<221> NAME/KEY: MOD_RES
<222> LOCATION: 5
<223> OTHER INFORMATION: C* is C or Pen in D or L form
<220> FEATURE:
<221> NAME/KEY: MOD_RES
<222> LOCATION: 6
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L form
<220> FEATURE:
<221> NAME/KEY: MOD_RES
<222> LOCATION: 7
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: 8
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: 9
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
<220> FEATURE:
<221> NAME/KEY: MOD_RES
<222> LOCATION: 10
<223> OTHER INFORMATION: P, P(3-OH), ?Pro, Pip, N-Me-A, P(3-OH), Y(3-I),
```

```
      b-h-Y, or Aib, in D or L form
<220> FEATURE:
<221> NAME/KEY: MOD_RES
<222> LOCATION: 11
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: 12
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: 13
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: 14
<223> OTHER INFORMATION: C* is C or Pen in D or L form

<400> SEQUENCE: 834

Xaa Xaa Xaa Xaa Xaa Xaa Xaa Xaa Xaa Xaa Xaa Xaa Xaa Xaa
1               5                   10

<210> SEQ ID NO 835
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: G, K, PP, GY, GV, GF, GH, GK(G), KK(K), Dpr,
      EAG, or PPG, in D or L form; and wherein the peptide has a length
      of 14 to 20 amino acids
<220> FEATURE:
<221> NAME/KEY: MOD_RES
<222> LOCATION: 2
<223> OTHER INFORMATION: Q, G, A, D, S, P, K, GQ, K(G), K(Y.G), K(V.G).
      K(F.G), K(H.H),  KK(K), Dpr, or Aib, in D or L form
<220> FEATURE:
<221> NAME/KEY: MOD_RES
<222> LOCATION: 3
<223> OTHER INFORMATION: any amino acid
<220> FEATURE:
<221> NAME/KEY: MOD_RES
<222> LOCATION: 4
<223> OTHER INFORMATION: any amino acid
<220> FEATURE:
<221> NAME/KEY: MOD_RES
<222> LOCATION: 5
<223> OTHER INFORMATION: C* is C or Pen in D or L form
<220> FEATURE:
<221> NAME/KEY: MOD_RES
<222> LOCATION: 6
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L form
<220> FEATURE:
<221> NAME/KEY: MOD_RES
<222> LOCATION: 7
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: 8
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: 9
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
      in D or L form
```

```
<220> FEATURE:
<221> NAME/KEY: MOD_RES
<222> LOCATION: 10
<223> OTHER INFORMATION: P, P(3-OH), ?Pro, Pip, N-Me-A, P(3-OH), Y(3-I),
      b-h-Y, or Aib, in D or L form
<220> FEATURE:
<221> NAME/KEY: MOD_RES
<222> LOCATION: 11
<223> OTHER INFORMATION: H, A, S, K, N, Y, T, D, R, W, P, Aib, or b-h-T,
      in D or L form
<220> FEATURE:
<221> NAME/KEY: MOD_RES
<222> LOCATION: 12
<223> OTHER INFORMATION: H, A, S, N, D, Y, W, Aib, Dpr, 2-Pal, 1-Nal,
      thien-W, W(5-OH), or b-h-W, in D or L form
<220> FEATURE:
<221> NAME/KEY: MOD_RES
<222> LOCATION: 13
<223> OTHER INFORMATION: Y, A, R, T, V, H, D, S, P, 1-Nal, Bip, DOPA,
      H-Tyr, H-Tyr(Me), F(3-OMe), Y(3-Cl), Y(2,6-Me2), Dip, F(4-NH2),
      or Aib, in D or L form
<220> FEATURE:
<221> NAME/KEY: MOD_RES
<222> LOCATION: 14
<223> OTHER INFORMATION: C* is C or Pen in D or L form

<400> SEQUENCE: 835

Xaa Xaa Xaa Xaa Xaa Xaa Xaa Xaa Xaa Xaa Xaa Xaa Xaa Xaa
1               5                   10

<210> SEQ ID NO 836
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 1
<223> OTHER INFORMATION: G
<220> FEATURE:
<221> NAME/KEY: MOD_RES
<222> LOCATION: 2
<223> OTHER INFORMATION: Q, D, or K(G)
<220> FEATURE:
<221> NAME/KEY: MOD_RES
<222> LOCATION: 3
<223> OTHER INFORMATION: any amino acid
<220> FEATURE:
<221> NAME/KEY: MOD_RES
<222> LOCATION: 4
<223> OTHER INFORMATION: any amino acid
<220> FEATURE:
<221> NAME/KEY: MOD_RES
<222> LOCATION: 5
<223> OTHER INFORMATION: C* is C or Pen in D or L form
<220> FEATURE:
<221> NAME/KEY: MOD_RES
<222> LOCATION: 6
<223> OTHER INFORMATION: T, A, K, V, I, S, Y, G, R, P, L, 3-NO2 Y,
      4-Pal, 4-CO2H-F, 4-tBu-F, F(4-NH2), Y(Bn, 3-Cl), b-h-S, Y(3-I),
      or Aib, in D or L form
<220> FEATURE:
<221> NAME/KEY: MOD_RES
<222> LOCATION: 7
<223> OTHER INFORMATION: T, A, N, S, Y, R, V, I, K, D, G, b-h-G, Orn,
      or Dpr, in D or L form
<220> FEATURE:
<221> NAME/KEY: MOD_RES
<222> LOCATION: 8
<223> OTHER INFORMATION: R, A, S, L, Y, D, K, G, P, Aib, Y(3-Cl), I,
      Cha, Abu, F(4-F), Dopa, Tle, Cit, b-h-D, or K(Boc), in D or L form
<220> FEATURE:
<221> NAME/KEY: MOD_RES
<222> LOCATION: 9
<223> OTHER INFORMATION: F, Bip, F(4-CF3), 4-Pal, 1-Nal, F(4-NO2), Hfe,
      Bpa, F(4-CN), F(4-NH2), F(3,4-OMe), 2-Nal, Y(3-Cl), Aib, or b-h-E,
```

```
        in D or L form
<220> FEATURE:
<221> NAME/KEY: MOD_RES
<222> LOCATION: 10
<223> OTHER INFORMATION: P, P(3-OH), ?Pro, Pip, N-Me-A, P(3-OH), Y(3-I),
        b-h-Y, or Aib, in D or L form
<220> FEATURE:
<221> NAME/KEY: MOD_RES
<222> LOCATION: 11
<223> OTHER INFORMATION: H, A, S, K, N, Y, T, D, R, W, P, Aib, or b-h-T,
        in D or L form
<220> FEATURE:
<221> NAME/KEY: MOD_RES
<222> LOCATION: 12
<223> OTHER INFORMATION: H, A, S, N, D, Y, W, Aib, Dpr, 2-Pal, 1-Nal,
        thien-W, W(5-OH), or b-h-W, in D or L form
<220> FEATURE:
<221> NAME/KEY: MOD_RES
<222> LOCATION: 13
<223> OTHER INFORMATION: Y, A, R, T, V, H, D, S, P, 1-Nal, Bip, DOPA,
        H-Tyr, H-Tyr(Me), F(3-OMe), Y(3-Cl), Y(2,6-Me2), Dip, F(4-NH2),
        or Aib, in D or L form
<220> FEATURE:
<221> NAME/KEY: MOD_RES
<222> LOCATION: 14
<223> OTHER INFORMATION: C* is C or Pen in D or L form

<400> SEQUENCE: 836

Xaa Xaa Xaa Xaa Xaa Xaa Xaa Xaa Xaa Xaa Xaa Xaa Xaa Xaa
1               5                   10
```